US007709218B2

(12) United States Patent
Gentz et al.

(10) Patent No.: US 7,709,218 B2
(45) Date of Patent: **\*May 4, 2010**

(54) TUMOR NECROSIS FACTOR RECEPTORS 6α AND 6β

(75) Inventors: Reiner L. Gentz, Belo Horizonte (BR); Reinhard Ebner, Gaithersburg, MD (US); Guo-Liang Yu, Berkeley, CA (US); Steven M. Ruben, Brookeville, MD (US); Jian Ni, Germantown, MD (US); Ping Feng, Germantown, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,301

(22) Filed: May 8, 2009

(65) Prior Publication Data

US 2009/0226456 A1    Sep. 10, 2009

Related U.S. Application Data

(60) Division of application No. 11/416,310, filed on May 3, 2006, now Pat. No. 7,534,428, which is a continuation of application No. 09/935,727, filed on Aug. 24, 2001, now Pat. No. 7,285,267, and a continuation-in-part of application No. 09/006,352, filed on Jan. 13, 1998, and a continuation-in-part of application No. 09/518,931, filed on Mar. 3, 2000, now Pat. No. 7,186,800, which is a continuation-in-part of application No. 09/006,352, filed on Jan. 13, 1998, said application No. 09/935,727 is a continuation-in-part of application No. 09/006,352, filed on Jan. 13, 1998, and a continuation-in-part of application No. 09/518,931, filed on Mar. 3, 2000, now Pat. No. 7,186,800.

(60) Provisional application No. 60/035,496, filed on Jan. 14, 1997, provisional application No. 60/121,774, filed on Mar. 4, 1999, provisional application No. 60/124,092, filed on Mar. 12, 1999, provisional application No. 60/131,279, filed on Apr. 27, 1999, provisional application No. 60/131,964, filed on Apr. 30, 1999, provisional application No. 60/146,371, filed on Aug. 2, 1999, provisional application No. 60/168,235, filed on Dec. 1, 1999, provisional application No. 60/227,598, filed on Aug. 25, 2000, provisional application No. 60/252,131, filed on Nov. 21, 2000, provisional application No. 60/303,224, filed on Jul. 6, 2001.

(51) Int. Cl.
G01N 33/53      (2006.01)
G01N 33/563     (2006.01)
G01N 33/577     (2006.01)
C07K 16/00      (2006.01)
C07K 16/18      (2006.01)
C07K 16/28      (2006.01)

(52) U.S. Cl. .................... 435/7.1; 435/7.2; 424/130.1; 424/133.1; 424/135.1; 424/141.1; 424/143.1; 530/387.1; 530/387.9; 530/388.1; 530/388.22

(58) Field of Classification Search ...................... None
See application file for complete search history.

(56) References Cited

U.S. PATENT DOCUMENTS

| 4,847,325 | A  | 7/1989  | Shadle et al.   |
|-----------|----|---------|-----------------|
| 5,194,596 | A  | 3/1993  | Tischer et al.  |
| 5,350,836 | A  | 9/1994  | Kopchick et al. |
| 5,620,889 | A  | 4/1997  | Lynch et al.    |
| 5,632,994 | A  | 5/1997  | Reed et al.     |
| 5,652,210 | A  | 7/1997  | Barr et al.     |
| 5,663,070 | A  | 9/1997  | Barr et al.     |
| 5,741,667 | A  | 4/1998  | Goeddel et al.  |
| 5,830,469 | A  | 11/1998 | Lynch et al.    |
| 5,874,546 | A  | 2/1999  | Nagata et al.   |
| 5,876,969 | A  | 3/1999  | Fleer et al.    |
| 5,885,800 | A  | 3/1999  | Emery et al.    |
| 5,985,614 | A  | 11/1999 | Rosen et al.    |
| 6,297,367 | B1 | 10/2001 | Tribouley       |
| 6,764,679 | B2 | 7/2004  | Ashkenazi et al.|
| 2006/0234285 | A1 | 10/2006 | Gentz et al.  |

FOREIGN PATENT DOCUMENTS

| EP | 0 861 850   | 9/1998  |
|----|-------------|---------|
| WO | WO-95/33051 | 12/1995 |

(Continued)

OTHER PUBLICATIONS

U.S. Appl. No. 09/912,293, Not Published, Rosen et al.
GenBank Accession No. AA025673 (Aug. 16, 1996).
Kwon et al., *J. Biol. Chem.*, 272:14272-14276 (1997).
GenBank Accession No. W67560 (Oct. 16 1996).
GenBank Accession No. M91489 (Oct. 29, 1992).
Gieser et al., *Genomics*, 13(3):873-876 (Jul. 1992).
Hiller et al., *Genome Res.*, 6:807-828 (1996).
Pitti et al., *Nature*, 396:699-703 (Dec. 17, 1998).
International Search Report mailed Jul. 11, 2000, in corresponding International Application No. PCT/US00/05686.

(Continued)

*Primary Examiner*—Christine J Saoud
*Assistant Examiner*—Jon M Lockard

(57) ABSTRACT

The present invention relates to novel Tumor Necrosis Factor Receptor proteins. In particular, isolated nucleic acid molecules are provided encoding the human TNFR-6α & -6β proteins. TNFR-6α & -6β polypeptides and antibodies that bind TNFR-6α & -6β polypeptides are also provided as are vectors, host cells and recombinant methods for producing the same. The invention further relates to screening methods for identifying agonists and antagonists of TNFR-6α & -6β activity. Also provided are diagnostic methods for detecting immune system-related disorders and therapeutic methods for treating immune system-related disorders.

15 Claims, 23 Drawing Sheets

FOREIGN PATENT DOCUMENTS

| WO | WO-96/34095 | 10/1996 |
|---|---|---|
| WO | WO-98/30694 | 7/1998 |
| WO | WO-98/56892 | 12/1998 |
| WO | WO-99/04001 | 1/1999 |
| WO | WO-99/07738 | 2/1999 |
| WO | WO-99/11791 | 3/1999 |
| WO | WO-99/14330 | 3/1999 |
| WO | WO-99/26977 | 6/1999 |
| WO | WO-99/31128 | 6/1999 |
| WO | WO-99/33980 | 7/1999 |
| WO | WO-99/46376 | 9/1999 |
| WO | WO-99/50413 | 10/1999 |
| WO | WO-00/01817 | 1/2000 |
| WO | WO-00/32221 | 6/2000 |
| WO | WO-00/34782 | 6/2000 |
| WO | WO-00/37094 | 6/2000 |
| WO | WO-00/46247 | 8/2000 |
| WO | WO-00/52028 A1 | 9/2000 |
| WO | WO-00/53223 | 9/2000 |
| WO | WO-00/53755 | 9/2000 |
| WO | WO-00/53758 | 9/2000 |
| WO | WO-00/58465 | 10/2000 |
| WO | WO-00/58466 | 10/2000 |
| WO | WO-00/60079 | 10/2000 |
| WO | WO-00/73452 | 12/2000 |
| WO | WO-00/75316 | 12/2000 |
| WO | WO-01/10908 | 2/2001 |
| WO | WO-01/18041 | 3/2001 |
| WO | WO-01/18055 | 3/2001 |
| WO | WO-01/18202 | 3/2001 |
| WO | WO-01/22920 A2 | 4/2001 |
| WO | WO-01/28582 A3 | 4/2001 |
| WO | WO-01/42434 A1 | 6/2001 |
| WO | WO-01/42463 A1 | 6/2001 |
| WO | WO-01/68912 A3 | 9/2001 |
| WO | WO-02/00677 A1 | 1/2002 |
| WO | WO-02/00928 A3 | 1/2002 |
| WO | WO-02/09668 A2 | 2/2002 |
| WO | WO-02/060317 A2 | 8/2002 |
| WO | WO-02/060947 A3 | 8/2002 |
| WO | WO-02/060949 A3 | 8/2002 |
| WO | WO-02/078524 A2 | 10/2002 |

OTHER PUBLICATIONS

Kikuno et al., "Prediction of the Coding Sequences of Unidentified Human Genes, XIV, the Complete Sequences of 100 New cDNA Clones from Brain Which Code for Large Proteins in vitro," *DNA Res.*, 6:197-205 (1999).

Bai et al., "Overexpression of M68/DcR3 in human gastrointestinal tract tumors independent of gene amplification and its location in a four-gene cluster," *PNAS*, 97(3):1230-1235 (Feb. 1, 2000).

Yu et al,, "A Newly Identified Member of Tumor Necrosis Factor Receptor Superfamily (TR6) Suppresses Light-mediated Apoptosis," *J. Biol. Chem.*, 274(20):13733-13736 (May 14, 1999).

Rabinowich et al., "Lymphocyte Apoptosis Induced by Fas Ligand-expressing Ovarian Carcinoma Cells," *J. Clin. Invest.*, 101(11):2579-2588 (Jun. 1998).

Walker et al., "Tumor expression of Fas ligand (CD95L) and the consequences," *Curr. Opin. Immunol.*, 10:564-572 (1998).

Gratas et al., "Up-Regulation of Fas (APO-1/CD95) Ligand and Down-Regulation of Fas Expression in Human Esophageal Cancer," *Cancer Res.*, 58:2057-2062 (May 15, 1998).

Buzyn et al., "Membrane-Bound Fas (Apo-1/CD95) Ligand on Leukemic Cells: A Mechanism of Tumor Immune Escape in Leukemia Patients," *Blood*, 94(9):3135-3140 (Nov. 1, 1999).

Duesterhoeft et al., GenBank Accession No. AL157435 (Feb. 15, 2000).

Zhang et al., "Modulation of T-cell Responses to Alloantigens by TR6/DcR3," *J. Clin. Invest.*, 107(11):1459-1468 (Jun. 2001).

Connolly et al,, "In Vivo Inhibition of Fas-Ligand-Mediated Killing by TR6, a Fas Ligand Decoy Receptor," *J. Pharmacol. Exper. Ther.*, 298(1):25-33 (2001).

Vukicevic et al., *PNAS USA* 93:9021-9026 (1996).

Yu et al., GenBank Accession No. AF134240 (May 11, 1999).

Ashkenazi and Dixit, "Apoptosis control by death and decoy receptors," *Curr. Opin. Cell Biol.*, 11(2):255-260 (1999).

Skolnick et al,, "From genes to protein structure and function: novel applications of computational approaches in the genomic era," *Trends in Biotech.*, 18:34-39 (Jan. 2000).

Kikuno et al., "Prediction of the coding sequences of identified human genes," PIR Accession No. T45294 (Jan. 31, 2000).

Bai et al., GenBank Accession No. AF217793 (Feb. 12, 2000).

Bai et al., GenBank Accession No. AF217794 (Feb. 12, 2000).

Bai et al., GenBank Accession No. AF217796 (Feb. 21, 2000).

Yan et al., "Two-Amino Acid Molecular Switch in an Epithelial Morphogen That Regulates Binding to Two Distinct Receptors," *Science*, 290:523-527 (Oct. 20, 2000).

Ohshima et al., "Amplification and expression of a decoy receptor for Fas ligand (DcR3) in virus (EBV or HTLV-I) associated lymphomas," *Cancer Letters*, 160 (1):89-97 (2000).

Locksley et al., "The TNF and TNF Receptor Superfamilies: Integrating Mammalian Biology," *Cell*, 104:487-501 (Feb. 23, 2001).

Wallis, GenBank Accession No. AL353715 (Apr. 18, 2001).

Matthews, GenBank Accession No. AL121845 (Jul. 6, 2001).

Pitti et al., GenBank Accession No. NM_032945 (Jul. 6, 2001).

Pitti et al., GenBank Accession No. NM_032957 (Jul. 17, 2001).

Adams et al., "Initial assessment of human gene diversity and expression patterns," *Nature*, 377(6547 Supp):3-174 (Sep. 28, 1995).

Adams et al., GenBank Accession No. AA325843 (Apr. 20, 1997).

Hillier et al., GenBank Accession No. AA025672 (Feb. 1, 1997).

Hillier et al., GenBank Accession No. AA155646 (Nov. 8, 1997).

Ksontini et al., "Disparate Roles for TNF-α and Fas Ligand in Concanavalin A-Induced Hepatitis," *J. Immunol.*, 160:4082-4089 (1998).

Kondo et al., "Essential roles of the Fas ligand in the development of hepatitis," *Nat. Med.*, 3:409-413 (1997).

Tagawa et al., "Suppression of concanavalin A-induced hepatitis in IFN-gamma(-/-) mice, but not in TNF-alpha(-/-) mice: role for IFN-gamma in activating apoptosis of hepatocytes," *J. Immunol.*, 159:1418-1428 (1997).

Ando et al., "Perforin, Fas/Fas ligand, and TNF-alpha pathways as specific and bystander killing mechanisms of hepatitis C virus-specific human CTL," *J. Immunol.*, 158:5283-5291 (1997).

Nagata, S., "Apoptosis by Death Factor," *Cell*, 88:355-365 (1997).

International Search Report mailed Aug. 21, 1998 in International Application No. PCT/US98/00153.

International Search Report mailed Jun. 28, 2002 in International Application No. PCT/US01/26396.

GCTCTCCCTGCTCCAGCAAGGACCATGAGGGCGCTGGAGGGGCCAGGCCTGTCGCTGCTG
                         M  R  A  L  E  G  P  G  L  S  L  L

TGCCTGGTGTTGGCGCTGCCTGCCCTGCTGCCGGTGCCGGCTGTACGCGGAGTGGCAGAA
 C  L  V  L  A  L  P  A  L  L  P  V  P  A  V  R  G  V  A  E

ACACCCACCTACCCCTGGCGGGACGCAGAGACAGGGGAGCGGCTGGTGTGCGCCCAGTGC
 T  P  T  Y  P  W  R  D  A  E  T  G  E  R  L  V  C  A  Q  C

CCCCCAGGCACCTTTGTGCAGCGGCCGTGCCGCCGAGACAGCCCCACGACGTGTGGCCCG
 P  P  G  T  F  V  Q  R  P  C  R  R  D  S  P  T  T  C  G  P

TGTCCACCGCGCCACTACACGCAGTTCTGGAACTACCTGGAGCGCTGCCGCTACTGCAAC
 C  P  P  R  H  Y  T  Q  F  W  N  Y  L  E  R  C  R  Y  C  N

GTCCTCTGCGGGGAGCGTGAGGAGGAGGCACGGGCTTGCCACGCCACCCACAACCGTGCC
 V  L  C  G  E  R  E  E  E  A  R  A  C  H  A  T  H  N  R  A

TGCCGCTGCCGCACCGGCTTCTTCGCGCACGCTGGTTTCTGCTTGGAGCACGCATCGTGT
 C  R  C  R  T  G  F  F  A  H  A  G  F  C  L  E  H  A  S  C

CCACCTGGTGCCGGCGTGATTGCCCCGGGCACCCCCAGCCAGAACACGCAGTGCCAGCCG
 P  P  G  A  G  V  I  A  P  G  T  P  S  Q  N  T  Q  C  Q  P

TGCCCCCCAGGCACCTTCTCAGCCAGCAGCTCCAGCTCAGAGCAGTGCCAGCCCCACCGC
 C  P  P  G  T  F  S  A  S  S  S  S  S  E  Q  C  Q  P  H  R

AACTGCACGGCCCTGGGCCTGGCCCTCAATGTGCCAGGCTCTTCCTCCCATGACACCCTG
 N  C  T  A  L  G  L  A  L  N  V  P  G  S  S  S  H  D  T  L

TGCACCAGCTGCACTGGCTTCCCCCTCAGCACCAGGGTACCAGGAGCTGAGGAGTGTGAG
 C  T  S  C  T  G  F  P  L  S  T  R  V  P  G  A  E  E  C  E

CGTGCCGTCATCGACTTTGTGGCTTTCCAGGACATCTCCATCAAGAGGCTGCAGCGGCTG
 R  A  V  I  D  F  V  A  F  Q  D  I  S  I  K  R  L  Q  R  L

CTGCAGGCCCTCGAGGCCCCGGAGGGCTGGGCTCCGACACCAAGGGCGGGCCGCGCGGCC
 L  Q  A  L  E  A  P  E  G  W  G  P  T  P  R  A  G  R  A  A

TTGCAGCTGAAGCTGCGTCGGCGGCTCACGGAGCTCCTGGGGGCGCAGGACGGGGCGCTG
 L  Q  L  K  L  R  R  R  L  T  E  L  L  G  A  Q  D  G  A  L

CTGGTGCGGCTGCTGCAGGCGCTGCGCGTGGCCAGGATGCCCGGGCTGGAGCGGAGCGTC
 L  V  R  L  L  Q  A  L  R  V  A  R  M  P  G  L  E  R  S  V

CGTGAGCGCTTCCTCCCTGTGCACTGATCCTGGCCCCCTCTTATTTATTCTACATCCTTG
 R  E  R  F  L  P  V  H  *

GCACCCCACTTGCACTGAAAGAGGCTTTTTTTTAAATAGAAGAAATGAGGTTTCTTAAAG

CTTATTTTTTATAAAGCTTTTTCATAAAAAAAAAAAAAAAAAAAAAAAAAAAAAAAAAAA

FIG.1

TGGCATGTCGGTCAGGCACAGCAGGGTCCTGTGTCCGCGCTGAGCCGCGCTCTCCCTGCT

CCAGCAAGGACCATGAGGGCGCTGGAGGGGCCAGGCCTGTCGCTGCTGTGCCTGGTGTTG
     M  R  A  L  E  G  P  G  L  S  L  L  C  L  V  L

GCGCTGCCTGCCCTGCTGCCGGTGCCGGCTGTACGCGGAGTGGCAGAAACACCCACCTAC
A  L  P  A  L  L  P  V  P  A  V  R  G  V  A  E  T  P  T  Y

CCCTGGCGGGACGCAGAGACAGGGGAGCGGCTGGTGTGCGCCCAGTGCCCCCCAGGCACC
P  W  R  D  A  E  T  G  E  R  L  V  C  A  Q  C  P  P  G  T

TTTGTGCAGCGGCCGTGCCGCCGAGACAGCCCCACGACGTGTGGCCCGTGTCCACCGCGC
F  V  Q  R  P  C  R  R  D  S  P  T  T  C  G  P  C  P  P  R

CACTACACGCAGTTCTGGAACTACCTGGAGCGCTGCCGCTACTGCAACGTCCTCTGCGGG
H  Y  T  Q  F  W  N  Y  L  E  R  C  R  Y  C  N  V  L  C  G

GAGCGTGAGGAGGAGGCACGGGCTTGCCACGCCACCCACAACCGTGCCTGCCGCTGCCGC
E  R  E  E  E  A  R  A  C  H  A  T  H  N  R  A  C  R  C  R

ACCGGCTTCTTCGCGCACGCTGGTTTCTGCTTGGAGCACGCATCGTGTCCACCTGGTGCC
T  G  F  F  A  H  A  G  F  C  L  E  H  A  S  C  P  P  G  A

GGCGTGATTGCCCCGGGTGAGAGCTGGGCGAGGGGAGGGGCCCCCAGGAGTGGTGGCCGG
G  V  I  A  P  G  E  S  W  A  R  G  G  A  P  R  S  G  G  R

AGGTGTGGCAGGGGTCAGGTTGCTGGTCCCAGCCTTGCACCCTGAGCTAGGACACCAGTT
R  C  G  R  G  Q  V  A  G  P  S  L  A  P  *

CCCCTGACCCTGTTCTTCCCTCCTGGCTGCAGGCACCCCCAGCCAGAACACGCAGTGCCA

GCCGTGCCCCCCAGGCACCTTCTCAGCCAGCAGCTCCAGCTCAGAGCAGTGCCAGCCCCA

CCGCAACTGCACGGCCCTGGGCCTGGCCCTCAATGTGCCAGGCTCTTCCTCCCATGACAC

CCTGTGCACCAGCTGCACTGGCTTCCCCCTCAGCACCAGGGTACCAGGTGAGCCAGAGGC

CTGAGGGGGCAGCACACTGCAGGCCAGGCCCACTTGTGCCCTCACTCCTGCCCCTGCACG

TGCATCTAGCCTGAGGCATGCCAGCTGGCTCTGGGAAGGGGCCACAGTGGATTTGAGGGG

TCAGGGGTCCCTCCACTAGATCCCCACCAAGTCTGCCCTCTCAGGGGTGGCTGAGAATTT

GGATCTGAGCCAGGGCACAGCCTCCCCTGGAGAGCTCTGGGAAAGTGGGCAGCAATCTCC

FIG.2A

TAACTGCCCGAGGGGAAGGTGGCTGGCTCCTCTGACACGGGGAAACCGAGGCCTGATGGT

AACTCTCCTAACTGCCTGAGAGGAAGGTGGCTGCCTCCTCTGACATGGGGAAACCGAGGC

CCAATGTTAACCACTGTTGAGAAGTCACAGGGGGAAGTGACCCCCTTAACATCAAGTCAG

GTCCGGTCCATCTGCAGGTCCCAACTCGCCCCTTCCGATGGCCCAGGAGCCCCAAGCCCT

TGCCTGGGCCCCCTTGCCTCTTGCAGCCAAGGTCCGAGTGGCCGCTCCTGCCCCCTAGGC

CTTTGCTCCAGCTCTCTGACCGAAGGCTCCTGCCCCTTCTCCAGTCCCCATCGTTGCACT

GCCCTCTCCAGCACGGCTCACTGCACAGGGATTTCTCTCTCCTGCAAACCCCCCGAGTGG

GGCCCAGAAAGCAGGGTACCTGGCAGCCCCCGCCAGTGTGTGTGGGTGAAATGATCGGAC

CGCTGCCTCCCCACCCCACTGCAGGAGCTGAGGAGTGTGAGCGTGCCGTCATCGACTTTG

TGGCTTTCCAGGACATCTCCATCAAGAGGAGCGGCTGCTGCAGGCCC

```
223  - EGSTGDFAL - - - - - - - - - - - CLLSLLF IGLMY - - - - - - - -  TNFR1
252  MGSSQPVVTRGTTDNLIPVYCS - - - PVGLIVGVTALGLLIGV V  TNFR2
236  - - - - - - - - - - - - - - - - - - - - - - - - VLFLLFTTVVGLVA - - - - -  NgFR
230  - - - - - - - - - - - - - - - - - - - - - - - - CLLLLPIPLIV - I - - - -  LTbR
178  - AD - - - - - - - - - - - - - - - - - - - - LFI LACAWMRHPS - -  FAS
164  KQEPDYYLDEAGRCTACVSCSRDDLVEKTPCAWNSSRTC - -  CD27
242  - - - - - - - - - - - - - - - - - - - - - - IFGILFAILLVFIKK - - -  CD30
200  - - - - - - - - - - - - - - - - - - - - - - - - - - - - - - - - - - - - -  CD40
190  - FFL - - - - - - - - - - - - - - - - - - - - - - - - - - - - - - - - - -  4-1BB
184  - ARPITVQPTEA - - - - - - - - - - - - - - - - - - - - - - - - - - - -  OX40
221  PVFREEY - - - - - - - - - - - - - FSVLNKVATSGFFTGENR  VC22
221  PVFRNGY - - - - - - - - - - - - - FSVLNEVATSGFFTGQNR  CRMB

208  AEECER - - - - - - - - - - - - - - AV I  TNFR-6a
143  - - - - - - - - - - - - - - - - - - - - - - - -  TNFR-6b
```

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| 405 | A | T | W | R | R | R | T | P | R | R | E | A | T | L | E | L | L | G | R | V | L | R | D | M | D | L | L | G | C | - | E | - | - | - | - | - | - | - | - | TNFR1 |
| 409 | - | - | - | - | - | - | - | - | - | - | - | - | - | - | - | - | - | - | - | - | - | - | - | - | - | - | - | - | - | - | - | - | - | - | - | - | - | - | - | TNFR2 |
| 388 | A | S | W | A | T | Q | D | S | S | A | T | L | D | A | - | P | K | D | E | - | - | - | Q | V | P | F | S | K | E | E | C | A | F | - | A | - | - | - | - | NGFR |
| 365 | - | - | - | - | - | - | - | - | R | G | P | G | D | P | - | P | A | P | P | - | - | - | - | - | - | - | - | - | - | - | - | - | - | - | - | - | - | - | - | LTbR |
| 279 | R | N | W | H | Q | L | H | G | K | K | E | A | - | Y | D | T | L | I | K | D | L | K | K | A | N | L | - | C | T | L | A | E | K | I | Q | - | - | - | - | FAS |
| 239 | - | - | - | - | - | - | E | E | G | S | T | I | - | - | - | - | - | - | - | - | - | - | - | - | - | - | - | - | - | - | - | - | - | - | - | - | - | Y | - | CD27 |
| 481 | E | S | L | P | L | Q | D | A | S | P | A | G | G | - | - | - | - | - | - | - | - | P | S | S | P | R | D | L | P | E | P | R | V | S | T | E | H | T | N | CD30 |
| 263 | - | - | - | - | - | - | - | - | - | - | - | - | - | - | - | - | - | - | - | - | - | - | - | - | - | - | - | - | - | - | - | - | - | N | N | K | I | E | K | CD40 |
| 222 | - | - | - | - | - | - | - | - | - | - | - | - | - | - | - | - | - | - | - | - | - | - | - | - | - | - | - | - | - | - | - | - | - | - | - | - | - | - | I | 4-1BB |
| 260 | - | - | - | - | - | - | - | - | - | - | - | - | - | - | - | - | - | - | - | - | - | - | - | - | - | - | - | - | - | - | - | - | - | - | - | - | - | Y | - | OX40 |
| 339 | - | - | - | - | - | - | - | - | - | - | - | - | - | - | - | - | - | - | - | - | - | - | - | - | - | - | - | P | I | T | N | S | K | N | - | - | - | - | - | VC22 |
| 342 | - | - | - | - | - | - | - | - | - | - | - | - | - | - | - | - | - | - | - | - | - | - | - | - | - | - | L | I | T | N | S | S | N | S | Q | Y | - | - | - | CRMB |
| 291 | - | - | - | - | - | - | - | - | - | - | - | - | - | - | - | - | - | - | - | - | - | - | - | - | - | - | - | - | - | - | - | - | - | - | - | - | - | - | - | TNFR-6a |
| 163 | - | - | - | - | - | - | - | - | - | - | - | - | - | - | - | - | - | - | - | - | - | - | - | - | - | - | - | - | - | - | - | - | - | - | - | - | - | - | - | TNFR-6b |

FIG. 3N

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
|434|L|E|D|I|E|E|A|L|C|G|P|A|A|L|P|-|-|-|-|R|-|S|G|-|L|P|T|L|L|G|S|-|T|E|E|K|-|TNFR1|
|431|-|-|-|-|-|-|-|-|-|-|-|-|-|-|-|-|-|-|-|-|-|-|-|-|L|L|A|A|L|R|R|-|I|Q|R|A|-|TNFR2|
|401|-|-|-|-|-|-|-|-|-|-|-|-|-|-|-|-|-|-|-|R|-|Q|P|-|L|S|T|P|Y|Q|E|D|G|K|K|A|W|NGFR|
|386|-|-|-|-|-|-|-|-|-|-|-|-|-|-|-|-|-|-|-|-|-|-|P|-|L|L|A|Y|L|S|T|-|E|R|A|D|-|LTbR|
|312|-|T|-|-|-|-|-|-|-|-|-|F|-|-|-|-|-|-|-|-|-|-|-|-|-|-|-|-|-|-|-|-|-|-|-|-|-|FAS|
|246|-|I|-|L|K|D|I|T|S|D|-|S|E|N|S|N|F|R|-|-|-|-|-|-|-|-|-|-|-|-|-|-|-|-|-|-|-|CD27|
|520|M|K|A|D|T|I|V|G|T|V|K|A|E|L|P|E|G|R|G|L|A|G|P|-|A|E|P|-|-|L|E|A|D|H|T|P|H|CD30|
|263|-|-|-|-|-|-|-|-|-|-|-|-|-|-|-|-|-|-|-|-|P|-|-|-|-|-|-|-|-|L|E|A|D|B|T|P|-|CD40|
|224|-|-|-|-|-|-|-|-|-|-|-|-|-|-|-|-|-|-|-|A|-|-|-|-|-|-|-|-|-|Q|E|D|G|K|E|S|-|4-1BB|
|260|-|-|-|-|-|-|-|-|-|-|-|-|-|-|-|-|-|-|-|-|-|-|-|-|-|-|-|-|-|Q|E|M|R|P|V|Q|T|OX40|
|345|F|K|-|-|-|-|-|-|-|-|-|-|-|-|-|-|-|-|-|-|-|-|-|-|-|Q|P|F|-|-|-|-|R|T|-|VC22|
|351|-|-|-|-|-|-|-|-|-|-|-|-|-|-|-|-|-|-|-|-|T|R|F|-|-|-|-|-|-|-|-|-|-|-|-|-|-|CRMB|
|||||||||||||||||||||||||P|T|H|F|||||||||||||
|291|-|-|-|-|-|-|-|-|-|-|-|-|-|-|-|-|-|-|-|-|P|T|-|-|-|-|-|-|-|-|-|-|S|V|R|E|R|TNFR-6a|
|163|-|-|-|-|-|-|-|-|-|-|-|-|-|-|-|-|-|-|-|-|-|-|-|-|-|-|-|-|-|-|-|-|V|A|G|P|S|TNFR-6b|

HELDI06R
GGCACGAGCA GGGTCCTGTN TCCGCCCTGA GCCGCGCTCT NCCTGCTCCA GCAAGGACCA
TGAGGGCGCT GGAGGGGCCA GGCCTGTCGC TGCTGTGCCT GGTGTTGGCG CTGCCTGCCC
TGCTGCCGGT GCCGGCTGTA CGCGGAGTGG CAGAAACACN NACNTACCCC TGGCGGGACG
NAGAGACAGG GGAGCGGCTG GTGTNTNCCC ANTGCCCCCC AGGCACCTTT NTGCAGCGGC
CGTGCCGNCG AGACAGCCCC ACGACGTGTG GCCCGTNTCC ACCGCGCCAC TACACGCATT
CTGGAACTAC CTGGAGCGCT GNCGTTACTN CAACGTCCTC TGCGGGGAGC GTNAGGAGGA
GGCACGGGTT TNCCACGNCA ACCACAACCG NGGNTTACCG TNGCCGNACC GGTTTCTTCG
NGGCAAGTTG GTTTTTNNTT TGGAGNAAGG ATTCGTGTTN CAATTNATTG ACGNAGTGAT
TNNNCNCGGG AAACTNAAA

HCEOW38R
CGCAACTGCA CGGCCCTGGG ACTGGCCCTC AATGTGCCAG GNTCTTCCTC CCATGACACC
CTGTGCACCA GCTGCACTGG CTTCCCCCTC AGCACCAGGG TACCANGAGC TGAGGAGTGT
GAGCNTGCCG TCATCGACTT TTTGGCTTTC CAGGACATCT CCATCAAGAG GCTGCAGCGG
CTGCTCANGC C

FIG.6

TUMOR NECROSIS FACTOR RECEPTORS 6α AND 6β

RELATED APPLICATIONS

This application is a divisional of U.S. Non-Provisional patent application Ser. No. 11/416,310, filed May 3, 2006, which is a continuation of U.S. Non-Provisional patent application Ser. No. 09/935,727, filed Aug. 24, 2001, now U.S. Pat. No. 7,285,267, which claims the benefit of priority under 35 U.S.C. §119(e) based on U.S. Provisional Application Ser. Nos. 60/303,224 filed Jul. 6, 2001; 60/252,131 filed Nov. 21, 2000; and 60/227,598 filed Aug. 25, 2000. U.S. Non-Provisional patent application Ser. No. 09/935,727, filed Aug. 24, 2001 is also a continuation-in-part of U.S. Non-Provisional patent application Ser. No. 09/518,931 filed Mar. 3, 2000, now U.S. Pat. No. 7,186,800, which claims the benefit of priority under 35 U.S.C. §119(e) based on U.S. Provisional Application Ser. Nos. 60/168,235 filed Dec. 1, 1999; 60/146,371 filed Aug. 2, 1999; 60/131,964 filed Apr. 30, 1999; 60/131,279 filed Apr. 27, 1999; 60/124,092 filed Mar. 12, 1999; and 60/121,774 filed Mar. 4, 1999. U.S. Non-Provisional patent application Ser. No. 09/518,931 is also a continuation-in-part of U.S. Non-Provisional patent application Ser. No. 09/006,352 filed Jan. 13, 1998 which claims the benefit of priority under 35 U.S.C. §119(e) based on U.S. Provisional Application Ser. No. 60/035,496 filed Jan. 14, 1997. U.S. Non-Provisional patent application Ser. No. 09/935,727, filed Aug. 24, 2001 is also a continuation-in-part of U.S. Non-Provisional application Ser. No. 09/006,352 filed Jan. 13, 1998. U.S. Non-Provisional patent application Ser. No. 11/416,310, filed May 3, 2006, is also a continuation-in-part of U.S. Non-Provisional patent application Ser. No. 09/518,931 filed Mar. 3, 2000. U.S. Non-Provisional patent application Ser. No. 11/416,310, filed May 3, 2006, is also a continuation-in-part of U.S. Non-Provisional application Ser. No. 09/006,352 filed Jan. 13, 1998. Each of the above U.S. Provisional and Non-Provisional Patent applications is hereby incorporated by reference in its entirety. Each of the above U.S. Provisional and Non-Provisional Patent applications is hereby incorporated by reference in its entirety.

REFERENCE TO SEQUENCE LISTING AS TEXT FILE

This application refers to a "Sequence Listing" listed below, which is provided as a text file. The text file contains a document entitled "PF454P2C1D1-SequenceListing.txt" (68,356 bytes, created Apr. 27, 2009), which is incorporated by reference in its entirety.

FIELD OF THE INVENTION

The present invention relates to novel human genes encoding polypeptides which are members of the TNF receptor family. More specifically, isolated nucleic acid molecules are provided encoding human polypeptides named tumor necrosis factor receptor-6α & -6β hereinafter sometimes referred to as "TNFR-6α & TNFR-6β" or generically as "TNFR polypeptides". TNFR polypeptides are also provided, as are vectors, host cells and recombinant methods for producing the same. The invention further relates to screening methods for identifying agonists and antagonists of TNFR polypeptide activity. Also provided are diagnostic and therapeutic methods utilizing such compositions.

BACKGROUND OF THE INVENTION

Many biological actions, for instance, response to certain stimuli and natural biological processes, are controlled by factors, such as cytokines. Many cytokines act through receptors by engaging the receptor and producing an intra-cellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, sixteen members of the TNF ligand superfamily have been identified and seventeen members of the TNF-receptor superfamily have been characterized.

Among the ligands there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals, 22:291-295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-inked immunodeficiency state characterized by high levels of immunoglobulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al., Cell 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., Science 264:667-668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., Cell 74:845 (1993)). Apoptosis, or programmed cell death, is a physiologic process essential to the normal development and homeostasis of multicellular organisms (H. Steller, Science 267, 1445-1449 (1995)). Derangements of apoptosis contribute to the pathogenesis of several human diseases including cancer, neurodegenerative disorders, and acquired immune deficiency syndrome (C. B. Thompson, Science 267, 1456-1462 (1995)). Recently, much attention has focused on the signal transduction and biological function of two cell surface death receptors, Fas/APO-1 and TNFR-1 (J. L. Cleveland, J. N. Ihle, Cell 81, 479-482 (1995); A. Fraser, G. Evan, Cell 85, 781-784 (1996); S. Nagata, P. Golstein, Science 267, 1449-56 (1995)). Both are members of the TNF receptor family which also include TNFR-2, low affinity NGFR, CD40, and CD30, among others (C. A. Smith, et al., Science 248, 1019-23 (1990); M. Tewari, V. M. Dixit, in Modular Texts in Molecular and Cell Biology M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the *Drosophila* suicide gene, reaper (P. Golstein, D. Marguet, V. Depraetere, Cell 81, 185-6 (1995); K. White et al., Science 264, 677-83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan, K. O'Rourke, M. Tewari, V. M. Dixit, Cell 81, 505-12 (1995); M. P. Boldin, et al., J. Biol Chem 270, 7795-8 (1995); F. C. Kischkel, et al., EMBO 14, 5579-5588 (1995)), which in turn binds and presumably activates FLICE/MACH1, a member of the ICE/CED-3 family of pro-apoptotic proteases (M. Muzio et al., Cell 85, 817-827 (1996); M. P. Boldin, T. M. Goncharov, Y. V. Goltsev, D. Wallach, Cell 85, 803-815 (1996)). While the central role of Fas/APO-1 is to trigger cell death, TNFR-1 can signal an array of diverse biological activities-many of which stem from its ability to activate NF-kB (L. A. Tartaglia, D. V. Goeddel, Immunol Today 13, 151-3 (1992)). Accordingly, TNFR-1 recruits the multivalent adapter molecule TRADD, which like FADD, also contains a death domain (H. Hsu, J. Xiong, D. V. Goeddel, Cell 81, 495-504 (1995); H. Hsu, H.-B. Shu, M.-P. Pan, D. V. Goeddel, Cell 84, 299-308 (1996)). Through its associations with a number of signaling molecules including FADD, TRAF2, and RIP, TRADD can signal both apoptosis and NF-kB activation (H. Hsu, H.-B. Shu, M.-P. Pan, D. V. Goeddel, Cell 84, 299-308 (1996); H. Hsu, J. Huang, H.-B. Shu, V. Baichwal, D. V. Goeddel, Immunity 4, 387-396 (1996)).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

SUMMARY OF THE INVENTION

The present invention provides isolated nucleic acid molecules comprising, or alternatively consisting of, a polynucleotide encoding at least a portion of a TNFR (i.e., TNFR-6α or TNFR-6β polypeptide) having the complete amino acid sequences shown in SEQ ID NOS:2 and 4, respectively, or the complete amino acid sequence encoded by a cDNA clone deposited as plasmid DNA as ATCC™ Deposit Number 97810 and 97809, respectively. The nucleotide sequence determined by sequencing the deposited TNFR-6 alpha and TNFR-6 beta clones, which are shown in FIGS. 1 and 2A-B (SEQ ID NOS: 1 and 3, respectively), contain open reading frames encoding complete polypeptides of 300 and 170 amino acid residues, respectively, including an initiation codon encoding an N-terminal methionine at nucleotide positions 25-27 and 73-75 in SEQ ID NOS: 1 and 3, respectively.

The TNFR proteins of the present invention share sequence homology with other TNF receptors. Splice variants TNFR-6 alpha and TNFR-6 beta show the highest degree of sequence homology with the translation products of the human mRNAs for TNFR-I and -II (FIGS. 3A-P) (SEQ ID NOS:5 and 6, respectively) also including multiple conserved cysteine rich domains.

The TNFR-6 alpha and TNFR-6 beta polypeptides have predicted leader sequences of 30 amino acids each; and the amino acid sequence of the predicted mature TNFR-6 alpha and TNFR-6 beta polypeptides are also shown in FIGS. 1 and 2A-B as amino acid residues 31-300 (SEQ ID NO:2) and 31-170 (SEQ ID NO:4), respectively.

Thus, one aspect of the invention provides an isolated nucleic acid molecule comprising, or alternatively consisting of, a polynucleotide having a nucleotide sequence selected from the group consisting of: (a) a nucleotide sequence encoding a TNFR polypeptide having the complete amino acid sequence in SEQ ID NO:2 or 4, or as encoded by the cDNA clone contained in ATCC™ Deposit No. 97810 or 97809; (b) a nucleotide sequence encoding a mature TNFR polypeptide having the amino acid sequence at positions 31-300 in SEQ ID NO:2, or 31-170 in SEQ ID NO:4, or as encoded by the cDNA clone contained in ATCC™ Deposit No. 97810 or 97809; (c) a nucleotide sequence encoding a soluble extracellular domain of a TNFR polypeptide having the amino acid sequence at positions 31 to 283 in SEQ ID NO:2 or 31 to 166 in SEQ ID NO:4, or as encoded by the cDNA clone contained in the ATCC™ Deposit No. 97810 or 97809; (d) a nucleotide sequence encoding a fragment of a TNFR polypeptide having the amino acid sequence at positions 31 to 283 in SEQ ID NO:2 or 31 to 166 in SEQ ID NO:4, or as encoded by the cDNA clone contained in the ATCC™ Deposit No. 97810 or 97809 wherein said fragment has TNFR-6α and/or TNFR-6β functional activity; and (e) a nucleotide sequence complementary to any of the nucleotide sequences in (a), (b), (c), or (d) above.

Further embodiments of the invention include isolated nucleic acid molecules that comprise, or alternatively consist of, a polynucleotide having a nucleotide sequence at least 90% identical, and more preferably at least 80%, 85%, 90%, 92%, or 95%, 96%, 97%, 98% or 99% identical, to any of the nucleotide sequences in (a), (b), (c), (d) and (e) above, or a polynucleotide which hybridizes under stringent hybridization conditions to a polynucleotide in (a), (b), (c), (d), or (e) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising, or alternatively consisting of, a polynucleotide which encodes the amino acid sequence of an epitope-bearing portion of a TNFR polypeptide having an amino acid sequence in (a), (b), (c), or (d) above.

The present invention also relates to recombinant vectors, which include the isolated nucleic acid molecules of the present invention, and to host cells containing the recombinant vectors, as well as to methods of making such vectors and host cells and for using them for production of TNFR polypeptides or peptides by recombinant techniques.

The invention further provides an isolated TNFR polypeptide comprising an amino acid sequence selected from the group consisting of: (a) the amino acid sequence of a full-length TNFR polypeptide having the complete amino acid sequence shown in SEQ ID NO:2 or 4 or as encoded by the cDNA clone contained in ATCC™ Deposit No. 97810 or 97809; (b) the amino acid sequence of a mature TNFR polypeptide having the amino acid sequence at positions 31-300 in SEQ ID NO:2, or 31-170 in SEQ ID NO:4, or as encoded by the cDNA clone contained in ATCC™ Deposit No. 97810 or 97809; (c) the amino acid sequence of a soluble extracellular domain of a TNFR polypeptide having the amino acid sequence at positions 31 to 283 in SEQ ID NO:2 or 31 to 166 in SEQ ID NO:4, or as encoded by the cDNA clone contained in ATCC™ Deposit No. 97810 or 97809; or (d) the amino acid sequence of a fragment of the TNFR polypeptide having the amino acid sequence at positions 31 to 283 in SEQ ID NO:2 or 31 to 166 in SEQ ID NO:4, or as encoded by the cDNA clone contained in ATCC™ Deposit No. 97810 or 97809, wherein said fragment has TNFR-6α and/or TNFR-6β functional activity.

The polypeptides of the present invention also include polypeptides having an amino acid sequence at least 80% identical, more preferably at least 85% identical, and still more preferably 90%, 92%, 95%, 96%, 97%, 98% or 99% identical to those described in (a), (b), (c) or (d) above, as well as polypeptides having an amino acid sequence with at least 90% similarity, and more preferably at least 80%, 85%, 90%, 92%, or 95% similarity, to those above.

An additional embodiment of this aspect of the invention relates to a peptide or polypeptide which comprises the amino acid sequence of an epitope-bearing portion of a TNFR polypeptide having an amino acid sequence described in (a), (b), (c) or (d), above. Peptides or polypeptides having the amino acid sequence of an epitope-bearing portion of a TNFR polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a TNFR polypeptide having an amino acid sequence described in (a), (b), (c) or (d) above. The invention further provides methods for isolating antibodies that bind specifically to a TNFR polypeptide having an amino acid sequence as described herein. Such antibodies are useful diagnostically or therapeutically as described below.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. The invention also provides for pharmaceutical compositions comprising TNFR polypeptides, particularly human TNFR polypeptides, which may be employed, for instance, to treat infectious disease including HIV infection, endotoxic shock, cancer, autoimmune diseases, graft vs. host disease, acute graft rejection, chronic graft rejection, neurodegenerative disorders, myelodysplastic syndromes, ischemic injury (e.g., ischemic cardiac injury), toxin-induced liver disease, septic shock, cachexia and anorexia. Methods of treating individuals in need of TNFR polypeptides are also provided.

The invention further provides compositions comprising a TNFR polynucleotide or a TNFR polypeptide for administration to cells in vitro, to cells ex vivo and to cells in vivo, or to a multicellular organism. In certain particularly preferred embodiments of this aspect of the invention, the compositions comprise a TNFR polynucleotide for expression of a TNFR polypeptide in a host organism for treatment of disease. Particularly preferred in this regard is expression in a human patient for treatment of a dysfunction associated with aberrant endogenous activity of a TNFR polypeptide.

In another aspect, a screening assay for agonists and antagonists is provided which involves determining the effect a candidate compound has on TNFR polypeptide binding to a TNF-family ligand. In particular, the method involves contacting the TNF-family ligand with a TNFR polypeptide and a candidate compound and determining whether TNFR polypeptide binding to the TNF-family ligand is increased or decreased due to the presence of the candidate compound. In this assay, an increase in binding of a TNFR polypeptide over the standard binding indicates that the candidate compound is an agonist of TNFR polypeptide binding activity and a decrease in TNFR polypeptide binding compared to the standard indicates that the compound is an antagonist of TNFR polypeptide binding activity.

TNFR-6 alpha and TNFR-6 beta are expressed in endothelial cells, keratinocytes, normal prostate and prostate tumor tissue. For a number of disorders of these tissues or cells, particularly of the immune system, significantly higher or lower levels of TNFR gene expression may be detected in certain tissues (e.g., cancerous tissues) or bodily fluids (e.g., serum, plasma, urine, synovial fluid or spinal fluid) taken from an individual having such a disorder, relative to a "standard" TNFR gene expression level, i.e., the TNFR expression level in healthy tissue from an individual not having the immune system disorder. Thus, the invention provides a diagnostic method useful during diagnosis of such a disorder, which involves: (a) assaying TNFR gene expression level in cells or body fluid of an individual; (b) comparing the TNFR gene expression level with a standard TNFR gene expression level, whereby an increase or decrease in the assayed TNFR gene expression level compared to the standard expression level is indicative of disorder in the immune system.

An additional aspect of the invention is related to a method for treating an individual in need of an increased level of TNFR polypeptide activity in the body comprising administering to such an individual a composition comprising a therapeutically effective amount of an isolated TNFR polypeptide of the invention or an agonist thereof.

A still further aspect of the invention is related to a method for treating an individual in need of a decreased level of TNFR polypeptide activity in the body comprising, administering to such an individual a composition comprising a therapeutically effective amount of a TNFR antagonist. Preferred antagonists for use in the present invention are TNFR-specific antibodies.

BRIEF DESCRIPTION OF THE FIGURES

FIG. 1 shows the nucleotide sequence (SEQ ID NO:1) and deduced amino acid sequence (SEQ ID NO:2) of TNFR-6α. The initial 30 amino acids (underlined) are the putative leader sequence.

FIGS. 2A-B the nucleotide sequence (SEQ ID NO:3) and deduced amino acid sequence (SEQ ID NO:4) of TNFR-6β. The initial 30 amino acids (underlined) are the putative leader sequence.

FIGS. 3A-P show an alignment created by the Clustal method using the Megaline program in the DNAstar suite comparing the amino acid sequences of TNFR-6α ("TNFR-6 alpha" (SEQ ID NO:2)), and TNFR-6β ("TNFR-6 beta" (SEQ ID NO:4)) with other TNF receptors, as follows: TNFR1 (SEQ ID NO:5); TNFR2 (SEQ ID NO:6); NGFR (SEQ ID NO:7); LTbR (SEQ ID NO:8); FAS (SEQ ID NO:9); CD27 (SEQ ID NO:10); CD30 (SEQ ID NO:11); CD40 (SEQ ID NO:12); 4-1BB (SEQ ID NO:13); OX40 (SEQ ID NO:14); VC22 (SEQ ID NO:15); and CRMB (SEQ ID NO:16).

Figure 4:
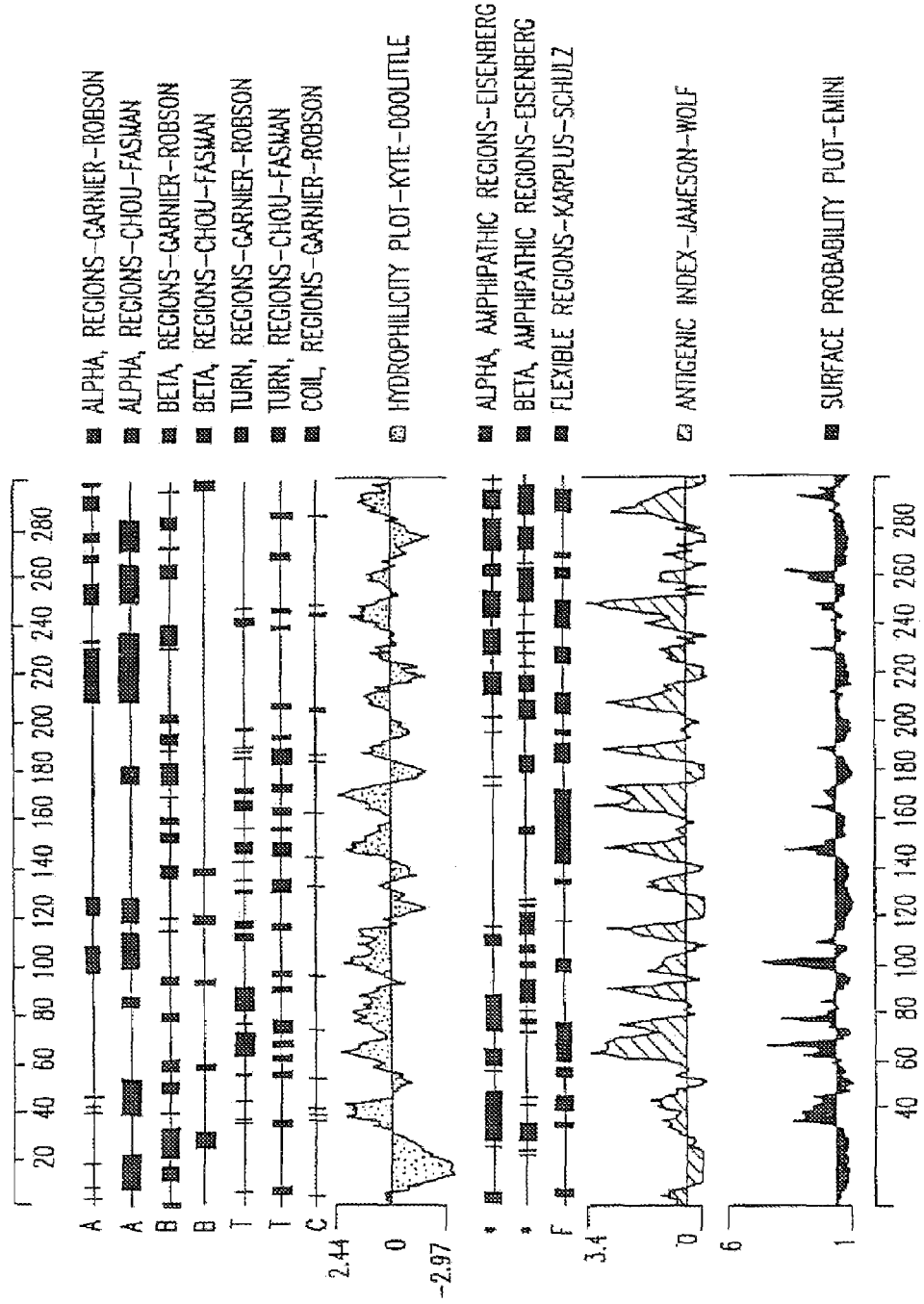
FIGS. 4 and 5 show separate analyses of the TNFR-6 alpha and TNFR-6 beta amino acid sequences, respectively. Alpha, beta, turn and coil regions; hydrophilicity; amphipathic regions; flexible regions; antigenic index and surface probability are shown, as predicted for the amino acid sequence of SEQ ID NO:2 and SEQ ID NO:4, respectively, using the default parameters of the recited computer programs. In the "Antigenic Index—Jameson-Wolf" graph, which indicates the location of the highly antigenic regions of TNFR-6α and TNFR-6β, i.e., regions from which epitope-bearing peptides of the invention may be obtained. Antigenic regions of TNFR-6α, include from about Ala-31 to about Thr-46, from about Phe-57 to about Thr-117, from about Cys-132 to about Thr-175, from about Gly-185 to about Thr-194, from about Val-205 to about Asp-217, from about Pro-239 to about Leu-264, and from about Ala-283 to about Pro-298 (SEQ ID NO:2). Antigenic regions of TNFR-6β, include from about Ala-31 to about Thr-46, from about Phe-57 to about Gln-80, from about Glu-86 to about His-106, from about Thr-108 to about PHz-119, from about His-129 to about Val-138, and from about Gly-142 to about Pro-166 (SEQ ID NO:4). These polypeptide fragments have been determined to bear antigenic epitopes of the TNFR-6 alpha and TNFR-6 beta polypeptides by the analysis of the Jameson-Wolf antigenic index.
Figure 5:
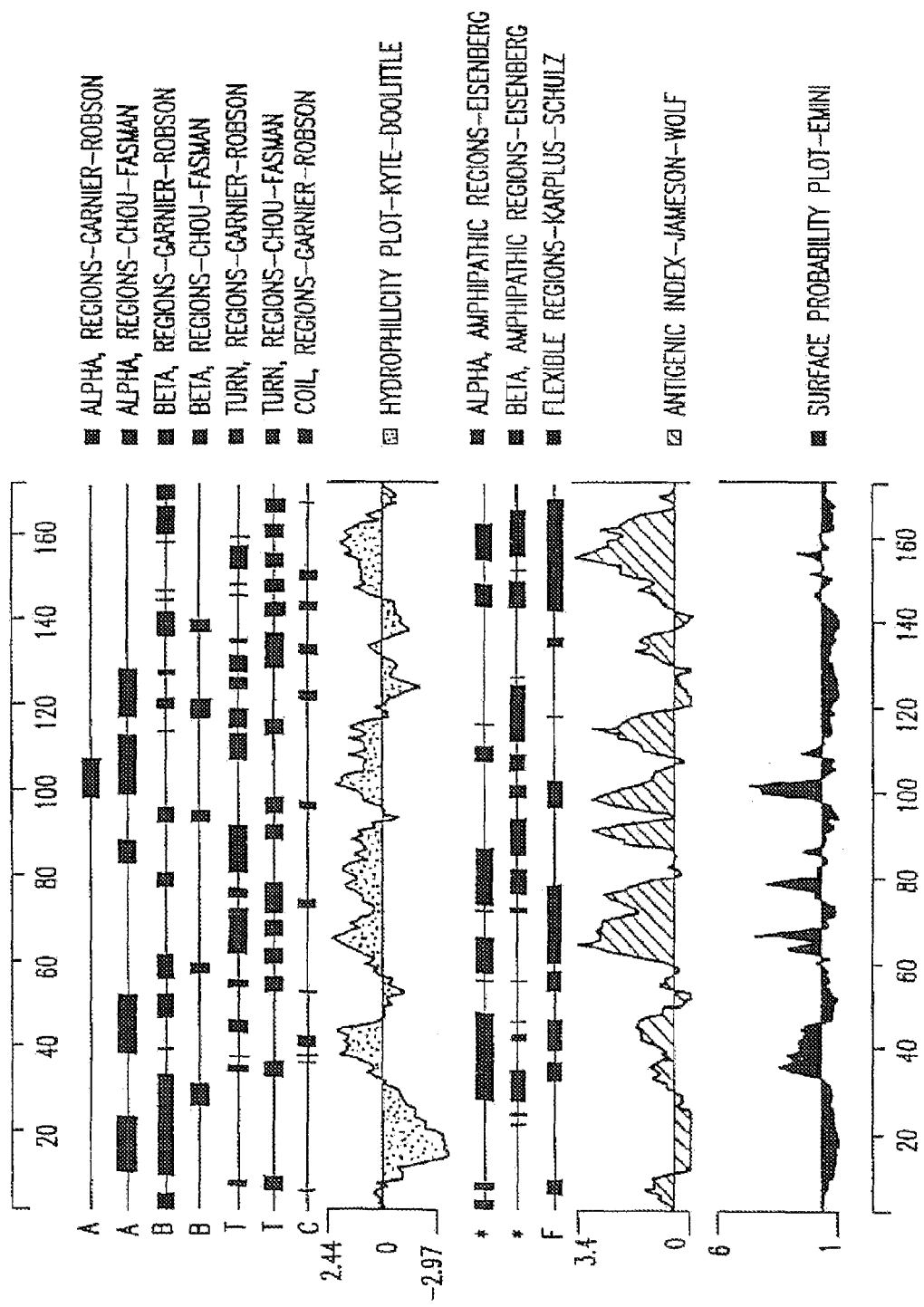

The data presented in FIGS. 4 and 5 are also represented in tabular form in Tables I and II, respectively. The columns are labeled with the headings "Res", "Position", and Roman Numerals I-XIV. The column headings refer to the following features of the amino acid sequence presented in FIG. 4, (Table I) and FIG. 5 (Table II): "Res": amino acid residue of SEQ ID NO:2 (FIG. 1) or SEQ ID NO:4 (FIG. 2A); "Position": position of the corresponding residue within of SEQ ID NO:2 (FIG. 1) or SEQ ID NO:4 (FIG. 2A); I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

FIG. 6 shows the nucleotide sequences of HELDI06R (SEQ ID NO:17) and HCEOW38R (SEQ ID NO:18) which are related to SEQ ID NOS:1 and 3.

Figure 7B:
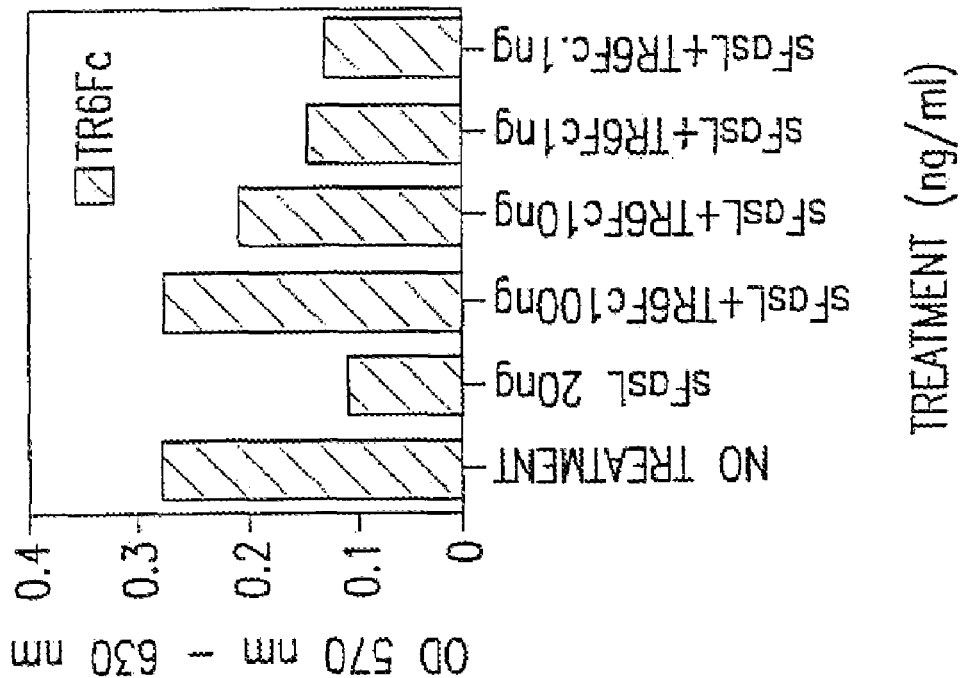
Figure 7A:
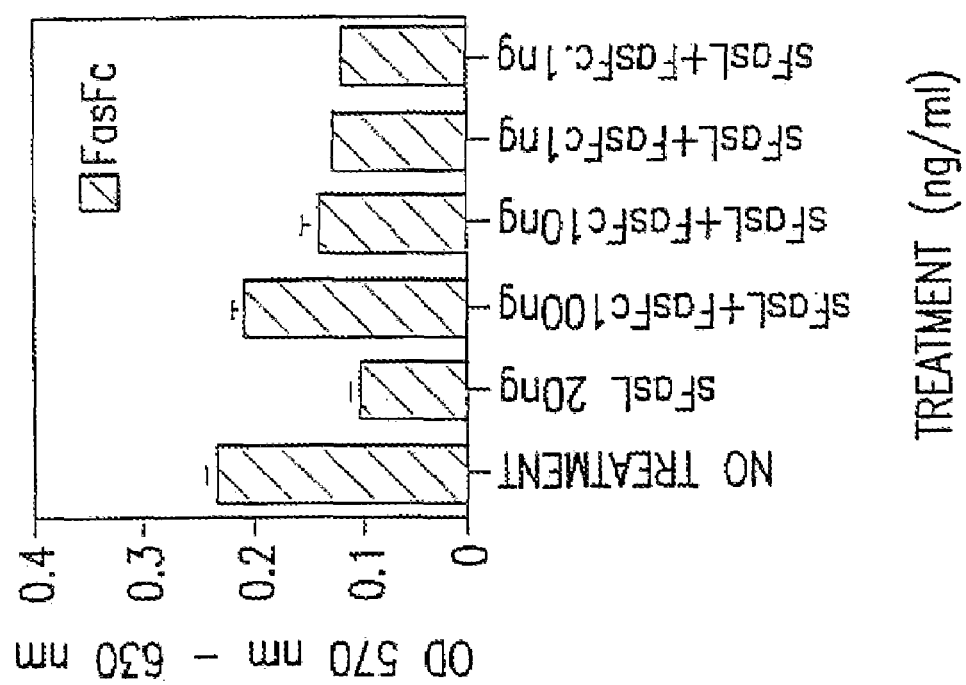

FIGS. 7A-B show TNFR6 alpha blocking of Fas ligand mediated cell death. Jurkat T-cells were treated with a combination of Fas ligand and TNFR 6 alpha Fc receptor for 16 hours. To measure the levels of viable cells after treatment, cells were incubated for 5 hours with 10% ALOMAR blue and examined spectrophotometrically at OD 570 nm-630 nm. All samples were tested in triplicate. TNFR6 alpha-Fc appears to block Fas ligand mediated apoptosis of Jurkat cells in a dose dependent manner as effectively as Fas-Fc.

DETAILED DESCRIPTION

The present invention provides isolated nucleic acid molecules comprising, or alternatively consisting of, a polynucleotide encoding a TNFR-6α or -6β polypeptide, generically "TNFR polypeptide(s)" having the amino acid sequence shown in SEQ ID NOS:2 and 4, respectively, which were determined by sequencing cloned cDNAs. The nucleotide sequences shown in FIGS. 1 and 2A-B (SEQ ID NOS:1 and 3) were obtained by sequencing the HPHAE52 and HTPCH84 clones, respectively, which were deposited on Nov. 22, 1996 at the American Type Culture Collection, 10801 University Boulevard, Manassas, Va. 20110-2209 and given accession numbers ATCC™ 97810 and 97809, respectively. The deposited clones are contained in the pBluescript SK(-) plasmid (Stratagene, La Jolla, Calif.).

The TNFR-6 alpha and TNFR-6 beta proteins of the present invention are splice variants which share an identical nucleotide and amino acid sequence over the N-terminal 142 residues of the respective proteins. The amino acid sequences of these proteins are about 23% similar to and share multiple conserved cysteine rich domains with the translation product of the human TNFR-2 mRNA (FIGS. 3A-P) (SEQ ID NO:6). Importantly, these proteins share substantial sequence similarity over a polypeptide sequence including four repeated cysteine rich motifs with significant intersubunit homology. TNFR-2 is thought to exclusively mediate human T-cell proliferation by TNF (PCT WO/94/09137).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequences in FIGS. 1 and 2A-B (SEQ ID NOS:1 and 3), a nucleic acid molecule of the present invention encoding a TNFR polypeptide may be obtained using standard cloning and screening procedures, such as those for cloning cDNAs using mRNA as starting material. Illustrative of the invention, the TNFR-6α and TNFR-6β clones (FIGS. 1 and 2A-B, respectively) were identified in cDNA libraries from the following tissues: endothelial cells, keratinocytes, normal prostate tissue, and prostate tumor tissue.

The determined nucleotide sequences of the TNFR cDNAs of FIGS. 1 and 2A-B (SEQ ID NOS:1 and 3) contain open reading frames encoding proteins of 300 and 170 amino acid residues, with an initiation codon at nucleotide positions 25-27 and 73-75 of the nucleotide sequences in FIGS. 1 and 2A-B (SEQ ID NOS:1 and 3), respectively.

The open reading frames of the TNFR-6α and TNFR-6β genes share sequence homology with the translation product of the human mRNA for TNFR-2, including the soluble extracellular domain of about residues 31-283 of SEQ ID NO:2 and 31-166 of SEQ ID NO:4, respectively.

As one of ordinary skill would appreciate, due to the possibilities of sequencing errors discussed above, the actual complete TNFR polypeptides encoded by the deposited cDNAs, which comprise about 300 and 170 amino acids, may be somewhat longer or shorter. More generally, the actual open reading frames may be anywhere in the range of ±20 amino acids, more likely in the range of ±10 amino acids, of that predicted from the first methionine codon from the N-terminus shown in FIGS. 1 and 2A-B (SEQ ID NOS:1 and 3), which is in-frame with the translated sequences shown in each respective figure. It will further be appreciated that, depending on the analytical criteria used for identifying various functional domains, the exact "address" of the extracellular and transmembrane domain(s) of the TNFR polypeptides may differ slightly from the predicted positions above. For example, the exact location of the extracellular domain or antigenic regions in SEQ ID NO:2 and SEQ ID NO:4 may vary slightly (e.g., the address may "shift" by about 1 to about 20 residues, more likely about 1 to about 5 residues) depending on the criteria used to define the domains and antigenic regions. In any event, as discussed further below, the invention further provides polypeptides having various residues deleted from the N-terminus of the complete polypeptide, including polypeptides lacking one or more amino acids from the N-terminus of the extracellular domain described herein, which constitute soluble forms of the extracellular domains of the TNFR-6α and TNFR-6β proteins.

The amino acid sequences of the complete TNFR proteins include a leader sequence and a mature protein, as shown in SEQ ID NOS:2 and 4. More in particular, the present invention provides nucleic acid molecules encoding mature forms of the TNFR proteins. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding a mature TNFR polypeptide having the amino acid sequence encoded by a cDNA clone identified as ATCC™ Deposit No. 97810 or 97809. By the "mature TNFR polypeptides having the amino acid sequence encoded by a cDNA clone contained in the plasmid deposited as ATCC™ Deposit No. 97810, or 97809" is meant the mature form(s) of the protein produced by expression in a mammalian cell (e.g., COS cells, as described below) of the complete open reading frame encoded by the human DNA sequence of the clone contained in the deposited vector.

In addition, methods for predicting whether a protein has a secretory leader as well as the cleavage point for that leader sequence are available. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75-80% (von Heinje, supra). However, the two methods do not always produce the same predicted cleavage point(s) for a given protein.

In the present case, the deduced amino acid sequence of the complete TNFR polypeptides were analyzed by a computer program "PSORT", available from Dr. Kenta Nakai of the Institute for Chemical Research, Kyoto University (see K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis of the TNFR amino acid sequences by this program provided the following results: TNFR-6α & TNFR-6β encode mature polypeptides having the amino acid sequences of residues 31-300 and 31-170 of SEQ ID NOS:2 and 4, respectively.

In certain preferred embodiments, TNFR-6α & TNFR-6β encode mature polypeptides having the amino acid sequences of residues 31-299 and 31-169 of SEQ ID NOS:2 and 4, respectively.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention. As discussed further herein, isolated nucleic acid molecules according to the present invention may be produced naturally, recombinantly, or synthetically.

Isolated nucleic acid molecules of the present invention include DNA molecules comprising an open reading frame (ORF) with an initiation codon at positions 25-27 and 73-75 of the nucleotide sequences shown in SEQ ID NOS:1 and 3, respectively.

Also included are DNA molecules comprising the coding sequence for the predicted mature TNFR polypeptides shown at positions 31-300 and 31-170 of SEQ ID NOS:2 and 4, respectively.

Also included are DNA molecules comprising the coding sequence for the predicted mature TNFR polypeptides shown at positions 31-299 and 31-169 of SEQ ID NOS:2 and 4, respectively.

In specific embodiments, the present invention encompasses isolated nucleic acid molecules comprising a polynucleotide sequence encoding exon 1 of TNFR-6 alpha, (i.e., a polynucleotide sequence comprising nucleotides 1-424 of SEQ ID NO:28 which corresponds to nucleotides 25-448 of SEQ ID NO:1). In other embodiments, the present invention encompasses isolated nucleic acid molecules comprising a polynucleotide sequence encoding exon 2 of TNFR-6 alpha, (i.e., a polynucleotide sequence comprising nucleotides 561-755 of SEQ ID NO:28 which corresponds to nucleotides 449-643 of SEQ ID NO:1). In other embodiments, the present invention encompasses isolated nucleic acid molecules comprising a polynucleotide sequence encoding exon 3 of TNFR-6 alpha, (i.e., a polynucleotide sequence comprising nucleotides 1513-1793 of SEQ ID NO:28 which corresponds to nucleotides 644-924 of SEQ ID NO:1).

In still other embodiments, the present invention comprises isolated nucleic acid molecules comprising a polynucleotide sequence encoding exons 1 and 2 of TNFR-6 alpha. In other embodiments, the present invention comprises isolated nucleic acid molecules comprising a polynucleotide sequence encoding exons 1 and 3 of TNFR-6 alpha. In other embodiments, the present invention comprises isolated nucleic acid molecules comprising a polynucleotide sequence encoding exons 2 and 3 of TNFR-6 alpha.

In addition, isolated nucleic acid molecules of the invention include DNA molecules which comprise a sequence substantially different from those described above but which, due to the degeneracy of the genetic code, still encode a TNFR protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as E. coli).

In another aspect, the invention provides isolated nucleic acid molecules encoding a TNFR polypeptide having an amino acid sequence encoded by the cDNA clone contained in the plasmid deposited as ATCC™ Deposit No. 97810 or 97809. Preferably, this nucleic acid molecule will encode the mature polypeptide encoded by the above-described deposited cDNA clone.

The invention further provides an isolated nucleic acid molecule having the nucleotide sequence shown in FIG. 1 or 2 (SEQ ID NO:1 or 3) or the nucleotide sequence of the TNFR cDNAs contained in the above-described deposited clones, or a nucleic acid molecule having a sequence complementary to one of the above sequences. Such isolated molecules, particularly DNA molecules, are useful, for example, as probes for gene mapping by in situ hybridization with chromosomes, and for detecting expression of the TNFR genes in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides polynucleotides having a nucleotide sequence representing the portion of SEQ ID NO:1 or 3 which consist of positions 25-924 and 73-582 of SEQ ID NOS:1 and 3, respectively. Also contemplated are polynucleotides encoding TNFR polypeptides which lack an amino terminal methionine such polynucleotides having a nucleotide sequence representing the portion of SEQ ID NOS:1 and 3 which consist of positions 28-924 and 76-582, respectively. Polypeptides encoded by such polynucleotides are also provided, such polypeptides comprising an amino acid sequence at positions 2-300 and 2-170 of SEQ ID NOS:2 and 4, respectively.

In addition, the invention provides nucleic acid molecules having nucleotide sequences related to extensive portions of SEQ ID NOS:1 and 3 as follows: HELDI06R (SEQ ID NO:17) and HCEOW38R (SEQ ID NO:18) are related to both SEQ ID NOS:1 and 3. Preferred are polynucleotide fragments of SEQ ID NOS:1 and 3 which are not SEQ ID NO:17 or 18 or subfragments of either SEQ ID NO:17 or 18. The sequences of HELDI06R and HCEOW38R are shown in FIG. 6.

More generally, by a fragment of an isolated nucleic acid molecule having the nucleotide sequence of the deposited cDNA or the nucleotide sequence shown in FIG. 1 or 2 (SEQ ID NOS:1 or 3) is intended fragments at least about 15 nt, and more preferably at least about 20 nt, still more preferably at least about 30 nt, and even more preferably, at least about 40 nt in length. These fragments have numerous uses, which include, but are not limited to, as diagnostic probes and primers as discussed herein. Of course, larger fragments 50-300 nt in length are also useful according to the present invention as are fragments corresponding to most, if not all, of the nucleotide sequence of the deposited cDNAs or as shown in FIGS. 1 and 2A-B (SEQ ID NOS:1 and 3). Especially preferred are fragments comprising at least 500 nucleotides which are at least 80%, 85%, 90%, 92%, or 95% identical to 500 contiguous nucleotides shown in SEQ ID NO:1. By a fragment at least about 20 nt in length, for example, is intended fragments which include 20 or more contiguous bases from the nucleotide sequence of a deposited cDNA or the nucleotide sequence as shown in FIGS. 1 and 2A-B (SEQ ID NOS:1 and 3). In this context "about" includes the particularly recited size, and those sizes that are larger or smaller by several (5, 4, 3, 2, or 1) nucleotides, at either terminus or at both termini. Preferred nucleic acid fragments of the present invention include nucleic acid molecules encoding epitope-bearing portions of the TNFR polypeptides as identified in FIGS. 4 and 5 and described in more detail below.

Representative examples of TNFR-6α nucleic acid fragments of the invention include, for example, fragments that comprise, or alternatively, consist of, a sequence from about nucleotide 1 to about nucleotide 25, about nucleotide 26 to about nucleotide 75, about nucleotide 76 to about nucleotide 114, about nucleotide 115 to about nucleotide 162, about nucleotide 163 to about nucleotide 216, about nucleotide 217 to about nucleotide 267, about nucleotide 268 to about nucleotide 318, about nucleotide 319 to about nucleotide 369, about nucleotide 370 to about nucleotide 420, about nucleotide 421 to about nucleotide 471, about nucleotide 472 to about nucleotide 522, about nucleotide 523 to about nucleotide 573, about nucleotide 574 to about nucleotide 625, about nucleotide 626 to about nucleotide 675, about nucleotide 676 to about nucleotide 714, about nucleotide 715 to about nucleotide 765, about nucleotide 766 to about nucleotide 816, about nucleotide 817 to about nucleotide 867, about nucleotide 868 to about nucleotide 924, about nucleotide 925 to about nucleotide 975 of SEQ ID NO:1, or the complementary strand thereto, or the cDNA contained in the plasmid deposited as ATCC™ Deposit No. 97810. In this context "about" includes the particularly recited ranges, and those ranges that are larger or smaller by several (5, 4, 3, 2, or 1) nucleotides, at either terminus or at both termini.

In specific embodiments, the nucleic acid fragments of the invention comprise, or alternatively, consist of, a polynucleotide sequence encoding amino acid residues 100 to 150, 150 to 200, 200 to 300, 220 to 300, 240 to 300, 250 to 300, 260 to 300, and/or 280 to 300, of SEQ ID NO:2, or the complementary strand thereto. Polynucleotides that hybridize to these polynucleotide fragments are also encompassed by the invention.

Representative examples of TNFR-6β nucleic acid fragments of the invention include, for example, fragments that comprise, or alternatively, consist of, a sequence from about nucleotide 1 to about nucleotide 36, about nucleotide 37 to about nucleotide 72, about nucleotide 73 to about nucleotide 123, about nucleotide 124 to about nucleotide 175, about nucleotide 176 to about nucleotide 216, about nucleotide 217 to about nucleotide 267, about nucleotide 268 to about nucleotide 318, about nucleotide 319 to about nucleotide 369, about nucleotide 370 to about nucleotide 420, about nucleotide 421 to about nucleotide 471, about nucleotide 472 to about nucleotide 522, about nucleotide 523 to about nucleotide 582, about nucleotide 583 to about nucleotide 622, about nucleotide 623 to about nucleotide 682, about nucleotide 683 to about nucleotide 750, about nucleotide 751 to about nucleotide 800, about nucleotide 801 to about nucleotide 850, about nucleotide 851 to about nucleotide 900, about nucleotide 901 to about nucleotide 950, about nucleotide 951 to about nucleotide 1000, about nucleotide 1001 to about nucleotide 1050, about nucleotide 1051 to about nucleotide 1100, about nucleotide 1101 to about nucleotide 1150, about nucleotide 1151 to about nucleotide 1200, about nucleotide 1201 to about nucleotide 1250, about nucleotide 1251 to about nucleotide 1300, about nucleotide 1301 to about nucleotide 1350, about nucleotide 1351 to about nucleotide 1400, about nucleotide 1401 to about nucleotide 1450, about nucleotide 1451 to about nucleotide 1500, about nucleotide 1501 to about nucleotide 1550, about nucleotide 1551 to about nucleotide 1600 about nucleotide 1601 to about nucleotide 1650, about nucleotide 1651 to about nucleotide 1667 of SEQ ID NO:3, or the complementary strand thereto, or the cDNA contained in the plasmid deposited as ATCC™ Deposit No. 97809. In this context "about" includes the particularly recited ranges, and those ranges that are larger or smaller by several (5, 4, 3, 2, or 1) nucleotides, at either terminus or at both termini.

In specific embodiments, the nucleic acid fragments of the invention comprise, or alternatively, consist of, a polynucleotide sequence encoding amino acid residues 50 to 100, 100 to 170, 110 to 170, 130 to 170, 140 to 170, 150 to 170, and/or 160 to 170, of SEQ ID NO:4, or the complementary strand thereto. Polynucleotides that hybridize to these polynucleotide fragments are also encompassed by the invention.

Preferably, the polynucleotide fragments of the invention encode a polypeptide which demonstrates a TNFR-6α and/or TNFR-6β functional activity. By a polypeptide demonstrating "functional activity" is meant, a polypeptide capable of displaying one or more known functional activities associated with a complete (full-length) or mature TNFR-6α and/or TNFR-6β polypeptide. Such functional activities include, but are not limited to, biological activity (e.g., inhibition or reduction of FasL mediated apoptosis, inhibition or reduction of AIM-II mediated apoptosis), antigenicity [ability to bind (or compete with a TNFR-6α and/or TNFR-6β polypeptide for binding) to an anti-TNFR-6α antibody and/or anti-TNFR-6β antibody], immunogenicity (ability to generate antibody which binds to a TNFR-6α and/or TNFR-6β polypeptide), ability to form multimers with TNFR-6α and/or TNFR-6β polypeptides of the invention, and ability to bind to a receptor or ligand for a TNFR-6α and/or TNFR-6β polypeptide (e.g., Fas ligand and/or AIM-II (International application publication number WO 97/34911, published Sep. 25, 1997)).

The functional activity of TNFR-6α and/or TNFR-6β polypeptides, and fragments, variants derivatives, and analogs thereof, can be assayed by various methods.

For example, in one embodiment where one is assaying for the ability to bind or compete with complete (full-length) or mature TNFR-6α and/or TNFR-6β polypeptide for binding to anti-TNFR-6α and/or anti-TNFR-6β antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a TNF-ligand is identified (e.g., Fas Ligand and/or AIM-II (International application publication number WO 97/34911, published Sep. 25, 1997)), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94-123 (1995). In another embodiment, physiological correlates of TNFR-6α and/or TNFR-6β binding to its substrates (signal transduction) can be assayed.

In addition, assays described herein (e.g., see Examples 7-9) and otherwise known in the art may routinely be applied or modified to measure the ability of TNFR-6α and/or TNFR-6β polypeptides and fragments, variants derivatives and analogs thereof, to elicit TNFR-6α and/or TNFR-6β related biological activity (e.g., to inhibit or reduce FasL mediated apoptosis in vitro or in vivo, or to inhibit or reduce AIM-II mediated apoptosis in vitro or in vivo).

For example, the ability of TNFR polypeptides of the invention to reduce or block FasL mediated apoptosis can be assayed using a Fas expressing T-cell line, such as Jurkat. In this assay, Jurkat cells treated with soluble FasL undergo apoptosis. Pretreatment of cells with TNFR and/or TNFR agonists prior to addition of FasL protects cells from undergoing apoptosis and results in a reduced level of apoptosis when compared to that observed when the same concentration of soluble FasL is contacted with the same concentration of the Fas expressing cells in the absence of the TNFR polypeptide or TNFR agonist. Alternatively mixing of the FasL protein with TNFR and/or TNFR agonist will also block the ability of FasL to bind the Jurkat cells and mediate apoptosis (see, e.g., Example 9).

In contrast, TNFR antagonists of the invention block TNFR mediated inhibition of FasL mediated apoptosis. Accordingly, TNFR antagonists of the invention can be assayed, for example, by combining the mature TNFR (known to bind FasL), the TNFR antagonist to be tested, and soluble FasL, and contacting this combination with the Fas expressing cell line. TNFR antagonists reduce or block TNFR mediated inhibition of FasL mediated apoptosis. Accordingly, Fas expressing T cells contacted with mature TNFR, TNFR antagonist and soluble FasL exhibit elevated apoptosis levels when compared with the same concentration of Fas expressing cells that have been contacted with the same concentrations of mature TNFR and FasL in the absence of the TNFR antagonist.

Apoptosis can be measured, for example, by increased staining with Annexin, which selectively binds apoptotic cells. In another example, the decrease in cell numbers due to apoptosis can be detected by a decrease in ALOMAR blue staining which detects viable cells.

Other methods will be known to the skilled artisan and are within the scope of the invention.

In additional embodiments, the polynucleotides of the invention encode functional attributes of TNFR-6α and/or TNFR-6β. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TNFR-6α and/or TNFR-6β polypeptides.

Certain preferred regions in this regard are set out in FIG. 4 (Table I) and FIG. 5 (Table II). The data presented in FIG. 4 and FIG. 5 and that presented in Table I and Table II, respectively, merely present a different format of the same results obtained when the amino acid sequence of SEQ ID NO:2 and the amino acid sequence of SEQ ID NO:4 is analyzed using the default parameters of the DNA*STAR computer algorithm.

The above-mentioned preferred regions set out in FIG. 4 (Table I) and FIG. 5 (Table II) include, but are not limited to, regions of the aforementioned types identified by analysis of the amino acid sequence set out in FIG. 1 and FIG. 2A. As set out in FIG. 4 (Table I) and FIG. 5 (Table II), such preferred regions include Garnier-Robson alpha-regions, beta-regions, turn-regions, and coil-regions, Chou-Fasman alpha-regions, beta-regions, and coil-regions, Kyte-Doolittle hydrophilic regions, Eisenberg alpha- and beta-amphipathic regions, Karplus-Schulz flexible regions, Emini surface-forming regions and Jameson-Wolf regions of high antigenic index. Among highly preferred polynucleotides in this regard are those that encode polypeptides comprising regions of TNFR-6α and/or TNFR-6β that combine several structural features, such as several (e.g., 1, 2, 3, or 4) of the features set out above.

Additionally, the data presented in columns VIII, IX, XIII, and XIV of Tables I and II can routinely be used to determine regions of TNFR-6α and/or TNFR-6β which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.06 | 0.09 | * | . | . | −0.10 | 0.60 |
| Arg | 2 | . | . | B | . | . | . | . | 0.10 | −0.34 | * | . | . | 0.50 | 0.82 |
| Ala | 3 | . | . | B | . | . | . | . | 0.28 | −0.34 | * | . | . | 0.50 | 0.63 |
| Leu | 4 | A | . | . | . | . | . | . | 0.32 | −0.34 | * | . | . | 0.50 | 0.99 |
| Glu | 5 | A | . | . | . | . | . | . | −0.10 | −0.53 | * | . | F | 0.95 | 0.50 |
| Gly | 6 | . | . | . | . | . | T | C | 0.20 | 0.16 | * | . | F | 0.45 | 0.41 |
| Pro | 7 | . | . | . | . | T | T | . | −0.72 | 0.04 | * | . | F | 0.65 | 0.66 |
| Gly | 8 | . | . | . | . | T | T | . | −0.94 | 0.04 | . | . | F | 0.65 | 0.32 |
| Leu | 9 | A | . | . | . | . | T | . | −0.80 | 0.73 | . | . | . | −0.20 | 0.26 |
| Ser | 10 | A | A | . | . | . | . | . | −1.61 | 0.87 | . | . | . | −0.60 | 0.09 |
| Leu | 11 | . | A | B | . | . | . | . | −2.12 | 1.13 | . | . | . | −0.60 | 0.08 |
| Leu | 12 | . | A | B | . | . | . | . | −2.72 | 1.34 | . | . | . | −0.60 | 0.07 |
| Cys | 13 | . | A | B | . | . | . | . | −2.97 | 1.34 | . | . | . | −0.60 | 0.04 |
| Leu | 14 | . | A | B | . | . | . | . | −2.97 | 1.46 | . | . | . | −0.60 | 0.05 |
| Val | 15 | . | A | B | . | . | . | . | −2.88 | 1.46 | . | . | . | −0.60 | 0.05 |
| Leu | 16 | . | A | B | . | . | . | . | −2.66 | 1.20 | . | . | . | −0.60 | 0.15 |
| Ala | 17 | . | A | B | . | . | . | . | −2.66 | 1.13 | . | . | . | −0.60 | 0.18 |
| Leu | 18 | . | A | B | . | . | . | . | −2.80 | 1.13 | . | . | . | −0.60 | 0.20 |
| Pro | 19 | A | A | . | . | . | . | . | −2.20 | 1.17 | . | . | . | −0.60 | 0.20 |
| Ala | 20 | . | A | B | . | . | . | . | −2.20 | 0.91 | . | . | . | −0.60 | 0.31 |
| Leu | 21 | . | A | B | . | . | . | . | −1.60 | 1.06 | . | * | . | −0.60 | 0.28 |
| Leu | 22 | . | A | B | . | . | . | . | −1.60 | 0.80 | . | . | . | −0.60 | 0.28 |
| Pro | 23 | . | A | B | . | . | . | . | −1.64 | 0.87 | . | * | . | −0.60 | 0.28 |
| Val | 24 | . | . | B | . | . | . | . | −1.32 | 1.01 | . | * | . | −0.40 | 0.25 |
| Pro | 25 | . | . | B | . | . | . | . | −1.08 | 0.33 | * | . | . | −0.10 | 0.60 |
| Ala | 26 | . | . | B | B | . | . | . | −1.12 | 0.07 | . | . | . | −0.30 | 0.38 |
| Val | 27 | . | . | B | B | . | . | . | −0.90 | 0.29 | * | * | . | −0.30 | 0.38 |
| Arg | 28 | . | . | B | B | . | . | . | −0.69 | 0.14 | * | * | . | −0.30 | 0.25 |
| Gly | 29 | . | . | B | B | . | . | . | −0.14 | −0.29 | * | * | . | 0.30 | 0.43 |
| Val | 30 | . | . | B | B | . | . | . | −0.14 | −0.30 | * | * | . | 0.30 | 0.83 |
| Ala | 31 | . | . | B | B | . | . | . | 0.13 | −0.51 | * | * | . | 0.60 | 0.66 |
| Glu | 32 | . | . | B | . | . | . | . | 0.74 | −0.03 | * | * | F | 0.65 | 0.96 |
| Thr | 33 | . | . | B | . | . | T | . | 0.42 | 0.30 | * | * | F | 0.40 | 2.02 |
| Pro | 34 | . | . | . | . | T | T | . | 0.48 | 0.09 | * | * | F | 0.80 | 3.10 |
| Thr | 35 | . | . | . | . | T | T | . | 1.44 | 0.50 | * | . | F | 0.50 | 1.88 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Tyr | 36 | . | . | . | . | . | T | C | 2.03 | 0.50 | * | . | . | 0.15 | 2.55 |
| Pro | 37 | . | . | . | . | T | . | . | 1.44 | 0.01 | * | . | . | 0.45 | 2.76 |
| Trp | 38 | . | A | . | . | . | . | C | 1.76 | 0.09 | * | . | . | 0.05 | 1.93 |
| Arg | 39 | . | A | B | . | . | . | . | 1.66 | −0.40 | * | . | F | 0.60 | 2.13 |
| Asp | 40 | A | A | . | . | . | . | . | 1.62 | −0.67 | * | . | F | 0.90 | 1.99 |
| Ala | 41 | . | A | . | . | . | . | C | 1.87 | −0.67 | * | . | F | 1.10 | 1.87 |
| Glu | 42 | A | A | . | . | . | . | . | 2.19 | −1.59 | * | * | F | 0.90 | 1.66 |
| Thr | 43 | A | A | . | . | . | . | . | 1.67 | −1.59 | * | . | F | 0.90 | 1.94 |
| Gly | 44 | . | A | . | . | T | . | . | 0.70 | −0.90 | * | . | F | 1.30 | 1.59 |
| Glu | 45 | A | A | . | . | . | . | . | 0.03 | −0.76 | * | * | F | 0.75 | 0.68 |
| Arg | 46 | A | A | . | . | . | . | . | 0.03 | −0.19 | * | . | F | 0.45 | 0.25 |
| Leu | 47 | A | A | . | . | . | . | . | 0.03 | −0.17 | * | . | . | 0.30 | 0.26 |
| Val | 48 | . | A | B | . | . | . | . | −0.32 | −0.20 | . | . | . | 0.30 | 0.26 |
| Cys | 49 | . | A | B | . | . | . | . | −0.19 | 0.37 | . | . | . | −0.30 | 0.07 |
| Ala | 50 | . | A | B | . | . | . | . | −0.40 | 0.80 | . | . | . | −0.60 | 0.13 |
| Gln | 51 | . | A | B | . | . | . | . | −0.86 | 0.54 | . | . | . | −0.60 | 0.28 |
| Cys | 52 | . | A | B | . | . | . | . | −0.36 | 0.33 | . | . | . | −0.30 | 0.51 |
| Pro | 53 | . | . | . | . | . | T | C | −0.20 | 0.24 | . | . | F | 0.45 | 0.73 |
| Pro | 54 | . | . | . | . | T | T | . | −0.39 | 0.53 | . | . | F | 0.35 | 0.36 |
| Gly | 55 | . | . | . | . | T | T | . | 0.20 | 0.77 | * | . | F | 0.35 | 0.50 |
| Thr | 56 | . | . | B | . | . | T | . | 0.31 | 0.60 | . | . | F | −0.05 | 0.56 |
| Phe | 57 | . | . | B | B | . | . | . | 0.77 | 0.17 | * | . | F | −0.15 | 0.71 |
| Val | 58 | . | . | B | B | . | . | . | 0.31 | 0.17 | * | . | . | 0.19 | 1.12 |
| Gln | 59 | . | . | B | B | . | . | . | 0.63 | 0.31 | * | . | F | 0.53 | 0.41 |
| Arg | 60 | . | . | B | . | . | T | . | 1.09 | −0.17 | * | . | F | 1.87 | 0.94 |
| Pro | 61 | . | . | B | . | . | T | . | 1.40 | −0.96 | * | . | F | 2.66 | 2.47 |
| Cys | 62 | . | . | . | . | T | T | . | 1.80 | −1.60 | * | . | F | 3.40 | 2.38 |
| Arg | 63 | . | . | . | . | T | T | . | 2.44 | −1.61 | * | . | F | 3.06 | 1.63 |
| Arg | 64 | . | . | . | . | T | . | . | 2.13 | −1.19 | * | . | F | 2.77 | 1.63 |
| Asp | 65 | . | . | . | . | T | . | . | 1.71 | −1.13 | * | . | F | 2.68 | 4.39 |
| Ser | 66 | . | . | . | . | T | T | . | 1.26 | −1.21 | . | . | F | 2.79 | 3.24 |
| Pro | 67 | . | . | . | . | T | T | . | 1.58 | −0.64 | . | . | F | 2.55 | 0.89 |
| Thr | 68 | . | . | . | . | T | T | . | 1.26 | −0.21 | . | . | F | 2.50 | 0.52 |
| Thr | 69 | . | . | . | . | T | T | . | 0.48 | 0.21 | . | . | F | 1.65 | 0.61 |
| Cys | 70 | . | . | . | . | T | . | . | 0.27 | 0.40 | . | . | F | 1.14 | 0.21 |
| Gly | 71 | . | . | . | . | T | T | . | 0.36 | 0.40 | * | . | F | 1.33 | 0.22 |
| Pro | 72 | . | . | . | . | T | T | . | 0.68 | 0.34 | * | . | F | 1.62 | 0.24 |
| Cys | 73 | . | . | . | . | . | T | C | 0.96 | −0.14 | * | . | F | 2.01 | 0.88 |
| Pro | 74 | . | . | . | . | . | T | C | 1.02 | −0.21 | * | . | F | 2.40 | 1.21 |
| Pro | 75 | . | . | . | . | T | T | . | 1.38 | 0.11 | * | * | F | 1.76 | 1.23 |
| Arg | 76 | . | . | . | . | T | . | . | 1.72 | 0.17 | * | * | F | 1.52 | 3.30 |
| His | 77 | . | . | B | . | . | T | . | 1.23 | 0.00 | * | * | F | 0.88 | 3.70 |
| Tyr | 78 | . | . | B | . | . | T | . | 1.61 | 0.36 | * | * | . | 0.49 | 2.07 |
| Thr | 79 | . | . | B | . | . | . | . | 1.82 | 0.84 | * | . | . | −0.25 | 1.11 |
| Gln | 80 | . | . | B | . | . | . | . | 1.79 | 1.24 | * | . | . | −0.25 | 1.31 |
| Phe | 81 | . | . | . | . | T | . | . | 0.87 | 1.50 | * | * | . | 0.15 | 1.31 |
| Trp | 82 | . | . | . | . | T | . | . | 0.90 | 1.43 | * | . | . | 0.00 | 0.75 |
| Asn | 83 | . | A | . | . | T | . | . | 1.26 | 0.94 | * | . | . | −0.20 | 0.75 |
| Tyr | 84 | . | A | . | . | T | . | . | 0.90 | 0.54 | * | * | . | −0.05 | 1.70 |
| Leu | 85 | . | A | . | . | T | . | . | 1.01 | 0.33 | * | * | . | 0.38 | 0.87 |
| Glu | 86 | . | A | . | . | T | . | . | 1.47 | −0.59 | * | * | . | 1.71 | 1.05 |
| Arg | 87 | . | A | . | . | T | . | . | 1.09 | −0.23 | . | * | . | 1.69 | 1.05 |
| Cys | 88 | . | . | . | . | T | T | . | 1.09 | −0.41 | . | * | . | 2.22 | 0.69 |
| Arg | 89 | . | . | . | . | T | T | . | 0.48 | −0.70 | . | * | . | 2.80 | 0.64 |
| Tyr | 90 | . | . | . | . | T | T | . | 0.48 | −0.06 | . | * | . | 2.22 | 0.24 |
| Cys | 91 | . | . | . | . | T | T | . | −0.19 | 0.63 | . | * | . | 1.04 | 0.37 |
| Asn | 92 | . | . | B | B | . | . | . | −0.64 | 0.63 | . | * | . | −0.04 | 0.10 |
| Val | 93 | . | . | B | B | . | . | . | 0.02 | 1.06 | . | * | . | −0.32 | 0.06 |
| Leu | 94 | . | . | B | B | . | . | . | 0.02 | 0.30 | . | . | . | −0.30 | 0.21 |
| Cys | 95 | . | . | B | . | . | . | . | 0.27 | −0.27 | . | . | . | 0.70 | 0.25 |
| Gly | 96 | . | . | . | . | . | T | C | 0.93 | −0.67 | . | . | F | 1.35 | 0.59 |
| Glu | 97 | A | . | . | . | . | T | . | 0.93 | −1.31 | . | . | F | 1.30 | 1.24 |
| Arg | 98 | A | . | . | . | . | T | . | 1.20 | −2.00 | . | * | F | 1.30 | 4.00 |
| Glu | 99 | A | A | . | . | . | . | . | 2.12 | −2.07 | . | * | F | 0.90 | 4.08 |
| Glu | 100 | A | A | . | . | . | . | . | 2.20 | −2.50 | . | * | F | 0.90 | 4.61 |
| Glu | 101 | A | A | . | . | . | . | . | 1.88 | −2.00 | . | * | F | 0.90 | 2.38 |
| Ala | 102 | A | A | . | . | . | . | . | 1.84 | −1.43 | . | . | F | 0.75 | 0.74 |
| Arg | 103 | A | A | . | . | . | . | . | 1.14 | −0.93 | . | . | . | 0.60 | 0.58 |
| Ala | 104 | A | A | . | . | . | . | . | 0.83 | −0.43 | . | * | . | 0.30 | 0.34 |
| Cys | 105 | A | A | . | . | . | . | . | 0.80 | 0.06 | . | * | . | −0.30 | 0.48 |
| His | 106 | A | A | . | . | . | . | . | 0.80 | 0.06 | * | * | . | −0.30 | 0.34 |
| Ala | 107 | A | A | . | . | . | . | . | 1.50 | 0.46 | * | * | . | −0.60 | 0.53 |
| Thr | 108 | A | A | . | . | . | . | . | 0.80 | −0.04 | * | * | . | 0.45 | 1.95 |
| His | 109 | . | A | . | . | T | . | . | 0.72 | −0.11 | * | . | . | 1.13 | 1.45 |
| Asn | 110 | . | A | . | . | T | . | . | 1.50 | −0.04 | * | . | . | 1.26 | 0.77 |
| Arg | 111 | . | A | . | . | T | . | . | 0.87 | −0.54 | . | * | . | 1.99 | 1.04 |
| Ala | 112 | . | A | . | . | T | . | . | 1.57 | −0.46 | . | * | . | 1.82 | 0.41 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 113 | . | . | . | . | T | T | . | 1.57 | −0.96 | . | * | . | 2.80 | 0.50 |
| Arg | 114 | . | . | B | . | . | T | . | 1.26 | −0.87 | * | * | . | 2.12 | 0.37 |
| Cys | 115 | . | . | . | . | T | T | . | 0.56 | −0.44 | * | * | . | 1.94 | 0.36 |
| Arg | 116 | . | . | . | . | T | T | . | −0.26 | −0.16 | . | * | . | 1.66 | 0.58 |
| Thr | 117 | . | A | . | B | T | . | . | −0.26 | 0.06 | . | * | F | 0.53 | 0.26 |
| Gly | 118 | . | A | . | B | T | . | . | 0.38 | 0.56 | . | * | . | −0.20 | 0.49 |
| Phe | 119 | . | A | B | B | . | . | . | −0.32 | 0.49 | . | * | . | −0.60 | 0.34 |
| Phe | 120 | . | A | B | B | . | . | . | −0.00 | 0.99 | . | * | . | −0.60 | 0.24 |
| Ala | 121 | A | A | . | B | . | . | . | −0.81 | 0.93 | . | * | . | −0.60 | 0.24 |
| His | 122 | A | A | . | . | . | . | . | −1.17 | 1.29 | . | . | . | −0.60 | 0.24 |
| Ala | 123 | A | A | . | . | . | . | . | −1.63 | 1.07 | . | * | . | −0.60 | 0.15 |
| Gly | 124 | A | A | . | . | . | . | . | −0.93 | 0.97 | . | * | . | −0.60 | 0.12 |
| Phe | 125 | A | A | . | . | . | . | . | −0.27 | 0.47 | . | . | . | −0.60 | 0.15 |
| Cys | 126 | A | A | . | . | . | . | . | −0.27 | 0.47 | . | * | . | −0.60 | 0.20 |
| Leu | 127 | A | A | . | . | . | . | . | −0.53 | 0.47 | . | . | . | −0.60 | 0.21 |
| Glu | 128 | A | A | . | . | . | . | . | −0.61 | 0.43 | . | . | . | −0.60 | 0.32 |
| His | 129 | . | . | . | . | T | T | . | −0.48 | 0.21 | . | . | . | 0.50 | 0.32 |
| Ala | 130 | . | . | . | . | T | T | . | 0.01 | 0.07 | . | . | . | 0.63 | 0.61 |
| Ser | 131 | . | . | . | . | T | T | . | 0.33 | −0.19 | . | . | . | 1.36 | 0.54 |
| Cys | 132 | . | . | . | . | . | T | C | 0.56 | 0.24 | . | . | . | 0.69 | 0.39 |
| Pro | 133 | . | . | . | . | . | T | C | 0.21 | 0.24 | . | . | F | 0.97 | 0.39 |
| Pro | 134 | . | . | . | . | . | T | T | −0.61 | 0.17 | . | . | F | 1.30 | 0.29 |
| Gly | 135 | . | . | . | . | . | T | T | −0.91 | 0.43 | . | . | F | 0.87 | 0.40 |
| Ala | 136 | . | . | . | . | . | T | . | −1.20 | 0.54 | . | . | . | 0.19 | 0.18 |
| Gly | 137 | . | . | B | B | . | . | . | −0.74 | 0.61 | . | . | . | −0.34 | 0.12 |
| Val | 138 | . | . | B | B | . | . | . | −0.88 | 0.61 | . | . | . | −0.47 | 0.19 |
| Ile | 139 | . | . | B | B | . | . | . | −0.98 | 0.61 | . | . | . | −0.60 | 0.18 |
| Ala | 140 | . | . | B | B | . | . | . | −0.84 | 0.60 | . | . | . | −0.60 | 0.27 |
| Pro | 141 | . | . | B | . | . | . | . | −0.56 | 0.60 | . | . | F | −0.25 | 0.55 |
| Gly | 142 | . | . | . | . | T | . | . | −0.21 | 0.34 | . | . | F | 0.88 | 1.06 |
| Thr | 143 | . | . | . | . | . | T | C | 0.64 | 0.06 | . | . | F | 1.16 | 1.82 |
| Pro | 144 | . | . | . | . | . | T | C | 1.22 | −0.04 | . | . | F | 2.04 | 1.89 |
| Ser | 145 | . | . | . | . | T | T | . | 1.81 | 0.01 | . | . | F | 1.92 | 2.76 |
| Gln | 146 | . | . | . | . | T | T | . | 1.36 | −0.01 | . | . | F | 2.80 | 3.31 |
| Asn | 147 | . | . | . | . | T | T | . | 1.70 | 0.07 | . | . | F | 1.92 | 1.15 |
| Thr | 148 | . | . | . | . | T | T | . | 1.80 | 0.04 | . | . | F | 1.64 | 1.48 |
| Gln | 149 | . | . | . | . | T | T | . | 1.34 | 0.09 | . | . | F | 1.36 | 1.32 |
| Cys | 150 | . | . | B | . | . | T | . | 1.43 | 0.26 | . | . | F | 0.53 | 0.44 |
| Gln | 151 | . | . | B | . | . | . | . | 1.22 | 0.29 | . | . | F | 0.05 | 0.47 |
| Pro | 152 | . | . | B | . | . | . | . | 0.88 | 0.23 | . | * | F | 0.05 | 0.42 |
| Cys | 153 | . | . | B | . | . | . | . | 0.88 | 0.26 | . | * | F | 0.05 | 0.78 |
| Pro | 154 | . | . | B | . | . | T | . | 0.18 | 0.17 | . | * | F | 0.25 | 0.65 |
| Pro | 155 | . | . | . | . | T | T | . | 0.54 | 0.56 | . | * | F | 0.35 | 0.36 |
| Gly | 156 | . | . | . | . | T | T | . | −0.04 | 0.51 | . | * | F | 0.35 | 0.91 |
| Thr | 157 | . | . | B | . | . | T | . | −0.13 | 0.44 | . | . | F | −0.05 | 0.59 |
| Phe | 158 | . | . | B | . | . | . | . | 0.23 | 0.40 | . | . | F | −0.25 | 0.51 |
| Ser | 159 | . | . | B | . | . | . | . | 0.14 | 0.36 | . | . | F | 0.39 | 0.70 |
| Ala | 160 | . | . | B | . | . | . | . | 0.06 | 0.31 | . | . | F | 0.73 | 0.65 |
| Ser | 161 | . | . | . | . | T | C | . | 0.10 | 0.21 | . | . | F | 1.62 | 1.00 |
| Ser | 162 | . | . | . | . | T | C | . | 0.41 | −0.19 | . | . | F | 2.56 | 1.00 |
| Ser | 163 | . | . | . | . | T | T | . | 1.11 | −0.57 | . | . | F | 3.40 | 1.72 |
| Ser | 164 | . | . | . | . | T | T | . | 0.74 | −0.67 | . | . | F | 3.06 | 2.22 |
| Ser | 165 | . | . | . | . | T | . | . | 1.33 | −0.49 | . | . | F | 2.07 | 0.89 |
| Glu | 166 | . | . | . | . | T | . | . | 1.42 | −0.47 | . | . | F | 1.88 | 1.15 |
| Gln | 167 | . | . | . | . | T | . | . | 1.69 | −0.43 | . | . | F | 1.82 | 1.32 |
| Cys | 168 | . | . | . | . | T | . | . | 2.10 | −0.31 | . | . | F | 1.76 | 1.34 |
| Gln | 169 | . | . | B | . | . | . | . | 2.40 | −0.70 | . | . | F | 1.94 | 1.52 |
| Pro | 170 | . | . | . | . | T | . | . | 2.03 | −0.30 | . | . | F | 2.32 | 1.41 |
| His | 171 | . | . | . | . | T | T | . | 1.72 | −0.13 | . | . | F | 2.80 | 1.41 |
| Arg | 172 | . | . | . | . | T | T | . | 1.13 | −0.21 | . | . | F | 2.52 | 1.18 |
| Asn | 173 | . | . | . | . | T | T | . | 0.99 | −0.11 | * | . | . | 1.94 | 0.77 |
| Cys | 174 | . | . | B | . | . | T | . | 0.64 | 0.14 | . | . | . | 0.66 | 0.47 |
| Thr | 175 | . | A | B | . | . | . | . | 0.04 | 0.07 | . | . | . | −0.02 | 0.24 |
| Ala | 176 | . | A | B | . | . | . | . | −0.51 | 0.76 | * | . | . | −0.60 | 0.12 |
| Leu | 177 | . | A | B | . | . | . | . | −1.43 | 0.86 | * | . | . | −0.60 | 0.23 |
| Gly | 178 | . | A | B | . | . | . | . | −1.43 | 0.97 | . | * | . | −0.60 | 0.13 |
| Leu | 179 | . | A | B | . | . | . | . | −1.62 | 0.89 | . | * | . | −0.60 | 0.21 |
| Ala | 180 | . | A | B | . | . | . | . | −1.52 | 1.03 | . | * | . | −0.60 | 0.19 |
| Leu | 181 | . | A | B | . | . | . | . | −1.28 | 0.77 | . | * | . | −0.60 | 0.29 |
| Asn | 182 | . | A | B | . | . | . | . | −0.77 | 0.77 | . | * | . | −0.60 | 0.35 |
| Val | 183 | . | . | B | . | . | T | . | −0.72 | 0.47 | . | * | F | −0.05 | 0.46 |
| Pro | 184 | . | . | . | . | T | C | . | −0.21 | 0.36 | . | * | F | 0.73 | 0.75 |
| Gly | 185 | . | . | . | . | T | T | . | 0.34 | 0.06 | . | * | F | 1.21 | 0.63 |
| Ser | 186 | . | . | . | . | T | T | . | 1.16 | 0.16 | . | * | F | 1.64 | 1.15 |
| Ser | 187 | . | . | . | . | T | C | . | 0.84 | −0.49 | . | . | F | 2.32 | 1.24 |
| Ser | 188 | . | . | . | . | T | T | . | 0.89 | −0.43 | . | . | F | 2.80 | 1.81 |
| His | 189 | . | . | B | . | . | T | . | 0.43 | −0.17 | . | . | F | 2.12 | 1.11 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 190 | . | . | . | . | T | T | . | 0.47 | 0.01 | . | . | F | 1.49 | 0.45 |
| Thr | 191 | . | . | B | . | . | . | . | 0.47 | 0.11 | . | . | F | 0.61 | 0.48 |
| Leu | 192 | . | . | B | . | . | . | . | 0.10 | 0.11 | . | . | . | 0.18 | 0.47 |
| Cys | 193 | . | . | B | . | . | T | . | 0.09 | 0.19 | . | . | . | 0.10 | 0.15 |
| Thr | 194 | . | . | B | . | . | T | . | −0.22 | 0.67 | . | . | . | −0.20 | 0.15 |
| Ser | 195 | . | . | B | . | . | T | . | −0.92 | 0.61 | * | . | F | −0.05 | 0.18 |
| Cys | 196 | . | . | B | . | . | T | . | −0.82 | 0.71 | . | . | F | −0.05 | 0.29 |
| Thr | 197 | . | . | . | . | T | . | . | −0.82 | 0.57 | . | . | F | 0.15 | 0.31 |
| Gly | 198 | . | . | . | . | T | . | . | −0.46 | 0.77 | . | . | . | 0.00 | 0.19 |
| Phe | 199 | . | . | B | . | . | . | . | −0.46 | 0.77 | . | * | . | −0.40 | 0.48 |
| Pro | 200 | . | . | B | . | . | . | . | −0.04 | 0.69 | * | * | . | −0.40 | 0.48 |
| Leu | 201 | . | . | B | . | . | . | . | −0.23 | 0.20 | * | * | . | −0.10 | 0.96 |
| Ser | 202 | . | . | B | . | . | . | . | −0.13 | 0.41 | * | * | F | 0.02 | 0.82 |
| Thr | 203 | . | . | B | . | . | . | . | −0.13 | 0.06 | . | * | F | 0.59 | 0.82 |
| Arg | 204 | . | . | . | . | . | . | C | −0.02 | 0.06 | . | * | F | 1.06 | 0.99 |
| Val | 205 | . | . | . | . | . | T | C | 0.19 | −0.13 | . | * | F | 2.13 | 0.74 |
| Pro | 206 | . | . | . | . | . | T | C | 1.00 | −0.51 | . | * | F | 2.70 | 0.89 |
| Gly | 207 | . | . | . | . | . | T | C | 0.63 | −1.00 | . | * | F | 2.43 | 0.79 |
| Ala | 208 | A | . | . | . | . | T | . | 0.94 | −0.43 | . | * | F | 1.66 | 0.57 |
| Glu | 209 | A | A | . | . | . | . | . | 0.94 | −1.07 | . | * | F | 1.29 | 0.64 |
| Glu | 210 | A | A | . | . | . | . | . | 1.21 | −1.50 | * | . | F | 1.17 | 1.26 |
| Cys | 211 | A | A | . | . | . | . | . | 0.57 | −1.43 | * | . | F | 0.90 | 1.26 |
| Glu | 212 | A | A | . | . | . | . | . | 0.02 | −1.29 | * | * | F | 0.75 | 0.54 |
| Arg | 213 | A | A | . | . | . | . | . | 0.61 | −0.60 | * | * | . | 0.60 | 0.22 |
| Ala | 214 | A | A | . | . | . | . | . | −0.09 | −0.60 | * | * | . | 0.60 | 0.68 |
| Val | 215 | A | A | . | . | . | . | . | −0.94 | −0.39 | * | * | . | 0.30 | 0.34 |
| Ile | 216 | A | A | . | . | . | . | . | −0.87 | 0.26 | * | * | . | −0.30 | 0.13 |
| Asp | 217 | A | A | . | . | . | . | . | −1.57 | 0.76 | * | * | . | −0.60 | 0.13 |
| Phe | 218 | A | A | . | . | . | . | . | −1.68 | 1.04 | * | * | . | −0.60 | 0.15 |
| Val | 219 | A | A | . | . | . | . | . | −1.09 | 0.80 | . | . | . | −0.60 | 0.37 |
| Ala | 220 | A | A | . | . | . | . | . | −1.12 | 0.11 | . | . | . | −0.30 | 0.37 |
| Phe | 221 | A | A | . | . | . | . | . | −0.53 | 0.80 | . | * | . | −0.60 | 0.30 |
| Gln | 222 | A | A | . | . | . | . | . | −1.42 | 0.40 | . | * | . | −0.60 | 0.54 |
| Asp | 223 | A | A | . | . | . | . | . | −0.68 | 0.44 | . | . | F | −0.45 | 0.38 |
| Ile | 224 | A | A | . | . | . | . | . | 0.29 | −0.06 | . | . | F | 0.45 | 0.87 |
| Ser | 225 | A | A | . | . | . | . | . | 0.07 | −0.84 | . | . | F | 0.75 | 0.99 |
| Ile | 226 | A | A | . | . | . | . | . | 0.77 | −0.56 | * | . | F | 0.75 | 0.49 |
| Lys | 227 | A | A | . | . | . | . | . | 0.88 | −0.16 | * | * | F | 0.60 | 1.20 |
| Arg | 228 | A | A | . | . | . | . | . | 0.07 | −0.84 | * | * | F | 0.90 | 1.76 |
| Leu | 229 | A | A | . | . | . | . | . | 0.14 | −0.54 | * | . | F | 0.90 | 2.07 |
| Gln | 230 | A | A | . | . | . | . | . | 0.44 | −0.54 | * | . | F | 0.75 | 0.85 |
| Arg | 231 | . | A | B | . | . | . | . | 0.74 | −0.14 | * | . | . | 0.30 | 0.76 |
| Leu | 232 | A | A | . | . | . | . | . | −0.11 | 0.36 | * | . | . | −0.30 | 0.93 |
| Leu | 233 | . | A | B | . | . | . | . | −0.22 | 0.36 | * | * | . | −0.30 | 0.44 |
| Gln | 234 | . | A | B | . | . | . | . | −0.00 | −0.04 | * | . | . | 0.30 | 0.39 |
| Ala | 235 | . | A | B | . | . | . | . | −0.21 | 0.46 | * | . | . | −0.60 | 0.48 |
| Leu | 236 | . | A | B | . | . | . | . | −0.32 | 0.20 | * | * | . | −0.30 | 0.89 |
| Glu | 237 | . | A | B | . | . | . | . | 0.14 | −0.49 | . | . | . | 0.30 | 0.89 |
| Ala | 238 | . | . | B | . | . | T | . | 0.67 | −0.46 | . | . | F | 0.85 | 0.88 |
| Pro | 239 | . | . | . | . | T | T | . | 0.32 | −0.04 | . | . | F | 1.40 | 1.12 |
| Glu | 240 | . | . | . | . | T | T | . | 0.70 | −0.30 | . | . | F | 1.25 | 0.64 |
| Gly | 241 | . | . | . | . | T | T | . | 1.20 | 0.13 | . | . | F | 0.65 | 0.98 |
| Trp | 242 | . | . | . | . | T | . | . | 0.99 | 0.11 | * | . | F | 0.45 | 0.91 |
| Gly | 243 | . | . | . | . | . | . | C | 1.69 | 0.11 | * | * | F | 0.59 | 0.81 |
| Pro | 244 | . | . | . | . | . | . | C | 1.31 | 0.11 | * | * | F | 1.08 | 1.61 |
| Thr | 245 | . | . | . | . | . | T | C | 0.97 | 0.19 | * | . | F | 1.62 | 1.55 |
| Pro | 246 | . | . | . | . | . | T | C | 1.42 | −0.30 | * | . | F | 2.56 | 1.55 |
| Arg | 247 | . | . | . | . | . | T | . | 1.12 | −0.73 | * | . | F | 3.40 | 1.96 |
| Ala | 248 | . | . | . | . | . | T | C | 0.88 | −0.66 | * | . | F | 2.86 | 1.37 |
| Gly | 249 | A | A | . | . | . | . | . | 0.28 | −0.64 | * | * | F | 1.77 | 0.90 |
| Arg | 250 | A | A | . | . | . | . | . | 0.59 | −0.39 | * | * | . | 0.98 | 0.38 |
| Ala | 251 | A | A | . | . | . | . | . | −0.01 | 0.01 | * | . | . | 0.04 | 0.65 |
| Ala | 252 | A | A | . | . | . | . | . | −0.08 | 0.20 | * | . | . | −0.30 | 0.54 |
| Leu | 253 | A | A | . | . | . | . | . | −0.30 | −0.23 | * | . | . | 0.30 | 0.55 |
| Gln | 254 | A | A | . | . | . | . | . | 0.16 | 0.46 | . | * | . | −0.60 | 0.45 |
| Leu | 255 | A | A | . | . | . | . | . | 0.16 | −0.04 | . | * | . | 0.30 | 0.87 |
| Lys | 256 | A | A | . | . | . | . | . | 0.86 | −0.54 | . | * | . | 0.75 | 2.07 |
| Leu | 257 | A | A | . | . | . | . | . | 0.63 | −1.23 | . | * | F | 0.90 | 2.34 |
| Arg | 258 | A | A | . | . | . | . | . | 1.13 | −0.94 | * | * | F | 0.90 | 2.34 |
| Arg | 259 | . | A | B | . | . | . | . | 1.13 | −1.14 | * | * | F | 0.90 | 1.69 |
| Arg | 260 | . | A | B | . | . | . | . | 1.13 | −1.14 | * | * | F | 0.90 | 3.55 |
| Leu | 261 | . | A | B | . | . | . | . | 0.28 | −1.14 | * | * | F | 0.90 | 1.49 |
| Thr | 262 | . | A | B | . | . | . | . | 0.74 | −0.46 | * | * | F | 0.45 | 0.63 |
| Glu | 263 | . | A | B | . | . | . | . | 0.04 | −0.03 | * | . | . | 0.30 | 0.32 |
| Leu | 264 | . | A | B | . | . | . | . | −0.07 | 0.47 | * | . | . | −0.60 | 0.39 |
| Leu | 265 | . | A | B | . | . | . | . | −0.18 | 0.19 | . | * | . | −0.30 | 0.47 |
| Gly | 266 | A | A | . | . | . | . | . | 0.29 | −0.30 | . | . | . | 0.30 | 0.45 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 267 | A | . | . | . | . | T | . | 0.01 | 0.13 | . | . | F | 0.25 | 0.54 |
| Gln | 268 | A | . | . | . | . | T | . | −0.80 | −0.06 | . | . | F | 0.85 | 0.66 |
| Asp | 269 | A | . | . | . | . | T | . | −0.80 | −0.06 | . | . | F | 0.85 | 0.55 |
| Gly | 270 | A | . | . | . | . | T | . | −0.84 | 0.20 | * | . | . | 0.10 | 0.45 |
| Ala | 271 | A | A | . | . | . | . | . | −0.39 | 0.34 | * | * | . | −0.30 | 0.19 |
| Leu | 272 | . | A | B | . | . | . | . | −0.61 | −0.06 | * | * | . | 0.30 | 0.23 |
| Leu | 273 | . | A | B | . | . | . | . | −1.42 | 0.63 | * | * | . | −0.60 | 0.19 |
| Val | 274 | A | A | . | . | . | . | . | −1.42 | 0.89 | * | * | . | −0.60 | 0.15 |
| Arg | 275 | A | A | . | . | . | . | . | −1.67 | 0.79 | * | * | . | −0.60 | 0.32 |
| Leu | 276 | A | A | . | . | . | . | . | −1.89 | 0.60 | * | * | . | −0.60 | 0.40 |
| Leu | 277 | A | A | . | . | . | . | . | −0.97 | 0.60 | * | * | . | −0.60 | 0.44 |
| Gln | 278 | A | A | . | . | . | . | . | −1.01 | −0.04 | * | * | . | 0.30 | 0.44 |
| Ala | 279 | A | A | . | . | . | . | . | −0.74 | 0.60 | * | * | . | −0.60 | 0.40 |
| Leu | 280 | A | A | . | . | . | . | . | −0.74 | 0.41 | * | * | . | −0.60 | 0.49 |
| Arg | 281 | . | A | B | . | . | . | . | −0.53 | −0.27 | * | * | . | 0.30 | 0.55 |
| Val | 282 | . | A | B | . | . | . | . | 0.07 | −0.06 | * | . | . | 0.30 | 0.54 |
| Ala | 283 | . | A | B | . | . | . | . | −0.28 | −0.13 | * | . | . | 0.72 | 1.01 |
| Arg | 284 | . | A | B | . | . | . | . | −0.50 | −0.39 | * | . | . | 0.84 | 0.51 |
| Met | 285 | . | . | B | . | . | T | . | 0.31 | 0.30 | . | * | . | 0.91 | 0.57 |
| Pro | 286 | . | . | . | . | . | T | C | 0.31 | −0.34 | . | * | F | 2.13 | 0.97 |
| Gly | 287 | . | . | . | . | . | T | C | 0.87 | −0.84 | * | * | F | 2.70 | 0.97 |
| Leu | 288 | A | . | . | . | . | T | . | 0.60 | −0.46 | * | * | F | 2.08 | 1.32 |
| Glu | 289 | A | . | . | . | . | . | . | 0.60 | −0.43 | * | * | F | 1.46 | 0.63 |
| Arg | 290 | A | . | . | . | . | . | . | 1.20 | −0.86 | * | * | F | 1.64 | 1.25 |
| Ser | 291 | A | . | . | . | . | . | . | 1.52 | −1.29 | * | * | F | 1.37 | 2.62 |
| Val | 292 | A | . | . | . | . | . | . | 1.17 | −1.97 | * | * | F | 1.10 | 2.97 |
| Arg | 293 | A | . | . | . | . | . | . | 1.17 | −1.19 | * | * | F | 1.10 | 1.31 |
| Glu | 294 | A | . | . | . | . | . | . | 0.96 | −0.50 | * | * | F | 0.65 | 0.81 |
| Arg | 295 | A | . | . | . | . | . | . | −0.01 | −0.46 | * | * | F | 0.80 | 1.68 |
| Phe | 296 | . | . | B | . | . | . | . | 0.26 | −0.46 | . | * | . | 0.50 | 0.64 |
| Leu | 297 | . | . | B | . | . | . | . | 0.72 | 0.04 | . | * | . | −0.10 | 0.50 |
| Pro | 298 | A | . | . | . | . | . | . | 0.22 | 0.47 | . | * | . | −0.40 | 0.33 |
| Val | 299 | A | . | . | . | . | . | . | −0.17 | 0.90 | * | . | . | −0.40 | 0.48 |
| His | 300 | A | . | . | . | . | . | . | −0.67 | 0.54 | . | . | . | −0.40 | 0.75 |

TABLE II

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.06 | 0.09 | * | . | . | −0.10 | 0.60 |
| Arg | 2 | . | . | B | . | . | . | . | 0.10 | −0.34 | * | . | . | 0.50 | 0.82 |
| Ala | 3 | . | . | B | . | . | . | . | 0.28 | −0.34 | * | . | . | 0.50 | 0.63 |
| Leu | 4 | . | . | B | . | . | . | . | 0.32 | −0.34 | . | . | . | 0.50 | 0.99 |
| Glu | 5 | . | . | B | . | . | . | . | −0.10 | −0.53 | . | . | F | 0.95 | 0.50 |
| Gly | 6 | . | . | . | . | . | T | C | 0.20 | 0.16 | * | . | F | 0.45 | 0.41 |
| Pro | 7 | . | . | . | . | T | T | . | −0.72 | 0.04 | * | . | F | 0.65 | 0.66 |
| Gly | 8 | . | . | . | . | T | T | . | −0.94 | 0.04 | . | . | F | 0.65 | 0.32 |
| Leu | 9 | . | . | B | . | . | T | . | −0.80 | 0.73 | . | . | . | −0.20 | 0.26 |
| Ser | 10 | . | A | B | . | . | . | . | −1.61 | 0.87 | . | . | . | −0.60 | 0.09 |
| Leu | 11 | . | A | B | . | . | . | . | −2.12 | 1.13 | . | . | . | −0.60 | 0.08 |
| Leu | 12 | . | A | B | . | . | . | . | −2.72 | 1.34 | . | . | . | −0.60 | 0.07 |
| Cys | 13 | . | A | B | . | . | . | . | −2.97 | 1.34 | . | . | . | −0.60 | 0.04 |
| Leu | 14 | . | A | B | . | . | . | . | −2.97 | 1.46 | . | . | . | −0.60 | 0.05 |
| Val | 15 | . | A | B | . | . | . | . | −2.88 | 1.46 | . | . | . | −0.60 | 0.05 |
| Leu | 16 | . | A | B | . | . | . | . | −2.66 | 1.20 | . | . | . | −0.60 | 0.15 |
| Ala | 17 | . | A | B | . | . | . | . | −2.66 | 1.13 | . | . | . | −0.60 | 0.18 |
| Leu | 18 | . | A | B | . | . | . | . | −2.80 | 1.13 | . | . | . | −0.60 | 0.20 |
| Pro | 19 | . | A | B | . | . | . | . | −2.20 | 1.17 | . | . | . | −0.60 | 0.20 |
| Ala | 20 | . | A | B | . | . | . | . | −2.20 | 0.91 | . | . | . | −0.60 | 0.31 |
| Leu | 21 | . | A | B | . | . | . | . | −1.60 | 1.06 | . | * | . | −0.60 | 0.28 |
| Leu | 22 | . | A | B | . | . | . | . | −1.60 | 0.80 | . | * | . | −0.60 | 0.28 |
| Pro | 23 | . | A | B | . | . | . | . | −1.64 | 0.87 | . | * | . | −0.60 | 0.28 |
| Val | 24 | . | . | B | . | . | . | . | −1.32 | 1.01 | . | * | . | −0.40 | 0.25 |
| Pro | 25 | . | . | B | . | . | . | . | −1.08 | 0.33 | . | . | . | −0.10 | 0.60 |
| Ala | 26 | . | . | B | B | . | . | . | −1.12 | 0.07 | . | . | . | −0.30 | 0.38 |
| Val | 27 | . | . | B | B | . | . | . | −0.90 | 0.29 | * | . | . | −0.30 | 0.38 |
| Arg | 28 | . | . | B | B | . | . | . | −0.69 | 0.14 | * | . | . | −0.30 | 0.25 |
| Gly | 29 | . | . | B | B | . | . | . | −0.14 | −0.29 | * | . | . | 0.30 | 0.43 |
| Val | 30 | . | . | B | B | . | . | . | −0.14 | −0.30 | * | . | . | 0.30 | 0.83 |
| Ala | 31 | . | . | B | B | . | . | . | 0.13 | −0.51 | * | . | . | 0.60 | 0.66 |
| Glu | 32 | . | . | B | . | . | . | . | 0.74 | −0.03 | * | . | F | 0.65 | 0.96 |
| Thr | 33 | . | . | B | . | . | T | . | 0.42 | 0.30 | * | * | F | 0.40 | 2.02 |
| Pro | 34 | . | . | . | . | T | T | . | 0.48 | 0.09 | * | * | F | 0.80 | 3.10 |
| Thr | 35 | . | . | . | . | T | T | . | 1.44 | 0.50 | * | . | F | 0.50 | 1.88 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Tyr | 36 | . | . | . | . | . | T | C | 2.03 | 0.50 | * | . | . | 0.15 | 2.55 |
| Pro | 37 | . | . | . | . | T | . | . | 1.44 | 0.01 | * | . | . | 0.45 | 2.76 |
| Trp | 38 | . | A | . | . | . | . | C | 1.76 | 0.09 | * | . | . | 0.05 | 1.93 |
| Arg | 39 | . | A | B | . | . | . | . | 1.66 | −0.40 | * | . | F | 0.60 | 2.13 |
| Asp | 40 | . | A | . | . | . | . | C | 1.62 | −0.67 | * | . | F | 1.10 | 1.99 |
| Ala | 41 | . | A | . | . | . | . | C | 1.87 | −0.67 | * | * | F | 1.10 | 1.87 |
| Glu | 42 | . | A | . | . | . | . | C | 2.19 | −1.59 | * | * | F | 1.10 | 1.66 |
| Thr | 43 | . | A | . | . | T | . | . | 1.67 | −1.59 | * | . | F | 1.30 | 1.94 |
| Gly | 44 | . | A | . | . | T | . | . | 0.70 | −0.90 | * | . | F | 1.30 | 1.59 |
| Glu | 45 | . | A | . | . | T | . | . | 0.03 | −0.76 | * | * | F | 1.15 | 0.68 |
| Arg | 46 | . | A | . | . | T | . | . | 0.03 | −0.19 | * | . | F | 0.85 | 0.25 |
| Leu | 47 | . | A | B | . | . | . | . | 0.03 | −0.17 | * | . | . | 0.30 | 0.26 |
| Val | 48 | . | A | B | . | . | . | . | −0.32 | −0.20 | . | . | . | 0.30 | 0.26 |
| Cys | 49 | . | A | B | . | . | . | . | −0.19 | 0.37 | . | . | . | −0.30 | 0.07 |
| Ala | 50 | . | A | B | . | . | . | . | −0.40 | 0.80 | . | . | . | −0.60 | 0.13 |
| Gln | 51 | . | A | B | . | . | . | . | −0.86 | 0.54 | . | . | . | −0.60 | 0.28 |
| Cys | 52 | . | A | B | . | . | . | . | −0.36 | 0.33 | . | . | . | −0.30 | 0.51 |
| Pro | 53 | . | . | . | . | . | T | C | −0.20 | 0.24 | . | . | F | 0.45 | 0.73 |
| Pro | 54 | . | . | . | . | T | T | . | −0.39 | 0.53 | . | . | F | 0.35 | 0.36 |
| Gly | 55 | . | . | . | . | T | T | . | 0.20 | 0.77 | * | . | F | 0.35 | 0.50 |
| Thr | 56 | . | . | B | . | . | T | . | 0.31 | 0.60 | . | . | F | −0.05 | 0.56 |
| Phe | 57 | . | . | B | B | . | . | . | 0.77 | 0.17 | * | . | F | −0.15 | 0.71 |
| Val | 58 | . | . | B | B | . | . | . | 0.31 | 0.17 | * | . | . | 0.19 | 1.12 |
| Gln | 59 | . | . | B | B | . | . | . | 0.63 | 0.31 | * | . | F | 0.53 | 0.41 |
| Arg | 60 | . | . | B | . | . | T | . | 1.09 | −0.17 | * | . | F | 1.87 | 0.94 |
| Pro | 61 | . | . | B | . | . | T | . | 1.40 | −0.96 | * | . | F | 2.66 | 2.47 |
| Cys | 62 | . | . | . | . | T | T | . | 1.80 | −1.60 | * | . | F | 3.40 | 2.38 |
| Arg | 63 | . | . | . | . | T | T | . | 2.44 | −1.61 | * | . | F | 3.06 | 1.63 |
| Arg | 64 | . | . | . | . | T | . | . | 2.13 | −1.19 | * | . | F | 2.77 | 1.63 |
| Asp | 65 | . | . | . | . | T | T | . | 1.71 | −1.13 | * | . | F | 2.68 | 4.39 |
| Ser | 66 | . | . | . | . | T | T | . | 1.26 | −1.21 | . | . | F | 2.79 | 3.24 |
| Pro | 67 | . | . | . | . | T | T | . | 1.58 | −0.64 | . | . | F | 2.55 | 0.89 |
| Thr | 68 | . | . | . | . | T | T | . | 1.26 | −0.21 | . | . | F | 2.50 | 0.52 |
| Thr | 69 | . | . | . | . | T | T | . | 0.48 | 0.21 | . | . | F | 1.65 | 0.61 |
| Cys | 70 | . | . | . | . | T | . | . | 0.27 | 0.40 | . | . | F | 1.14 | 0.21 |
| Gly | 71 | . | . | . | . | T | T | . | 0.36 | 0.40 | . | * | F | 1.33 | 0.22 |
| Pro | 72 | . | . | . | . | T | T | . | 0.68 | 0.34 | . | * | F | 1.62 | 0.24 |
| Cys | 73 | . | . | . | . | . | T | C | 0.96 | −0.14 | * | . | F | 2.01 | 0.88 |
| Pro | 74 | . | . | . | . | . | T | C | 1.02 | −0.21 | * | . | F | 2.40 | 1.21 |
| Pro | 75 | . | . | . | . | T | T | . | 1.38 | 0.11 | * | * | F | 1.76 | 1.23 |
| Arg | 76 | . | . | . | . | T | . | . | 1.72 | 0.17 | * | * | F | 1.52 | 3.30 |
| His | 77 | . | . | B | . | . | T | . | 1.23 | 0.00 | * | * | F | 0.88 | 3.70 |
| Tyr | 78 | . | . | B | . | . | T | . | 1.61 | 0.36 | * | * | . | 0.49 | 2.07 |
| Thr | 79 | . | . | B | . | . | . | . | 1.82 | 0.84 | * | * | . | −0.25 | 1.11 |
| Gln | 80 | . | . | B | . | . | . | . | 1.79 | 1.24 | * | * | . | −0.25 | 1.31 |
| Phe | 81 | . | . | . | . | T | . | . | 0.87 | 1.50 | * | * | . | 0.15 | 1.31 |
| Trp | 82 | . | . | . | . | T | . | . | 0.90 | 1.43 | * | . | . | 0.00 | 0.75 |
| Asn | 83 | . | A | . | . | T | . | . | 1.26 | 0.94 | * | * | . | −0.20 | 0.75 |
| Tyr | 84 | . | A | . | . | T | . | . | 0.90 | 0.54 | * | * | . | −0.05 | 1.70 |
| Leu | 85 | . | A | . | . | T | . | . | 1.01 | 0.33 | * | * | . | 0.38 | 0.87 |
| Glu | 86 | . | A | . | . | T | . | . | 1.47 | −0.59 | * | * | . | 1.71 | 1.05 |
| Arg | 87 | . | A | . | . | T | . | . | 1.09 | −0.23 | . | * | . | 1.69 | 1.05 |
| Cys | 88 | . | . | . | . | T | T | . | 1.09 | −0.41 | . | * | . | 2.22 | 0.69 |
| Arg | 89 | . | . | . | . | T | T | . | 0.48 | −0.70 | . | * | . | 2.80 | 0.64 |
| Tyr | 90 | . | . | . | . | T | T | . | 0.48 | −0.06 | . | * | . | 2.22 | 0.24 |
| Cys | 91 | . | . | . | . | T | T | . | −0.19 | 0.63 | . | * | . | 1.04 | 0.37 |
| Asn | 92 | . | . | B | B | . | . | . | −0.64 | 0.63 | . | * | . | −0.04 | 0.10 |
| Val | 93 | . | . | B | B | . | . | . | 0.02 | 1.06 | . | * | . | −0.02 | 0.06 |
| Leu | 94 | . | . | B | B | . | . | . | 0.02 | 0.30 | . | . | . | 0.30 | 0.21 |
| Cys | 95 | . | . | B | . | . | T | . | 0.27 | −0.27 | . | . | . | 1.60 | 0.25 |
| Gly | 96 | . | . | . | . | . | T | C | 0.93 | −0.67 | . | . | F | 2.55 | 0.59 |
| Glu | 97 | . | . | . | . | . | T | C | 0.93 | −1.31 | . | . | F | 3.00 | 1.24 |
| Arg | 98 | A | . | . | . | . | T | . | 1.20 | −2.00 | . | * | F | 2.50 | 4.00 |
| Glu | 99 | A | A | . | . | . | . | . | 2.12 | −2.07 | . | * | . | 1.80 | 4.08 |
| Glu | 100 | A | A | . | . | . | . | . | 2.20 | −2.50 | . | * | F | 1.50 | 4.61 |
| Glu | 101 | A | A | . | . | . | . | . | 1.88 | −2.00 | . | * | F | 1.20 | 2.38 |
| Ala | 102 | A | A | . | . | . | . | . | 1.84 | −1.43 | . | . | F | 0.75 | 0.74 |
| Arg | 103 | A | A | . | . | . | . | . | 1.14 | −0.93 | . | . | . | 0.60 | 0.58 |
| Ala | 104 | A | A | . | . | . | . | . | 0.83 | −0.43 | . | * | . | 0.30 | 0.34 |
| Cys | 105 | A | A | . | . | . | . | . | 0.80 | 0.06 | . | * | . | −0.30 | 0.48 |
| His | 106 | A | A | . | . | . | . | . | 0.80 | 0.06 | * | * | . | −0.30 | 0.34 |
| Ala | 107 | . | A | . | . | . | T | . | 1.50 | 0.46 | * | * | . | −0.20 | 0.53 |
| Thr | 108 | . | A | . | . | . | T | . | 0.80 | −0.04 | * | * | . | 0.85 | 1.95 |
| His | 109 | . | A | . | . | . | T | . | 0.72 | −0.11 | * | * | . | 1.13 | 1.45 |
| Asn | 110 | . | A | . | . | . | T | . | 1.50 | −0.04 | * | . | . | 1.26 | 0.77 |
| Arg | 111 | . | A | . | . | . | T | . | 0.87 | −0.54 | . | * | . | 1.99 | 1.04 |
| Ala | 112 | . | A | . | . | . | T | . | 1.57 | −0.46 | . | * | . | 1.82 | 0.41 |

TABLE II-continued

| Res | Position I | II | III | IV | V | VI | VII | VIII | IX | X | XI | XII | XIII | XIV |
|---|---|---|---|---|---|---|---|---|---|---|---|---|---|---|
| Cys | 113 | . | . | . | . | T | T | . | 1.57 | −0.96 | . | * | . | 2.80 | 0.50 |
| Arg | 114 | . | B | . | . | . | T | . | 1.26 | −0.87 | . | * | . | 2.12 | 0.37 |
| Cys | 115 | . | . | . | . | T | T | . | 0.56 | −0.44 | * | * | . | 1.94 | 0.36 |
| Arg | 116 | . | . | . | . | T | T | . | −0.26 | −0.16 | . | * | . | 1.66 | 0.58 |
| Thr | 117 | . | A | . | B | T | . | . | −0.26 | 0.06 | . | * | F | 0.53 | 0.26 |
| Gly | 118 | . | A | . | B | T | . | . | 0.38 | 0.56 | . | * | . | −0.20 | 0.49 |
| Phe | 119 | . | A | B | B | . | . | . | −0.32 | 0.49 | . | * | . | −0.60 | 0.34 |
| Phe | 120 | . | A | B | B | . | . | . | −0.00 | 0.99 | . | * | . | −0.60 | 0.24 |
| Ala | 121 | . | A | B | B | . | . | . | −0.81 | 0.93 | . | * | . | −0.60 | 0.24 |
| His | 122 | . | A | . | . | . | . | C | −1.17 | 1.29 | . | * | . | −0.40 | 0.24 |
| Ala | 123 | . | A | . | . | . | . | C | −1.63 | 1.07 | . | * | . | −0.40 | 0.15 |
| Gly | 124 | . | A | . | . | T | . | . | −0.93 | 0.97 | . | * | . | −0.20 | 0.12 |
| Phe | 125 | . | A | . | . | T | . | . | −0.27 | 0.47 | . | . | . | −0.20 | 0.15 |
| Cys | 126 | . | A | . | . | T | . | . | −0.27 | 0.47 | . | * | . | −0.20 | 0.20 |
| Leu | 127 | . | A | B | . | . | . | . | −0.53 | 0.47 | . | . | . | −0.60 | 0.21 |
| Glu | 128 | . | A | B | . | T | . | . | −0.61 | 0.43 | . | . | . | −0.20 | 0.32 |
| His | 129 | . | . | . | . | T | T | . | −0.48 | 0.21 | . | . | . | 0.50 | 0.32 |
| Ala | 130 | . | . | . | . | T | T | . | 0.01 | 0.07 | . | . | . | 0.63 | 0.61 |
| Ser | 131 | . | . | . | . | T | T | . | 0.33 | −0.19 | . | . | . | 1.36 | 0.54 |
| Cys | 132 | . | . | . | . | . | T | C | 0.56 | 0.24 | . | . | . | 0.69 | 0.39 |
| Pro | 133 | . | . | . | . | . | T | C | 0.21 | 0.24 | . | . | F | 0.97 | 0.39 |
| Pro | 134 | . | . | . | . | T | T | . | −0.61 | 0.17 | . | . | F | 1.30 | 0.29 |
| Gly | 135 | . | . | . | . | T | T | . | −0.91 | 0.43 | . | . | F | 0.87 | 0.40 |
| Ala | 136 | . | . | B | . | . | T | . | −1.20 | 0.54 | . | . | . | 0.19 | 0.18 |
| Gly | 137 | . | . | B | B | . | . | . | −0.74 | 0.61 | . | . | . | −0.34 | 0.12 |
| Val | 138 | . | . | B | B | . | . | . | −0.88 | 0.61 | . | . | . | −0.47 | 0.19 |
| Ile | 139 | . | . | B | B | . | . | . | −0.67 | 0.61 | . | . | . | −0.60 | 0.18 |
| Ala | 140 | . | . | B | . | . | T | . | −0.62 | 0.11 | . | . | . | 0.10 | 0.32 |
| Pro | 141 | . | . | B | . | . | T | . | −0.32 | 0.07 | . | . | F | 0.25 | 0.58 |
| Gly | 142 | . | . | . | . | . | T | C | −0.57 | 0.34 | * | * | F | 0.45 | 0.86 |
| Glu | 143 | . | . | . | . | . | T | C | 0.40 | 0.16 | * | * | F | 0.45 | 0.86 |
| Ser | 144 | . | . | B | . | . | . | . | 0.94 | −0.34 | * | * | F | 0.80 | 1.10 |
| Trp | 145 | . | . | . | . | T | . | . | 1.19 | −0.34 | * | * | F | 1.20 | 1.10 |
| Ala | 146 | . | . | B | . | . | T | . | 0.81 | −0.34 | * | * | F | 0.85 | 0.63 |
| Arg | 147 | . | . | . | . | T | T | . | 0.94 | 0.16 | * | * | F | 0.65 | 0.47 |
| Gly | 148 | . | . | . | . | T | T | . | 1.06 | 0.20 | . | * | F | 0.65 | 0.69 |
| Gly | 149 | . | . | . | . | . | T | C | 1.06 | −0.71 | . | . | F | 1.84 | 1.35 |
| Ala | 150 | . | . | . | . | . | . | C | 1.00 | −0.83 | . | . | F | 1.83 | 0.92 |
| Pro | 151 | . | . | . | . | . | . | C | 1.24 | −0.40 | . | * | F | 1.87 | 0.92 |
| Arg | 152 | . | . | . | . | T | T | . | 1.24 | −0.40 | . | . | F | 2.61 | 0.92 |
| Ser | 153 | . | . | . | . | T | T | . | 1.70 | −0.83 | * | . | F | 3.40 | 1.78 |
| Gly | 154 | . | . | . | . | T | T | . | 1.38 | −1.33 | * | * | F | 3.06 | 2.26 |
| Gly | 155 | . | . | . | . | T | T | . | 1.62 | −1.19 | * | * | F | 2.57 | 0.62 |
| Arg | 156 | . | . | . | . | T | . | . | 1.94 | −0.76 | * | * | F | 2.26 | 0.46 |
| Arg | 157 | . | . | . | . | T | . | . | 1.49 | −1.14 | * | * | F | 2.15 | 0.90 |
| Cys | 158 | . | . | B | . | . | . | . | 1.79 | −1.14 | * | * | F | 1.64 | 0.90 |
| Gly | 159 | . | . | . | . | T | T | . | 1.28 | −1.17 | * | * | F | 2.47 | 0.80 |
| Arg | 160 | . | . | B | . | . | T | . | 1.03 | −0.53 | * | * | F | 2.30 | 0.30 |
| Gly | 161 | . | . | B | . | . | T | . | 0.58 | −0.03 | * | * | F | 1.77 | 0.57 |
| Gln | 162 | . | . | B | . | . | T | . | 0.26 | −0.17 | * | * | F | 1.54 | 0.57 |
| Val | 163 | . | . | B | . | . | . | . | 0.62 | −0.17 | . | * | F | 1.11 | 0.45 |
| Ala | 164 | . | . | B | . | . | . | . | 0.16 | 0.21 | . | * | F | 0.28 | 0.61 |
| Gly | 165 | . | . | B | . | . | T | . | −0.54 | 0.47 | . | * | F | −0.05 | 0.29 |
| Pro | 166 | . | . | B | . | . | T | . | −0.41 | 0.57 | . | . | F | −0.05 | 0.40 |
| Ser | 167 | . | . | . | . | . | T | C | −0.80 | 0.36 | . | . | F | 0.45 | 0.61 |
| Leu | 168 | . | . | B | . | . | T | . | −0.33 | 0.29 | . | . | . | 0.10 | 0.78 |
| Ala | 169 | . | . | B | . | . | . | . | −0.13 | 0.29 | . | . | . | −0.10 | 0.65 |
| Pro | 170 | . | . | B | . | . | . | . | −0.18 | 0.29 | . | . | . | −0.10 | 0.62 |

Additional preferred nucleic acid fragments of the present invention comprise, or alternatively consist of, nucleic acid molecules encoding one or more epitope-bearing portions of TNFR-6α and/or TNFR-6β. In particular, such nucleic acid fragments of the present invention include nucleic acid molecules encoding: a polypeptide comprising, or alternatively consisting of, amino acid residues from about Phe-57 to about Thr-117, from about Cys-132 to about Thr-175, from about Gly-185 to about Three-194, from about Val-205 to about Asp-217, from about Pro-239 to about Leu-264, and/or from about Ala-283 to about Pro-298 in SEQ ID NO:2. In additional embodiments, nucleic acid fragments of the present invention comprise, or alternatively consist of nucleic acid molecules encoding one or more epitope bearing portions of TNFR-6β from about Ala-31 to about Thr-46, from about Phe-57 to about Gln-80, from about Glu-86 to about His-106, from about Thr-108 to about Phe-119, from about His-129 to about Val-138, and/or from about Gly-142 to about Pro-166 in SEQ ID NO:4. In this context "about" includes the particularly recited ranges and rangers larger or smaller by several (5, 4, 3, 2, or 1) amino acids at either terminus or at both termini. These polypeptide fragments have been determined to bear antigenic epitopes of the TNFR-6α and TNFR-6β polypeptides respectively, by the analysis of the Jameson-Wolf antigenic index, as shown in FIGS. 4 and 5, above. Further, polypeptide fragments which bear antigenic epitopes of TNFR-6α and/or TNFR-6β may be easily determined by one of skill in the art using the above-described analysis of the Jameson-Wolf antigenic index, as shown in FIGS. 4 and 5. Methods for determining other such epitope-bearing portions of TNFR-6α and/or TNFR-6β are described in detail below.

In specific embodiments, the nucleic acids of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, nucleic acids of the invention comprise at least 15, at least 30, at least 50, at least 100, or at least 250, at least 500, or at least 1000 contiguous nucleotides of TNFR coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide sequence set forth in FIG. 1 (SEQ ID NO:1) or FIGS. 2A-B (SEQ ID NO:3). Infer embodiments, nucleic acids of the invention comprise at least 15, at least 30, at least 50, at least 100, or at least 250, at least 500, or at least 1000 contiguous nucleotides of TNFR coding sequence, but do not comprise all or a portion of any TNFR intron. In another embodiment, the nucleic acid comprising TNFR coding sequence does not contain coding sequences of a genomic flanking gene (i.e., 5' or 3' to the TNFR gene in the genome). In other embodiments, the nucleic acids of the invention do not contain the coding sequence of more than 1000, 500, 250, 100, 50, 25, 20, 15, 10, 5, 4, 3, 2, or 1 genomic flanking gene(s).

In another aspect, the invention provides an isolated nucleic acid molecule comprising, or alternatively consisting of, a polynucleotide which hybridizes under stringent hybridization conditions to a portion of the polynucleotide in a nucleic acid molecule of the invention described above, for instance, the cDNA contained in the plasmid deposited as ATCC™ Deposit No. 97810 or 97809, or a fragment of the polynucleotide sequence disclosed in FIG. 1 and/or FIGS. 2A-B. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 (e.g., 50) nt of the reference polynucleotide. These have uses that include, but are not limited to, as diagnostic probes and primers as discussed above and in more detail below.

By a portion of a polynucleotide of "at least about 20 nt in length," for example, is intended 20 or more contiguous nucleotides from the nucleotide sequence of the reference polynucleotide (e.g., a deposited cDNA or a nucleotide sequence as shown in FIG. 1 or 2 (SEQ ID NO:1 or 3)). In this context "about" includes the particularly recited size, and those sizes that are larger or smaller by several (5, 4, 3, 2, or 1) nucleotides, at either terminus or at both termini. Of course, a polynucleotide which hybridizes only to a poly A sequence (such as the 3' terminal poly(A) tract of a TNFR cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone that has been generated using oligo dT as a primer).

As indicated, nucleic acid molecules of the present invention which encode a TNFR polypeptide may include, but are not limited to, those encoding the amino acid sequence of the mature polypeptide, by itself; and the coding sequence for the mature polypeptide and additional sequences, such as those encoding the about 26-35 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include a TNFR-6α or TNFR-6β fused to Fc at the N- or C-terminus.

The present invention further relates to variants of the nucleic acid molecules of the present invention, which encode portions, analogs or derivatives of a TNFR polypeptide. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells et al., Philos. Trans. R. Soc. London SerA 317:415 (1986)).

Thus, the invention also encompasses TNFR variants (e.g., derivatives and analogs) that have one or more amino acid residues deleted, added, or substituted to generate TNFR polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the TNFR polypeptides of the invention, and/or an amino acid deletion at the second position of any one or more such recognition sequences will prevent glycosylation of the TNFR at the modified tripeptide sequence (see, e.g., Miyajimo et al., *EMBO J.* 5(6):1193-97). Additionally, one or more of the amino acid residues of the polypeptides of the invention (e.g., arginine and lysine residues) may be deleted or substituted with another residue to eliminate undesired processing by proteases such as, for example, furins or kexins. For example, polypeptides of the invention containing carboxy terminal TNFR polypeptide sequences may have the amino acid residue corresponding to the arginine residue at position 290 and/or 295 of SEQ ID NO:2 deleted or substituted with another residue.

Variants of the invention include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TNFR polypeptide or portions thereof. Also especially preferred in this regard are conservative substitutions.

Highly preferred are nucleic acid molecules encoding a mature protein having an amino acid sequence shown in SEQ ID NOS:2 and 4 or the mature TNFR polypeptide sequences encoded by the cDNA clone contained in the plasmid deposited as ATCC™ Deposit No. 97810 or ATCC™ Deposit No. 97809.

Further embodiments include an isolated nucleic acid molecule comprising, or alternatively consisting of, a polynucleotide having a nucleotide sequence at least 90% identical, and more preferably at least 80%, 85%, 90%, 92%, or 95%, 96%, 97%, 98% or 99% identical to a polynucleotide selected from the group consisting of: (a) a nucleotide sequence encoding a TNFR polypeptide having the complete amino acid sequence in SEQ ID NO:2 or 4, or as encoded by the cDNA clone contained in the plasmid deposited as ATCC™ Deposit No. 97810 or 97809; (b) a nucleotide sequence encoding a mature TNFR polypeptide having an amino acid sequence at positions 31-300 or 31-170 in SEQ ID NO:2 or 4, respectively, or as encoded by the cDNA clone contained in the plasmid deposited as ATCC™ Deposit No. 97810 or 97809; (c) a nucleotide sequence encoding a soluble extracellular domain of a TNFR polypeptide having the amino acid sequence at positions 31-283 and 31-166 of SEQ ID NOS:2 and 4, respectively; (d) a nucleotide sequence encoding a fragment of the TNFR polypeptide having the complete amino acid sequence in SEQ ID NO:2 or 4, or as encoded by the cDNA clone contained in the plasmid deposited as ATCC™ Deposit No. 97810 or 97809, wherein the fragment has TNFR-6α and/or TNFR-6β functional activity; and (e) a nucleotide sequence complementary to any of the nucleotide sequences in (a), (b), (c) or (d) above. Polypeptides encoded by the polynucleotides are also encompassed by the invention.

Further embodiments of the invention include isolated nucleic acid molecules that comprise a polynucleotide having a nucleotide sequence at least 90% identical, and more preferably at least 80%, 85%, 90%, 92%, or 95%, 96%, 97%, 98% or 99% identical, to any of the nucleotide sequences in (a), (b), (c), (d), or (e), above, or a polynucleotide which hybridizes under stringent hybridization conditions to a polynucleotide in (a), (b), (c), (d), or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising, or alternatively consisting of, a polynucleotide which encodes the amino acid sequence of an epitope-bearing portion of a TNFR polypeptide having an amino acid sequence in (a), (b), (c), (d), or (e), above.

By a polynucleotide having a nucleotide sequence at least, for example, 95% "identical" to a reference nucleotide sequence encoding a TNFR polypeptide is intended that the nucleotide sequence of the polynucleotide is identical to the reference sequence except that the polynucleotide sequence may include up to five point mutations per each 100 nucleotides of the reference nucleotide sequence encoding the TNFR polypeptide. In other words, to obtain a polynucleotide having a nucleotide sequence at least 80%, 85%, 90%, 92%, or 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference sequence may be the entire TNFR-6α and/or TNFR-6β encoding sequence shown in FIG. 1 (SEQ ID NO:1 and 2) and FIGS. 2A-B (SEQ ID NO:3 and 4) or any fragment, variant, derivative or analog thereof, as described herein.

As a practical matter, whether any particular nucleic acid molecule is at least 90%, 95%, 96%, 97%, 98% or 99% identical to, for instance, a nucleotide sequence shown in FIG. 1 or 2, or to the nucleotides sequence contained in one or both of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. The reference (query) sequence may be the entire TNFR encoding nucleotide sequence shown in FIG. 1 (SEQ ID NO:1), FIGS. 2A-B (SEQ ID NO:3) or any TNFR-6α and/or TNFR-6β polynucleotide fragment (e.g., a polynucleotide encoding the amino acid sequence of any of the N or C terminal deletions described herein), variant, derivative or analog, as described herein.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to a nucleic acid sequence shown in FIG. 1 or 2 (SEQ ID NO:1 or 3), to the nucleic acid sequence of a deposited cDNA and/or to a nucleic acid sequence otherwise disclosed herein (e.g., encoding polypeptide having the amino acid sequence of a N and/or C terminal deletion disclosed herein, such as, for example, a nucleic acid molecule encoding amino acids Val-30 to His-300 of SEQ ID NO:2), irrespective of whether they encode a polypeptide having TNFR functional activity. This is because even where a particular nucleic acid molecule does not encode a polypeptide having TNFR functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TNFR functional activity include, inter alia, (1) isolating a TNFR gene or allelic variants thereof in a cDNA library; (2) in situ hybridization (e.g., "FISH") to metaphase chromosomal spreads to provide precise chromosomal location of the TNFR gene, as described in Verma et al., Human Chromosomes: A Manual of Basic Techniques, Pergamon Press, New York (1988); and Northern Blot analysis for detecting TNFR mRNA expression in specific tissues.

Preferred, however, are nucleic acid molecules having sequences at least 90%, 95%, 96%, 97%, 98% or 99% identical to a nucleic acid sequence shown in FIG. 1 or 2 (SEQ ID NOS:1 or 3) or to the nucleic acid sequence of the cDNA clone contained in the plasmid deposited as ATCC™ Deposit No. 97810 or ATCC™ Deposit No. 97809, and/or to a nucleic acid sequence otherwise disclosed herein (e.g., encoding polypeptide having the amino acid sequence of a N and/or C terminal deletion disclosed herein), which do, in fact, encode polypeptides having TNFR (i.e., TNFR-6α and/or TNFR-6β) protein functional activity. By "a polypeptide having TNFR functional activity" is intended polypeptides exhibiting activity similar, but not necessarily identical, to an activity of a TNFR-6α and/or TNFR-6β protein of the invention (e.g., complete (full-length), mature, and extracellular domain as measured, for example, in a particular immunoassay or biological assay. For example, TNFR-6α and/or TNFR-6β activity can be measured by determining the ability of a TNFR-6α and/or TNFR-6β polypeptide to bind a TNFR-6α and/or -6β ligand (e.g., Fas Ligand and/or AIM-II (International application publication number WO 97/34911, published Sep. 25, 1997). In another example, TNFR-6α and/or TNFR-6β functional activity is measured by determining the ability of a polypeptide, such as cognate ligand which is free or expressed on a cell surface, to induce apoptosis.

The TNF family ligands induce various cellular responses by binding to TNF-family receptors, including the TNFR-6α and TNFR-6β of the present invention. Cells which express the TNFR proteins are believed to have a potent cellular response to TNFR-I receptor ligands including B lymphocytes (CD19+), both CD4 and CD8+ T lymphocytes, monocytes and endothelial cells. By a "cellular response to a TNF-family ligand" is intended any genotypic, phenotypic, and/or morphological change to a cell, cell line, tissue, tissue culture or patient that is induced by a TNF-family ligand. As indicated, such cellular responses include not only normal physiological responses to TNF-family ligands, but also diseases associated with increased cell proliferation or the inhibition of increased cell proliferation, such as by the inhibition of apoptosis.

Screening assays for the forgoing are known in the art. One such screening assay involves the use of cells which express the receptor (for example, transfected CHO cells) in a system which measures extracellular pH changes caused by receptor activation, for example, as described in Science 246:181-296 (October 1989). For example, a TNF-family ligand may be contacted with a cell which expresses the mature form of the receptor polypeptide of the present invention and a second messenger response, e.g., signal transduction or pH changes, may be measured to determine whether the TNFR polypeptide is active.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the cDNA clone deposited as ATCC™ Deposit No. 97810 or 97809, the nucleic acid sequence shown in FIG. 1 or 2 (SEQ ID NO:1 and 3), or fragments thereof, will encode a polypeptide "having TNFR protein functional activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TNFR protein functional activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated nucleic acid molecules of the present invention, host cells which are genetically engineered with the recombinant vectors, or which are otherwise engineered to produce the polypeptides of the invention, and the production of TNFR polypeptides, or fragments thereof, by recombinant techniques.

In one embodiment, the polynucleotides of the invention are joined to a vector (e.g., a cloning or expression vector). The vector may be, for example, a phage, plasmid, viral or retroviral vector. Retroviral vectors may be replication competent or replication defective. In the latter case, viral propagation generally will occur only in complementing host cells. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

In one embodiment, the DNA of the invention is operatively associated with an appropriate heterologous regulatory element (e.g., promoter or enhancer), such as, the phage lambda PL promoter, the *E. coli* lac, trp, phoA, and tac promoters, the SV40 early and late promoters and promoters of retroviral LTRs, to name a few. Other suitable promoters will be known to the skilled artisan.

As indicated, the expression vectors will preferably include at least one selectable marker. Such markers include dihydrofolate reductase, glutamine synthase, G418 or neomycin resistance for eukaryotic cell culture and tetracycline, kanamycin or ampicillin resistance genes for culturing in *E. coli* and other bacteria.

Vectors which use glutamine synthase (GS) or DHFR as the selectable markers can be amplified in the presence of the drugs methionine sulphoximine or methotrexate, respectively. The availability of drugs which inhibit the function of the enzymes encoded by these selectable markers allows for selection of cell lines in which the vector sequences have been amplified after integration into the host cell's DNA. An advantage of glutamine synthase based vectors are the availability of cell lines (e.g., the murine myeloma cell line, NS0) which are glutamine synthase negative. Vectors containing glutamine synthase can also be amplified in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors that may be used according to the present invention are commercially available from suppliers including, for example, Lonza Biologics, Inc. (Portsmouth, N.H.). Expression and production of monoclonal antibodies using a GS expression system in murine myeloma cells is described in Bebbington et al., *Bio/technology* 10:169 (1992) and in Biblia and Robinson *Biotechnol. Prog.* 11:1 (1995) which are herein incorporated by reference.

Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed. Selection of appropriate vectors and promoters for expression in a host cell is a well known procedure and the requisite techniques for expression vector construction, introduction of the vector into the host and expression in the host are routine skills in the art.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice. As a representative, but nonlimiting example, useful expression vectors for bacterial use can comprise a selectable marker and bacterial origin of replication derived from commercially available plasmids comprising genetic elements of the well known cloning vector pBR322 (ATCC™ 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. Among vectors preferred for use in bacteria include pHE4-5 (ATCC™ Accession No. 209311; and variations thereof), pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Various mammalian cell culture systems can also be employed to express recombinant protein. Examples of mammalian expression systems include the COS-7 lines of monkey kidney fibroblasts, described by Gluzman (Cell 23:175 (1981)), and other cell lines capable of expressing a compatible vector, for example, the C127, 3T3, CHO, NSO HeLa and BHK cell lines. NSO cell lines are particularly suitable host cells for transformation with polynucleotides and expression vectors of the invention. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TNFR coding sequence), and/or to include genetic material (e.g., heterologous polynucleotide sequences) that is operably associated with TNFR polynucleotides of the invention, and which activates, alters, and/or amplifies endogenous TNFR polynucleotides. For example, techniques known in the art may be used to operably associate heterologous control regions (e.g., promoter and/or enhancer) and endogenous TNFR polynucleotide sequences via homologous recombination (see, e.g., U.S. Pat. No. 5,641,670, issued Jun. 24, 1997; International application publication number WO 96/29411, published Sep. 26, 1996; International application publication number WO 94/12650, published Aug. 4, 1994; Koller et al., *Proc. Natl. Acad. Sci. USA* 86:8932-8935 (1989); and Zijlstra et al., *Nature* 342:435-438 (1989), the disclosures of each of which are incorporated by reference in their entireties).

The host cells described infra can be used in a conventional manner to produce the gene product encoded by the recombinant sequence. Alternatively, cell-free translation systems can also be employed to produce the polypeptides of the invention using RNAs derived from the DNA constructs of the present invention.

The polypeptide of the invention may be expressed or synthesized in a modified form, such as a fusion protein (comprising the polypeptide joined via a peptide bond to a heterologous protein sequence (of a different protein), e.g., the signal peptide of CK-beta8 (amino acids -21 to -1 of the CK-beta8 sequence disclosed in published PCT application PCT/US95/09058; filed Jun. 23, 1995) or the signal peptide of stanniocalcin (See ATCC™ Accession No. 75652, deposited Jan. 25, 1994)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one embodiment, polynucleotides encoding TNFR-6 alpha and/or TNFR-6 beta polypeptides of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, the signal sequence of chemokine-beta-8, and the signal sequence of alkaline phosphatase. Several vectors are commercially available for the construction of fusion proteins which will direct the localization of a protein, such as the pMAL series of vectors (particularly the pMAL-p series)

available from New England Biolabs. In a specific embodiment, polynucleotides encoding TNFR-6 alpha and/or TNFR-6 beta polypeptides of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to a polypeptide of the invention in order to direct its secretion in mammalian cells include, but are not limited to, the MPIF-1 signal sequence (amino acids 1-21 of GenBank Accession number AAB51134), the stanniocalcin signal sequence (MLQNSAVLLLLVISASA, SEQ ID NO:29), and a consensus signal sequence (MPTWAWWLFLVLLLALWAPARG, SEQ ID NO:30). A suitable signal sequence that may be used in conjunction with baculoviral expression systems is the gp67 signal sequence, (amino acids 1-19 of GenBank Accession Number AAA72759).

A preferred fusion protein comprises a heterologous region from immunoglobulin that is useful to stabilize and purify proteins. For example, EP-A-0 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). In preferred embodiments, the IgG1 m(f) allele is used to generate Fc fusion proteins of the invention. In other embodiments, the IgG1 m(f) allele in which the cysteine residue at position 220 in the hinge region of the constant region is substituted with a serine amino acid residue is used. Alternatively, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. As an example, an enterokinase cleavage site between the protein of the invention and the fusion moiety (e.g. Fc constant region) may be engineered. Subsequently, the protein of the invention may be separated from the fusion moiety by digestion with enterokinase. In drug discovery, for example, human proteins, such as hIL-5 has been fused with Fc portions for the purpose of high-throughput screening assays to identify antagonists of hIL-5. See, D. Bennett et al., *J. Molecular Recognition* 8:52-58 (1995) and K. Johanson et al., *J. Biol. Chem.* 270:9459-9471 (1995). In another example, preferred fusion proteins of the invention comprise a portion of an immunoglobulin light chain (i.e., a portion of a kappa or lambda light chain). In specific embodiments the fusion proteins of the invention comprise a portion of the constant region of a kappa or lambda light chain.

Polypeptides of the invention (including antibodies of the invention, see below) may also be fused to albumin (including but not limited to recombinant human serum albumin (HSA) (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides (including antibodies) of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Such human serum albumin TNFR-6 alpha and TNFR-6 beta fusion proteins may be used therapeutically in accordance with the invention, in the same manner as, for example, the TNFR-6α- and TNFR-6β-Fc fusion proteins described herein, below (see, e.g., Examples 22 and 23).

Other fusion proteins of the invention include fusion of TNFR-6 alpha or TNFR-6 beta, or even TNFR-6 alpha-Fc fusion protein, TNFR-6 beta-Fc fusion protein, TNFR-6 alpha-HSA fusion protein, or TNFR-6 beta-HSA fusion protein, fused to glucoamylase (e.g., GenBank Accession Number P23176 or PO4064). Nucleic acids encoding such fusion proteins operably associated with appropriate regulatory sequences and/or selectable markers may be expressed in fungal cells including, for example, *Saccharomyces* species such as *S. cerevisiae*, *Aspergillus* species such as *A. niger* and *Chrysosporium* species such as *C. lucknowense*.

Exemplary fragments of TNFR-6 alpha, that may be fused to a heterologous polypeptide, for example, immunoglobulin Fc domain or human serum albumin include, but are not limited to, amino acid residues 1-299, 1-300, 23-300, 34-300, 30-300, 1-195, 1-221, 1-254, 1-271, 35-300, 42-300, 47-300, and 48-300 of SEQ ID NO:2. In preferred embodiments, amino acid residues 30-300 of SEQ ID NO:2 are fused to an immunoglobulin Fc domain or human serum albumin.

In specific embodiments, the present invention provides TNFR-6 alpha expression constructs for expressing TNFR-6 alpha or fragments, variants or fusion proteins thereof, in which the polynucleotide encoding the TNFR-6 alpha polypeptide comprises exons 1, 2, and 3 of TNFR-6 alpha as well as the intervening introns, see for example SEQ ID NO:27, wherein exon 1 consists of nucleotides 425-560 of SEQ ID NO:27 and exon 2 consists of nucleotides 756-1512 of SEQ ID NO:27. In particular embodiments, the above expression constructs comprising TNFR-6 alpha exons and introns may also be designed so that the TNFR-6 alpha protein will be expressed as a fusion protein (e.g., an Fc fusion protein or a human serum albumin fusion protein). The proteins expressed by these expression constructs are also encompassed by the present invention.

In other embodiments, the present invention provides TNFR-6 alpha expression constructs that express fragments of TNFR-6 alpha and/or TNFR-6 beta containing the cysteine rich domains (e.g., amino acid residues 1-195 of SEQ ID NO:2) either alone or as a fusion protein (e.g., an Fc fusion protein or a human serum albumin fusion protein). The proteins expressed by these expression constructs as well as polynucleotides encoding the proteins expressed by these expression constructs, are also encompassed by the present invention.

In other embodiments, the present invention provides TNFR-6 alpha expression constructs for expressing TNFR-6 alpha and/or TNFR-6 beta as a fusion protein with TR2 (SEQ ID NO:31, also described in International Publication Numbers WO96/34095 and WO98/18824 which are herein incorporated by reference in their entireties). In specific embodiments, the present invention encompasses an expression vector for expressing a TR2-TNFR-6 alphaTR2 fusion protein comprising amino acids M1-S41 of TR2 (SEQ ID NO:31) fused to C48-S195 of TNFR-6 alpha (SEQ ID NO:2) fused to S186-A192 of TR2 (SEQ ID NO:31). In other embodiments the TR2-TNFR-6 alpha-TR2 fusion protein is additionally fused to an immunoglobulin Fc region or to human serum albumin. The proteins expressed by these expression constructs as well as polynucleotides encoding the proteins expressed by these expression constructs, are also encompassed by the present invention.

In other embodiments, the present invention provides TNFR-6 alpha expression constructs for expressing TNFR-6 alpha fusions proteins in which the last 6 amino acids of TNFR-6 alpha have been deleted and replaced with the amino acid sequence NIT. Such fusion proteins have the TNFR-6 alpha protein N-terminal of the fusion protein moiety (e.g., an immunoglobulin Fc region or human serum albumin). The NIT sequence may serve as a glycosylation site. As a non-limiting mechanism, the carbohydrate moieties on a glycosylated TNFR-6 alpha (M1-E294 of SEQ ID NO:2)-NIT-fusion protein may mask the fusion protein junction and prevent cleavage of the protein in the host cell. The TNFR-6 alpha (M1-E294 of SEQ ID NO:2)-NIT-fusion proteins (glycosylated and non-glycosylated) are also encompassed by the present invention, as are polynucleotides encoding the TNFR-6 alpha (M1-E294 of SEQ ID NO:2)-NIT-fusion proteins.

The present invention encompasses TNFR-6 alpha proteins which contain alanine-160 to asparagine (A160N) and/or serine-186 to asparagine (S186N) point mutations. The present invention also encompasses TNFR-6 alpha (A160N, S186N) fusion polypeptides (e.g., TNFR6-alpha (A160N, S186N) fused to an immunoglobulin Fc domain or to human serum albumin). Polynucleotides encoding these TNFR-6 alpha (A160N, S186N) polypeptides (both fusion and non-fusion) as well as vectors comprising polynucleotides encoding these TNFR-6 alpha (A160N, S186N) polypeptides, are also encompassed by the invention.

In other embodiments, the present invention provides TNFR-6 alpha expression constructs which comprise a polynucleotide encoding mammalian synthetic TNFR-6 alpha (SEQ ID NO:32). In preferred embodiments, the present invention provides TNFR-6 alpha expression constructs which comprise a polynucleotide encoding mammalian synthetic TNFR-6 alpha (SEQ ID NO:32) operably linked to a heterologous regulatory sequence. In still other embodiments, the present invention provides TNFR-6 alpha expression constructs which comprise a polynucleotide encoding mammalian synthetic TNFR-6 alpha (SEQ ID NO:32) fused in frame to a polynucleotide encoding a heterologous polypeptide, such as a polynucleotide encoding an immunoglobulin constant domain or human serum albumin.

In other embodiments, the present invention provides TNFR-6 alpha expression constructs which comprise a polynucleotide encoding TNFR-6 alpha which has been codon optimized for expression in yeast (SEQ ID NO:33). In preferred embodiments, the present invention provides TNFR-6 alpha expression constructs which comprise polynucleotide encoding TNFR-6 alpha which has been codon optimized for expression in yeast (SEQ ID NO:33) operably linked to a heterologous regulatory sequence. In still other embodiments, the present invention provides TNFR-6 alpha expression constructs which polynucleotide encoding TNFR-6 alpha which has been codon optimized for expression in yeast (SEQ ID NO:33) fused in frame to a polynucleotide encoding a heterologous polypeptide such as, a polynucleotide encoding an immunoglobulin constant domain or human serum albumin.

Proteins of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Proteins of the invention can be chemically synthesized using techniques known in the art (e.g., see Creighton, 1983, *Proteins: Structures and Molecular Principles*, W.H. Freeman & Co., N.Y., and Hunkapiller, M., et al, *Nature* 310:105-111 (1984)). For example, a peptide corresponding to a fragment of the complete TNFR (i.e., TNFR-6α and/or TNFR-6β) polypeptides of the invention can be synthesized by use of a peptide synthesizer. Furthermore, if desired, nonclassical amino acids or chemical amino acid analogs can be introduced as a substitution or addition into the TNFR polypeptide sequence. Non-classical amino acids include, but are not limited to, the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The TNFR-6 alpha and/or TNFR-6 beta proteins may be modified by either natural processes, such as posttranslational processing, or by chemical modification techniques which are well known in the art. It will be appreciated that the same type of modification may be present in the same or varying degrees at several sites in a given TNFR-6 alpha and/or TNFR-6 beta protein. Also, a given TNFR-6 alpha and/or TNFR-6 beta protein may contain many types of modifications. TNFR-6 alpha and/or TNFR-6 beta proteins may be branched, for example, as a result of ubiquitination, and they may be cyclic, with or without branching. Cyclic, branched, and branched cyclic TNFR-6 alpha and/or TNFR-6 beta proteins may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The invention encompasses TNFR-6α, and/or TNFR-6β proteins which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

The present invention further encompasses TNFR-6α and/or TNFR-6β polypeptides or fragments thereof conjugated to a diagnostic agent (e.g. a detectable agent) and/or therapeutic agent. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the polypeptide (or fragment thereof) or indirectly, through an intermediate (such as, for example, a linker known in the art) using techniques known in the art. See, for example, U.S. Pat. No. 4,741,900 for metal ions which can be conjugated to polypeptides for use as diagnostics and/or therapeutics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}I$, $^{123}I$, $^{125}I$, $^{131}I$), carbon ($^{14}C$), sulfur ($^{35}S$), tritium (3H), indium ($^{111}In$, $^{112}In$, $^{113}In$, $^{115m}In$), technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$. A preferred radioisotope label is $^{111}I$. Another preferred radioactive label is $^{90}Y$. Another preferred radioactive label is $^{131}I$.

Further, TNFR-6α and/or TNFR-6β polypeptides or fragments or variants thereof may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$ or other radioisotopes such as, for example, $^{103}Pd$, $^{133}Xe$, $^{131}I$, $^{68}Ge$, $^{57}Co$, $^{65}Zn$, $^{85}Sr$, $^{32}P$, $^{35}S$, $^{90}Y$, $^{153}Sm$, $^{153}Gd$, $^{169}Yb$, $^{51}Cr$, $^{54}M$, $^{75}Se$, $^{113}Sn$, $^{90}Y$, $^{117}Tin$, $^{186}Re$, $^{188}Re$ and $^{166}Ho$. In specific embodiments, TNFR-6α and/or TNFR-6β polypeptides or fragments or variants thereof are attached to macrocyclic chelators useful for conjugating radiometal ions, including but not limited to, $^{177}Lu$, $^{90}Y$, $^{166}Ho$, and $^{153}Sm$, to polypeptides. In a preferred embodiment, the radiometal ion associated with the macrocyclic chelators attached to TNFR-6α and/or TNFR-6β polypeptides of the invention is $^{111}In$. In another preferred embodiment, the radiometal ion associated with the macrocyclic chelator attached to TNFR-6α and/or TNFR-6β polypeptides of the invention is $^{90}Y$. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition U.S. Pat. Nos. 5,652,361 and 5,756,065, which disclose chelating agents that may be conjugated to antibodies, and methods for making and using them, are hereby incorporated by reference in their entireties.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

Also provided by the invention are chemically modified derivatives of TNFR-6α and/or TNFR-6β which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera Drug Carrier Sys.* 9:249-304 (1992).

The TNFR proteins can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

TNFR Proteins

The invention further provides for the proteins containing polypeptide sequences encoded by the polynucleotides of the invention.

The TNFR proteins of the invention may be in monomers or multimers (i.e., dimers, trimers, tetramers, and higher multimers). Accordingly, the present invention relates to monomers and multimers of the TNFR proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TNFR proteins of the invention (including TNFR fragments, variants, and fusion proteins, as described herein). These homomers may contain TNFR proteins having identical or different polypeptide sequences. In a specific embodiment, a homomer of the invention is a multimer containing only TNFR proteins having an identical polypeptide sequence. In another specific embodiment, a homomer of the invention is a multimer containing TNFR proteins having different polypeptide sequences. In specific embodiments, the multimer of the invention is a homodimer (e.g., containing TNFR proteins having identical or different polypeptide sequences) or a homotrimer (e.g., containing TNFR proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the TNFR gene) in addition to the TNFR proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TNFR proteins of the invention. Such covalent associations may involve one or more amino acid residues contained in the polypeptide sequence of the protein (e.g., the polypeptide sequence recited in SEQ ID NO:2 or SEQ ID NO:4, contained in the polypeptide encoded by the cDNA clone contained in ATCC™ Deposit No. 97810), contained in the polypeptide encoded by the cDNA clone contained in ATCC™ Deposit No. 97809). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TNFR fusion protein. In one example, covalent associations are between the heterologous sequence contained in a fusion protein of the invention (see, e.g., U.S. Pat. No. 5,478,925). In a specific example, the covalent associations are between the heterologous sequence contained in a TNFR-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International application publication number WO 98/49305, the contents of which are herein incorporated by reference in its entirety). In another embodiment, two or more TR6-alpha and/or TR6-beta polypeptides of the invention are joined through peptide linkers. Examples include those peptide linkers described in U.S. Pat. No. 5,073,627 (hereby incorporated by reference). Proteins comprising multiple TR6-alpha and/or TR6-beta polypeptides separated by peptide linkers may be produced using conventional recombinant DNA technology.

Another method for preparing multimer TR6-alpha and/or TR6-beta polypeptides of the invention involves use of TR6-alpha and/or TR6-beta polypeptides fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR6-alpha and/or TR6-beta proteins are those described in PCT application WO 94/10308, hereby incorporated by reference. Recombinant fusion proteins comprising a soluble TR6-alpha and/or TR6-beta polypeptide fused to a peptide that dimerizes or trimerizes in solution are expressed in suitable host cells, and the resulting soluble multimeric TR6-alpha and/or TR6-beta is recovered from the culture supernatant using techniques known in the art.

Certain members of the TNF family of proteins are believed to exist in trimeric form (Beutler and Huffel, Science 264:667, 1994; Banner et al., Cell 73:431, 1993). Thus, trimeric TR6-alpha and/or TR6-beta may offer the advantage of enhanced biological activity. Preferred leucine zipper moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric TR6-alpha and/or TR6-beta.

In further preferred embodiments, TR6-alpha or TR6-beta polynucleotides of the invention are fused to a polynucleotide encoding a FLAG® polypeptide (DYKDDDDK). Thus, a TR6-alpha-FLAG or a TR6-beta-FLAG fusion protein is encompassed by the present invention. The FLAG® antigenic polypeptide may be fused to a TR6-alpha or a TR6-beta polypeptide of the invention at either or both the amino or the carboxy terminus. In preferred embodiments, a TR6-alpha-FLAG or a TR6-beta-FLAG fusion protein is expressed from a pFLAG-CMV™-5a or a pFLAG-CMV™-1 expression vector (available from Sigma, St. Louis, Mo., USA). See, Andersson, S., et al., J. Biol. Chem. 264:8222-29 (1989); Thomsen, D. R., et al., Proc. Natl. Acad. Sci. USA, 81:659-63 (1984); and Kozak, M., Nature 308:241 (1984) (each of which is hereby incorporated by reference). In further preferred embodiments, a TR6-alpha-FLAG or a TR6-beta-FLAG fusion protein is detectable by anti-FLAG® monoclonal antibodies (also available from Sigma).

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In one embodiment, the invention provides isolated TNFR proteins comprising, or alternatively, consisting of, the amino acid sequence of the complete (full-length) TNFR polypeptide encoded by the cDNA contained in ATCC™ Deposit No. 97810, the amino acid sequence of the complete (full-length) TNFR polypeptide encoded by the cDNA contained in ATCC™ Deposit No. 97809, the amino acid sequence of the complete TNFR-6α polypeptide disclosed in FIG. 1 (SEQ ID NO:2), the amino acid sequence of the complete TNFR-6β polypeptide disclosed in FIG. 2A (SEQ ID NO:4), or a portion of the above polypeptides.

In another embodiment, the invention provides isolated TNFR proteins comprising, or alternatively consisting of, the amino acid sequence of the mature TNFR polypeptide encoded by the cDNA contained in ATCC™ Deposit No. 97810, the amino acid sequence of the mature TNFR polypeptide encoded by the cDNA contained in ATCC™ Deposit No. 97809, amino acid residues 31 to 300 of the TNFR-6α sequence disclosed in FIG. 1 (SEQ ID NO:2), amino acid residues 31 to 170 of the TNFR-60 sequence disclosed in FIG. 2 (SEQ ID NO:4), or a portion (i.e., fragment) of the above polypeptides.

Polypeptide fragments of the present invention include polypeptides comprising or alternatively, consisting of, an amino acid sequence contained in SEQ ID NO:2, an amino acid sequence contained in SEQ ID NO:4, an amino acid sequence encoded by the cDNA plasmid deposited as ATCC™ Deposit No. 97810, an amino acid sequence encoded by the cDNA plasmid deposited as ATCC™ Deposit No. 97809, or an amino acid sequence encoded by a nucleic acid which hybridizes (e.g., under stringent hybridization conditions) to the nucleotide sequence of the cDNA contained in ATCC™ Deposit No. 97810 and/or 97809, or shown in FIGS. 1 and/or 2 (SEQ ID NO:1 and SEQ ID NO:3, respectively) or the complementary strand thereto. Polynucleotides that hybridize to these polynucleotide fragments are also encompassed by the invention. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from amino acid residues: 1 to 31, 32 to 50, 51 to 100, 101 to 150, 151 to 200, 201 to 250, and/or 251 to 300 of SEQ ID NO:2. Additional representative examples of polypeptide fragments of the invention include polypeptide fragments that comprise, or alternatively, consist of from amino acids 1 to 31, 32 to 70, 70 to 100, 100 to 125, 126 to 150, and/or 151 to 170 of SEQ ID NO:4. Moreover, polypeptide fragments can be at least 10, 20, 30, 40, 50, 60, 70, 80, 90, 100, 110, 120, 130, 140, 150, 175 or 200 amino acids in length. Polynucleotides encoding these polypeptides are also encompassed by the invention.

In specific embodiments, polypeptide fragments of the invention comprise, or alternatively consist of, amino acid residues: 100 to 150, 150 to 200, 200 to 300, 210 to 300, 220 to 300, 230 to 300, 240 to 300, 250 to 300, 260 to 300, 270 to 300, 280 to 300, and/or 290 to 300 as depicted in FIG. 1 (SEQ ID NO:2). Polynucleotides encoding these polypeptides are also encompassed by the invention.

TNFR comprises two domains having different structural and functional properties. The amino terminal domain spanning residues 30 to 196 of SEQ ID NO:2 shows homology to other members of the TNFR family, through conservation of four cysteine rich domains characteristic of TNFR families. Amino acid sequences contained in each of the four domains include amino acid residues 34 to 70, 73 to 113, 115 to 150, and 153 to 193, of SEQ ID NO:2, respectively. The carboxy terminal domain, spanning amino acid residues 197 to 300 of SEQ ID NO:2, has no significant homology to any known sequences. Unlike a number of other TNF receptor family members, TNFR appears to be exclusively a secreted protein and does not appear to be synthesized as a membrane associated form. While the amino terminal domain of TNFR appears to be required for biological activity of TNFR, the carboxy-terminal domain appears to be important for multimerization of TNFR.

In one embodiment, the polypeptides of the invention comprise, or alternatively consist of, amino acid residues 34 to 70, 73 to 113, 115 to 150, and 153 to 193, and/or 30-196 of SEQ ID NO:2. Polynucleotides encoding these polypeptides are also encompassed by the invention.

In another embodiment, the polypeptides of the invention comprise, or alternatively consist of, amino acid residues 197 to 240, 241 to 270, 271-300, and/or 197 to 300 of SEQ ID NO:2. Polynucleotides encoding these polypeptides are also encompassed by the invention. Since these polypeptide sequences are believed to be associated with multimerization of TNFR, proteins having one or more of these polypeptide sequences would be expected to form dimers, trimers and higher multimers, which may have advantageous properties, such as, increased binding affinity, greater stability, and longer circulating half life compared to monomeric forms. In a specific embodiment, the invention provides for fusion proteins comprising fusions of one or more of the above polypeptides to a heterologous sequence of a cell signaling molecule, such as a receptor, an extracellular domain thereof, and an active fragment, derivative, or analog of a receptor or an extracellular domain. In a preferred embodiment, heterologous sequences are selected from the family of TNR-like receptors. Such sequences preferably include functional extracellular ligand binding domains and lack functional transmembrane and/or cytoplasmic domains. Such fusion proteins are useful for detecting molecules which interact with the fused heterologous sequences and thereby identifying potential new receptors and ligands. The fusion proteins are also useful for treatment of a variety of disorders, for example, those related to receptor binding. In one embodiment, fusion proteins of the invention comprising TNF/TNFR and TNF receptor/TNFR sequences are used to treat TNF and TNF receptor mediated disorders, such as, inflammation, autoimmune diseases, cancer, and disorders associated with excessive or alternatively, reduced apoptosis.

Additional embodiments TNFR polypeptide fragments comprising, or alternatively, consisting of, functional regions of polypeptides of the invention, such as the Garnier-Robson alpha-regions, beta-regions, turn-regions, and coil-regions, Chou-Fasman alpha-regions, beta-regions, and coil-regions, Kyte-Doolittle hydrophilic regions, Eisenberg alpha- and beta-amphipathic regions, Karplus-Schulz flexible regions, Emini surface-forming regions and Jameson-Wolf regions of high antigenic index set out in FIG. 4 (Table I) and FIG. 5 (Table 2) and as described herein. In a preferred embodiment, the polypeptide fragments of the invention are antigenic. The data presented in columns VIII, IX, XIII, and XIV of Tables I and II can be used to routinely determine regions of TNFR which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response. Among highly preferred fragments of the invention are those that comprise regions of TNFR that combine several structural features, such as several (e.g., 1, 2, 3 or 4) of the features set out above. Polynucleotides encoding these polypeptides are also encompassed by the invention.

The present invention encompasses polypeptides comprising, or alternatively consisting of, an epitope of the polypeptide having an amino acid sequence of SEQ ID NOS:2 and 4, respectively, or an epitope of the polypeptide sequence encoded by a polynucleotide sequence contained in deposited clone ATCC™ Deposit Number 97810 and 97809, respectively, or encoded by a polynucleotide that hybridizes to the complement of the sequence of SEQ ID NOS:1 and 3, respectively, or contained in deposited clone ATCC™ Deposit Number 97810 and 97809, respectively, under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NOS:1 and/or 3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Non-limiting examples of antigenic polypeptides or peptides that can be used to generate TNFR-specific antibodies include: a polypeptide comprising, or alternatively consisting of, amino acid residues from about Ala-31 to about Thr-46, from about Phe-57 to about Thr-117, from about Cys-132 to about Thr-175, from about Gly-185 to about Thr-194, from about Val-205 to about Asp-217, from about Pro-239 to about Leu-264, and from about Ala-283 to about Pro-298 in SEQ ID NO:2; and from about Ala-31 to about Thr-46, from about Phe-57 to about Gln-80, from about Glu-86 to about His-106, from about Thr-108 to about Phe-119, from about His-129 to about Val-138, and from about Gly-142 to about Pro-166 in SEQ ID NO:4. These polypeptide fragments have been determined to bear antigenic epitopes of the TNFR-6 alpha and TNFR-6 beta polypeptides respectively, by the analysis of the Jameson-Wolf antigenic index, as shown in FIGS. 4 and 5, above.

Fragments that function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

Epitope bearing peptides of the invention may also be synthesized as multiple antigen peptides (MAPs), first described by J. P. Tam in *Proc. Natl. Acad. Sci. U.S.A.* 85:5409 which is incorporated by reference herein in its entirety. MAPs consist of multiple copies of a specific peptide attached to a non-immunogenic lysine core. Map peptides usually contain four or eight copies of the peptide often referred to as MAP-4 or MAP-8 peptides. By way of non-limiting example, MAPs may be synthesized onto a lysine core matrix attached to a polyethylene glycol-polystyrene (PEG-PS) support. The peptide of interest is synthesized onto the lysine residues using 9-fluorenylmethoxycarbonyl (Fmoc) chemistry. For example, Applied Biosystems (Foster City, Calif.) offers MAP resins, such as, for example, the Fmoc Resin 4 Branch and the Fmoc Resin 8 Branch which can be used to synthesize MAPs. Cleavage of MAPs from the resin is performed with standard trifloroacetic acid (TFA)-based cocktails known in the art. Purification of MAPS, except for desalting, is not necessary. MAP peptides may be used as an immunizing vaccine which elicits antibodies that recognize both the MAP and the native protein from which the peptide was derived.

Epitope bearing polypeptides of the invention may be modified, for example, by the addition of amino acids at the amino- and/or carboxy-termini of the peptide. Such modifications may be performed, for example, to alter the conformation of the epitope bearing polypeptide such that the epitope will have a conformation more closely related to the structure of the epitope in the native protein. An example of a modified epitope-bearing polypeptide of the invention is a polypeptide in which one or more cysteine residues have been added to the polypeptide to allow for the formation of a disulfide bond between two cysteines, resulting in a stable loop structure of the epitope bearing polypeptide under non-reducing conditions. Disulfide bonds may form between a cysteine residue added to the polypeptide and a cysteine residue of the naturally occurring epitope, or may form between two cysteines which have both been added to the naturally occurring epitope bearing polypeptide. Additionally, it is possible to modify one or more amino acid residues of the naturally occurring epitope bearing polypeptide by substituting them with cysteines to promote the formation of disulfide bonded loop structures. Cyclic thioether molecules of synthetic peptides may be routinely generated using techniques known in the art and are described in PCT publication WO 97/46251, incorporated in its entirety by reference herein. Other modifications of epitope-bearing polypeptides contemplated by this invention include biotinylation.

Animals such as, for example, rabbits, rats, and mice are immunized with either free or carrier-coupled peptides, or MAP peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or FLAG® tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

The techniques of gene-shuffling, motif-shuffling, exon-shuffling, and/or codon-shuffling (collectively referred to as "DNA shuffling") may be employed to modulate the activities of TR6-alpha and/or TR6-beta thereby effectively generating agonists and antagonists of TR6-alpha and/or TR6-beta. See generally, U.S. Pat. Nos. 5,605,793, 5,811,238, 5,830,721, 5,834,252, and 5,837,458, and Patten, P. A., et al., *Curr. Opinion Biotechnol.* 8:724-33 (1997); Harayama, S. *Trends Biotechnol.* 16(2):76-82 (1998); Hansson, L. O., et al., *J. Mol. Biol.* 287:265-76 (1999); and Lorenzo, M. M. and Blasco, R. *Biotechniques* 24(2):308-13 (1998) (each of these patents and publications are hereby incorporated by reference). In one embodiment, alteration of TR6-alpha and/or TR6-beta polynucleotides and corresponding polypeptides may be achieved by DNA shuffling. DNA shuffling involves the assembly of two or more DNA segments into a desired TR6-alpha and/or TR6-beta molecule by homologous, or site-specific, recombination. In another embodiment, TR6-alpha and/or TR6-beta polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TR6-alpha and/or TR6-beta may be recombined with one or more components, motifs, sections, parts, domains, fragments, etc. of one or more heterologous molecules. In preferred embodiments, the heterologous molecules are TNF-alpha, TNF-beta, lymphotoxin-alpha, lymphotoxin-beta, FAS ligand, APRIL. In further preferred embodiments, the heterologous molecules are any member of the TNF family.

Additionally, the techniques of gene-shuffling, motif-shuffling, exon-shuffling, and/or codon-shuffling (collectively referred to as "DNA shuffling") may be employed to modulate the activities of TNFR thereby effectively generating agonists and antagonists of TNFR. See generally, U.S. Pat. Nos. 5,605,793, 5,811,238, 5,830,721, 5,834,252, and 5,837,458, and Patten et al, *Curr. Opinion Biotechnol.* 8:724-33 (1997); Harayama, *Trends Biotechnol.* 16(2):76-82 (1998); Hansson et al., *J. Mol. Biol.* 287:265-76 (1999); and Lorenzo and Blasco, *Biotechniques* 24(2):308-13 (1998) (each of these patents and publications are hereby incorporated by reference). In one embodiment, alteration of TNFR polynucleotides and corresponding polypeptides may be achieved by DNA shuffling. DNA shuffling involves the assembly of two or more DNA segments into a desired TNFR molecule by homologous, or site-specific, recombination. In another embodiment, TNFR polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TNFR may be recombined with one or more components, motifs, sections, parts, domains, fragments, etc. of one or more heterologous molecules. In preferred embodiments, the heterologous molecules include, but are not limited to, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (*J. Exp. Med.* 188(6):1185-1190), endokine-alpha (International Publication No. WO 98/07880), neutrokine alpha (International Publication No. WO98/18921), TR6 (International Publication No. WO 98/30694), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153. In further preferred embodiments, the heterologous molecules are any member of the TNF family.

To improve or alter the characteristics of a TNFR polypeptide, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.,* 268:2984-2988 (1993) reported modified KGF proteins that had heparin binding activity even if 3, 8, or 27 amino-terminal amino acid residues were missing.

In the present case, since the proteins of the invention are members of the TNFR polypeptide family, deletions of N-terminal amino acids up to the Cysteine at position 49 of SEQ ID NOS:2 and 4 (TNFR-6 alpha and TNFR-6 beta) may retain some biological activity such as, for example regulation of cellular proliferation and apoptosis (e.g., of lymphoid cells), ability to bind Fas ligand (FasL), and ability to bind AIM-II. Polypeptides having further N-terminal deletions including the Cys-49 residue in SEQ ID NOS:2 and 4, would not be expected to retain such biological activities because it is known that these residues in a TNFR-related polypeptide are required for forming a disulfide bridge to provide structural stability which is needed for receptor/ligand binding and signal transduction. However, even if deletion of one or more amino acids from the N-terminus of a protein results in modification of loss of one or more biological functions of the protein, other functional activities may still be retained. Thus, the ability of the shortened protein to induce and/or bind to antibodies which recognize the complete or mature TNFR or extracellular domain of TNFR protein generally will be retained when less than the majority of the residues of the complete TNFR, mature TNFR, or extracellular domain of TNFR are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides comprising. or alternatively consisting of, one or more residues deleted from the amino terminus of the amino acid sequence of the TNFR shown in SEQ ID NOS:2 and 4, up to the cysteine residue at position number 49, and polynucleotides encoding such polypeptides. In particular, the present invention provides TNFR polypeptides comprising, or alternatively consisting of, the amino acid sequence of residues m-300 of FIG. 1 (SEQ ID NO:2) and/or residues n-170 of FIG. 2A (SEQ ID NO:4), where m and n are integers in the range of 1-49 and where 49 is the position of the first cysteine residue from the N-terminus of the complete TNFR-6α and TNFR-6β polypeptides (shown in SEQ ID NOS:2 and 4, respectively) believed to be required for activity of the TNFR-6α and TNFR-6β proteins.

More in particular, the invention provides polynucleotides encoding polypeptides having (i.e., comprising) or alternatively consisting of, the amino acid sequence of a member selected from the group consisting of residues: 1-300, 2-300, 3-300, 4-300, 5-300, 6-300, 7-300, 8-300, 9-300, 10-300, 11-300, 12-300, 13-300, 14-300, 15-300, 16-300, 17-300, 18-300, 19-300, 20-300, 21-300, 22-300, 23-300, 24-300, 25-300, 26-300, 27-300, 28-300, 29-300, 30-300, 31-300, 32-300, 33-300, 34-300, 35-300, 36-300, 37-300, 38-300, 39-300, 40-300, 41-300, 42-300, 43-300, 44-300, 45-300, 46-300, 47-300, 48-300, and 49-300 of SEQ ID NO:2; and 1-170, 2-170, 3-170, 4-170, 5-170, 6-170, 7-170, 8-170, 9-170, 10-170, 11-170, 12-170, 13-170, 14-170, 15-170, 16-170, 17-170, 18-170, 19-170, 20-170, 21-170, 22-170, 23-170, 24-170, 25-170, 26-170, 27-170, 28-170, 29-170, 30-170, 31-170, 32-170, 33-170, 34-170, 35-170, 36-170, 37-170, 38-170, 39-170, 40-170, 41-170, 42-170, 43-170, 44-170, 45-170, 46-170, 47-170, 48-170, and 49-170 of SEQ ID NO:4. Polypeptides encoded by these polynucleotide fragments are also encompassed by the invention.

In a specific embodiment, the invention provides polynucleotides encoding polypeptides comprising, or alternatively consisting of, the amino acid sequence of a member selected from the group consisting of residues: Val-30 to His-300 of SEQ ID NO:2. Polypeptides encoded by these polynucleotide fragments are also encompassed by the invention.

In other specific embodiments, the invention provides polynucleotides encoding polypeptides comprising, or alternatively consisting of, the amino acid sequence of a member selected from the group consisting of residues: P-23 to H-300, and/or P-34 to H-300 of SEQ ID NO:2. Polypeptides encoded by these polynucleotides are also encompassed by the invention.

As mentioned above, even if deletion of one or more amino acids from the N-terminus of a protein results in modification of loss of one or more biological functions of the protein, other functional activities (e.g., biological activities) may still be retained. Thus, the ability of shortened TNFR muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TNFR mutein with a large number of deleted N-terminal amino acid residues may retain some biological or immunogenic activities. In fact, peptides composed of as few as six TNFR amino acid residues may often evoke an immune response.

Accordingly, the present invention further provides polypeptides having one or more residues deleted from the amino terminus of the TNFR-6α amino acid sequence shown in FIG. 1 (i.e., SEQ ID NO:2), up to the arginine residue at position number 295 and polynucleotides encoding such polypeptides. In particular, the present invention provides polypeptides comprising or alternatively consisting of, the amino acid of residues $n^1$-300 of FIG. 1 (SEQ ID NO:2), where $n^1$ is an integer from 49 to 295, corresponding to the position of the amino acid residue in FIG. 1 (SEQ ID NO:2).

More in particular, the invention provides polynucleotides encoding polypeptides comprising, or alternatively consisting of, the amino acid sequence of a member selected from the group consisting of residues of C-49 to H-300; A-50 to H-300; Q-51 to H-300; C-52 to H-300; P-53 to H-300; P-54 to H-300; G-55 to H-300; T-56 to H-300; F-57 to H-300; V-58 to H-300; Q-59 to H-300; R-60 to H-300; P-61 to H-300; C-62 to H-300; R-63 to H-300; R-64 to H-300; D-65 to H-300; S-66 to H-300; P-67 to H-300; T-68 to H-300; T-69 to H-300; C-70 to H-300; G-71 to H-300; P-72 to H-300; C-73 to H-300; P-74 to H-300; P-75 to H-300; R-76 to H-300; H-77 to H-300; Y-78 to H-300; T-79 to H-300; Q-80 to H-300; F-81 to H-300; W-82 to H-300; N-83 to H-300; Y-84 to H-300; L-85 to H-300; E-86 to H-300; R-87 to H-300; C-88 to H-300; R-89 to H-300; Y-90 to H-300; C-91 to H-300; N-92 to H-300; V-93 to H-300; L-94 to H-300; C-95 to H-300; G-96 to H-300; E-97 to H-300; R-98 to H-300; E-99 to H-300; E-100 to H-300; E-101 to H-300; A-102 to H-300; R-103 to H-300; A-104 to H-300; C-105 to H-300; H-106 to H-300; A-107 to H-300; T-108 to H-300; H-109 to H-300; N-10 to H-300; R-111 to H-300; A-112 to H-300; C-113 to H-300; R-114 to H-300; C-115 to H-300; R-116 to H-300; T-117 to H-300; G-118 to H-300; F-119 to H-300; F-120 to H-300; A-121 to H-300; H-122 to H-300; A-123 to H-300; G-124 to H-300; F-125 to H-300; C-126 to H-300; L-127 to H-300; E-128 to H-300; H-129 to H-300; A-130 to H-300; S-131 to H-300; C-132 to H-300; P-133 to H-300; P-134 to H-300; G-135 to H-300; A-136 to H-300; G-137 to H-300; V-138 to H-300; 1-139 to H-300; A-140 to H-300; P-141 to H-300; G-142 to H-300; T-143 to H-300; P-144 to H-300; S-145 to H-300; Q-146 to H-300; N-147 to H-300; T-148 to H-300; Q-149 to H-300; C-150 to H-300; Q-151 to H-300; P-152 to H-300; C-153 to H-300; P-154 to H-300; P-155 to H-300; G-156 to H-300; T-157 to H-300; F-158 to H-300; S-159 to H-300; A-160 to H-300; S-161 to H-300; S-162 to H-300; S-163 to H-300; S-164 to H-300; S-165 to H-300; E-166 to H-300; Q-167 to H-300; C-168 to H-300; Q-169 to H-300; P-170 to H-300; H-171 to H-300; R-172 to H-300; N-173 to H-300; C-174 to H-300; T-175 to H-300; A-176 to H-300; L-177 to H-300; G-178 to H-300; L-179 to H-300; A-180 to H-300; L-181 to H-300; N-182 to H-300; V-183 to H-300; P-184 to H-300; G-185 to H-300; S-186 to H-300; S-187 to H-300; S-188 to H-300; H-189 to H-300; D-190 to H-300; T-191 to H-300; L-192 to H-300; C-193 to H-300; T-194 to H-300; S-195 to H-300; C-196 to H-300; T-197 to H-300; G-198 to H-300; F-199 to H-300; P-200 to H-300; L-201 to H-300; S-202 to H-300; T-203 to H-300; R-204 to H-300; V-205 to H-300; P-206 to H-300; G-207 to H-300; A-208 to H-300; E-209 to H-300; E-210 to H-300; C-211 to H-300; E-212 to H-300; R-213 to H-300; A-214 to H-300; V-215 to H-300; I-216 to H-300; D-217 to H-300; F-218 to H-300; V-219 to H-300; A-220 to H-300; F-221 to H-300; Q-222 to H-300; D-223 to H-300; I-224 to H-300; S-225 to H-300; 1-226 to H-300; K-227 to H-300; R-228 to H-300; L-229 to H-300; Q-230 to H-300; R-231 to H-300; L-232 to H-300; L-233 to H-300; Q-234 to H-300; A-235 to H-300; L-236 to H-300; E-237 to H-300; A-238 to H-300; P-239 to H-300; E-240 to H-300; G-241 to H-300; W-242 to H-300; G-243 to H-300; P-244 to H-300; T-245 to H-300; P-246 to H-300; R-247 to H-300; A-248 to H-300; G-249 to H-300; R-250 to H-300; A-251 to H-300; A-252 to H-300; L-253 to H-300; Q-254 to H-300; L-255 to H-300; K-256 to H-300; L-257 to H-300; R-258 to H-300; R-259 to H-300; R-260 to H-300; L-261 to H-300; T-262 to H-300; E-263 to H-300; L-264 to H-300; L-265 to H-300; G-266 to H-300; A-267 to H-300; Q-268 to H-300; D-269 to H-300; G-270 to H-300; A-271 to H-300; L-272 to H-300; L-273 to H-300; V-274 to H-300; R-275 to H-300; L-276 to H-300; L-277 to H-300; Q-278 to H-300; A-279 to H-300; L-280 to H-300; R-281 to H-300; V-282 to H-300; A-283 to H-300; R-284 to H-300; M-285 to H-300; P-286 to H-300; G-287 to H-300; L-288 to H-300; E-289 to H-300; R-290 to H-300; S-291 to H-300; V-292 to H-300; R-293 to H-300; E-294 to H-300; and R-295 to H-300 of the TNFR-6α sequence shown in FIG. 1 (SEQ ID NO:2). Polypeptides encoded by these polynucleotide fragments are also encompassed by the invention.

Similarly, many examples of biologically functional C-terminal deletion muteins are known. For instance, interferon gamma shows up to ten times higher activities by deleting 8-10 amino acid residues from the carboxy terminus of the protein (Döbeli et al., *J. Biotechnology* 7:199-216 (1988)). In the present case, since the protein of the invention is a member of the TNFR polypeptide family, deletions of C-terminal amino acids up to the cysteine at position 193 and 132 of SEQ ID NOS:2 and 4, respectively, may retain some functional activity, such as, for example, a biological activity (such as, for example, regulation of proliferation and apoptosis (e.g., of lymphoid cells, ability to bind Fas ligand, and ability to bind AIM-II)). Polypeptides having further C-terminal deletions including the cysteines at positions 193 and 132 of SEQ ID NOS:2 and 4, respectively, would not be expected to retain such biological activities because it is known that these residues in TNF receptor-related polypeptides are required for forming disulfide bridges to provide structural stability which is needed for receptor binding.

However, even if deletion of one or more amino acids from the C-terminus of a protein results in modification or loss of one or more biological functions of the protein, other functional activities (e.g., biological activities, the ability to multimerize, and the ability to bind ligand (e.g., Fas ligand and AIM-II)) may still be retained. Thus, the ability of the shortened protein to induce and/or bind to antibodies which recognize the complete or mature form of the protein generally will be retained when less than the majority of the residues of the complete or mature form protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of TNFR-6 alpha and TNFR-6 beta shown in SEQ ID NOS:2 and 4 up to the cysteine at position 193 and 132 of SEQ ID NOS:2 and 4, respectively, and polynucleotides encoding such polypeptides. In particular, the present invention provides polypeptides comprising, or alternatively consisting of, the amino acid sequence of a member selected from the group consisting of residues 1-y and 1-z of the amino acid sequence in SEQ ID NOS:2 and 4, respectively, where y is any integer in the range of 193-300 and z is any integer in the range of 132-170. Polynucleotides encoding these polypeptides also are provided.

In certain preferred embodiments, the present invention provides polypeptides comprising, or alternatively, consisting of, the amino acid sequence of a member selected from the group consisting of residues 1-y' and 1-z' of the amino acid sequence in SEQ ID NOS:2 and 4, respectively, where y' is any integer in the range of 193-299 and z' is any integer in the range of 132-169. Polynucleotides encoding these polypeptides also are provided.

In additional preferred specific embodiments, the present invention provides polypeptides comprising, or alternatively consisting of, the amino acid sequence of a member selected from the group consisting of residues Pro-23 to His-300, Val-30 to His-300, and Pro-34 to His-300 of SEQ ID NO:2 and polypeptides having the amino acid sequence of a member selected from the group consisting of residues Pro-23 to Pro-170, Val-30 to Pro-170, and Pro-34 to His-Pro-170 of SEQ ID NO:4. As described herein, these polypeptides may be fused to heterologous polypeptide sequences. Polynucleotides encoding these polypeptides and these fusion polypeptides are also provided.

The invention also provides polypeptides having one or more amino acids deleted from both the amino and the carboxyl termini, which may be described generally as having residues m-y of SEQ ID NO:2 and n-z of SEQ ID NO:4, where m, n, y and z are integers as described above.

Also as mentioned above, even if deletion of one or more amino acids from the C-terminus of a protein results in modification or loss of one or more biological functions of the protein, other functional activities (e.g., biological activities, the ability to form homomultimers, and the ability to bind ligand (e.g., Fas ligand and AIM-II)) may still be retained. For example, the ability of the shortened TNFR mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TNFR mutein with a large number of deleted C-terminal amino acid residues may retain some biological or immunogenic activities. In fact, peptides composed of as few as six TNFR amino acid residues may often evoke an immune response.

Accordingly, the present invention further provides polypeptides having one or more residues deleted from the carboxy terminus of the amino acid sequence of the TNFR polypeptide shown in FIG. 1 (SEQ ID NO:2), up to the glycine residue at position number 6, and polynucleotides encoding such polypeptides. In particular, the present invention provides polypeptides comprising, or alternatively consisting of, the amino acid sequence of residues 1-$m^1$ of FIG. 1 (i.e., SEQ ID NO:2), where $m^1$ is an integer from 6 to 299, corresponding to the position of the amino acid residue in FIG. 1 (SEQ ID NO:2).

More in particular, the invention provides polynucleotides encoding polypeptides comprising, or alternatively consisting of, the amino acid sequence of a member selected from the group consisting of residues M-1 to V-299; M-1 to P-298; M-1 to L-297; M-1 to F-296; M-1 to R-295; M-1 to E-294; M-1 to R-293; M-1 to V-292; M-1 to S-291; M-1 to R-290; M-1 to E-289; M-1 to L-288; M-1 to G-287; M-1 to P-286; M-1 to M-285; M-1 to R-284; M-1 to A-283; M-1 to V-282; M-1 to R-281; M-1 to L-280; M-1 to A-279; M-1 to Q-278; M-1 to L-277; M-1 to L-276; M-1 to R-275; M-1 to V-274; M-1 to L-273; M-1 to L-272; M-1 to A-271; M-1 to G-270; M-1 to D-269; M-1 to Q-268; M-1 to A-267; M-1 to G-266; M-1 to L-265; M-1 to L-264; M-1 to E-263; M-1 to T-262; M-1 to L-261; M-1 to R-260; M-1 to R-259; M-1 to R-258; M-1 to L-257; M-1 to K-256; M-1 to L-255; M-1 to Q-254; M-1 to L-253; M-1 to A-252; M-1 to A-251; M-1 to R-250; M-1 to G-249; M-1 to A-248; M-1 to R-247; M-1 to P-246; M-1 to T-245; M-1 to P-244; M-1 to G-243; M-1 to W-242; M-1 to G-241; M-1 to E-240; M-1 to P-239; M-1 to A-238; M-1 to E-237; M-1 to L-236; M-1 to A-235; M-1 to Q-234; M-1 to L-233; M-1 to L-232; M-1 to R-231; M-1 to Q-230; M-1 to L-229; M-1 to R-228; M-1 to K-227; M-1 to 1-226;

M-1 to S-225; M-1 to 1-224; M-1 to D-223; M-1 to Q-222; M-1 to F-221; M-1 to A-220; M-1 to V-219; M-1 to F-218; M-1 to D-217; M-1 to I-216; M-1 to V-215; M-1 to A-214; M-1 to R-213; M-1 to E-212; M-1 to C-211; M-1 to E-210; M-1 to E-209; M-1 to A-208; M-1 to G-207; M-1 to P-206; M-1 to V-205; M-1 to R-204; M-1 to T-203; M-1 to S-202; M-1 to L-201; M-1 to P-200; M-1 to F-199; M-1 to G-198; M-1 to T-197; M-1 to C-196; M-1 to S-195; M-1 to T-194; M-1 to C-193; M-1 to L-192; M-1 to T-191; M-1 to D-190; M-1 to H-189; M-1 to S-188; M-1 to S-187; M-1 to S-186; M-1 to G-185; M-1 to P-184; M-1 to V-183; M-1 to N-182; M-1 to L-181; M-1 to A-180; M-1 to L-179; M-1 to G-178; M-1 to L-177; M-1 to A-176; M-1 to T-175; M-1 to C-174; M-1 to N-173; M-1 to R-172; M-1 to H-171; M-1 to P-170; M-1 to Q-169; M-1 to C-168; M-1 to Q-167; M-1 to E-166; M-1 to S-165; M-1 to S-164; M-1 to S-163; M-1 to S-162; M-1 to S-161; M-1 to A-160; M-1 to S-159; M-1 to F-158; M-1 to T-157; M-1 to G-156; M-1 to P-155; M-1 to P-154; M-1 to C-153; M-1 to P-152; M-1 to Q-151; M-1 to C-150; M-1 to Q-149; M-1 to T-148; M-1 to N-147; M-1 to Q-146; M-1 to S-145; M-1 to P-144; M-1 to T-143; M-1 to G-142; M-1 to P-141; M-1 to A-140; M-1 to 1-139; M-1 to V-138; M-1 to G-137; M-1 to A-136; M-1 to G-135; M-1 to P-134; M-1 to P-133; M-1 to C-132; M-1 to S-131; M-1 to A-130; M-1 to H-129; M-1 to E-128; M-1 to L-127; M-1 to C-126; M-1 to F-125; M-1 to G-124; M-1 to A-123; M-1 to H-122; M-1 to A-121; M-1 to F-120; M-1 to F-119; M-1 to G-118; M-1 to T-117; M-1 to R-116; M-1 to C-115; M-1 to R-114; M-1 to C-113; M-1 to A-112; M-1 to R-111; M-1 to N-110; M-1 to H-109; M-1 to T-108; M-1 to A-107; M-1 to H-106; M-1 to C-105; M-1 to A-104; M-1 to R-103; M-1 to A-102; M-1 to E-101; M-1 to E-100; M-1 to E-99; M-1 to R-98; M-1 to E-97; M-1 to G-96; M-1 to C-95; M-1 to L-94; M-1 to V-93; M-1 to N-92; M-1 to C-91; M-1 to Y-90; M-1 to R-89; M-1 to C-88; M-1 to R-87; M-1 to E-86; M-1 to L-85; M-1 to Y-84; M-1 to N-83; M-1 to W-82; M-1 to F-81; M-1 to Q-80; M-1 to T-79; M-1 to Y-78; M-1 to H-77; M-1 to R-76; M-1 to P-75; M-1 to P-74; M-1 to C-73; M-1 to P-72; M-1 to G-71; M-1 to C-70; M-1 to T-69; M-1 to T-68; M-1 to P-67; M-1 to S-66; M-1 to D-65; M-1 to R-64; M-1 to R-63; M-1 to C-62; M-1 to P-61; M-1 to R-60; M-1 to Q-59; M-1 to V-58; M-1 to F-57; M-1 to T-56; M-1 to G-55; M-1 to P-54; M-1 to P-53; M-1 to C-52; M-1 to Q-51; M-1 to A-50; M-1 to C-49; M-1 to V-48; M-1 L-47; M-1 to R-46; M-1 to E-45; M-1 to G-44; M-1 to T-43; M-1 to E-42; M-1 to A-41; M-1 to D-40; M-1 to R-39; M-1 to W-38; M-1 to P-37; M-1 to Y-36; M-1 to T-35; M-1 to P-34; M-1 to T-33; M-1 to E-32; M-1 to A-31; M-1 to V-30; M-1 to G-29; M-1 to R-28; M-1 to V-27; M-1 to A-26; M-1 to P-25; M-1 to V-24; M-1 to P-23; M-1 to L-22; M-1 to L-21; M-1 to A-20; M-1 to P-19; M-1 to L-18; M-1 to A-17; M-1 to L-16; M-1 to V-15; M-1 to L-14; M-1 to C-13; M-1 to L-12; M-1 to L-11; M-1 to S-10; M-1 to L-9; M-1 to G-8; M-1 to P-7; and M-1 to G-6 of the sequence of the TFNR sequence shown in FIG. 1 (SEQ ID NO:2). Polypeptides encoded by these polynucleotide fragments are also encompassed by the invention.

In specific embodiments, the invention provides polynucleotides encoding polypeptides comprising or alternatively consisting of the amino acid sequence of a member selected from the group consisting of residues: M-1 to A-271, M-1 to Q-254 and/or M-1 to F-221 of SEQ ID NO:2. Polypeptides encoded by these polynucleotide fragments are also encompassed by the invention.

The invention also provides polypeptides having one or more amino acids deleted from both the amino and the carboxyl termini of a TNFR polypeptide, which may be described generally as having residues $n^1$-$m^1$ of FIG. 1 (i.e., SEQ ID NO:2), where $n^1$ and $m^1$ are integers as described above.

In additional embodiments, the present invention provides polypeptides comprising. or alternatively consisting of, the amino acid sequence of residues 30-$m^3$ of FIG. 1 (i.e., SEQ ID NO:2), where $m^3$ is an integer from 36 to 299, corresponding to the position of the amino acid residue in FIG. 1 (SEQ ID NO:2). For example, the invention provides polynucleotides encoding polypeptides comprising, or alternatively consisting of, the amino acid sequence of a member selected from the group consisting of residues V-30 to V-299; V-30 to P-298; V-30 to L-297; V-30 to F-296; V-30 to R-295; V-30 to E-294; V-30 to R-293; V-30 to V-292; V-30 to S-291; V-30 to R-290; V-30 to E-289; V-30 to L-288; V-30 to G-287; V-30 to P-286; V-30 to M-285; V-30 to R-284; V-30 to A-283; V-30 to V-282; V-30 to R-281; V-30 to L-280; V-30 to A-279; V-30 to Q-278; V-30 to L-277; V-30 to L-276; V-30 to R-275; V-30 to V-274; V-30 to L-273; V-30 to L-272; V-30 to A-271; V-30 to G-270; V-30 to D-269; V-30 to Q-268; V-30 to A-267; V-30 to G-266; V-30 to L-265; V-30 to L-264; V-30 to E-263; V-30 to T-262; V-30 to L-261; V-30 to R-260; V-30 to R-259; V-30 to R-258; V-30 to L-257; V-30 to K-256; V-30 to L-255; V-30 to Q-254; V-30 to L-253; V-30 to A-252; V-30 to A-251; V-30 to R-250; V-30 to G-249; V-30 to A-248; V-30 to R-247; V-30 to P-246; V-30 to T-245; V-30 to P-244; V-30 to G-243; V-30 to W-242; V-30 to G-241; V-30 to E-240; V-30 to P-239; V-30 to A-238; V-30 to E-237; V-30 to L-236; V-30 to A-235; V-30 to Q-234; V-30 to L-233; V-30 to L-232; V-30 to R-231; V-30 to Q-230; V-30 to L-229; V-30 to R-228; V-30 to K-227; V-30 to I-226; V-30 to S-225; V-30 to 1-224; V-30 to D-223; V-30 to Q-222; V-30 to F-221; V-30 to A-220; V-30 to V-219; V-30 to F-218; V-30 to D-217; V-30 to 1-216; V-30 to V-215; V-30 to A-214; V-30 to R-213; V-30 to E-212; V-30 to C-211; V-30 to E-210; V-30 to E-209; V-30 to A-208; V-30 to G-207; V-30 to P-206; V-30 to V-205; V-30 to R-204; V-30 to T-203; V-30 to S-202; V-30 to L-201; V-30 to P-200; V-30 to F-199; V-30 to G-198; V-30 to T-197; V-30 to C-196; V-30 to S-195; V-30 to T-194; V-30 to C-193; V-30 to L-192; V-30 to T-191; V-30 to D-190; V-30 to H-189; V-30 to S-188; V-30 to S-187; V-30 to S-186; V-30 to G-185; V-30 to P-184; V-30 to V-183; V-30 to N-182; V-30 to L-181; V-30 to A-180; V-30 to L-179; V-30 to G-178; V-30 to L-177; V-30 to A-176; V-30 to T-175; V-30 to C-174; V-30 to N-173; V-30 to R-172; V-30 to H-171; V-30 to P-170; V-30 to Q-169; V-30 to C-168; V-30 to Q-167; V-30 to E-166; V-30 to S-165; V-30 to S-164; V-30 to S-163; V-30 to S-162; V-30 to S-161; V-30 to A-160; V-30 to S-159; V-30 to F-158; V-30 to T-157; V-30 to G-156; V-30 to P-155; V-30 to P-154; V-30 to C-153; V-30 to P-152; V-30 to Q-151; V-30 to C-150; V-30 to Q-149; V-30 to T-148; V-30 to N-147; V-30 to Q-146; V-30 to S-145; V-30 to P-144; V-30 to T-143; V-30 to G-142; V-30 to P-141; V-30 to A-140; V-30 to 1-139; V-30 to V-138; V-30 to G-137; V-30 to A-136; V-30 to G-135; V-30 to P-134; V-30 to P-133; V-30 to C-132; V-30 to S-131; V-30 to A-130; V-30 to H-129; V-30 to E-128; V-30 to L-127; V-30 to C-126; V-30 to F-125; V-30 to G-124; V-30 to A-123; V-30 to H-122; V-30 to A-121; V-30 to F-120; V-30 to F-119; V-30 to G-118; V-30 to T-117; V-30 to R-116; V-30 to C-115; V-30 to R-114; V-30 to C-113; V-30 to A-112; V-30 to R-111; V-30 to N-110; V-30 to H-109; V-30 to T-108; V-30 to A-107; V-30 to H-106; V-30 to C-105; V-30 to A-104; V-30 to R-103; V-30 to A-102; V-30 to E-101; V-30 to E-100; V-30 to E-99; V-30 to R-98; V-30 to E-97; V-30 to G-96; V-30 to C-95; V-30 to L-94; V-30 to V-93; V-30 to N-92; V-30 to C-91; V-30 to Y-90; V-30 to R-89; V-30 to C-88; V-30 to R-87; V-30 to E-86; V-30 to L-85; V-30 to Y-84; V-30 to N-83; V-30 to W-82; V-30 to F-81; V-30 to Q-80; V-30 to T-79; V-30 to Y-78; V-30 to H-77; V-30 to R-76; V-30 to P-75; V-30 to P-74; V-30 to C-73; V-30 to P-72; V-30 to G-71; V-30 to C-70; V-30 to T-69; V-30 to T-68; V-30 to P-67; V-30 to S-66; V-30 to D-65; V-30 to R-64; V-30 to R-63; V-30 to C-62; V-30 to P-61; V-30 to R-60; V-30 to Q-59; V-30 to V-58; V-30 to F-57; V-30 to T-56; V-30 to G-55; V-30 to P-54; V-30 to P-53; V-30 to C-52; V-30 to Q-51; V-30 to A-50; V-30 to C-49; V-30 to V-48; V-30 to L-47; V-30 to R-46; V-30 to E-45; V-30 to G-44; V-30 to T-43; V-30 to E-42; V-30 to A-41; V-30 to D-40; V-30 to R-39; V-30 to W-38; V-30 to P-37; and V-30 to Y-36 of the sequence of the TFNR sequence shown in FIG. 1 (SEQ ID NO:2). Polypeptides encoded by these polynucleotide fragments are also encompassed by the invention. In specific embodiments, the invention provides polynucleotides encoding polypeptides comprising or alternatively consisting of the amino acid sequence of a member selected from the group consisting of residues: V-30 to A-271, V-30 to Q-254 and/or V-30 to F-221 of SEQ ID NO:2. Polypeptides encoded by these polynucleotides are also encompassed by the invention. The present application is also directed to polynucleotides or polypeptides comprising, or alternatively, consisting of, a polynucleotide or polypeptide sequence at least 80%, 85%, 90%, 92%, 95%, 96%, 97%, 98% or 99% identical to a polypeptide or polypeptide sequence described above, respectively. The present invention also encompasses the above polynucleotide or polypeptide sequences fused to a heterologous polynucleotide or polypeptide sequence, respectively.

With respect to fragments of TNFR-6β, as mentioned above, even if deletion of one or more amino acids from the N-terminus of a protein results in modification of loss of one or more biological functions of the protein, other functional activities (e.g., biological activities, the ability to multimerize, the ability to bind ligand (e.g., Fas ligand and/or AIM-II)) may still be retained. For example, the ability of shortened TNFR muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TNFR mutein with a large number of deleted N-terminal amino acid residues may retain some biological or immunogenic activities. In fact, peptides composed of as few as six TNFR amino acid residues may often evoke an immune response.

Accordingly, the present invention further provides polypeptides comprising, or alternatively, consisting of, one or more residues deleted from the amino terminus of the TNFR-6β amino acid sequence shown in FIG. 2A (i.e., SEQ ID NO:4), up to the glycine residue at position number 165 and polynucleotides encoding such polypeptides. In particular, the present invention provides polypeptides comprising, or alternatively consisting of, the amino acid sequence of residues $n^2$-170 of FIG. 2A (SEQ ID NO:4), where $n^2$ is an integer from 2 to 165, corresponding to the position of the amino acid residue in FIG. 2A (SEQ ID NO:4).

More in particular, the invention provides polynucleotides encoding polypeptides comprising, or alternatively consisting of, the amino acid sequence of a member selected from the group consisting of residues of R-2 to P-170; A-3 to P-170; L-4 to P-170; E-5 to P-170; G-6 to P-170; P-7 to P-170; G-8 to P-170; L-9 to P-170; S-10 to P-170; L-11 to P-170; L-12 to P-170; C-13 to P-170; L-14 to P-170; V-15 to P-170; L-16 to P-170; A-17 to P-170; L-18 to P-170; P-19 to P-170; A-20 to P-170; L-21 to P-170; L-22 to P-170; P-23 to P-170; V-24 to P-170; P-25 to P-170; A-26 to P-170; V-27 to P-170; R-28 to P-170; G-29 to P-170; V-30 to P-170; A-31 to P-170; E-32 to P-170; T-33 to P-170; P-34 to P-170; T-35 to P-170; Y-36 to P-170; P-37 to P-170; W-38 to P-170; R-39 to P-170; D-40 to P-170; A-41 to P-170; E-42 to P-170; T-43 to P-170; G-44 to P-170; E-45 to P-170; R-46 to P-170; L-47 to P-170; V-48 to P-170; C-49 to P-170; A-50 to P-170; Q-51 to P-170; C-52 to P-170; P-53 to P-170; P-54 to P-170; G-55 to P-170; T-56 to P-170; F-57 to P-170; V-58 to P-170; Q-59 to P-170; R-60 to P-170; P-61 to P-170; C-62 to P-170; R-63 to P-170; R-64 to P-170; D-65 to P-170; S-66 to P-170; P-67 to P-170; T-68 to P-170; T-69 to P-170; C-70 to P-170; G-71 to P-170; P-72 to P-170; C-73 to P-170; P-74 to P-170; P-75 to P-170; R-76 to P-170; H-77 to IP-170; Y-78 to P-170; T-79 to P-170; Q-80 to P-170; F-81 to P-170; W-82 to P-170; N-83 to P-170; Y-84 to P-170; L-85 to P-170; E-86 to P-170; R-87 to P-170; C-88 to P-170; R-89 to P-170; Y-90 to P-170; C-91 to P-170; N-92 to P-170; V-93 to P-170; L-94 to P-170; C-95 to P-170; G-96 to P-170; E-97 to P-170; R-98 to P-170; E-99 to P-170; E-100 to P-170; E-101 to P-170; A-102 to P-170; R-103 to P-170; A-104 to P-170; C-105 to P-170; H-106 to P-170; A-107 to P-170; T-108 to P-170; H-109 to P-170; N-110 to P-170; R-111 to P-170; A-112 to P-170; C-113 to P-170; R-114 to P-170; C-115 to P-170; R-116 to P-170; T-117 to P-170; G-118 to P-170; F-119 to P-170; F-120 to P-170; A-121 to P-170; H-122 to P-170; A-123 to P-170; G-124 to P-170; F-125 to P-170; C-126 to P-170; L-127 to P-170; E-128 to P-170; H-129 to P-170; A-130 to P-170; S-131 to P-170; C-132 to P-170; P-133 to P-170; P-134 to P-170; G-135 to P-170; A-136 to P-170; G-137 to P-170; V-138 to P-170; I-139 to P-170; A-140 to P-170; P-141 to P-170; G-142 to P-170; E-143 to P-170; S-144 to P-170; W-145 to P-170; A-146 to P-170; R-147 to P-170; G-148 to P-170; G-149 to P-170; A-150 to P-170; P-151 to P-170; R-152 to P-170; S-153 to P-170; G-154 to P-170; G-155 to P-170; R-156 to P-170; R-157 to P-170; C-158 to P-170; G-159 to P-170; R-160 to P-170; G-161 to P-170; Q-162 to P-170; V-163 to P-170; A-164 to P-170; and G-165 to P-170 of the TNFR-6β sequence shown in FIG. 2A (SEQ ID NO:4). Polypeptides encoded by these polynucleotide fragments are also encompassed by the invention.

Also as mentioned above, even if deletion of one or more amino acids from the C-terminus of a protein results in modification of loss of one or more biological functions of the protein, other functional activities (e.g., biological activities, the ability to multimerize, ability to bind ligand (e.g., Fas ligand and/or AIM-II) may still be retained. For example, the ability of the shortened TNFR-6β mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TNFR-6β mutein with a large number of deleted C-terminal amino acid residues may retain some biological or immunogenic activities. In fact, peptides composed of as few as six TNFR-6β amino acid residues may often evoke an immune response.

Accordingly, the present invention further provides polypeptides comprising, or alternatively consisting of one or more residues deleted from the carboxy terminus of the amino acid sequence of the TNFR-6β polypeptide shown in FIG. 2A (SEQ ID NO:4), up to the glycine residue at position number 6, and polynucleotides encoding such polypeptides.

In particular, the present invention provides polypeptides comprising, or alternatively consisting of, the amino acid sequence of residues 1-$m^2$ of FIG. 2A (i.e., SEQ ID NO:4), where $m^2$ is an integer from 6 to 169, corresponding to the position of the amino acid residue in FIG. 2A (SEQ ID NO:4).

More in particular, the invention provides polynucleotides encoding polypeptides comprising, or alternatively consisting of, the amino acid sequence of a member selected from the group consisting of residues M-1 to A-169; M-1 to L-168; M-1 to S-167; M-1 to P-166; M-1 to G-165; M-1 to A-164; M-1 to V-163; M-1 to Q-162; M-1 to G-161; M-1 to R-160; M-1 to G-159; M-1 to C-158; M-1 to R-157; M-1 to R-156; M-1 to G-155; M-1 to G-154; M-1 to S-153; M-1 to R-152; M-1 to P-151; M-1 to A-150; M-1 to G-149; M-1 to G-148; M-1 to R-147; M-1 to A-146; M-1 to W-145; M-1 to S-144; M-1 to E-143; M-1 to G-142; M-1 to P-141; M-1 to A-140; M-1 to I-139; M-1 to V-138; M-1 to G-137; M-1 to A-136; M-1 to G-135; M-1 to P-134; M-1 to P-133; M-1 to C-132; M-1 to S-131; M-1 to A-130; M-1 to H-129; M-1 to E-128; M-1 to L-127; M-1 to C-126; M-1 to F-125; M-1 to G-124; M-1 to A-123; M-1 to H-122; M-1 to A-121; M-1 to F-120; M-1 to F-119; M-1 to G-118; M-1 to T-117; M-1 to R-116; M-1 to C-115; M-1 to R-114; M-1 to C-113; M-1 to A-112; M-1 to R-111; M-1 to N-110; M-1 to H-109; M-1 to T-108; M-1 to A-107; M-1 to H-106; M-1 to C-105; M-1 to A-104; M-1 to R-103; M-1 to A-102; M-1 to E-101; M-1 to E-100; M-1 to E-99; M-1 to R-98; M-1 to E-97; M-1 to G-96; M-1 to C-95; M-1 to L-94; M-1 to V-93; M-1 to N-92; M-1 to C-91; M-1 to Y-90; M-1 to R-89; M-1 to C-88; M-1 to R-87; M-1 to E-86; M-1 to L-85; M-1 to Y-84; M-1 to N-83; M-1 to W-82; M-1 to F-81; M-1 to Q-80; M-1 to T-79; M-1 to Y-78; M-1 to H-77; M-1 to R-76; M-1 to P-75; M-1 to P-74; M-1 to C-73; M-1 to P-72; M-1 to G-71; M-1 to C-70; M-1 to T-69; M-1 to T-68; M-1 to P-67; M-1 to S-66; M-1 to D-65; M-1 to R-64; M-1 to R-63; M-1 to C-62; M-1 to P-61; M-1 to R-60; M-1 to Q-59; M-1 to V-58; M-1 to F-57; M-1 to T-56; M-1 to G-55; M-1 to P-54; M-1 to P-53; M-1 to C-52; M-1 to Q-51; M-1 to A-50; M-1 to C-49; M-1 to V-48; M-1 to L-47; M-1 to R-46; M-1 to E-45; M-1 to G-44; M-1 to T-43; M-1 to E-42; M-1 to A-41; M-1 to D-40; M-1 to R-39; M-1 to W-38; M-1 to P-37; M-1 to Y-36; M-1 to T-35; M-1 to P-34; M-1 to T-33; M-1 to E-32; M-1 to A-31; M-1 to V-30; M-1 to G-29; M-1 to R-28; M-1 to V-27; M-1 to A-26; M-1 to P-25; M-1 to V-24; M-1 to P-23; M-1 to L-22; M-1 to L-21; M-1 to A-20; M-1 to P-19; M-1 to L-18; M-1 to A-17; M-1 to L-16; M-1 to V-15; M-1 to L-14; M-1 to C-13; M-1 to L-12; M-1 to L-11; M-1 to S-10; M-1 to L-9; M-1 to G-8; M-1 to P-7; and M-1 to G-6 of the sequence of the TNFR-6β shown in FIG. 2A (SEQ ID NO:4). Polypeptides encoded by these polynucleotide fragments are also encompassed by the invention.

The invention also provides polypeptides comprising, or alternatively consisting of, one or more amino acids deleted from both the amino and the carboxyl termini of a TNFR-6β polypeptide, which may be described generally as having residues $n^2$-$m^2$ of FIG. 2A (i.e., SEQ ID NO:4), where $n^2$ and $m^2$ are integers as described above.

The present application is also directed to nucleic acid molecules comprising, or alternatively, consisting of, a polynucleotide sequence at least 90%, 92%, 95%, 96%, 97%, 98% or 99% identical to the polynucleotide sequence encoding a TNFR polypeptide set forth herein as m-y, n-z, $n^1$-$m^1$, 30-$m^3$, and/or $n^2$-$m^2$. In preferred embodiments, the application is directed to nucleic acid molecules comprising, or alternatively, consisting of, a polynucleotide sequence at least 90%, 92%, 95%, 96%, 97%, 98% or 99% identical to the polynucleotide sequences encoding polypeptides having the amino acid sequence of the specific N- and C-terminal deletions recited herein. The present invention also encompasses the above polynucleotide sequences fused to a heterologous polynucleotide sequence. Polypeptides encoded by these nucleic acids and/or polynucleotide sequences are also encompassed by the invention.

Also included are a nucleotide sequence encoding a polypeptide consisting of a portion of a complete TNFR amino acid sequence encoded by a cDNA clone contained in ATCC™ Deposit No. 97810, or 97809, where this portion excludes from 1 to about 49 amino acids from the amino terminus of the complete amino acid sequence encoded by the cDNA clone contained in ATCC™ Deposit No. 97810 and 97809, respectively, or from 1 to about 107 or 58 amino acids from the carboxy terminus of the complete amino acid sequence encoded by the cDNA clone contained in ATCC™ Deposit No. 97810 and 97809, respectively, or any combination of the above amino terminal and carboxy terminal deletions, of the complete amino acid sequence encoded by the cDNA clone contained in ATCC™ Deposit No. 97810 or 97809. Polypeptides encoded by all of the above polynucleotides are also encompassed by the invention.

In addition to terminal deletion forms of the protein discussed above, it also will be recognized by one of ordinary skill in the art that some amino acid sequences of the TNFR polypeptides can be varied without significant effect on the structure or function of the proteins. If such differences in sequence are contemplated, it should be remembered that there will be critical areas on the protein which determine activity.

Thus, the invention further includes variations of the TNFR polypeptides which show substantial TNFR polypeptide functional activity (e.g., immunogenic activity, biological activity) or which include regions of TNFR protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Thus, the fragment, derivative or analog of the polypeptide of SEQ ID NO:2, 4 or 6, or that encoded by a deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature or soluble extracellular polypeptide is fused with another compound, such as a compound to increase the half-life of the polypeptide (for example, polyethylene glycol), or (iv) one in which the additional amino acids (such as, for example, an IgG Fc peptide fusion and/or an immunoglobulin light chain constant region peptide), a leader or secretory sequence, or a sequence which is employed for purification of the TNFR polypeptide) are fused to a TNFR polypeptide described herein. Such fragments, derivatives and analogs are deemed to be within the scope of those skilled in the art from the teachings herein.

Thus, the TNFR of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table III).

TABLE III

| Conservative Amino Acid Substitutions. | |
| --- | --- |
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TNFR proteins of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for functional activity such as, for example, ligand/receptor (e.g., Fas ligand and/or AIM-II) receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331-340 (1967); Robbins et al., *Diabetes* 36: 838-845 (1987); Cleland et al., *Crit. Rev. Therapeutic Drug Carrier Systems* 10:307-377 (1993).

Replacement of amino acids can also change the selectivity of the binding of a ligand to cell surface receptors. For example, Ostade et al., *Nature* 361:266-268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

Since TNFR-6 alpha and TNFR-6 beta are members of the TNF receptor-related protein family, to modulate rather than completely eliminate biological activities of TNFR preferably mutations are made in sequences encoding amino acids in the TNFR conserved extracellular domain, more preferably in residues within this region which are not conserved among members of the TNF receptor family. Also forming part of the present invention are isolated polynucleotides comprising nucleic acid sequences which encode the above TNFR mutants.

The polypeptides of the present invention are preferably provided in an isolated form, and preferably are substantially purified. A recombinantly produced version of the TNFR polypeptides can be substantially purified by the one-step method described in Smith and Johnson, *Gene* 67:31-40 (1988). Polypeptides of the invention also can be purified from natural or recombinant sources using anti-TNFR-6 alpha and TNFR-6 beta antibodies of the invention in methods which are well known in the art of protein purification.

The invention further provides isolated TNFR polypeptides comprising an amino acid sequence selected from the group consisting of: (a) the amino acid sequence of a full-length TNFR polypeptide having the complete amino acid sequence shown in SEQ ID NO:2 or 4 or as encoded by the cDNA clone contained in the plasmid deposited as ATCC™ Deposit No. 97810 or 97809; (b) the amino acid sequence of a mature TNFR polypeptide having the amino acid sequence at positions 31-300 in SEQ ID NO:2 or 31-170 in SEQ ID NO:4, or as encoded by the cDNA clone contained in the plasmid deposited as ATCC™ Deposit No. 97810 or 97809; or (c) the amino acid sequence of a soluble extracellular domain of a TNFR polypeptide having the amino acid sequence at positions 31 to 283 in SEQ ID NO:2 or 31 to 166 in SEQ ID NO:4, or as encoded by the cDNA clone contained in the plasmid deposited as ATCC™ Deposit No. 97810 or 97809.

Further polypeptides of the present invention include polypeptides which have at least 90% similarity, more preferably at least 80%, 85%, 90%, 92%, or 95% similarity, and still more preferably at least 96%, 97%, 98% or 99% similarity to those described above. The polypeptides of the invention also comprise those which are at least 80% identical, more preferably at least 85%, 90%, 92% or 95% identical, still more preferably at least 96%, 97%, 98% or 99% identical to the polypeptide encoded by the deposited cDNA (ATCC™ Deposit Nos. 97810 or 97809) or to the polypeptide of SEQ ID NO:2 or 4, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a reference amino acid sequence of a TNFR polypeptide is intended that the amino acid sequence of the polypeptide is identical to the reference sequence except that the polypeptide sequence may include up to five amino acid alterations per each 100 amino acids of the reference amino acid of the TNFR polypeptide. In other words, to obtain a polypeptide having an amino acid sequence at least 80%, 85%, 90%, or 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NO:2 or 4, or to an amino acid sequence encoded by the cDNA contained in the deposits having ATCC™ Deposit No. 97810, or 97809, or fragments thereof (e.g., the sequence of any of the polypeptides corresponding to N or C terminal deletions of TNFR, as described herein (e.g., the polypeptide having the sequence of amino acids 30 to 300 of SEQ ID NO:2)) can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty-0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptide of the present invention have uses which include, but are not limited to, as molecular weight markers on SDS-PAGE gels or on molecular sieve gel filtration columns using methods well known to those of skill in the art. As described in detail below, the polypeptides of the present invention can also be used to raise polyclonal and monoclonal antibodies, which are useful in assays for detecting TNFR protein expression as described below or as agonists and antagonists capable of enhancing or inhibiting TNFR protein function. Further, such polypeptides can be used in the yeast two-hybrid system to "capture" TNFR protein binding proteins which are also candidate agonists and antagonists according to the present invention. The yeast two hybrid system is described in Fields and Song, *Nature* 340:245-246 (1989).

Transgenics

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691-698 (1994); Carver et al., *Biotechnology (NY)* 11:1263-1270 (1993); Wright et al, *Biotechnology (NY)* 9:830-834 (1991); and Hoppe et al., U.S. Pat. No. 4,873,191 (1989)); retrovirus mediated gene transfer into germ lines (Van der Putten et al., *Proc. Natl. Acad. Sci, USA* 82:6148-6152 (1985)), blastocysts or embryos; gene targeting in embryonic stem cells (Thompson et al., *Cell* 56:313-321 (1989)); electroporation of cells or embryos (Lo, *Mol. Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717-723 (1989)); etc. For a review of such techniques, see Gordon, "Transgenic Animals," *Intl. Rev. Cytol* 115:171-229 (1989), which is incorporated by reference herein in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64-66 (1996); Wilmut et al., *Nature* 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Female transgenic mice that secrete a TNFR-6 alpha and/or TNFR-6 beta polypeptide in their milk may be generated using the pBC1 Milk Expression Vector Kit, available from Invitrogen Corp. (Carlsbad, Calif.; Catalog Number K270-01). Transgenic mice can be made using the pBC1 vector according to protocols well-known in the art. Milk may be harvested from the mice and TNFR-6 alpha and/or TNFR-6 beta polypeptides purified from the milk according to the manufacturer's instructions published in the package insert that accompanies the pBC1 Milk Expression Vector Kit (Version B, 000829; 25-0264).

Transgenic and "knock-out" animals of the invention have uses which include, but are not limited to, animal model systems useful in elaborating the biological function of TNFR polypeptides, studying conditions and/or disorders associated with aberrant TNFR expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In a preferred embodiment, the immunoglobulin is an IgG1 isotype. In another preferred embodiment, the immunoglobulin is an IgG4 isotype.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferred binding affinities include those with a dissociation constant or Kd less than $5\times10^{-6}$ M, $10^{-6}$ M, $5\times10^{-7}$ M, $10^{-7}$ M, $5\times10^{-8}$ M, or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-2}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen, et al., Cancer Res. 58(16):3668-3678 (1998); Harrop et al., J. Immunol. 161(4): 1786-1794 (1998); Zhu et al., Cancer Res. 58(15):3209-3214 (1998); Yoon, et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17): 11295-11301 (1997); Taryman et al., Neuron 14(4): 755-762 (1995); Muller et al., Structure 6(9):1153-1167 (1998); Bartmunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

By way of another non-limiting example, antibodies of the invention may be administered to individuals as a form of passive immunization. Alternatively, antibodies of the present invention may be used for epitope mapping to identify the epitope(s) bound by the antibody. Epitopes identified in this way may, in turn, for example, be used as vaccine candidates, i.e., to immunize an individual to elicit antibodies against the naturally occurring forms of TNFR-6 alpha and/or TNFR-6 beta.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387. Additional antibodies of the invention may be to albumin, as described above.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well-known in the art and are discussed in detail in Example 11. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV. In general, the sample containing human B cells is innoculated with EBV, and cultured for 34 weeks. A typical source of EBV is the culture supernatant of the B95-8 cell line (ATCC™ #VR-1492). Physical signs of EBV transformation can generally be seen towards the end of the 3-4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human×mouse; e.g, SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; 5,939,598; 6,075,181; and 6,114,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby activate or block TNFR mediated inhibition of apoptosis.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or 4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334: 544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038-1041).

Methods of Producing Antibodies

The antibodies of the invention can be produced by any method known in the art for the synthesis of antibodies, in particular, by chemical synthesis or preferably, by recombinant expression techniques. Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260: 926-932; and Morgan and Anderson, 1993, Ann. Rev. Biochem. 62:191-217; May, 1993, TIB TECH 11(5):155-215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. It is also possible to amplify vectors that utilize glutamine synthase selection in glutamine synthase expressing cells (e.g., Chinese Hamster Ovary (CHO) cells), however, by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., Bio/technology 10:169 (1992) and in Biblia and Robinson Biotechnol. Prog. 11:1 (1995) which are herein incorporated by reference.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270: 3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995)0.

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the FLAG® tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$M $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators useful for chelating radiometal ions, including but not limited to, $^{177}$Lu, $^{90}$Y, $^{166}$Ho, and $^{153}$Sm, to polypeptides. In a preferred embodiment, the radiometal ion associated with the macrocyclic chelators attached to antibodies of the invention is $^{111}$In. In another preferred embodiment, the radiometal ion associated with the macrocyclic chelator attached to antibodies of the invention is $^{90}$Y. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition U.S. Pat. Nos. 5,652,361 and 5,756,065, which disclose chelating agents that may be conjugated to antibodies, and methods for making and using them, are hereby incorporated by reference in their entireties.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label polypeptides and antibodies (as well as fragments and variants of polypeptides and antibodies) of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the described disorders. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein). The antibodies of the invention can be used to treat or prevent diseases and disorders associated with aberrant expression and/or activity of a polypeptide of the invention, including, but not limited to, diseases and/or disorders such as autoimmune diseases and/or deficiencies, as discussed herein. The treatment and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-retroviral agents, and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than 5×10–6 M, 10–6 M, 5×10–7 M, 10–7 M, 5×10–8 M, 10–8 M, 5×10–9 M, 10–9 M, 5×10–10 M, 10–10 M, 5×10–11 M, 10–11 M, 5×10–12 M, 10–12 M, 5×10–13 M, 10–13 M, 5×10–14 M, 10–14 M, 5×10–15 M, and 10–15 M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932-8935; Zijlstra et al., 1989, Nature 342:435-438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, viral vectors that contains nucleic acid sequences encoding an antibody of the invention are used. For example, a retroviral vector can be used (see Miller et al., 1993, Meth. Enzymol. 217:581-599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Assaying TR6-alpha and/or TR6-beta polypeptide levels in a biological sample can occur using antibody-based techniques. Antibodies of the invention can be used to assay protein levels in a biological sample using classical immunohistological methods known to those of skill in the art (e.g., see Jalkanen, M., et al., J. Cell. Biol. 101:976-985 (1985); Jalkanen, M., et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No.

5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI.

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Immune System-Related Disorders

Diagnosis

The present inventors have discovered that TNFR-6 alpha and TNFR-6 beta are expressed in hematopoietic and transformed tissues. For a number of immune system-related disorders, substantially altered (increased or decreased) levels of TNFR gene expression can be detected in immune system tissue or other cells or bodily fluids (e.g., sera and plasma) taken from an individual having such a disorder, relative to a "standard" TNFR gene expression level, that is, the TNFR expression level in immune system tissues or other cells or bodily fluids from an individual not having the immune system disorder. Thus, the invention provides a diagnostic method useful during diagnosis of an immune system disorder, which involves measuring the expression level of the gene encoding the TNFR protein in immune system tissue or other cells or body fluid from an individual and comparing the measured gene expression level with a standard TNFR gene expression level, whereby an increase or decrease in the gene expression level compared to the standard is indicative of an immune system disorder.

In particular, it is believed that certain tissues in mammals with cancer (e.g., colon, breast and lung cancers) have elevated copy numbers of TNFR genes and/or express significantly elevated levels of the TNFR protein and mRNA encoding the TNFR when compared to a corresponding "standard" level. Further, it is believed that elevated levels of the TNFR protein can be detected in certain cells or body fluids (e.g., sera and plasma) from mammals with such a cancer when compared to sera from mammals of the same species not having the cancer.

Thus, the invention provides a diagnostic method useful during diagnosis of an immune system disorder, including cancers which involves measuring the expression level of the gene encoding the TNFR protein in immune system tissue or other cells or body fluid from an individual and comparing the measured gene expression level with a standard TNFR gene expression level, whereby an increase or decrease in the gene expression level compared to the standard is indicative of an immune system disorder.

Where a diagnosis of a disorder in the immune system including diagnosis of a tumor has already been made according to conventional methods, the present invention is useful as a prognostic indicator, whereby patients exhibiting depressed gene expression will experience a worse clinical outcome relative to patients expressing the gene at a level nearer the standard level.

By "assaying the expression level of the gene encoding a TNFR protein" is intended qualitatively or quantitatively measuring or estimating the level of the TNFR-6α and/or TNFR-6β protein or the level of the mRNA encoding the TNFR-6α and/or TNFR-6β protein in a first biological sample either directly (e.g., by determining or estimating absolute protein level or mRNA level) or relatively (e.g., by comparing to the TNFR protein level or mRNA level in a second biological sample). Preferably, the TNFR protein level or mRNA level in the first biological sample is measured or estimated and compared to a standard TNFR protein level or mRNA level, the standard being taken from a second biological sample obtained from an individual not having the disorder or being determined by averaging levels from a population of individuals not having a disorder of the immune system. As will be appreciated in the art, once standard TNFR protein levels or mRNA levels are known, they can be used repeatedly as a standard for comparison.

By "biological sample" is intended any biological sample obtained from an individual, body fluid, cell line, tissue culture, or other source which contains TNFR protein or mRNA. As indicated, biological samples include body fluids (such as sera, plasma, urine, synovial fluid and spinal fluid) which contain free extracellular domain(s) (or soluble form(s)) of a TNFR protein, immune system tissue, and other tissue sources found to express complete TNFR, mature TNFR, or extracellular domain of a TNFR. Methods for obtaining tissue biopsies and body fluids from mammals are well known in the art. Where the biological sample is to include mRNA, a tissue biopsy is the preferred source.

The invention also contemplates the use of a gene of the present invention for diagnosing mutations in a TNFR gene. For example, if a mutation is present in one of the genes of the present invention, conditions would result from a lack of production of the receptor polypeptides of the present invention. Further, mutations which enhance receptor polypeptide activity would lead to diseases associated with an over expression of the receptor polypeptide, e.g., cancer. Mutations in the genes can be detected by comparing the sequence of the defective gene with that of a normal one. Subsequently one can verify that a mutant gene is associated with a disease condition or the susceptibility to a disease condition. That is, a mutant gene which leads to the underexpression of the receptor polypeptides of the present invention would be associated with an inability of TNFR to inhibit Fas ligand and/or AIM-II mediated apoptosis, and thereby result in irregular cell proliferation (e.g., tumor growth).

Other immune system disorders which may be diagnosed by the foregoing assays include, but are not limited to, hypersensitivity, allergy, infectious disease, graft-host disease, Immunodificiency, autoimmune diseases and the like.

Individuals carrying mutations in the genes of the present invention may be detected at the DNA level by a variety of techniques. Nucleic acids used for diagnosis may be obtained from a patient's cells, such as from blood, urine, saliva and tissue biopsy among other tissues. The genomic DNA may be used directly for detection or may be amplified enzymatically by using PCR (Saiki et al., *Nature*, 324:163-166 (1986)) prior to analysis. RNA or cDNA may also be used for the same purpose. As an example, PCR primers complementary to the nucleic acid of the instant invention can be used to identify and analyze mutations in the human genes of the present invention. For example, deletions and insertions can be detected by a change in the size of the amplified product in comparison to the normal genotype. Point mutations can be identified by hybridizing amplified DNA to radiolabeled RNA or alternatively, radiolabeled antisense DNA sequences of the present invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primer used with double stranded PCR product or a single stranded template molecule generated by a modified PCR product. The sequence determination is performed by conventional procedures with radiolabeled nucleotides or by automatic sequencing procedures with fluorescent tags.

Sequence changes at the specific locations may be revealed by nuclease protection assays, such as RNase and S1 protection or the chemical cleavage method (for example, Cotton et al., *PNAS*, 85:4397-4401 (1985)).

Assaying TNFR protein levels in a biological sample can occur using antibody-based techniques. For example, TNFR protein expression in tissues can be studied with classical immunohistological methods (Jalkanen, M., et al., *J. Cell. Biol.* 101:976-985 (1985); Jalkanen, M., et al., *J. Cell. Biol.* 105:3087-3096 (1987)). Other antibody-based methods useful for detecting TNFR gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying TNFR protein levels in a biological sample obtained from an individual, TNFR proteins can also be detected in vivo by imaging. Antibody labels or markers for in vivo imaging of TNFR proteins include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TNFR-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TNFR protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors Gene Structure and Biological Activities," *Symp. Quant. Biol.* 51:597-609 (1986), Cold Spring Harbor; Beutler, B., and Cerami, A., *Annu. Rev. Biochem.* 57:505-518 (1988); Old, L. J., *Sci. Am.* 258:59-75 (1988); Fiers, W., *FEBS Lett.* 285:199-224 (1991)). The TNF-family ligands induce such various cellular responses by binding to TNF-family receptors.

TNFR-6 alpha and/or TNFR-6 beta polynucleotides and polypeptides of the invention may be used in developing treatments for any disorder mediated (directly or indirectly) by defective, or insufficient amounts of TNFR-6 alpha and/or TNFR-6 beta. TNFR-6 alpha and/or TNFR-6 beta polypeptides may be administered to a patient (e.g., mammal, preferably human) afflicted with such a disorder. Alternatively, a gene therapy approach may be applied to treat such disorders. Disclosure herein of TNFR-6 alpha and/or TNFR-6 beta nucleotide sequences permits the detection of defective TNFR-6 alpha and/or TNFR-6 beta genes, and the replacement thereof with normal TNFR-6 alpha and/or TNFR-6 beta-encoding genes. Defective genes may be detected in in vitro diagnostic assays, and by comparison of a TNFR-6 alpha and/or TNFR-6 beta nucleotide sequence disclosed herein with that of a TNFR-6 alpha and/or TNFR-6 beta gene derived from a patient suspected of harboring a defect in this gene.

In another embodiment, the polypeptides of the present invention are used as a research tool for studying the biological effects that result from inhibiting Fas ligand/TNFR-6 alpha and/or TNFR-6 beta and/or AIM-II interactions on different cell types. TNFR-6 alpha and/or TNFR-6 beta polypeptides also may be employed in in vitro assays for detecting Fas ligand, AIM-1, or TNFR-6 alpha and/or TNFR-6 beta or the interactions thereof.

In another embodiment, a purified TNFR-6 alpha and/or TNFR-6 beta polypeptide of the invention is used to inhibit binding of Fas ligand and/or AIM-II to endogenous cell surface Fas ligand and/or AIM-II receptors. Certain ligands of the TNF family (of which Fas ligand and AIM-II are members) have been reported to bind to more than one distinct cell surface receptor protein. AIM-II likewise is believed to bind multiple cell surface proteins. By binding Fas ligand and/or AIM-II, soluble TNFR-6 alpha and/or TNFR-6 beta polypeptides of the present invention may be employed to inhibit the binding of Fas ligand and/or AIM-II not only to endogenous TNFR-6 alpha and/or TNFR-6 beta, but also to Fas ligand and AIM-II receptor proteins that are distinct from TNFR-6 alpha and/or TNFR-6 beta. Thus, in another embodiment, TNFR-6 alpha and/or TNFR-6 beta is used to inhibit a biological activity of Fas ligand and/or AIM-II, in in vitro or in vivo procedures. By inhibiting binding of Fas ligand and/or AIM-II to cell surface receptors, TNFR-6 alpha and/or TNFR-6 beta polypeptides of the invention also inhibit biological effects that result from the binding of Fas ligand and/or AIM-II to endogenous receptors. Various forms of TNFR-6 alpha and/or TNFR-6 beta may be employed, including, for example, the above-described TNFR-6 alpha and/or TNFR-6 beta fragments, derivatives, and variants that are capable of binding Fas ligand and/or AIM-II. In a preferred embodiment, a soluble TNFR-6 alpha and/or TNFR-6 beta polypeptide of the invention is administered to inhibit a biological activity of Fas ligand and/or AIM-II, e.g., to inhibit Fas ligand-mediated and/or AIM-II-mediated apoptosis of cells susceptible to such apoptosis.

In a further embodiment, a TNFR-6 alpha and/or TNFR-6 beta polypeptide of the invention is administered to a mammal to treat a Fas ligand-mediated and/or AIM-II-mediated disorder. Such Fas ligand-mediated and/or AIM-II-mediated (e.g., a human) disorders include conditions caused (directly or indirectly) or exacerbated by Fas ligand and/or AIM-II.

There are numerous autoimmune diseases in which FasL/Fas interactions play a role. In patients experiencing GVHD, serum levels of FasL were abnormally high as was the number of FasL$^+$ T cells. The CNS plaques from patients with MS have been shown to express high levels of Fas and FasL. This is particularly significant since Fas and FasL expression is normally absent in the mature CNS. As with NOD mice, patients with IDDM have a superabundance of FasL$^+$ T cells associated with their islet cells. As evidence of FasL/Fas mediated cell killing, patients with chronic renal failure have been reported to have a 50 fold increase in the number of apoptotic nephrons compared to normal. This has been ascribed to renal tubule epithelial cell expression of both FasL and Fas, leading to cellular fratricide. In the joints of rheumatoid arthritic patients, activated T cells expressing FasL are seen in conjunction with Fas expressing chondrocytes. In ulcerative colitis (UC), Fas expression is observed on colonic epithelial cells, and FasL on lamina propria lymphocytes. This lead to the observation that FasL positive lymphocytes are present only in the lamina propria of UC patients with active lesions but not in tissues from inactive UC patients.

Two clinical indications in which the role of FasL-mediated killing is most apparent are myelodisplastic syndrome (MDS) and the neutropenia associated with large granular lymphocyte (LGL) leukemia. In MDS, bone marrow hematopoetic cells suffer an abnormally high level of apoptosis, associated with the upregulation of bone marrow Fas expression and lymphocyte FasL expression. The neutropenia seen in patients with LGL leukemia has been attributed to the high levels of circulating serum FasL. When leukemic LGL serum was incubated in vitro for 24 hours with normal neutrophils, the degree of apoptosis significantly increased above that of cells incubated with normal serum.

As described in detail in Example 22, below, TNFR6-Fc is a potent inhibitor FasL-mediated killing. Thus, the FasL-associated disorders listed above may be treated and/or prevented, in accordance with the invention, through administration of the TNFR6-containing polypeptides and polynucleotides described herein.

Suitable animal models for examining the effectiveness of TNFR6 in treating disease include but are not limited to mouse models of graft versus host disease (GVHD), murine allergic encephalomyelitis (EAE), an assay used as a central nervous system (CNS) model of multiple sclerosis (MS); non-obese diabetic (NOD) mouse model of insulin-dependant diabetes mellitus (IDDM), which is characterized by FasL$^+$ T cell destruction of islet cells, while Fas$^-$ NOD mice fail to develop diabetes. NOD mice can also be used to model Sjogren's disease, since apoptosis in the salivary and lacrimal glands of these mice has been reported. In a mouse model of chronic renal failure, ROP-Os/+ mice developed spontaneous tubular atrophy and renal failure correlated with upregulation of Fas and FasL in these tissues. The invention encompasses the treatment and prevention of the human diseases corresponding to these animal models, through administration of the TNFR6 polypeptides and polynucleotides of the present invention.

In addition, TNFR6 binds to LIGHT (TL3), a regulator of T cell function. As detailed in Example 23, below, TNFR6-Fc can ameliorate the effects of transplantation, including the inhibition of transplant or graft rejection and the inhibition of graft versus host disease (GVHD). The methods encompass the treatment of graft rejection or GVHD wherein the grafted tissue or organ is one or more of a variety of tissues and/or organs, including, but not limited to, heart, lung, kidney, liver, pancreas, islet cells, bone marrow, and skin. Such methods of preventing FasL-mediated killing or ameliorating the effects of transplantation may be carried out, in accordance with the present invention, using TNFR6-human serum albumin fusions, in lieu of Fc fusions.

Cells which express a TNFR polypeptide and have a potent cellular response to TNFR-6α and TNFR-6β ligands include lymphocytes, endothelial cells, keratinocytes, and prostate tissue. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Additionally, as described herein, TNFR polypeptides of the invention bind Fas ligand and AIM-II and consequently block Fas ligand and AIM-II mediated apoptosis. Apoptosis-programmed cell death is a physiological mechanism involved in the deletion of B and/or T lymphocytes of the immune system, and its disregulation can lead to a number of different pathogenic processes (J.C. Ameisen AIDS 8:1197-1213 (1994); P. H. Kramner et al., Curr. Opin. Immunol. 6:279-289 (1994)).

Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis (e.g., proliferative glomerulonephritis), autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. In preferred embodiments, TNFR polynucleotides, polypeptides, and/or antagonists of the invention are used to inhibit growth, progression, and/or metastasis of cancers, in particular those listed above.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis (e.g., proliferative glomerulonephritis), autoimmune gastritis, thrombocytopenic purpura, and rheumatoid arthritis) myelodysplastic syndromes (such as aplastic anemia), graft vs. host disease (acute and/or chronic), ischemic injury (such as ischemic cardiac injury and that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia. In preferred embodiments, TNFR polynucleotides, polypeptides and/or agonists are used to treat or prevent the diseases and disorders listed above.

In a specific embodiment, TNFR polynucleotides, polypeptides, or agonists of the invention are used to treat and/or prevent glomerulonephritis. In a further embodiment, TNFR polynucleotides, polypeptides, or agonists of the invention are used to treat and/or prevent chronic glomerulonephritis and/or cell/tissue damage (e.g., glomerular cell death) and/or medical conditions associated with this disease. In a further nonexclusive embodiment, TNFR polynucleotides, polypeptides, or agonists of the invention are used to treat and/or prevent proliferative glomerulonephritis and/or cell/tissue damage (e.g., glomerular cell death) and/or medical conditions associated with this disease.

In a specific embodiment, TNFR polynucleotides, polypeptides, or agonists of the invention are used treat or prevent biliary cirrhosis and/or medical conditions associated with this disease.

In a specific embodiment, TNFR polynucleotides, polypeptides, or agonists of the invention are used treat or prevent disease, such as, for example, alcoholic liver disease and/or medical conditions associated with this disease (e.g., cirrhosis).

In a specific embodiment, TNFR polynucleotides, polypeptides, or agonists of the invention are used to treat and/or prevent graft vs host disease. In a specific embodiment TNFR polynucleotides, polypeptides, or agonists of the invention are used to treat (e.g., reduce) or prevent tissue or cell damage or destruction (e.g., lymphoid cell depletion associated with graft vs host disease) and/or other medical conditions associated with this disease. In another non exclusive specific embodiment, the TNFR polynucleotides, polypeptides, or agonists of the invention are used to treat (e.g., reduce) and/or prevent diarrhea during graft vs host disease.

In a specific embodiment, TNFR polynucleotides, polypeptides, and/or agonists or antagonists of the invention are used to treat and/or prevent Sjogren's disease and/or to reduce tissue/cell damage or destruction (e.g., damage or destruction of salivary and/or lacrimal tissues) and/or other medical conditions associated with this disease.

In a specific embodiment, TNFR polynucleotides, polypeptides, or agonists of the invention are used to treat and/or prevent multiple sclerosis and/or to reduce tissue damage or destruction (such as, for example, neurological tissue (e.g., CNS tissue) damage or destruction) and/or lesions or other medical conditions associated with this disease.

In a specific embodiment, TNFR polynucleotides, polypeptides, or agonists, including antibody and antibody fragments, of the invention are used to treat and/or prevent Alzheimer's disease and/or to reduce tissue damage or destruction (e.g., damage or destruction of neurological tissue or cells) and/or medical conditions associated with this disease.

In a specific embodiment, TNFR polynucleotides, polypeptides, or agonists of the invention are used to treat, prevent Parkinson's disease and/or to reduce tissue damage or destruction (e.g., damage or destruction of neurological tissue or cells, such as, for example neuronal cells) and/or medical conditions associated with this disease.

In a specific embodiment, TNFR polynucleotides, polypeptides, or agonists of the invention are used before, during, immediately after, and/or after a stroke to treat, prevent, or reduce damage of cells or tissue (such as, for example, neurological tissue) and/or medical conditions associated with stroke.

In a specific embodiment, TNFR polynucleotides, polypeptides, or agonists of the invention are used to treat, prevent, or reduce ischemic injury (such as, for example, ischemic cardiac injury) and/or medical conditions associated with ischemic injury. In a specific embodiment, TNFR polynucleotides, polypeptides, or agonists of the invention are used before, during, immediately after, and/or after a heart attack to treat, prevent, or reduce ischemic cardiac injury.

In another specific embodiment, TNFR polynucleotides, polypeptides, and/or agonists of the invention are used to treat or prevent myelodysplastic syndromes (MDS) and/or medical conditions associated with MDS.

In another specific embodiment, TNFR polynucleotides, polypeptides, or agonists of the invention are used to increase circulating blood cell numbers in patients suffering from cytopenia, lymphopenia and/or anemia.

In a specific embodiment, TNFR polynucleotides, polypeptides, or agonists of the invention are used to treat and/or prevent Hashimoto's thyroiditis and/or to reduce destruction or damage of tissue or cells (e.g., thyroid gland) and/or to treat or prevent medical conditions associated with this disease.

In a specific embodiment, TNFR polynucleotides, polypeptides, or agonists of the invention are used to treat (e.g., reduce) and/or prevent autoimmune gastritis and/or medical conditions associated with this disease.

In a specific embodiment, TNFR polynucleotides, polypeptides, or agonists of the invention are used to treat and/or prevent ulcerative colitis and/or cell/tissue damage (e.g., ulceration in the colon) and/or medical conditions associated with this disease.

In a specific embodiment, TNFR polynucleotides, polypeptides, and/or agonists or antagonists of the invention are used to treat and/or prevent rheumatoid arthritis and/or medical conditions associated with this disease.

Additionally, a number of cancers secrete FasL which binds Fas positive T cells and kills them. Any cancer which expresses FasL could therefor be a target for treatment by TNFR and TNFR agonists of the invention. Such cancers include, but are not limited to, malignant myeloma, leukemia and lymphoma.

Many of the pathologies associated with HIV are mediated by apoptosis, including HIV-induced nephropathy and HIV encephalitis. Thus, in additional preferred embodiments, TNFR polynucleotides, polypeptides, and/or TNFR agonists of the invention are used to treat or prevent AIDS and pathologies associated with AIDS. Another embodiment of the present invention is directed to the use of TNFR-6 alpha and/or TNFR-6 beta (e.g., TR6-alpha- and/or TR6-beta-Fc or albumin fusion proteins) to reduce Fas ligand and/or AIM-II-mediated death of T cells in HIV-infected patients.

The state of Immunodificiency that defines AIDS is secondary to a decrease in the number and function of CD4$^+$ T-lymphocytes. Recent reports estimate the daily loss of CD4$^+$ T cells to be between $3.5 \times 10^7$ and $2 \times 10^9$ cells (Wei X., et al., Nature 373:117-122 (1995)). One cause of CD4$^+$ T cell depletion in the setting of HIV infection is believed to be HIV-induced apoptosis (see, for example, Meyaard et al., Science 257:217-219, (1992); Groux et al., J. Exp. Med., 175:331, (1992); and Oyaizu et al., in Cell Activation and Apoptosis in HIV Infection, Andrieu and Lu, Eds., Plenum Press, New York, 1995, pp. 101-114). Indeed, HIV-induced apoptotic cell death has been demonstrated not only in vitro but also, more importantly, in infected individuals (Ameisen, J. C., AIDS 8:1197-1213 (1994); Finkel, T. H., and Banda, N. K., Curr. Opin. Immunol. 6:605-615 (1995); Muro-Cacho, C. A. et al., J. Immunol. 154:5555-5566 (1995)). Furthermore, apoptosis and CD4$^+$ T-lymphocyte depletion is tightly correlated in different animal models of AIDS (Brunner, T., et at, Nature 373:441-444 (1995); Gougeon, M. L., et at, AIDS Res. Hum. Retroviruses 9:553-563 (1993)) and, apoptosis is not observed in those animal models in which viral replication does not result in AIDS (Gougeon, M. L. et at, AIDS Res. Hum. Retroviruses 9:553-563 (1993)). Further data indicates that uninfected but primed or activated T lymphocytes from HIV-infected individuals undergo apoptosis after encountering the Fas Ligand. Using monocytic cell lines that result in death following HIV infection, it has been demonstrated that infection of U937 cells with IV results in the de novo expression of Fas ligand and that Fas ligand mediates HIV-induced apoptosis (Badley, A. D. et al, J. Virol. 70:199-206 (1996)). Further the TNF-family ligand was detectable in uninfected macrophages and its expression was upregulated following HIV infection resulting in selective killing of uninfected CD4 T-lymphocytes (Badley, A. D et at, J. Virol 70:199-206 (1996)). Further, additional studies have implicated Fas-mediated apoptosis in loss of T cells in HIV individuals (Katsikis et al., *J. Exp. Med.* 181:2029-2036, 1995).

Thus, by the invention, a method for treating HIV+ individuals is provided which involves administering TNFR and/or TNFR agonists of the present invention to reduce selective killing of CD4 T-lymphocytes. Modes of administration and dosages are discussed in detail below.

It is also possible that T cell apoptosis occurs through multiple mechanisms. Further at least some of the T cell death seen in HIV patients may be mediated by AIM-II. While not wishing to be bound by theory, such Fas ligand and/or AIM-II-mediated T cell death is believed to occur through the mechanism known as activation-induced cell death (AICD).

Activated human T cells are induced to undergo programmed cell death (apoptosis) upon triggering through the CD3/T cell receptor complex, a process termed activated-induced cell death (AICD). AICD of CD4 T cells isolated from HIV-Infected asymptomatic individuals has been reported (Groux et al., supra). Thus, AICD may play a role in the depletion of CD4+ T cells and the progression to AIDS in HIV-infected individuals. Thus, the present invention provides a method of inhibiting Fas ligand-mediated and/or AIM-II-mediated T cell death in IV patients, comprising administering a TNFR-6 alpha and/or TNFR-6 beta polypeptide of the invention to the patients. In one embodiment, the patient is asymptomatic when treatment with TNFR-6 alpha and/or TNFR-6 beta commences. If desired, prior to treatment, peripheral blood T cells may be extracted from an HIV patient, and tested for susceptibility to Fas ligand-mediated and/or AIM-II-mediated cell death by conventional procedures. In one embodiment, a patient's blood or plasma is contacted with TNFR-6 alpha and/or TNFR-6 beta ex vivo. The TNFR-6 alpha and/or TNFR-6 beta may be bound to a suitable chromatography matrix known in the art by conventional procedures. The patient's blood or plasma flows through a chromatography column containing TNFR-6 alpha and/or TNFR-6 beta polypeptides of the invention bound to the matrix, before being returned to the patient. The immobilized TNFR-6 alpha and/or TNFR-6 beta binds Fas ligand and/or AIM-II, thus removing Fas ligand and/or AIM-II protein from the patient's blood.

In additional embodiments a TNFR-6 alpha and/or TNFR-6 beta polypeptide of the invention may be administered in combination with other inhibitors of T cell apoptosis. For example, at least some of the T cell death seen in HIV patients is believed to be mediated by TRAIL (International application publication number WO 97/01633 hereby incorporated by reference). Thus, for example, a patient susceptible to both Fas ligand mediated and TRAIL mediated T cell death may be treated with both an agent that blocks TRAIL/TRAIL-receptor interactions and an agent that blocks Fas-ligand/Fas interactions. Suitable agents that may be administered with the polynucleotides and/or polypeptides of the invention to block binding of TRAIL to TRAIL receptors include, but are not limited to, soluble TRAIL receptor polypeptides (e.g., a soluble form of OPG, DR4 (International application publication number WO 98/32856); TR5 (International application publication number WO 98/30693); DR5 (International application publication number WO 98/41629); TR10 (International application publication number WO 98/54202)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

Suitable agents, which also block binding of Fas-ligand to Fas that may be administered with the polynucleotides and polypeptides of the present invention include, but are not limited to, soluble Fas polypeptides; multimeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Examples of suitable agents for blocking Fas-L/Fas interactions, including blocking anti-Fas monoclonal antibodies, are described in International application publication number WO 95/10540, hereby incorporated by reference.

Suitable agents that may be administered with the polynucleotides and/or polypeptides of the invention to block binding of AIM-II to AIM-II receptors include, but are not limited to, soluble AIM-II receptor polypeptides (e.g., a soluble form of TR2 (International application publication number WO 96/34095); LT beta receptor; and TR8 (International application publication number WO 98/54201)); multimeric forms of soluble AIM-II receptor polypeptides; and AIM-II receptor antibodies that bind the AIM-II receptor without transducing the biological signal that results in apoptosis, anti-AIM-II antibodies that block binding of AIM-II to one or more AIM-II receptors, and muteins of AIM-II that bind AIM-II receptors but do not transduce the biological signal that results in apoptosis. Preferably, the antibodies employed according to this method are monoclonal antibodies.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence the immune system is already at the effector stage. Antagonists of the present invention are able to suppress the immune response to both allografts and xenografts because lymphocytes activated and differentiated into effector cells will express the TNFR polypeptide, and thereby are susceptible to compounds which enhance TNFR activity. Thus, the present invention further provides a method for creating immune privileged tissues. Antagonist of the invention can further be used in the treatment of Inflammatory Bowel-Disease.

TNFR polynucleotides, polypeptides, and agonists of the invention may also be used to suppress immune responses. In one embodiment, the TNFR polynucleotides, polypeptides, and agonists of the invention are used to minimize untoward effects associated with transplantation. In a specific embodiment, the TNFR polynucleotides, polypeptides, and agonists of the invention are used to suppress Fas mediated immune responses (e.g., in a manner similar to an immunosuppressant such as, for example, rapamycin or cyclosporin). In another specific embodiment, the TNFR polynucleotides, polypeptides, and agonists of the invention are used to suppress AIM-II mediated immune responses.

Additionally, both graft rejection and graft vs. host disease are in part triggered by apoptosis. Accordingly, an additional preferred embodiment, TNFR polynucleotides, polypeptides, and/or TNFR agonists of the invention are used to treat and prevent and/or reduce graft rejection. In a further preferred embodiment, TNFR polynucleotides, polypeptides, and/or TNFR agonists of the invention are used to treat and prevent and/or reduce graft vs. host disease.

Additionally, TNFR-6 alpha and/or TNFR-6 beta polypeptides, polynucleotides, and/or agonists may be used to treat or prevent graft rejection (e.g., xenograft and allograft rejection (e.g, acute allograft rejection)) and/or medical conditions associated with graft rejection. In a specific embodiment, TNFR-6 alpha and/or TNFR-6 beta polypeptides, polynucleotides, and/or agonists of the invention are used to treat or prevent acute allograft rejection and/or medical conditions associated with acute allograft rejection. In a further specific embodiment, TNFR-6 alpha and/or TNFR-6 beta polypeptides, polynucleotides, and/or agonists of the invention are used to treat or prevent acute allograft rejection of a kidney and/or medical conditions associated with acute allograft rejection of a kidney.

Fas ligand is a type II membrane protein that induces apoptosis by binding to Fas. Fas ligand is expressed in activated T cells, and works as an effector of cytotoxic lymphocytes. Molecular and genetic analysis of Fas and Fas ligand have indicated that mouse lymphoproliferation mutation (lpr) and generalized lymphoproliferative disease (gld) are mutations of Fas and Fas ligand respectively. The lpr of gld mice develop lymphadenopathy, and suffer from autoimmune disease. Based on these phenotypes and other studies, it is believed that the Fas system is involved in the apoptotic process during T-cell development, specifically peripheral clonal deletion or activation-induced suicide of mature T cells. In addition to the activated lymphocytes, Fas is expressed in the liver, heart and lung. Administration of agonistic anti-Fas antibody into mice has been shown to induce apoptosis in the liver and to quickly kill the mice, causing liver damage. These findings indicate that the Fas system plays a role not only in the physiological process of lymphocyte development, but also in the cytotoxic T-lymphocyte-mediated disease such as fulminant hepatitis and/or hepatitis resulting from viral infection or toxic agents. As discussed herein, TNFR-6 alpha and/or TNFR-6 beta binds Fas ligand, and thus functions as an antagonist of Fas-ligand mediated activity. Accordingly, the TNFR-6 alpha and/or TNFR-6 beta polypeptides and/or polynucleotides of the invention, and/or agonists thereof, may be used to treat or prevent lymphoproliferative disorders (e.g., lymphadenopathy and others described herein), autoimmune disorders (e.g., autoimmune diabetes, systemic lupus erythematosus, Grave's disease, Hashimoto's thyroiditis, immune-related glomerulonephritis, autoimmune gastritis, autoimmune thrombocytopenic purpura, multiple sclerosis, rheumatoid arthritis, and others described herein), and/or liver disease (e.g., acute and chronic hepatitis, and cirrhosis).

In a specific embodiment, TNFR polynucleotides, polypeptides, and/or agonists of the invention are used to treat or prevent hepatitis and/or tissue/cell damage or destruction and/or medical conditions associated with hepatitis. In a specific embodiment TNFR polynucleotides, polypeptides, and/or agonists of the invention are used to treat or prevent fulminant hepatitis and/or medical conditions associated with fulminant hepatitis.

In a specific embodiment, TNFR polynucleotides, polypeptides, and/or agonists of the invention are used to treat or prevent systemic lupus erythematosus (SLE) and/or tissue/cell damage or destruction and/or medical conditions associated with SLE. In a further specific embodiment, TNFR polynucleotides, polypeptides, and/or agonists of the invention are used to treat or prevent skin lesions in SLE patients.

In a specific embodiment, TNFR polynucleotides, polypeptides, and/or agonists of the invention are used to treat or prevent insulin-dependent diabetes mellitus and/or tissue/cell damage or destruction and/or medical conditions associated with insulin-dependent diabetes mellitus. In a further specific embodiment, TNFR polynucleotides, polypeptides, and/or agonists of the invention are prior to, during, or immediately after the onset of diabetes to reduce or prevent damage to islet cells and/or to reduce exogenous insulin requirement.

In a specific embodiment TNFR polynucleotides, polypeptides, and/or agonists of the invention are used to treat or prevent toxic epidermal necrolysis (TEN) and/or tissue/cell damage or destruction, and/or medical conditions associated with TEN. In a further specific embodiment, TNFR polynucleotides, polypeptides, and/or agonists of the invention are used to treat or prevent Lyell's syndrome.

Hepatitis virus (e.g., Hepatitis B virus and Hepatitis C virus) is a major causative agent of chronic liver disease. In Hepatitis infection, Fas expression in hepatocytes is up-regulated in accordance with the severity of liver inflammation. When Hepatitis virus-specific T cells migrate into hepatocytes and recognize the viral antigen via the T cell receptor, they become activated and express Fas ligand that can transduce the apoptotic death signal to Fas-bearing hepatocytes. Thus, the Fas system plays an important role in liver cell injury by viral hepatitis. Accordingly, in specific embodiments, the TNFR-6 alpha and/or TNFR-6 beta polypeptides and/or polynucleotides of the invention and/or agonists or antagonists thereof, are used to treat or prevent hepatitis resulting from viral infection (e.g., infection resulting form Hepatitis B virus or Hepatitis C virus infection). In one embodiment, a patient's blood or plasma is contacted with TNFR-6 alpha and/or TNFR-6 beta polypeptides of the invention ex vivo. The TNFR-6 alpha and/or TNFR-6 beta may be bound to a suitable chromatography matrix by conventional procedures. According to this embodiment, the patient's blood or plasma flows through a chromatography column containing TNFR-6 alpha and/or TNFR-6 beta bound to the matrix, before being returned to the patient. The immobilized TNFR-6 alpha and/or TNFR-6 beta binds Fas-ligand, thus removing Fas-ligand protein from the patient's blood.

In a specific embodiment, TNFR-6 alpha and/or TNFR-6 beta polypeptides, polynucleotides, and/or agonists or antagonists of the invention may be used to treat or prevent renal failure (e.g., chronic renal failure), and/or tissue/cell damage or destruction (e.g., tubular epithelial cell deletion) and/or medical conditions associated with renal failure.

In a specific embodiment, TNFR-6 alpha and/or TNFR-6 beta polypeptides, polynucleotides, and/or agonists or antagonists of the invention may be used to regulate (i.e., stimulate or inhibit) bone growth. In specific embodiments TNFR-6 alpha and/or TNFR-6 beta polypeptides, polynucleotides, and/or agonists or antagonists of the invention are used to stimulate bone growth. Specific diseases or conditions that may be treated or prevented with the compositions of the invention include, but are not limited to, bone fractures, and defects, and disorders which result in weakened bones such as osteoporosis, osteomalacia, and age-related loss of bone mass.

TNFR-6 alpha and/or TNFR-6 beta polypeptides or polynucleotides encoding TNFR-6 alpha and/or TNFR-6 beta of the invention, and/or agonists or antagonists thereof may be used to treat or prevent cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as atherosclerosis, arrhythmias, carcinoid heart disease, high cardiac output, low cardiac output, cardiac tamponade, endocarditis (including bacterial), heart aneurysm, cardiac arrest, congestive heart failure (e.g., chronic congestive heart failure), congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary fibrosis, pulmonary heart disease, rheumatic heart disease, ventricular dysfunction, hyperemia, cardiovascular pregnancy complications, Scimitar Syndrome, cardiovascular syphilis, and cardiovascular tuberculosis.

In a specific embodiment, TNFR-6 alpha and/or TNFR-6 beta polynucleotides, polypeptides, or agonists of the invention may be used to treat and/or prevent chronic congestive heart failure and/or medical conditions associated chronic congestive heart failure.

In another specific embodiment, TNFR-6 alpha and/or TNFR-6 beta polynucleotides, polypeptides, or agonists of the invention may be used to treat and/or prevent pulmonary injury or disease (e.g., pulmonary fibrosis and chronic obstructive pulmonary diseases, such as, for example, emphysema and chronic bronchitis), and/or tissue/cell damage or destruction (e.g., alveolar wall and/or bronchiolar wall destruction) and/or medical conditions associated with pulmonary injury or disease.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thromboses include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, TNFR-6 alpha and/or TNFR-6 beta polypeptides, polynucleotides and/or agonists or antagonists of the invention are used to treat or prevent thrombotic microangiopathies. One such disorder is thrombotic thrombocytopenic purpura (TTP) (Kwaan, H. C., *Semin. Hematol.* 24:71 (1987); Thompson et al., Blood 80:1890 (1992)). Increasing TTP-associated mortality rates have been reported by the U.S. Centers for Disease Control (Torok et al., *Am. J.*

*Hematol.* 50:84 (1995)). Plasma from patients afflicted with TTP (including HIV+ and HIV- patients) induces apoptosis of human endothelial cells of dermal microvascular origin, but not large vessel origin (Laurence et al., *Blood* 87:3245 (1996)). Plasma of TTP patients thus is thought to contain one or more factors that directly or indirectly induce apoptosis. An anti-Fas blocking antibody has been shown to reduce TTP plasma-mediated apoptosis of microvascular endothelial cells (Lawrence et al, *Blood* 87:3245 (1996); hereby incorporated by reference). Accordingly, Fas ligand present in the serum of TTP patients is likely to play a role in inducing apoptosis of microvascular endothelial cells. Another thrombotic microangiopathy is hemolytic-uremic syndrome (HUS) (Moake, J. L., *Lancet*, 343:393, (1994); Melnyk et al., (*Arch. Intern. Med.*, 155:2077, (1995); Thompson et al., supra). Thus, in one embodiment, the invention is directed to use of TNFR-6 alpha and/or TNFR-6 beta to treat or prevent the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated using TNFR-6 alpha and/or TNFR-6 beta polypeptides and/or polynucleotides of the invention. Such conditions include, but are not limited to, those described herein. For example, cardiac problems seen in about 5-10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated. In one embodiment, a patient's blood or plasma is contacted with TNFR-6 alpha and/or TNFR-6 beta polypeptides of the invention ex vivo. The TNFR-6 alpha and/or TNFR-6 beta may be bound to a suitable chromatography matrix using techniques known in the art. According to this embodiment, the patient's blood or plasma flows through a chromatography column containing TNFR-6 alpha and/or TNFR-6 beta bound to the matrix, before being returned to the patient. The immobilized TNFR-6 alpha and/or TNFR-6 beta binds Fas ligand and/or AIM-II, thus removing Fas ligand protein from the patient's blood. Alternatively, TNFR-6 alpha and/or TNFR-6 beta may be administered in vivo to a patient afflicted with a thrombotic microangiopathy. In one embodiment, a TNFR-6 alpha and/or TNFR-6 beta polynucleotide or polypeptide of the invention is administered to the patient. Thus, the present invention provides a method for treating a thrombotic microangiopathy, involving use of an effective amount of a TNFR-6 alpha and/or TNFR-6 beta polypeptide of the invention. A TNFR-6 alpha and/or TNFR-6 beta polypeptide may be employed in in vivo or ex vivo procedures, to inhibit Fas ligand-mediated and/or AIM-II-mediated damage to (e.g., apoptosis of) microvascular endothelial cells.

TNFR-6 alpha and/or TNFR-6 beta polypeptides and polynucleotides of the invention may be employed in conjunction with other agents useful in treating a particular disorder. For example, in an in vitro study reported by Laurence et al. (*Blood* 87:3245, 1996), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated in combination with an additional agent that inhibits Fas-ligand-mediated apoptosis of endothelial cells such as, for example, an agent described above. In one embodiment, TNFR-6 alpha and/or TNFR-6 beta polypeptides of the invention and an anti-FAS blocking antibody are administered to a patient afflicted with a disorder characterized by thrombotic microangiopathy, such as TTP or HUS. Examples of blocking monoclonal antibodies directed against Fas antigen (CD95) are described in International Application publication number WO 95/10540, hereby incorporated by reference.

The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.*, 333:1757-1763 (1995); Auerbach et al., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment of diseases or disorders associated with neovascularization by administration of the TNFR-6 alpha and/or TNFR-6 beta polynucleotides and/or polypeptides of the invention. Malignant and metastatic conditions which can be treated with the polynucleotides and polypeptides of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)):

Ocular disorders associated with neovascularization which can be treated with the TNFR-6 alpha and/or TNFR-6 beta polynucleotides and polypeptides of the present invention (including TNFR agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

In another embodiment, TNFR-6 alpha and/or TNFR-6 beta polypeptides, polynucleotides and/or agonists or antagonists of the invention are used to stimulate differentiation and/or survival of photoreceptor cells and/or to treat or prevent diseases, disorders, or conditions associated with decreased number, differentiation and/or survival of photoreceptor cells.

Additionally, disorders which can be treated with the TNFR-6 alpha and/or TNFR-6 beta polynucleotides and polypeptides of the present invention (including TNFR agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

In additional embodiments, TNFR-6 alpha and/or TNFR-6 beta polynucleotides, polynucleotides and/or other compositions of the invention (e.g., TNFR-6 alpha and/or TNFR-6 beta Fc- or albumin-fusion proteins or anti-TNFR-6 alpha and/or anti-TNFR-6 beta antibodies) are used to treat or prevent diseases or conditions associated with allergy and/or inflammation.

As demonstrated in Example 24 below, it has been shown that TR6-alpha and TR6-beta interact with TNF-gamma-beta, a TNF ligand family member described in detail in International Publication Numbers WO96/14328, WO00/66608, and WO00/08139. TNF-gamma-beta is a proinflammatory molecule as evidenced by its ability to induce T cell proliferation and secretion of Interferon-gamma and GM-CSF by T cells. TNF-gamma-beta is also able to enhance an in vivo mixed lymphocyte reaction (MLR) as measured by the parent-into-F1 model of acute graft vs. host disease in which C57BL/6 splenic T cells are transferred into (BALB/c× C57BL/6) F1 mice. Thus, the ability of TNFR-6 alpha to bind TNF-gamma-beta and to prevent TNF-gamma-beta induced activities (see Example 24) suggests that TNFR-6 alpha and or TNF-6beta polynucleotides and polypeptides are useful as inhibitors of TNF-gamma-beta function.

In specific embodiments, TNFR-6 alpha and/or TNFR-6 beta polynucleotides and polypeptides and fragments or variants thereof (e.g. soluble forms of TNFR-6 alpha such as TNFR-6 alpha Fc fusion proteins or TNFR-6 alpha albumin fusion proteins) are useful for the prevention, diagnosis and treatment of inflammation and/or inflammatory diseases and disorders. In particular embodiments, the present invention provides a method of diagnosing, diagnosing, treating, preventing or ameliorating inflammatory diseases or disorders comprising or alternatively consisting of, administering to an animal, preferably a human, in which such treatment, prevention or amelioration is desired, a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) in an amount effective to treat prevent or ameliorate the inflammatory disease or disorder. In specific embodiments, the inflammatory disease or disorder is inflammatory bowel disease. In specific embodiments, the inflammatory disease or disorder is encephalitis. In specific embodiments, the inflammatory disease or disorder is atherosclerosis. In specific embodiments, the inflammatory disease or disorder is psoriasis. The present invention further provides compositions comprising the TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) and a carrier for use in the above-described method of diagnosing, treating, preventing or ameliorating inflammatory diseases and disorders.

In specific embodiments, the present invention provides a method of diagnosing, treating, preventing or ameliorating inflammation comprising or alternatively consisting of, administering to an animal, preferably a human, in which such treatment, prevention or amelioration is desired, a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) in an amount effective to treat prevent or ameliorate the inflammation. The present invention further provides compositions comprising a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) and a carrier for use in the above-described method of diagnosing, treating, preventing or ameliorating inflammation.

In specific embodiments, the present invention provides a method of diagnosing, treating, preventing or ameliorating graft versus host disease (GVHD) comprising or alternatively consisting of, administering to an animal, preferably a human, in which such treatment, prevention or amelioration is desired, a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) in an amount effective to treat prevent or ameliorate the GVHD. The present invention further provides compositions comprising a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) and a carrier for use in the above-described method of diagnosing, treating, preventing or ameliorating GVHD.

In other embodiments, the present invention provides a method of diagnosing, treating, preventing or ameliorating autoimmune diseases and disorders comprising or alternatively consisting of, administering to an animal, preferably a human, in which such treatment, prevention or amelioration is desired, a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) in an amount effective to treat prevent or ameliorate the autoimmune disease or disorder. In specific embodiments, the autoimmune disease or disorder is systemic lupus erythematosus. In specific embodiments, the autoimmune disease or disorder is arthritis, particularly rheumatoid arthritis. In specific embodiments, the autoimmune disease or disorder is multiple sclerosis. In specific embodiments, the autoimmune disease or disorder is Crohn's disease. In specific embodiments, the autoimmune disease or disorder is autoimmune encephalitis. The present invention further provides compositions comprising a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) and a carrier for use in the above-described method of diagnosing, treating, preventing or ameliorating autoimmune diseases and disorders.

In specific embodiments, the present invention provides a method of diagnosing, treating, preventing or ameliorating allergy or asthma comprising or alternatively consisting of, administering to an animal, preferably a human, in which such treatment, prevention or amelioration is desired, a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) or fragment or variant thereof in an amount effective to treat prevent or ameliorate the allergy or asthma. The present invention further provides compositions comprising a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) and a carrier for use in the above-described method of diagnosing, treating, preventing or ameliorating allergy or asthma.

The present invention further encompasses methods and compositions for reducing T cell activation, comprising, or alternatively consisting of, contacting an effective amount of a TNFR-6 alpha and/or TNFR-6 beta polypeptide or a fragment or variant thereof (e.g. soluble forms of TNFR-6 alpha and/or TNFR-6 beta such as a TNFR-6 alpha and/or TNFR-6 beta Fc- or albumin-fusion protein) with cells of hematopoietic origin, wherein the effective amount of the TNFR-6 alpha and/or TNFR-6 beta polypeptide or a fragment or variant thereof (e.g. soluble forms of TNFR-6 alpha and/or TNFR-6 beta such as a TNFR-6 alpha and/or TNFR-6 beta Fc- or albumin-fusion protein) reduces T cell activation. In preferred embodiments, the cells of hematopoietic origin are T cells. In other preferred embodiments, the effective amount of a TNFR-6 alpha and/or TNFR-6 beta polypeptide or a fragment or variant thereof (e.g. soluble forms of TNFR-6 alpha and/or TNFR-6 beta such as a TNFR-6 alpha and/or TNFR-6 beta Fc- or albumin-fusion protein) reduces TNF-gamma-alpha and/or TNF-gamma beta induced T cell activation.

The present invention further encompasses methods and compositions for reducing T cell activation comprising, or alternatively consisting of, administering to an animal, preferably a human, in which such reduction is desired, a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) or fragment or variant thereof in an amount effective to reduce T cell activation. The present invention further provides compositions comprising a TNFR-6 alpha and/or TNFR-6 beta polynucleotide or polypeptide or a fragment or variant thereof (e.g. soluble forms of TNFR-6 alpha and/or TNFR-6 beta such as a TNFR-6 alpha and/or TNFR-6 beta Fc- or albumin-fusion protein) and a carrier for use in the above-described method of reducing T cell activation.

In a specific embodiment TNFR polynucleotides, polypeptides and/or agonists or antagonists thereof may be used to treat or prevent thyroid-associated opthalmopathy and/or tissue/cell damage or destruction, and/or medical conditions associated with thyroid-associated opthalmopathy.

In a specific embodiment, TNFR polynucleotides, polypeptides, or agonists of the invention are used to prolong protein expression after gene therapy by inhibiting or reducing elimination of transgene expressing cells.

In further embodiments, the TNFR-6 alpha and/or TNFR-6 beta polynucleotides and/or polynucleotides, and/or agonists or antagonists thereof, are used to promote wound healing.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.))), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, regulating hematopoiesis and wound healing (e.g., wounds, burns, and bone fractures).

Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

In one aspect, the present invention is directed to a method for enhancing apoptosis induced by a TNF-family ligand, which involves administering to a patient (preferably a human) a TNFR antagonists (e.g., an anti-TNFR antibody or TNFR polypeptide fragment). Preferably, the TNFR antagonist is administered to treat a disease or condition wherein increased cell survival is exhibited. Antagonists of the invention include soluble forms of TNFR and monoclonal antibodies directed against the TNFR polypeptide.

By "antagonist" is intended naturally occurring and synthetic compounds capable of enhancing or potentiating apoptosis. By "agonist" is intended naturally occurring and synthetic compounds capable of inhibiting apoptosis. Whether any candidate "agonist" or "antagonist" of the present invention can inhibit or enhance apoptosis can be determined using art-known TNF-family ligand/receptor cellular response assays, including those described in more detail below.

One such screening procedure involves the use of melanophores which are transfected to express the receptor of the present invention. Such a screening technique is described in International application publication number WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246: 181-296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus oocytes* to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia, L. A., and Goeddel, D. V., *J. Biol. Chem.* 267(7):4304-4307 (1992).

Thus, in a further aspect, a screening method is provided for determining whether a candidate agonist or antagonist is capable of enhancing or inhibiting a cellular response to a TNF-family ligand. The method involves contacting cells which express the TNFR polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TNFR polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457-1458 (1995)). Further preferred agonists include polyclonal and monoclonal antibodies raised against the TNFR polypeptide, or a fragment thereof. Such agonist antibodies raised against a TNF-family receptor are disclosed in Tartaglia, L. A., et al., *Proc. Natl. Acad. Sci. USA* 88:9292-9296 (1991); and Tartaglia, L. A., and Goeddel, D. V., *J. Biol. Chem.* 267 (7):4304-4307 (1992) See, also, International application publication number WO 94/09137.

Antagonists according to the present invention include naturally occurring and synthetic compounds such as, for example, the CD40 ligand, neutral amino acids, zinc, estrogen, androgens, viral genes (such as Adenovirus ElB, Baculovirus p35 and M4P, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and -Hexachlorocyclohexane). Other antagonists include polyclonal and monoclonal antagonist antibodies raised against the TNFR polypeptides or a fragment thereof. Such antagonist antibodies raised against a TNF-family receptor are described in Tartaglia, L. A., and Goeddel, D. V., *J. Biol. Chem.* 267(7):4304-4307 (1992) and Tartaglia, L. A. et al., *Cell* 73:213-216 (1993). See, also, International application publication number WO 94/09137.

In specific embodiments, antagonists according to the present invention are nucleic acids corresponding to the sequences contained in TNFR, or the complementary strand thereof, and/or to nucleotide sequences contained in the deposited clones (ATCC™ Deposit Nos. 97810 and 97809). In one embodiment, antisense sequence is generated internally by the organism, in another embodiment, the antisense sequence is separately administered (see, for example, O'Connor, J., *Neurochem.* 56:560 (1991) and Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., *Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the TNFR antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TNFR antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TNFR, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., *Cell* 22:787-797 (1980), the herpes thymidine promoter (Wagner et al., *Proc. Natl. Acad. Sci. U.S.A.* 78:1441-1445 (1981), the regulatory sequences of the metallothionein gene (Brinster, et al., *Nature* 296:39-42 (1982)), etc.

The antisense nucleic acids of the invention comprise a sequence complementary to at least a portion of an RNA transcript of a TNFR gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TNFR antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TNFR RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions of the TNFR shown in FIGS. 1 and 2A-B could be used in an antisense approach to inhibit translation of endogenous TNFR mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TNFR mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625-6641 (1987)). The oligonucleotide is a 2¢-0-methylribonucleotide (Inoue et al., *Nucl. Acids Res.* 15:6131-6148 (1987)), or a chimeric RNA-DNA analogue (Inoue et al., *FEBS Lett.* 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448-7451 (1988)), etc.

While antisense nucleotides complementary to the TNFR coding region sequence could be used, those complementary to the transcribed untranslated region are most preferred.

Potential antagonists according to the invention also include catalytic RNA, or a ribozyme (See, e.g., International application publication number WO 90/11364, published Oct. 4, 1990; Sarver et al, *Science* 247:1222-1225 (1990). While ribozymes that cleave mRNA at site specific recognition sequences can be used to destroy TNFR mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). There are numerous potential hammerhead ribozyme cleavage sites within the nucleotide sequence of TNFR-6α (FIG. 1, SEQ ID NO: 1) and TNFR-6β (FIGS. 2A-B, SEQ ID NO:3). Preferably, the ribozyme is engineered so that the cleavage recognition site is located near the 5' end of the TNFR mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express TNFR in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TNFR messages and inhibit translation. Since ribozymes unlike antisense molecules, are catalytic, a lower intracellular concentration is required for efficiency.

Endogenous gene expression can also be reduced by inactivating or "knocking out" the TNFR gene and/or its promoter using targeted homologous recombination. (E.g., see Smithies et al., *Nature* 317:230-234 (1985); Thomas & Capecchi, *Cell* 51:503-512 (1987); Thompson et al., *Cell* 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

Antibodies according to the present invention may be prepared by any of a variety of standard methods using TNFR immunogens of the present invention. Such TNFR immunogens include the TNFR protein shown in FIGS. 1 and 2A-B (SEQ ID NO:2 and SEQ ID NO:4, respectively) (which may or may not include a leader sequence) and polypeptide fragments of TNFR comprising the ligand binding and/or extracellular domains of TNFR.

Polyclonal and monoclonal antibody agonists or antagonists according to the present invention can be raised according to the methods disclosed herein and/or known in the art, such as, for example, those methods described in Tartaglia and Goeddel, *J. Biol. Chem.* 267(7):4304-4307 (1992); Tartaglia et al., *Cell* 73:213-216 (1993), and International application publication number WO 94/09137 (the contents of each of these three applications are herein incorporated by reference in their entireties), and are preferably specific to polypeptides of the invention having the amino acid sequence of SEQ ID NO:2 and/or SEQ ID NO:4. Antibodies according to the present invention may be prepared by any of a variety of methods described herein, and known in the art.

Further antagonist according to the present invention include soluble forms of TNFR, e.g., TNFR fragments that include the ligand binding domain from the extracellular region of the full length receptor. Such soluble forms of the receptor, which may be naturally occurring or synthetic, antagonize TNFR mediated signaling by competing with the cell surface TNFR for binding to TNF-family ligands and/or antagonize TNFR mediated inhibition of apoptosis by, for example, disrupting the ability of TNFR to multimerize and/or to bind to and thereby neutralize apoptosis inducing ligands, such as, for example, Fas ligand and AIM-II. Thus, soluble forms of the receptor that include the ligand binding domain are novel cytokines capable of reducing TNFR-mediated inhibition of tumor necrosis induced by TNF-family ligands. Other such cytokines are known in the art and include Fas B (a soluble form of the mouse Fas receptor) that acts physiologically to limit apoptosis induced by Fas ligand (Hughes, D. P. and Crispe, I. N., *J. Exp. Med.* 182:1395-1401 (1995)).

Proteins and other compounds which bind the extracellular domains are also candidate agonist and antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, J. et al., *Cell* 75:791-803 (1993); Zervos, A. S. et al, *Cell* 72:223-232 (1993)).

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, the TNFR-6α & -6β ligands, TNF-α, lymphotoxin-α (LT-α, also known as TNF-β), LT-β, FasL, CD40, CD27, CD30, 4-IBB, OX40, TRAIL, AIM-II, and nerve growth factor (NGF).

Formulation and Administration

The TNFR polypeptide composition will be formulated and dosed in a fashion consistent with good medical practice, taking into account the clinical condition of the individual patient (especially the side effects of treatment with TNFR-6α or -6β polypeptide alone), the site of delivery of the TNFR polypeptide composition, the method of administration, the scheduling of administration, and other factors known to practitioners. The "effective amount" of TNFR polypeptide for purposes herein is thus determined by such considerations.

As a general proposition, the total pharmaceutically effective amount of TNFR polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TNFR polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to TNFR-6α or -6β polypeptide during therapy may also play an important role in determining a therapeutically and/or pharmacologically effective dosing regime. Variations of dosing such as repeated administrations of a relatively low dose of TNFR-6α or -6β polypeptide for a relatively long period of time may have an effect which is therapeutically and/or pharmacologically distinguishable from that achieved with repeated administrations of a relatively high dose of TNFR-6α or -6β polypeptide for a relatively short period of time.

Using the equivalent surface area dosage conversion factors supplied by Freireich, E. J., et al. (*Cancer Chemotherapy Reports* 50(4):219-44 (1966)), one of ordinary skill in the art is able to conveniently convert data obtained from the use of TNFR-6α or -6β polypeptide in a given experimental system into an accurate estimation of a pharmaceutically effective amount of TNFR-6α or -6β polypeptide to be administered per dose in another experimental system. Experimental data obtained through the administration of TNFR6-Fc in mice (see, for instance, Example 21) may converted through the conversion factors supplied by Freireich, et al., to accurate estimates of pharmaceutically effective doses of TNFR-6 in rat, monkey, dog, and human. The following conversion table (Table IV) is a summary of the data provided by Freireich, et al. Table IV gives approximate factors for converting doses expressed in terms of mg/kg from one species to an equivalent surface area dose expressed as mg/kg in another species tabulated.

TABLE IV

Equivalent Surface Area Dosage Conversion Factors.

| FROM | TO | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Human | 12 | 7 | 3 | 2 | 1 |

Thus, for example, using the conversion factors provided in Table IV, a dose of 50 mg/kg in the mouse converts to an appropriate dose of 12.5 mg/kg in the monkey because (50 mg/kg)×(1/4)=12.45 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

TNFR-6 alpha and/or TNFR-6 beta polypeptides of the invention may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. TNFR-6 alpha and/or TNFR-6 polypeptides of the invention may be administered as part of a pharmaceutical composition, described in more detail below. Methods of delivering TNFR-6 alpha and/or TNFR-6 beta polynucleotides of the invention are known in the art and described in more detail herein.

Pharmaceutical compositions containing the TNFR of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The term "parenteral" as used herein refers to modes of administration which include intravenous, intramuscular, intraperitoneal, intrasternal, subcutaneous and intraarticular injection and infusion.

The TNFR polypeptide is also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly (2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(–)-3-hydroxybutyric acid (EP 133,988).

In a preferred embodiment, compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific preferred embodiments the compositions of the invention are formulated using the ATRIGEL® Biodegradable System of Atrix Laboratories, Inc. (Fort Collins, Colo.).

Examples of biodegradable polymers which can be used in the formulation of compositions of the invention include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of compositions of the invention are poly (lactide-co-glycolides). Polymer properties such as molecular weight, hydrophobicity, and lactide/glycolide ratio may be modified to obtain the desired drug release profile (See, e.g., Ravivarapu et al., Journal of Pharmaceutical Sciences 89:732-741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alchohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alcohol, benzyl benzoate, dipropylene glycol, tributyrin, ethyl oleate, glycerin, glycofurol, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising compositions of the invention and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C.sub.6-C.sub.12 alkanols, 2-ethoxyethanol, and the like. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the compositions of the invention are formulated using the BEMA™ BioErodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.). In other specific embodiments, compositions of the invention are formulated using the ProLease® sustained release system available from Alkermes, Inc. (Cambridge, Mass.).

Sustained-release compositions also include liposomally entrapped compositions of the invention (see generally, Langer, *Science* 249:1527-1533 (1990); Treat et al., in *Liposomes in the Therapy of Infectious Disease and Cancer*, Lopez-Berestein and Fidler (eds.), Liss, New York, pp. 317-327 and 353-365 (1989)). Liposomes containing TNFR polypeptides my be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal TNFR polypeptide therapy.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527-1533 (1990)).

For parenteral administration, in one embodiment, the TNFR polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TNFR polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The TNFR polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of TNFR polypeptide salts.

TNFR polypeptides to be used for therapeutic administration must be sterile. Sterility is readily accomplished by filtration through sterile filtration membranes (e.g., 0.2 micron membranes). Therapeutic TNFR polypeptide compositions generally are placed into a container having a sterile access port, for example, an intravenous solution bag or vial having a stopper pierceable by a hypodermic injection needle.

TNFR polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TNFR polypeptide solution, and the resulting mixture is lyophilized. The infusion solution is prepared by reconstituting the lyophilized TNFR polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The compositions of the invention may be administered alone or in combination with other therapeutic agents, including but not limited to, chemotherapeutic agents, anti-opportunistic infection agents, antivirals, antibiotics, steroidal and non-steroidal anti-inflammatories, immunosuppressants, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, CD27L, CD30L, CD40L, 4-1BBL, DcR3, OX40L, TNF-gamma International application publication number WO 96/14328), AIM-I (International application publication number WO 97/33899), AIM-II (International application publication number WO 97/34911), APRIL (J. Exp. Med. 188(6):1185-1190), endokine-alpha (International Publication No. WO 98/07880), OPG, and neutrokine-alpha (International application publication number WO 98/18921), TWEAK, OX40, and nerve growth factor (NGF), and soluble forms of Fas, CD30, CD27, CD40 and 4-IBB, TR2 (International application publication number WO 96/34095), DR3 (International Publication No. WO 97/33904), DR4 (International application publication number WO 98/32856), TR5 (International application publication number WO 98/30693), TR7 (International application publication number WO 98/41629), TRANK, TR9 (International application publication number WO 98/56892), TR10 (International application publication number WO 98/54202), 312C2 (International application publication number WO 98/06842), and TR12.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™(efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM- SULFAMETHOXAZOLE™, DAPSONE™, PENTAMIDINE™, ATOVAQUONE™, ISONMAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In an additional embodiment, the compositions of the invention are administered alone or in combination with an anti-inflammatory agent. Anti-inflammatory agents that may be administered with the compositions of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21. In a preferred embodiment, the compositions of the invention are administered in combination with TNF-alpha. In another preferred embodiment, the compositions of the invention are administered in combination with IFN-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PDGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B 186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE 19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNAs herein disclosed are used to clone genomic DNA of a TNFR protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of TNFR-6 Alpha and TNFR-6 Beta in *E. coli*

The bacterial expression vector pQE60 is used for bacterial expression in this example (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequences encoding the desired portions of TNFR-6 alpha and TNFR-6 beta proteins comprising the mature forms of the TNFR-6 alpha and TNFR-6 beta amino acid sequences are amplified from the deposited cDNA clones using PCR oligonucleotide primers which anneal to the amino terminal sequences of the desired portions of the TNFR-6α or -6β proteins and to sequences in the deposited constructs 3' to the cDNA coding sequence. Additional nucleotides containing restriction sites to facilitate cloning in the pQE60 vector are added to the 5' and 3' sequences, respectively.

For cloning the mature form of the TNFR-6α protein, the 5' primer has the sequence 5'CGC CCATGGCAGAAACACCCACCTAC 3' (SEQ ID NO: 19) containing the underlined NcoI restriction site. One of ordinary skill in the art would appreciate, of course, that the point in the protein coding sequence where the 5' primer begins may be varied to amplify a desired portion of the complete protein shorter or longer than the mature form. The 3' primer has the sequence 5'CGC AAGCTTCTCTTTCAGTGCAAGTG 3' (SEQ ID NO:20) containing the underlined HindIII restriction site. For cloning the mature form of the TNFR-6β protein, the 5' primer has the sequence of SEQ ID NO:19 above, and the 3' primer has the sequence 5' CGCAAGCTTCTCCTCAGCTCCTGCAGTG 3' (SEQ ID NO:21) containing the underlined HindIII restriction site.

The amplified TNFR-6 alpha and TNFR-6 beta DNA fragments and the vector pQE60 are digested with NcoI and HindIII and the digested DNAs are then ligated together. Insertion of the TNFR-6 alpha and TNFR-6 beta DNA into the restricted pQE60 vector places the TNFR-6 alpha and TNFR-6 beta protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing TNFR-6α or -6β protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the TNFR-6 alpha and TNFR-6 beta polypeptide, the cells are then stirred for 3-4 hours at 4° C. in 6M guanidine-HCl, pH 8. The cell debris is removed by centrifugation, and the supernatant containing the TNFR-6 alpha and TNFR-6 beta is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure TNFR-6 alpha and TNFR-6 beta protein. The purified protein is stored at 4° C. or frozen at −80° C.

The following alternative method may be used to purify TNFR-6α or -6β expressed in *E coli* when it is present in the form of inclusion bodies. Unless otherwise specified, all of the following steps are conducted at 4-10° C.

Upon completion of the production phase of the *E. coli* fermentation, the cell culture is cooled to 4-10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GnHCl) for 2-4 hours. After 7000×g centrifugation for 15 min., the pellet is discarded and the TNFR-6α or -6β polypeptide-containing supernatant is incubated at 4° C. overnight to allow further GnHCl extraction.

Following high speed centrifugation (30,000×g) to remove insoluble particles, the GnHCl solubilized protein is refolded by quickly mixing the GnHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded TNF receptor polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perspective Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the TNF receptor polypeptide are then pooled and mixed with 4 volumes of water. The diluted sample is then loaded onto a previously prepared set of tandem columns of strong anion (Poros HQ-50, Perspective Biosystems) and weak anion (Poros CM-20, Perspective Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the TNFR-6α or -6β polypeptide (determined, for instance, by 16% SDS-PAGE) are then pooled.

The resultant TNF receptor polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2

Cloning and Expression of TNFR-6 Alpha and TNFR-6 Beta Proteins in a Baculovirus Expression System In this illustrative example, the plasmid shuttle vector pA2 is used to insert the cloned DNA encoding complete protein, including its naturally associated secretory signal (leader) sequence, into a baculovirus to express the mature TNFR-6α or -6β protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the full length TNFR-6α or -6β protein in a deposited clone, including the AUG initiation codon and the naturally associated leader sequence shown in SEQ ID NO:2 or 4 is amplified using PCR oligonucleotide primers corresponding to the 5' and 3' sequences of the gene. The 5' primer for TNFR-6 alpha and TNFR-6 beta has the sequence 5'CGC GGATCCGCCATCATGAGGGCGTGGAGGGGCCAG 3' (SEQ ID NO:22) containing the underlined BamHI restriction enzyme site. All of the previously described primers encode an efficient signal for initiation of translation in eukaryotic cells, as described by Kozak, M., *J. Mol. Biol.* 196:947-950 (1987). The 3' primer for TNFR-6α has the sequence 5'CGCGGTACCCTCTTTCAGTGCAAGTG 3' (SEQ ID NO:23) containing the underlined Asp718 restriction site. The 3' primer for TNFR-6β has the sequence 5'CGC GGTACCCTCCTCAGCTCCTGCAGTG 3' (SEQ ID NO:24) containing the underlined Asp718 restriction site.

The amplified fragment is isolated from a 1% agarose gel using a commercially available kit ("Geneclean," BIO 101 Inc., La Jolla, Calif.). The fragment then is digested with the appropriate restriction enzyme for each of the primers used, as specified above, and again is purified on a 1% agarose gel.

The plasmid is digested with the same restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and dephosphorylated plasmid are ligated together with T4 DNA ligase. *E. coli* HB 101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human TNF receptor gene by digesting DNA from individual colonies using the enzymes used immediately above and then analyzing the digestion product by gel electrophoresis. The sequence of the cloned fragment is confirmed by DNA sequencing. This plasmid is designated herein pA2-TNFR-6α or pA2TNFR-6β (collectively pA2-TNFR).

Five μg of the plasmid pA2-TNFR is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413-7417 (1987). One μg of BaculoGold™ virus DNA and 5 μg of the plasmid pA2-TNFR are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC™ CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the TNF receptor gene Sf9 cells are grown in Grace's medium supplemented with 10% heat-inactivated FBS. The cells are infected with the recombinant baculovirus at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the TNF receptor protein.

Example 3

Cloning and Expression of TNFR-6 Alpha and TNFR-6 Beta in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC™ 37152), pSV2dhfr (ATCC™ 37146) and pBC12MI (ATCC™ 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTNFR-α-HA and -6β-HA, is made by cloning a portion of the cDNA encoding the mature form of the TNF receptor protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete TNF receptor polypeptide is cloned into the polylinker region of the vector so that recombinant protein expression is directed by the CMV promoter. The plasmid construction strategy is as follows. The TNF receptor cDNA of a deposited clone is amplified using primers that contain convenient restriction sites, much as described above for construction of vectors for expression of a TNF receptor in *E. coli*. Suitable primers can easily be designed by those of ordinary skill in the art.

The PCR amplified DNA fragment and the vector, pcDNAI/Amp, are digested with XbaI and EcoRI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the TNFR-α and -6β polypeptides.

For expression of recombinant TNFR-α and -6β, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TNFR by the vector.

Expression of the pTNFR-α-HA and -6β-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TNFR-6 alpha and TNFR-6 beta polypeptides. Plasmid pC4 is a derivative of the plasmid pSV2-dhfr (ATCC™ Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438-447) plus a fragment isolated from the enhancer of the immediate early gene of human cytomegalovirus (CMV) (Boshart et al., *Cell* 41:521-530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TNF receptor polypeptide in a regulated way in mammalian cells (Gossen, M., & Bujard, H., *Proc. Natl. Acad. Sci. USA* 89:5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418, or hygromycin. It is advantageous to use more than one selectable marker in the beginning, e.g., G418 plus methotrexate.

The plasmid pC4 is digested with the restriction enzymes appropriate for the specific primers used to amplify the TNF receptor of choice as outlined below and then dephosphorylated using calf intestinal phosphates by procedures known in the art. The vector is then isolated from a 1% agarose gel.

The DNA sequence encoding the TNF receptor polypeptide is amplified using PCR oligonucleotide primers corresponding to the 5' and 3' sequences of the desired portion of the gene. The 5' primer for TNFR-6 alpha and TNFR-6 beta containing the underlined BamHI site, has the following sequence: 5'CGCGGATCCGCCATCATGAGGGCGTG-GAGGGGCCAG 3' (SEQ ID NO:22). The 3' primer for TNFR-6α has the sequence 5'CGCGGTAC-CCTCTTTCAGTGCAAGTG 3' (SEQ ID NO:23) containing the underlined Asp718 restriction site. The 3' primer for TNFR-6β has the sequence 5'CGCGGTACCCTCCT-CAGCTCCTGCAGTG 3' (SEQ ID NO:24) containing the underlined Asp718 restriction site.

The amplified fragment is digested with the endonucleases which will cut at the engineered restriction site(s) and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100-200 µM. Expression of the desired gene product is analyzed, for instance, by SDS-PAGE and Western blot or by reversed phase HPLC analysis.

Example 4

Tissue Distribution of TNF Receptor mRNA Expression

Northern blot analysis is carried out to examine TNFR-6α or -6β gene expression in human tissues, using methods described by, among others, Sambrook et al., cited above. A cDNA probe containing the entire nucleotide sequence of a TNF receptor protein (SEQ ID NO: 1 or 3) is labeled with $^{32}$P using the Rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for TNF receptor mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples. Numerous modifications and variations of the present invention are possible in light of the above teachings and, therefore, are within the scope of the appended claims.

Example 5

Gene Therapy Using Endogenous TNFR-6 Gene

Another method of gene therapy according to the present invention involves operably associating the endogenous TNFR (i.e., TNFR-6) sequence with a promoter via homologous recombination as described, for example, in U.S. Pat. No. 5,641,670, issued Jun. 24, 1997; International application publication number WO 96/29411, published Sep. 26, 1996; International application publication number WO 94/12650, published Aug. 4, 1994; Koller et al., *Proc. Natl. Acad. Sci. USA* 86:8932-8935 (1989); and Zijlstra et al., *Nature* 342: 435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TNFR-6, flanking the promoter. The targeting sequence will be sufficiently near the 5' end of TNFR-6 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TNFR-6 sequence. This results in the expression of TNFR-6 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the TNFR-6 locus, plasmid pUC18 (MBI Fermentas, Amherst, N.Y.) is digested with HindIII. The CMV promoter is amplified by PCR with an XbaI site on the 5' end and a BamHI site on the 3' end. Two TNFR-6 non-coding sequences are amplified via PCR: one TNFR-6 non-coding sequence (TNFR-6 fragment 1) is amplified with a HindIII site at the 5' end and an Xba site at the 3' end; the other TNFR-6 non-coding sequence (TNFR-6 fragment 2) is amplified with a BamHI site at the Send and a HindIII site at the 3' end. The CMV promoter and TNFR-6 fragments are digested with the appropriate enzymes (CMV promoter—XbaI and BamHI; TNFR-6 fragment 1—XbaI; TNFR-6 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 6

Effect of TNFR in Treating Graft-versus-host Disease in Mice

The invention also encompasses a method for the treatment of refractory/severe acute GVHD in patients comprising administering to the patients (preferably human), TNFR polypeptides or TNFR agonists of the invention.

An analysis of the use of soluble TNFR polypeptides of the invention (e.g., TNFR-6) to treat graft-versus-host disease (GVHD) is performed through the use of a C57BL/6 parent into (BALB/c X C57BL/6) F1 mouse model. This parent into F1 mouse model is a well-characterized and reproducible animal model of GVHD in bone marrow transplant patients, which is well known to one of ordinary skill in the art (see, e.g., Gleichemann et al, *Immunol Today* 5:324, 1984, which is herein incorporated by reference in its entirety). Soluble TNFR is expected to bind to FasL and inhibit FasL-mediated apoptosis, which plays a critical pathogenic role in the hepatic, cutaneous and lymphoid organ damage observed in this animal model of GVHD (Baker et al, *J. Exp. Med.* 183: 2645, (1996); Charles et al, *J. Immunol.* 157:5387, (1996); and Hattori et al, *Blood* 91:4051, (1998), each of which is herein incorporated by reference in its entirety).

Initiation of the GVHD condition is induced by the intravenous injection of $\sim 1-3 \times 10^8$ spleen cells from C57BL/6 mice into (BALB/c X C57BL/6) F1 mice (both are available from Jackson Lab, Bar Harbor, Me.). Groups of 6 to 8 mice receive either 0.1 to 5.0 mg/kg of TNFR or human IgG isotype control intraperitoneally or intradermally on every other day following the injection of spleen cells. The effect of TNFR on liver enzyme release in the sera, an indicator of liver damage, is analyzed twice per week for at least 3 weeks. When there is a significant amount of liver enzymes being detected in human IgG-treated mice, the animals are sacrificed for histological evaluation of the relative degree of tissue damage in the liver, spleen, skin and intestine, and for the therapeutic effect TNFR has elicited on these organs.

The ability of TNFR to ameliorate systems associated with refractory/severe acute GVHD is indicated by a reduction of liver enzyme release in the sera, tissue damage and/or reduced cachexia, loss of body weight and/or lethality when compared to the control.

Finally, TNFR- and human IgG-treated animals undergo a clinical evaluation every other day to assess cachexia, body weight and lethality.

TNFR in combination therapy with TNF-α inhibitors may also be examined in this GVHD murine model.

Example 7

TNFR-6α (DcR3) Suppresses AIM-II-mediated Apoptosis

BACKGROUND

The members of the tumor necrosis factor (TNF) family are involved in regulating diverse biological activities such as regulation of cell proliferation, differentiation, cell survival, cell death, cytokine production, lymphocyte co-stimulation, immunoglobulin secretion, and isotype switching (Armitage, R., *Curr. Opin. Immunol.* 6, 407-413 (1994); Tewari, M. et al., *Curr. Opin. Genet. Dev.* 6, 39-44 (1996)). Receptors in this family share a common structural motif in their extracellular domains consisting of multiple cysteine-rich repeats of approximately 30 to 40 amino acids (Gruss, H.-J., et al., Blood 85, 3378-3404 (1995)). While TNFR1, CD95/Fas/APO-1, DR3/TRAMP/APO-3, DR4/TRAIL-R1/APO-2, DR5/TRAIL-R2, and DR6 receptors contain a conserved intracellular motif of 30-40 amino acids called death domain, associated with the activation of apoptotic signaling pathways, other members which contain a low sequence identity in the intracellular domains, stimulate the transcription factors NF-κB and AP-1 (Armitage, R., Curr. Opin. Immunol. 6, 407-413 (1994); Tewari, M. et al., Curr. Opin. Genet. Dev. 6, 39-44 (1996); Gruss, H.-J. et al., Blood 85, 3378-3404 (1995)).

Most TNF receptors contain functional cytoplasmic domain and they include TNFR1 (Loetscher, H et al., Cell 61, 351-356 (1990); Schall, T. J., et al., Cell 61, 361-370 (1990)), TNFR2 (Smith, C. A., et al., Science 248, 1019-1023 (1990)), lymphotoxin β receptor (LTβR) (Baens, M., et al., Genomics 16, 214-218 (1993)), 4-1BB (Kwon, B. S., et al., Proc. Natl. Acad. Sci. USA 86, 1963-1967 (1989)), HVEM/TR2/ATAR (Kwon, B. S., et al., J. Biol. Chem. 272, 14272-14276 (1997); Montgomery, R. I., et al., Cell 87, 427-436 (1996); Hsu, H., et al., J. Biol. Chem 272, 13471-13474 (1997)), NGFR (Johnson, D., et al., Cell 47, 545-554 (1986)), CD27 (Van Lier, R. A., et al., J. Immunol. 139, 1589-1596 (1987)), CD30 (Durkorp, H., et al., Cell 68, 421-427 (1992)), CD40 (Banchereau, J., et al., Cell 68, 421-427 (1994)), OX40 (Mallett, S., et al., EMBO J. 9, 1063-1068 (1990)), Fas (Itoh, N., et al., Cell 66, 233-243 (1991)), DR3/TRAMP (Chinnaiyan, A. M., et al., Science 274, 990-992 (1996)), DR4/TRAIL-R1 (Pan, G., et al., Science 276, 111-113 (1996)), DR5/TRAIL-R2 (Pan, G., et al., Science 277, 815-818) (1997), and RANK (Anderson, D. et al., Nature 390, 175-179 (1997)). Some members of the TNFR superfamily do not have cytoplasmic domains and are secreted, such as osteoprotegerin (OPG) (Simmonet, et al., Cell 89, 309-319 (1997)), or linked to the membrane through a glycophospholipid tail, such as TRID/DcR1/TRAIL-R3 (Degli-Esposti, M. A., et al., J. Exp. Med. 186, 1165-1170 (1997); Sheridan, J. P., et al., Science 277, 818-821 (1997)). Viral open reading frames encoding soluble TNFRs have also been identified, such as SFV-T2 (Smith, C. A., et al., Science 248, 1019-1023 (1990)), Va53 (Howad, S. T., et al., Virology 180, 633-647 (1991)), G4RG (Hu, F. Q., et al., Virology 204, 343-356 (1994)), and crmB (Gruss, H.-J, et al., Blood 85, 3378-3404 (1995)).

By searching an expressed sequence tag (EST) database, a new member of the TNFR superfamily was identified, named TNFR-6α, and was characterized as a soluble cognate ligand for AIM-II and FasL/CD95L. AIM-II and FasL mediate the apoptosis, which is the most common physiological form of cell death and occurs during embryonic development, tissue remodeling, immune regulation and tumor regression.

AIM-II is highly induced in activated T lymphocytes and macrophages. AIM-II was characterized as a cellular ligand for HVEM/TR2 and LTβR (Mauri, D. N., et al., Immunity 8, 21-30 (1998)). HVEM/TR2 is a receptor for herpes simplex virus type 1 (HSV-1) entry into human T lymphoblasts. Soluble form of HVEM/TR2-Fc and antibodies to HVEM/TR2 were shown to inhibit a mixed lymphocyte reaction, suggesting a role for this receptor or its ligand in T lymphocyte proliferation (Kwon, B. et al., J. Biol. Chem. 272, 14272-14276 (1997); Mauri, D. N., et al., Immunity, 21-30 (1998); Harrop, J. A., et al, J. Immunol. 161, 1786-1794 (1998)). The level of LTβR expression is prominent on epithelial cells but is absent in T and B lymphocytes. Signaling via LTβR triggers cell death in some adenocarcinomas (Browning, J. L., et al., J. Exp. Med. 183, 867-878 (1996)). AIM-II produced by activated lymphocytes could evoke immune modulation from hematopoietic cells expressing only HVEM/TR2, and induce apoptosis of tumor cells, which express both LTβR and HVEM/TR2 receptors (Zhai, Y., et al., J. Clin. Invest. 102, 1142-1151 (1998); Harrop, J. A., et al., J. Biol. Chem. 273, 27548-27556 (1998)).

FasL is one of the major effectors of cytotoxic T lymphocytes and natural killer cells. It is also involved in the establishment of peripheral tolerance, in the activation-induced cell death of lymphocytes. Moreover, expression of FasL in nonlymphoid and tumor cells contributes to the maintenance of immune privilege of tissues by preventing the infiltration of Fas-sensitive lymphocytes (Nagata, S., Cell 88, 355-365 (1997)). FasL is also processed and shed from the surface of human cell (Schneider, P., et al., J. Exp. Med. 187, 1205-1213 (1998)).

Here, we demonstrate that TNFR-6α, a new member of the TNFR superfamily binds AIM-II and FasL. Therefore TNFR-6α, may act as an inhibitor in AIM-II-induced tumor cell death by blocking AIM-II interaction with its receptors.

Materials and Methods

Identification and Cloning of New Members of the TNFR Superfamily.

An EST cDNA database, obtained from more than 600 different cDNA libraries, was screened for sequence homology with the cysteine-rich motif of the TNFR superfamily, using the blastn and tblastn algorithms. Three EST clones containing an identical open reading frame whose amino acid sequence showed significant homology to TNFR-II were identified from cDNA libraries of human normal prostate and pancreas tumor. A full-length TNFR-6 alpha cDNA clone encoding an intact N-terminal signal peptide was obtained from a human normal prostate library.

RT-PCR Analysis.

For RT-PCR analysis, total RNA was isolated using Trizol (GIBCO) from various human cell lines before and after stimulation with PMA/Ionomycin or LPS. RNA was converted to cDNA by reverse transcription and amplified for 35 cycles by PCR. Primers used for amplification of the TNFR-6 alpha fragment are according to the sequence of TNFR-6 alpha. β-actin was used as an internal control for RNA integrity. PCR products were run on 2% agarose gel, stained with ethidium bromide and visualized by UV illumination.

Recombinant Protein Production and Purification.

The recombinant TNFR-6 alpha protein was produced with hexa-histidine at the C-terminus. TNFR-6 alpha-(His) encoding the entire TNFR-6 alpha protein was amplified by PCR. For correctly oriented cloning, a HindIII site on the 5' end of the forward primer (5'-AGACCCAAGCTTCCT-GCTCCA GCAAGGACCATG-3':SEQ ID NO:25) and a BamHI site on the 5' end of the reverse primer (5'-AGACGG-GATCCTTAGTGGTGGTGGTGGTGGTGCAC AGGGAGGAAGCGCTC-3':SEQ ID NO:26) were created. The amplified fragment was cut with HindIII/BamHI and cloned into mammalian expression vector, pCEP4 (Invitrogen). The TNFR-6 alpha-(His)/pCEP4 plasmid was stably transfected into HEK 293 EBNA cells to generate recombinant TNFR-6 alpha-(His). Serum free culture media from cells transfected TNFR-6 alpha-(His)/pCEP4 were passed through Ni-column (Novagen). The column eluents were fractionated by SDS-PAGE and TNFR-6 alpha-(His) was detected by western blot analysis using the anti-poly(His)$_6$ antibody (Sigma).

Production of HVEM/TR2-Fc, LTβR-Fc and Flag-tagged soluble AIM-II (soluble AIM-II) fusion proteins were previously described (Zhai, Y., et al., *J. Clin. Invest.* 102, 1142-1151 (1998)). Fc fusion protein-containing supernatants were filtered and trapped onto protein-G Sepharose beads. Flag-tagged soluble AIM-II proteins were purified with anti-FLAG® mAb affinity column.

Immunoprecipitation.

TNFR-6 alpha-(His) was incubated overnight with various Flag-tagged ligands of TNF superfamily and anti-FLAG® agarose in binding buffer (150 mM NaCl, 0.1% NP-40, 0.25% gelatin, 50 mM HEPES, pH 7.4) at 4° C., and then precipitated. The bound proteins were resolved by 12.5% SDS-PAGE and detected by western blot with HRP-conjugated anti-poly(His)$_6$ or anti-human IgG1 antibodies.

Cell-binding Assay.

For cell-binding assays, HEK 293 EBNA cells were stably transfected using calcium phosphate method with pCEP4/full sequence of AIM-II cDNA or pCEP4 vector alone. After selection with Hygromycin B, cells were harvested with 1 mM EDTA in PBS and incubated with TNFR-6 alpha-(His), HVEM/TR2-Fc, or LTβR-Fc for 20 minutes on ice. For detecting Fc-fusion protein, cells were stained with FITC-conjugated goat anti-human IgG. To detect TNFR-6 alpha binding, cells were stained with anti-poly(His)$_6$ and FITC conjugated goat anti-mouse IgG consecutively. The cells were analyzed by FACScan (Becton Dickinson).

Cytotoxicity Assay.

Cytotoxicity assays using HT29 cells were carried out as described previously (Browning, J. L., et al., *J. Exp. Med.* 183, 867-878 (1996)). Briefly, 5000 HT29 cells were seeded in 96-well plates with 1% FBS, DMEM and treated with soluble AIM-II (10 ng/ml) and 10 units/ml human recombinant interferon-γ (IFN-γ). Serial dilutions of TNFR-6 alpha-(His) were added in quadruplicate to microtiter wells. Cells treated with IFN-γ and soluble AIM-II were incubated with various amounts of TNFR-6 alpha-(His) for 4 days before the addition of [$^3$H]thymidine for the last 6 h of culture. Cells were harvested, and thymidine incorporation was determined using a liquid scintillation counter.

Results and Discussion

TNFR-6 Alpha is a New Member of the TNFR Superfamily

TNFR-6 alpha was identified by searching an EST database. Three clones containing an identical open reading frame were identified from cDNA libraries of human normal prostate and pancreas tumor. A full-length TNFR-6 alpha cDNA encoding an intact N-terminal signal peptide was obtained from a human normal prostate library. The open reading frame of TNFR-6 alpha encodes 300 amino acids. To determine the N-terminal amino acid sequence of mature TNFR-6 alpha, hexa-histidine tagged TNFR-6 alpha was expressed in mammalian cell expression system and the N-terminal amino acid sequence were determined by peptide sequencing. The N-terminal sequence of the processed mature TNFR-6 alpha-(His) started from amino acid 30, indicating that the first 29 amino acids constituted the signal sequence. Therefore, the mature protein of TNFR-6 alpha was composed of 271 amino acids with no transmembrane region. There was one potential N-linked glycosylation site (Asn173) in TNFR-6 alpha. Like OPG (Simmonet, W. et al., *Cell* 89, 309-319 (1997)), the predicted protein was a soluble, secreted protein and the recombinant TNFR-6 alpha expressed in mammalian cells was ~40 kD as estimated on polyacrylamide gel. Alignment of the amino sequences of TNFR-I, TNFR-II, 4-1BB, TR2/HVEM, LTβR, TR1/OPG and TNFR-6 alpha illustrated the existence of a potential cysteine-rich motif. TNFR-6 alpha contained two perfect and two imperfect cysteine-rich motifs and its amino acid sequence was remarkably similar to TR1/OPG amino acid sequence. TNFR-6 alpha shares ~30% sequence homology with OPG and TNFR-II.

mRNA Expression

We analyzed expression of TNFR-6 alpha mRNA in human multiple tissues by Northern blot hybridization. Northern blot analyses indicated that TNFR-6 alpha mRNA was ~1.3 kb in length and was expressed predominantly in lung tissue and colorectal adenocarcinoma cell line SW480. RT-PCR analyses were performed to determine the expression patterns of TNFR-6 alpha in various cell lines. TNFR-6 alpha transcript was detected weakly in most hematopoietic cell lines. The expression of TNFR-6 alpha was induced upon activation in Jurkat T leukemia cells. Interestingly, TNFR-6 alpha mRNA was constitutively expressed in endothelial cell line, HUVEC at high level.

Identification of the Ligand for TNFR-6 Alpha

To identify the ligand for TNFR-6 alpha, several Flag-tagged soluble proteins of TNF ligand family members were screened for binding to recombinant TNFR-6 alpha-(His) protein by immuno-precipitation. TNFR-6 alpha-(His) selectively bound AIM-II-Flag and FasL-Flag among Flag-tagged soluble TNF ligand members tested. This result indicates that TNFR-6 alpha binds at least two ligands, AIM-II and FasL. AIM-II exhibits significant sequence homology with the C-terminal receptor-binding domain of FasL (31%) but soluble AIM-II is unable to bind to Fas (Mauri, D. N., et al., *Immunity* 8, 21-30 (1998); Zhai, Y., et al., *J. Clin. Invest* 102, 1142-1151 (1998)). They may have a similar binding epitope for TNFR-6 alpha binding.

Previously, Zhai and Harrop (Zhai, Y., et al., *J. Clin. Invest.* 102, 1142-1151 (1998); Harrop, J. A., et al., *J. Biol. Chem.* 273, 27548-27556 (1998)) reported the biological functions of AIM-II and its possible mechanisms of action as a ligand for HVEM/TR2 and/or LTβR. AIM-II is expressed in activated T cells. AIM-II, in conjunction with serum starvation or addition of IFN-γ, inhibits the cell proliferation in tumor cells, MDA-MB-231 and HT29.

To determine whether TNFR-6 alpha might act as an inhibitor to AIM-II interactions with HVEM/TR2 or LTβR, TNFR-6 alpha-(His) was used as a competitive inhibitor in AIM-II-HVEM/TR2 interaction. When AIM-II was immunoprecipitated with HVEM/TR2-Fc in the presence of TNFR-6 alpha-(His), HVEM/TR2-Fc binding to AIM-II was decreased competitively by TNFR-6 alpha-(His) but TNFR-6 alpha-(His) binding to AIM-II was not changed by HVEM/TR2-Fc. Furthermore, the binding of HVEM/TR2-Fc (6 nM) or LTβR (6 nM) was completely inhibited by 20 nM of TNFR-6 alpha-(His) protein in immunoprecipitation assays. These results support the notion that TNFR-6 alpha may act as a strong inhibitor of AIM-II function through HVEM/TR2 and LTβR.

Binding of TNFR-6 Alpha-(His) to AIM-II-transfected Cells

To determine whether TNFR-6 alpha binds to AIM-II expressed on cell surface, we performed binding assay using AIM-II-transfected HEK 293 EBNA cells by flow cytometry. AIM-II-transfected HEK 293 EBNA cells were stained significantly by TNFR-6 alpha-(His) as well as by HVEM/TR2-Fc and LTβR-Fc. No binding was detected by HVEM/TR2-Fc or LTβR-Fc on pCEP4 vector-transfected HEK 293 EBNA cells. Furthermore, control isotype did not bind to AIM-II-transfected HEK 293 EBNA cells, and any of above fusion proteins did not bind to vector-transfected cells, confirming the specificity of these bindings. These bindings indicate that TNFR-6 alpha can bind to both soluble and membrane-bound forms of AIM-II.

TNFR-6 Alpha Inhibits AIM-II-induced Cytotoxicity in HT29 Cells

Browning et al. (*J. Exp. Med.* 183, 867-878 (1996)) have shown that Fas activation leads to rapid cell death (12-24 h) whereas LTβR takes 2-3 days in induction of apoptosis for colorectal adenocarcinoma cell line, HT29. Zhai et al. (*J. Clin. Invest.* 102, 1142-1151 (1998)) also reported that AIM-II leads to the death of the cells expressing both LTβR and HVEM/TR2 but not the cells expressing only the LTβR or HVEM/TR2 receptor. Both HVEM/TR2 and LTβR are involved cooperatively in AIM-II-mediated killing of HT29 cells (Zhai, Y., et al., *J. Clin. Invest.* 102, 1142-1151 (1998)).

To determine whether binding of TNFR-6 alpha inhibits AIM-II-mediated cytotoxicity, HT29 cells were incubated with 10 ng/ml of soluble AIM-II and IFN-γ (10 U/ml) in the presence of 200 ng/ml of LTβR-Fc or TNFR-6 alpha-(His). TNFR-6 alpha-(His) blocked significantly the AIM-II-mediated cell killing. Cells were also incubated with soluble AIM-II and/or IFN-γ in the presence of varying concentration of TNFR-6 alpha-(His). TNFR-6 alpha-(His) blocked soluble AIM-II-induced cell death in a dose-dependent manner. Taken together, TNFR-6 alpha appears to act as a natural inhibitor of AIM-II-induced tumor cell killing. The data also suggest that TNFR-6 alpha contributes to immune evasion of tumors.

AIM-II interaction with HVEM/TR2 and/or LTβR may trigger the distinct biological events, such as T cell proliferation, blocking of HVEM-dependent HSV1 infection and anti-tumor activity (Mauri, D. N., et al., *Immunity* 8, 21-30 (1998); Zhai, Y., et al., *J. Clin. Invest.* 102, 1142-1151 (1998); Harrop, J. A., et al., *J. Biol. Chem.* 273, 27548-27556 (1998)). TNFR-6 alpha may act as an inhibitor of AIM-II interaction and may play diverse roles in different cell types. TNFR-6 alpha may act as a decoy receptor and contribute to immune evasion both in slow and rapid tumor cell death, that are mediated by AIM-II and/or FasL mediated apoptosis pathway.

HUVEC cells constitutively expressed TNFR-6 alpha in RT-PCR analysis. AIM-II and FasL have been known to be expressed in activated T cells. Therefore TNFR-6 alpha and its ligands may be important for interactions between activated T lymphocytes and endothelium. TNFR-6 alpha may be involved in activated T cell trafficking as well as endothelial cell survival.

Example 8

Activation-induced Apoptosis Assay

Activation-induced apoptosis is assayed using SupT-13 T leukemia cells and is measured by cell cycle analysis. The assay is performed as follows. SupT-13 cells are maintained in RPMI containing 10% FCS in logarithmic growth (about $1\times10^6$). Sup-T13 cells are seeded in wells of a 24 well plate at $0.5\times10^6$/ml, 1 ml/well. AIM II protein or Fas Ligand protein (0.01, 0.1, 1, 10, 100, 1000 ng/ml) or buffer control is added to the wells and the cells are incubated at 37° C. for 24 hours in the presence or absence of the TNFR polypeptides of the invention. The wells of another 24 well plate are prepared with or without anti-CD3 antibody by incubating purified BC3 mAb at a concentration of 10 μg/ml in sterile-filtered 0.05M bicarbonate buffer, pH 9.5 or buffer alone in wells at 0.5 ml/well. The plate is incubated at 4° C. overnight. The wells of antibody coated plates are washed 3 times with sterile PBS, at 4° C. The treated Sup-T13 cells are transferred to the antibody coated wells and incubated for 18 hrs., at 37° C. Apoptosis is measured by cell cycle analysis using propidium iodide and flow cytometry. Proliferation of treated cells is measured by taking a total of 3001 μl of each treatment well and delivering in to triplicate wells (100 μl/well) of 96 well plates. To each well add 20 μl/well $^3$H-thymidine (0.5 μCi/20 μl, 2 Ci/mM) and incubate 18 hr., at 37° C. Harvest and count $^3$H-thymidine uptake by the cells. This measurement may be used to confirm an effect on apoptosis if observed by other methods. The positive controls for the assay is Anti-CD3 crosslinking alone, Fas Ligand alone, and/or AIM-II alone. In addition, profound and reproducible apoptosis in this line using anti-Fas monoclonal antibody (500 ng/ml in soluble form-IgM mAb) has been demonstrated. The negative control for the assay is medium or buffer alone. Also, crosslinking with another anti-CD3 mAB (OKT3) has been shown to have no effect. TNFR agonists according to the invention will demonstrate a reduced apoptosis when compared to the treatment of the Sup-T13 cells with AIM-II or Fas Ligand in the absence of the TNFR agonist. TNFR antagonists of the invention can be identified by combining TNFR polypeptides having Fas Ligand or AIM-II binding affinity (e.g., mature TNFR) with the TNFR polypeptide to be tested and contacting this combination in solution with AIM-II or Fas Ligand and the Sup-T13 cells. The negative control for this assay is a mixture containing the mature TNFR, Sup-T13 cells, and AIM-II or Fas Ligand (FasL) alone. Samples containing TNFR antagonists of the invention will demonstrate increased apoptosis when compared to the negative control.

If an effect is observed by cell cycle analysis the cells can be further stained for the TUNEL assay for flow cytometry or with Annexin V, using techniques well known to those skilled in the art.

Example 9

Blocking of Fas Ligand Mediated Apoptosis of Jurkat T-cells by TNFR6 Alpha-Fc

Methods.

Jurkat T-cells which express the Fas receptor were treated either with sFas ligand alone or with sFas ligand in combination with Fas-Fc, or TNFR6 alpha-Fc (corresponding to the full length TNFR 6 alpha protein (amino acids 1-300 of SEQ ID NO:2) fused to an Fc domain, as described herein). The sFas ligand protein utilized was obtained from Alexis Corporation and contains a FLAG® epitope tag at its N-terminus. As it has been demonstrated previously that cross-linking of Fas ligand utilizing the monoclonal FLAG® epitope enhances significantly the ability of Fas ligand to mediate apoptosis, the anti-FLAG® antibody was included in this study. Specifically, 106 Jurkat cells (RPMI+5% serum) were treated with Fas ligand (Alexis) (20 ng/ml) and anti-FLAG® Mab (200 ng/ml) and then incubated at 37° C. for 16 hrs. When TNFR6 alpha-Fc was included in the assay, the receptor was preincubated with the Fas ligand and anti-FLAG® Mab for 15 mins.

Results

After incubation, cells were harvested, resuspended in PBS and subjected to Flow Cytometric Analyses (Table V). In the absence of Fas ligand (FasL), approximately 1% of cells appear to be undergoing apoptosis as measured by high annexin staining and poor propidium iodide staining (Table V). Treatment with soluble Fas ligand alone resulted in an approximate 7-fold increase in the number of apoptotic cells which as expected could be blocked in the presence of Fas-Fc. Similar to Fas-Fc, TNFR6 alpha-Fc was also capable of blocking Fas mediated apoptosis with the blocking by TNFR6 alpha-Fc observed in a dose dependent manner over three logarithmic scales (Table V). The ability of TNFR6 alpha-Fc to block Fas mediated killing of Jurkat cells was also determined in a cell death assay (FIGS. 7A-B). In this assay, cells were again treated with combinations of Fas ligand and TNFR6 alpha-Fc for 16 hrs. To measure the levels of viable cells after treatment, cells were incubated for 5 hrs with 10% ALOMAR blue and examined spectrophotometrically at OD 570 nm-630 nm. Treatment with Fas ligand resulted in a 50% decrease in cell viability (FIGS. 7A-B). The decrease in cell viability can be overcome by either Fas-Fc or TNFR6 alpha-Fc but not TR5-Fc (FIGS. 7A-B), confirming the ability of TNFR6 alpha to interfere with Fas ligand mediated activity. The ability of TNFR6 alpha-Fc at both 100 ng/ml and at 10 ng/ml to block Fas ligand mediated activity in this assay is statistically different (p<0.05) than when no TNFR6 alpha-Fc is added (FIGS. 7A-B). Furthermore, the ability of TNFR6 alpha-Fc to block Fas ligand mediated cell death and apoptosis appears to be as efficient with Fas-Fc (Table V and FIGS. 7A-B).

Table V. FACS Analysis Revealing Blocking of Fas Ligand Mediated Apoptosis:

$10^6$ Jurkat cells (RPMI+5% serum) were treated with Fas ligand (Allexis; 20 ng/ml) and anti-FLAG® antibody (200 ng/ml) and then incubated at 37° C. for 16 hours. When Fc receptor was included in the assay, the receptor was preincubated with the Fas ligand and anti-FLAG® antibody Mab for 15 minutes. After incubation, cells were harvested, resuspended in PBS and subjected to Flow Cytometric Analyses.

| Treatment | % Cells undergoing apoptosis |
| --- | --- |
| Control (buffer) | 1.24 |
| FasL (20 ng) | 8.87 |
| FasL (20 ng) + Fas-Fc (100 ng) | 1.78 |
| FasL (20 ng) + TNFR6 alpha-Fc (100 ng) | 1.24 |
| FasL (20 ng) + TNFR6 alpha-Fc (10 ng) | 2.79 |
| FasL (20 ng) + TNFR6 alpha-Fc (1 ng) | 7.95 |
| FasL (20 ng) + TNFR6 alpha-Fc (0.1 ng) | 8.58 |

Conclusions.

TNFR6 alpha-Fc appears to block Fas ligand mediated apoptosis of Jurkat cells in a dose dependent manner as effectively as Fas ligand.

Example 10

Protein Fusions of TNFR-6 Alpha and/or TNFR-6 Beta

TNFR-6 alpha and/or TNFR-6 beta polypeptides of the invention are optionally fused to other proteins. These fusion proteins can be used for a variety of applications. For example, fusion of TNFR-6 alpha and/or TNFR-6 beta polypeptides to His-tag, HA-tag, protein A, IgG domains, and maltose binding protein facilitates purification. (See EP A 394,827; Traunecker, et al., Nature 331:84-86 (1988).) Similarly, fusion to IgG-1, IgG-3, and albumin increases the half-life time in vivo. Nuclear localization signals fused to TNFR-6 alpha and/or TNFR-6 beta polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and TNFR-6 alpha and/or TNFR-6 beta polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., International application publication number WO 96/34891.)

Human IgG Fc region:

(SEQ ID NO: 27)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 11

Production of an Antibody

Hybridoma Technology

The antibodies of the present invention can be prepared by a variety of methods. (See, Current Protocols, Chapter 2.) As one example of such methods, cells expressing TR6-alpha and/or TR6-beta are administered to an animal to induce the production of sera containing polyclonal antibodies. In a preferred method, a preparation of TR6-alpha and/or TR6-beta protein is prepared and purified to render it substantially free of natural contaminants. Such a preparation is then introduced into an animal in order to produce polyclonal antisera of greater specific activity.

Monoclonal antibodies specific for protein TR6-alpha and/or TR6-beta are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981)). In general, an animal (preferably a mouse) is immunized with TR6-alpha and/or TR6-beta polypeptide or, more preferably, with a secreted TR6-alpha and/or TR6-beta polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC™. After fusion, the resulting hybridoma cells are selectively maintained in HAT medium, and then cloned by limiting dilution as described by Wands et al. (Gastroenterology 80:225-232 (1981). The hybridoma cells obtained through such a selection are then assayed to identify clones which secrete antibodies capable of binding the TR6-alpha and/or TR6-beta polypeptide.

Alternatively, additional antibodies capable of binding to TR6-alpha and/or TR6-beta polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the TR6-alpha and/or TR6-beta protein-specific antibody can be blocked by TR6-alpha and/or TR6-beta. Such antibodies comprise anti-idiotypic antibodies to the TR6-alpha and/or TR6-beta protein-specific antibody and are used to immunize an animal to induce formation of further TR6-alpha and/or TR6-beta protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against TR6-Alpha and/or TR6-Beta from a Library of scFvs Naturally occurring V-genes isolated from human PBLs are constructed into a library of antibody fragments which contain reactivities against TR6-alpha and/or TR6-beta to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 $E.$ $coli$ harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×10$^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log $E.$ $coli$ TG1 by incubating eluted phage with bacteria for 30 minutes at 37° C. The $E.$ $coli$ are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect $E.$ $coli$ HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing.

Example 12

Method of Determining Alterations in the TNFR-6 Alpha and/or TNFR-6 Beta Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of TNFR-6 alpha and/or TNFR-6 beta are also determined and genomic PCR products analyzed to confirm the results. PCR products harboring suspected mutations in TNFR-6 alpha and/or TNFR-6 beta is then cloned and sequenced to validate the results of the direct sequencing.

PCR products of TNFR-6 alpha and/or TNFR-6 beta are cloned into T-tailed vectors as described in Holton, T. A. and Graham, M. W., *Nucleic Acids Research,* 19:1156 (1991) and sequenced with T7 polymerase (United States Biochemical). Affected individuals are identified by mutations in TNFR-6 alpha and/or TNFR-6 beta not present in unaffected individuals.

Genomic rearrangements are also observed as a method of determining alterations in the TNFR-6 alpha and/or TNFR-6 beta gene. Genomic clones isolated using techniques known in the art are nick-translated with digoxigenindeoxy-uridine 5'-triphosphate (Boehringer Manheim), and FISH performed as described in Johnson, et al., *Methods Cell Biol.* 35:73-99 (1991). Hybridization with the labeled probe is carried out using a vast excess of human cot-1 DNA for specific hybridization to the TNFR-6 alpha and/or TNFR-6 beta genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, et al., *Genet. Anal. Tech. Appl.,* 8:75 (1991).) Image collection, analysis and chromosomal fractional length measurements are performed using the ISee Graphical Program System. (Inovision Corporation, Durham, N.C.) Chromosome alterations of the genomic region of TNFR-6 alpha and/or TNFR-6 beta (hybridized by the probe) are identified as insertions, deletions, and translocations. These TNFR-6 alpha and/or TNFR-6 beta alterations are used as a diagnostic marker for an associated disease.

Example 13

Method of Detecting Abnormal Levels of TNFR-6 Alpha and/or TNFR-6 Beta in a Biological Sample TNFR-6 alpha and/or TNFR-6 beta polypeptides can be detected in a biological sample, and if an increased or decreased level of TNFR-6 alpha and/or TNFR-6 beta is detected, this polypeptide is a marker for a particular phenotype. Methods of detection are numerous, and thus, it is understood that one skilled in the art can modify the following assay to fit their particular needs.

For example, antibody-sandwich ELISAs are used to detect TNFR-6 alpha and/or TNFR-6 beta in a sample, preferably a biological sample. Wells of a microtiter plate are coated with specific antibodies to TNFR-6 alpha and/or TNFR-6 beta, at a final concentration of 0.2 to 10 ug/ml. The antibodies are either monoclonal or polyclonal and are produced using technique known in the art. The wells are blocked so that non-specific binding of TNFR-6 alpha and/or TNFR-6 beta to the well is reduced.

The coated wells are then incubated for >2 hours at RT with a sample containing TNFR-6 alpha and/or TNFR-6 beta. Preferably, serial dilutions of the sample should be used to validate results. The plates are then washed three times with deionized or distilled water to remove unbounded TNFR-6 alpha and/or TNFR-6 beta.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TNFR-6 alpha and/or TNFR-6 beta polypeptide concentration in a sample is then interpolated using the standard curve based on the measured flourescence of that sample.

Example 14

Method of Treating Decreased Levels of TNFR-6 Alpha and/or TNFR-6 Beta

The present invention relates to a method for treating an individual in need of a decreased level of TNFR-6 alpha and/or TNFR-6 beta biological activity in the body comprising, administering to such an individual a composition comprising a therapeutically effective amount of TNFR-6 alpha and/or TNFR-6 beta antagonist. Preferred antagonists for use in the present invention are TNFR-6 alpha and/or TNFR-6 beta-specific antibodies.

Moreover, it will be appreciated that conditions caused by a decrease in the standard or normal expression level of TNFR-6 alpha and/or TNFR-6 beta in an individual can be treated by administering TNFR-6 alpha and/or TNFR-6 beta, preferably in a soluble and/or secreted form. Thus, the invention also provides a method of treatment of an individual in need of an increased level of TNFR-6 alpha and/or TNFR-6 beta polypeptide comprising administering to such an individual a pharmaceutical composition comprising an amount of TNFR-6 alpha and/or TNFR-6 beta to increase the biological activity level of TNFR-6 alpha and/or TNFR-6 beta in such an individual.

For example, a patient with decreased levels of TNFR-6 alpha and/or TNFR-6 beta polypeptide receives a daily dose 0.1-100 ug/kg of the polypeptide for six consecutive days. Preferably, the polypeptide is in a soluble and/or secreted form.

Example 15

Method of Treating Increased Levels of TNFR-6 Alpha and/or TNFR-6 Beta

The present invention also relates to a method for treating an individual in need of an increased level of TNFR-6 alpha and/or TNFR-6 beta biological activity in the body comprising administering to such an individual a composition comprising a therapeutically effective amount of TNFR-6 alpha and/or TNFR-6 beta or an agonist thereof.

Antisense technology is used to inhibit production of TNFR-6 alpha and/or TNFR-6 beta. This technology is one example of a method of decreasing levels of TNFR-6 alpha and/or TNFR-6 beta polypeptide, preferably a soluble and/or secreted form, due to a variety of etiologies, such as cancer.

For example, a patient diagnosed with abnormally increased levels of TNFR-6 alpha and/or TNFR-6 beta is administered intravenously antisense polynucleotides at 0.5, 1.0, 1.5, 2.0 and 3.0 mg/kg day for 21 days. This treatment is repeated after a 7-day rest period if the is determined to be well tolerated.

Example 16

Method of Treatment Using Gene Therapy—Ex Vivo

One method of gene therapy transplants fibroblasts, which are capable of expressing soluble and/or mature TNFR-6 alpha and/or TNFR-6 beta polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TNFR-6 alpha and/or TNFR-6 beta can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted TNFR-6 alpha and/or TNFR-6 beta.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TNFR-6 alpha and/or TNFR-6 beta gene is then added to the media and the packaging cells transduced with the vector. The packaging cells now produce infectious viral particles containing the TNFR-6 alpha and/or TNFR-6 beta gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TNFR-6 alpha and/or TNFR-6 beta protein is produced.

The engineered fibroblasts are then transplanted onto the host, either alone or after having been grown to confluence on cytodex 3 microcarrier beads.

Example 17

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TNFR-6 alpha and/or TNFR-6 beta sequences into an animal to increase or decrease the expression of the TNFR-6 alpha and/or TNFR-6 beta polypeptide. The TNFR-6 alpha and/or TNFR-6 beta polynucleotide may be operatively linked to a promoter or any other genetic elements necessary for the expression of the TNFR-6 alpha and/or TNFR-6 beta polypeptide by the target tissue. Such gene therapy and delivery techniques and methods are known in the art, see, for example, International Application publication number WO90/11092, International Application publication number WO98/11779; U.S. Pat. Nos. 5,693,622, 5,705,151, 5,580, 859; Tabata H. et al., *Cardiovasc. Res.* 35:470-479 (1997); Chao J. et al., *Pharmacol. Res.* 35:517-522 (1997); Wolff J. A. *Neuromuscul. Disord.* 7:314-318 (1997); Schwartz B. et al., *Gene Ther.* 3:405-411 (1996); Tsurumi Y. et al., *Circulation* 94:3281-3290 (1996) (incorporated herein by reference).

The TNFR-6 alpha and/or TNFR-6 beta polynucleotide constructs may be delivered by any method that delivers injectable materials to the cells of an animal, such as, injection into the interstitial space of tissues (heart, muscle, skin, lung, liver, intestine and the like). The TNFR-6 alpha and/or TNFR-6 beta polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TNFR-6 alpha and/or TNFR-6 beta polynucleotides may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The TNFR-6 alpha and/or TNFR-6 beta polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TNFR-6 alpha and/or TNFR-6 beta polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TNFR-6 alpha and/or TNFR-6 beta polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TNFR-6 alpha and/or TNFR-6 beta polynucleotide constructs can be delivered to arteries during angioplasty by the catheter used in the procedure.

The dose response effects of injected TNFR-6 alpha and/or TNFR-6 beta polynucleotide in muscle in vivo is determined as follows. Suitable TNFR-6 alpha and/or TNFR-6 beta template DNA for production of mRNA coding for TNFR-6 alpha and/or TNFR-6 beta polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TNFR-6 alpha and/or TNFR-6 beta template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for TNFR-6 alpha and/or TNFR-6 beta protein expression. A time course for TNFR-6 alpha and/or TNFR-6 beta protem expression may be done in a similar fashion except that quadriceps from different mice are harvested at different times. Persistence of TNFR-6 alpha and/or TNFR-6 beta DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TNFR-6 alpha and/or TNFR-6 beta naked DNA.

Example 18

Rescue of Ischemia in Rabbit Lower Limb Model

To study the in vivo effects of TNFR-6 alpha and/or TNFR-6 beta on ischemia, a rabbit hindlimb ischemia model is created by surgical removal of one femoral arteries as described previously (Takeshita, S. et al., *Am J. Pathol* 147: 1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, et al, *Am J. Pathol* 147:1649-1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked TNFR-6 alpha and/or TNFR-6 beta expression plasmid by arterial gene transfer technology using a hydrogel-coated balloon catheter as described (Riessen, R. et al., *Hum Gene Ther.* 4:749-758 (1993); Leclerc, G. et al., *J. Clin. Invest* 90: 936-944 (1992)). When is used in the treatment, a single bolus of 500 mg protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score— This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example test activity in TNFR-6 proteins. However, one skilled in the art could easily modify the exemplified studies to test the activity of polynucleotides (e.g., gene therapy), agonists, and/or antagonists of TNFR-6 alpha and/or TNFR-6 beta.

Example 19

Diabetic Mouse and Glucocorticoid-Impaired Wound Healing Models

A. Diabetic db+/db+ Mouse Model.

To demonstrate that TNFR-6 accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283-293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1-7 (1983); Leiter et al., *Am. J. of Pathol.* 114:46-55 (1985)). Peripheral neuropathy, myocardial complications, and microvascular lesions, basement membrane thickening and glomerular filtration abnormalities have been described in these animals (Norido, F. et al., *Exp. Neurol.* 83(2):221-232 (1984); Robertson et al., *Diabetes* 29(1):60-67 (1980); Giacomelli et al., *Lab Invest.* 40(4):460-473 (1979); Coleman, D. L., *Diabetes* 31 (Suppl): 1-6 (1982)). These homozygous diabetic mice develop hyperglycemia that is resistant to insulin analogous to human type II diabetes (Mandel et al., *J. Immunol.* 120:1375-1377 (1978)).

The characteristics observed in these animals suggests that healing in this model may be similar to the healing observed in human diabetes (Greenhalgh, et al., *Am. J. of Pathol.* 136: 1235-1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and were 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245-251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

TNFR-6 alpha and/or TNFR-6 beta is administered using at a range different doses of TNFR-6 protein, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) TNFR-6 alpha and/or TNFR-6 beta.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 was 64 mm$^2$, the corresponding size of the dermal punch. Calculations were made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with TNFR-6. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranting of these sections is based on the extent of proliferation on a scale of 0-8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280-302 (1989); Wahl, S. M. et al., *J. Immunol.* 115: 476-481 (1975); Werb, Z. et al., *J. Exp. Med* 147:1684-1694 (1978)). Glucocorticoids retard wound healing by inhibiting angiogenesis, decreasing vascular permeability (Ebert, R. H., et al., *An. Intern. Med.* 37:701-705 (1952)), fibroblast proliferation, and collagen synthesis (Beck, L. S. et al., *Growth Factors.* 5: 295-304 (1991); Haynes, B. F. et al., *J. Clin. Invest.* 61: 703-797 (1978)) and producing a transient reduction of circulating monocytes (Haynes, B. F., et al., *J. Clin. Invest.* 61: 703-797 (1978); Wahl, S. M., "Glucocorticoids and wound healing", In: Antiinflammatory Steroid Action: Basic and Clinical Aspects, Academic Press, New York, pp. 280-302 (1989)). The systemic administration of steroids to impaired wound healing is a well establish phenomenon in rats (Beck, L. S. et al., *Growth Factors.* 5: 295-304 (1991); Haynes, B. F., et al., *J. Clin. Invest.* 61: 703-797 (1978); Wahl, S. M., "Glucocorticoids and wound healing", In: Antiinflammatory Steroid Action: Basic and Clinical Aspects, Academic Press, New York, pp. 280-302 (1989); Pierce, G. F. et al., *Proc. Natl. Acad. Sci. USA* 86: 2229-2233 (1989)).

To demonstrate that TNFR-6 alpha and/or TNFR-6 beta can accelerate the healing process, the effects of multiple topical applications of TNFR-6 on full thickness excisional skin wounds in rats in which healing has been impaired by the systemic administration of methylprednisolone is assessed.

Young adult male Sprague Dawley rats weighing 250-300 g (Charles River Laboratories) are used in this example. The animals are purchased at 8 weeks of age and were 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1-5 and on day 8. Wounds are measured horizontally and vertically using a calibrated Jameson caliper. Wounds are considered healed if granulation tissue was no longer visible and the wound is covered by a continuous epithelium.

TNFR-6 alpha and/or TNFR-6 beta is administered using at a range different doses of TNFR-6 protein, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) were evaluated: 1) Untreated group 2) Vehicle placebo control 3) TNFR-6 treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 was 64 mm$^2$, the corresponding size of the dermal punch. Calculations were made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining was performed on cross-sections of bisected wounds. Histologic examination of the wounds allows assessment of whether the healing process and the morphologic appearance of the repaired skin was improved by treatment with TNFR-6 alpha and/or TNFR-6 beta. A calibrated lens micrometer is used by a blinded observer to determine the distance of the wound gap.

Experimental data are analyzed using an unpaired t test. A p value of <0.05 is considered significant.

The studies described in this example test activity in TNFR-6 protein. However, one skilled in the art could easily modify the exemplified studies to test the activity of polynucleotides (e.g., gene therapy), agonists, and/or antagonists of TNFR-6 alpha and/or TNFR-6 beta.

Example 20

Lymphadema Animal Model

The purpose of this experimental approach is to create an appropriate and consistent lymphedema model for testing the therapeutic effects of in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located.

The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5-7. The plateau edematous peak are then observed. To evaluate the intensity of the lymphedema, the circumference and volumes of 2 designated places on each paw are measured before operation and daily for 7 days. The effect plasma proteins on lymphedema is determined and whether protein analysis is a useful testing parameter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people and the readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and the conclusion to the experiment to measure for total protein and Ca2+ comparison.

Limb Weight Comparison: After drawing blood, the animal is prepared for tissue collection. The limbs were amputated using a quillitine, then both experimental and control legs were cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80 degree C. until sectioning. Upon sectioning, the muscle was observed under fluorescent microscopy for lymphatics. Other immuno/histological methods are currently being evaluated.

The studies described in this example test activity in TNFR-6 proteins. However, one skilled in the art could easily modify the exemplified studies to test the activity of polynucleotides (e.g., gene therapy), agonists, and/or antagonists of TNFR-6 alpha and/or TNFR-6 beta.

It will be clear that the invention may be practiced otherwise than as particularly described in the foregoing description and examples. Numerous modifications and variations of the present invention are possible in light of the above teachings and, therefore, are within the scope of the appended claims.

Example 21

TNFR6-Fc Inhibits FasL Mediated Toxicity in a ColA Mouse Model of Liver Injury

The intravenous administration of Concanavalin A to mice activates T lymphocytes and induces both apoptotic and necrotic cell death of hepatocytes, mimicking aspects of the pathophysiology of chronic active hepatitis (Tiegs et al., J. Clin. Invest. 90: 196. (1992)). Fas-Fc protein, a dimeric form of Fas expected to inhibit Fas ligand activity, has been reported to reduce liver injury in this model via inhibition of Fas ligand demonstrating an involvement of Fas pathway in the pathology (Ksontini et al., J. Immunol.; 60(8):4082-4089 (1998)).

Validation of Model:

To validate the ConA mouse model, Con A was administered intravenously to Balb/c mice at 10, 15, and 20 mg/kg dose of ConA along with placebo or Fas-Fc at 97.5 micrograms/mouse. 10 Balb/c mice were used per treatment group. The mice were sacrificed 22 hours after treatment, serum collected and biochemical analysis performed using a Clinical Chemistry Analyzer ILAB900 (Instrumentation Laboratory) to determine the levels of the liver specific transaminases, alanine aminotransferase (ALT) and aspartate aminotransferase (AST), which are released in the serum upon liver damage ((Tiegs et al., J. Clin. Invest. 90: 196. (1992)). The administration of FasFc at a dose of 97.5 micrograms/mouse (about 5 mg/kg) was found to significantly inhibit the elevated liver enzymes at ConA doses of 10 and 15 mg/kg but not at 20 mg/kg (data not shown), thus validating the model.

Balb/C mice were injected intravenously with ConA (15 mg/kg) together with or without a three log dose of TNFR6-Fc (0.6, 6.60 ug/mouse). The TNFR6-Fc fusion protein used in this example corresponds to the full length TNFR-6 alpha polypeptide sequence (amino acids 1-300 of SEQ ID NO:2) fused to an Fc domain. 10 Balb/c mice were used per treatment group. The mice were sacrificed 22 hours after treatment and serum levels of ALT and AST were determined using a Clinical Chemistry Analyzer ILAB900 (Instrumentation Laboratory). The administration of TNFR6-Fc significantly inhibited both ALT and AST levels at the highest dose tested (60 micrograms/mouse, 3 mg/kg) by 50% (data not shown). Thus TNFR6-Fc significantly reduced ConA induced serum AST and ALT in a dose response fashion.

Effect of TNFR6-Fc on ConA Induced Apoptotic Events in the Liver

Since the elevation in serum liver enzyme levels reflects both apoptotic and non-apoptotic pathways of hepatocyte destruction, a more critical determination of the extent of liver injury can be derived via direct measurement of apoptotic events. Thus apoptosis was analyzed using whole liver cell suspensions isolated from mice treated with TNFR6-Fc and Con A. Three independent markers of apoptosis were assessed on the same sample. These include changes in surface expression of phosphatidylserine, measurements of DNA damage, and caspase activation.

Balb/C mice were injected intravenously with ConA (15 mg/kg) together with or without a three log dose of TNFR6-Fc (0.6, 6.60 ug/mouse). Cell suspensions were isolated from the livers of 3 mice/group and liver cells were isolated by placing the intact liver tissue on a 70 μm cell strainer and teased apart with the stopper of a 5 cc syringe using RPMI 1640/10% FBS. To remove red blood cells and large piece of tissue debris, the filtered cell suspension was layered over lymphocyte separation medium (density 1.0770 g/ml). The interface layer was collected, washed and the cells were counted. Prior to FACS analysis, the cell suspension was refiltered over a 40 μm filter.

For measurement of Annexin V binding (an indicator of apoptosis), cells were first incubated with fluorochrome-conjugated monoclonal antibodies CD45 CyChrome and B220 or anti-TCRβ PE (Pharmingen, San Diego, Calif.). Cells were washed with binding buffer (Pharmingen) then incubated with Annexin V FITC (Pharmingen). Stained cells were acquired and analyzed using a Becton Dickinson FACScan (Becton Dickinson, San Jose, Calif.). Only CD45 positive events were collected. Cells staining brightly for B220 and Annexin V were considered apoptotic B cells; cells staining brightly for anti-TCRβ and Annexin V were considered apoptotic T cells.

The level of DNA degradation (another hallmark of apoptosis) was determined by Terminal UTP nick-end labeling (TUNEL) which measures this degradation by using TdT enzyme to add FITC-labeled dUTP to the 3' ends of nicked DNA using the Apo-DIRECT kit (Pharmingen) according to manufacturer's directions. Briefly, cells were fixed in 1% paraformaldhyde, washed in PBS and then fixed with ice-cold 70% ethanol. Cells were washed twice in washing buffer, then incubated with staining solution containing TdT enzyme and dUTP-FITC at 37° C. for one hour. Cells were washed twice with rinsing buffer, re-suspended in propidium iodide solution and acquired on the FACScan. For analysis, an electronic gate was set on singlet events, and cells staining brightly for dUTP-FITC were considered apoptotic cells.

To determine the presence of the active form of caspase-3 (an early indicator of apoptosis) cells were incubated in IC FIX (BioSource International, Camarillo, Calif.), washed twice in PBS, then permeablized with IC PERM (BioSource). Cells were incubated with 5 μg rabbit anti-caspase-3 PE (Pharmingen) in IC PERM, washed in IC PERM, then washed twice with PBS. Cells were acquired on the FACScan and analyzed for PE mean fluorescence.

For all three indicators of apoptosis, TNFR6-Fc inhibited apoptosis in livers of mice as compared to mice treated with ConA alone (Table VI). Using DNA damage as a marker and TUNEL analysis, a dose-dependent trend of inhibition with TR6-Fc was observed. These data support a role for TNFR6-Fc in inhibition of apoptosis in ConA-induced hepatitis.

TABLE VI

Apoptosis of liver cells isolated from TNFR6-Fc-treated mice.[1]

| Treatment | Percent % Apoptotic Cells measured by: | | | |
|---|---|---|---|---|
| | Tunel | Caspase-3 | Annexin V/TcRβ | Annexin V/B220 |
| Untreated Control | — | 18.7 | 2.0 | 6.1 |
| ConA (15 mg/kg) Control | 24.4 | 35.2 | 7.0 | 12.2 |
| TNFR6-Fc (0.6 μg/mouse) | 15.6 | 22.7 | 3.5 | 6.3 |
| TNFR6Fc (6.0 μg/mouse) | 13.6 | 22.5 | 2.3 | 2.9 |
| TNFR6-Fc (60 μg/mouse) | 9.5 | 20.3 | 3.0 | 4.2 |

[1]Liver cell suspensions were analyzed for apoptosis using one of three independent measures. DNA degradation was measured using TUNEL staining; caspase activation by the analysis of the active form of caspase-3; and annexin V staining of surface membrane changes. Cell suspensions were isolated from the livers of 3 mice/group and pooled. The resulting pooled suspension was used to perform each analysis. For Annexin-V staining, only liver CD45+ cells were acquired and Annexin-V staining assessed on cells costained for B220 or TcRβ.

Conclusion:

The findings that TNFR6-Fc reduced both ConA induced serum AST and ALT levels and ConA induced liver cell apoptosis supports the therapeutic application of TNFR-6 alpha and TNFR-6 beta polypeptides of the invention for the treatment and/or prevention of hepatitis and other forms of liver injury.

Example 22

In Vitro and In Vivo Inhibition of FasL Mediated Killing by TNFR-6 Alpha

Fas (CD95/Apo1) and Fas ligand (FasL/CD95L), are a pair of pro-apoptotic mediators of the TNF receptor and ligand family that induce apoptosis upon receptor/ligand engagement. Fas/FasL-mediated apoptosis is a normal and important homeostatic mechanism useful in the down-regulation of hyper-immune responses and the deletion of activated lymphocytes. Fas/FasL-induced apoptosis is also important in host protection and surveillance, preventing damage to immune privileged sites, and eliminating virus-infected or transformed cells. While necessary for normal physiological processes, unregulated apoptosis mediated by the Fas/FasL system is implicated in organ-specific tissue injury both in experimental animal models and several human disease states.

This example describes the synthesis and biological activity of a TNFR-6 alpha (in this Example, hereinafter "TR6") fusion protein produced using the full length coding region of TR6 and an Fc domain of IgG1. Biochemical and biological characterization of this TR6-Fc form revealed it to, not only bind FasL and inhibit apoptosis in-vitro, but also to block the mortality associated with iv injection of cross-linked FasL into Fas$^+$ mice. This is the first demonstration of TR6-mediated inhibition of FasL activity in an in-vivo model. These results show the therapeutic potential of TR6-Fc in diseases where Fas/FasL is implicated in mediating organ damage.

Methods of Example 22

Animals

Female Balb/c mice (20-25 g) were obtained from Charles River Laboratories (Raleigh, N.C.). Female MLR/lpr mice (30-35 g) were obtained from Jackson Laboratories (Bar Harbor, Me.). Mice were housed five per cage, and kept under standard conditions for one week before being used in experiments. The animals were maintained according to National Research Council standards for the care and use of laboratory animals. The animal protocols used in this study were reviewed and approved by the HGS Institutional Animal Care and Use Committee.

Human TR6-Fc, TR6-non Fc and Fas-Fc Expression Vectors

Cells infected with baculovirus clone, pA2Fc:TR6 (M1-H300), were grown in media containing 1% ultra low IgG serum. Conditioned culture supernatant (20 L) was adjusted to pH 7.0, filtered through 0.22 micron filter and loaded on a Protein A column (BioSepra Ceramic HyperD) previously conditioned with 20 mM phosphate buffer with 0.5 M NaCl, pH7.2. The column was washed with 15 CV of 20 mM phosphate buffer containing 0.5 M NaCl, pH 7.2, and followed by 5 CV of 0.1 M citric acid (pH 5.0). TR6-Fc eluted with 0.1 M citric acid (pH 2.4)/20% glycerol, and fractions were neutralized with 1M Tris-HCl, pH 9.2. The human TR6-Fc positive fractions were determined by SDS-PAGE. The peak fractions were pooled and concentrated using an Amicon concentrator. The TR6-Fc concentrate was then loaded onto a Superdex 200 column containing PBS containing 0.5 M NaCl (Pharmacia) and TR6-Fc positive fractions determined by non-reducing SDS-PAGE. The TR6-Fc positive fractions eluting as disulfide-linked dimers were pooled and further concentrated with CentriPlus 10K cutoff spin concentrators.

The TR6-Fc protein bound to the Protein A resin contained both disulfide-linked Fc dimers and higher disulfide-linked aggregates. Aggregates were removed by Superdex 200 size-exclusion chromatography. The typical yield for TR6-Fc was 2 mg/L culture supernatant having a purity of 98% by Reverse-Phase HPLC assay and 92% by N-terminal sequence assay. The N-terminus started at residue Val 30. The pure protein behaved as disulfide linked dimer and was biologically active as it bound FasL in a BIAcore assay to a degree comparable to Fas-Fc.

To confirm purity, TR6-Fc protein was blotted to a ProBlott membrane cartridge (PE Biosystems, Inc). After staining with Ponceau S (0.2% in 4% acetic acid), the membrane was placed in a "Blot Cartridge", and subjected to N-terminal amino acid sequence analysis using a model ABI-494 sequencer (PE Biosystems, Inc.) and the Gas-phase Blot cycles. Proteins were subject to reverse-phase HPLC (Beckmann) analysis to access purity. In the case of Fas-Fc the N-terminus was deblocked using pyroglutamate aminopeptidase ( ) followed by N-terminal sequence analysis.

Human Fas(M1-G169)-Fc fusion protein was purified from CHO conditioned media by capture on a Poros 50 Protein A affinity column with elution at 0.1M citrate pH 2.0 as described for TR6-Fc. Further purification was effected by size separation on a Superdex-200 gel filtration resin in PBS/glycerol. N-terminal sequence of Fas-Fc was blocked and protein identity was confirmed post digestion with pyroglutamate aminopeptidase to deblock the N-terminus and 16% SDS-PAGE, respectively. The protein behaved as disulfide linked dimer as expected for a Fc fusion protein.

BIAcore Chip Preparation and Analysis

The extra-cellular portion of FasL (Oncogene Research Products), amino acids 103-281, were dialyzed against 10 mM sodium acetate buffer, pH 5 and a BIAcore flow cell prepared having 2020 RU of FasL. TR6-Fc and Fas-Fc fusion proteins were analyzed at 5 ug/mL in 50 uL HBS buffer and were injected onto the FasL chip at a flow rate of 15 ul per minute. After injection of the sample the flow cell was equilibrated with HBS and amount of net bound protein determined.

In Vitro Soluble Human FasL Mediated Cytotoxicity

The HT-29 cell line, a human colon adenocarcinoma cell line obtained from the ATCC™ (code ATCC™ HTB-38) is sensitive to FasL mediated cytotoxicity, presumably through activation of its Fas receptor. HT-29 cells were grown in D-MEM/10% FBS/2 mM Glutamine/pen/strep. To measure FLAG-FasL induced cytotoxicity, target cells were trypsinized, washed and plated in a 96-well plate at 50,000 cells/well. HT-29 cells were treated with cross-linked FLAG-FasL+anti-FLAG® antibody (1 ng/ml), or with cross-linked FLAG-FasL in combination with Fas-Fc, or TR6. Although uncross-linked FasL can induce cytotoxity in this assay, antibody cross-linking of FasL via its FLAG® domain significantly enhances the ability of FasL to mediate apoptosis, and thus the anti-FLAG® antibody was included. The final volume in each well was 200 ul. After 5 days of culture, the plate was harvested and 20 ul of Alamar Blue reagent added. To assess final viability, cells were incubated for four hours and the plate analyzed in a CytoFluor fluorescence plate reader with excitation of 530 μm and emission of 590 nm.

The Jurkat human T cell line, which also expresses the Fas receptor, and is sensitive to FasL, was tested in an in vitro cytotoxicity assay similar to that used on HT-29 cells. In addition, Jurkat cells were evaluated by FACS analysis in an apoptosis assay. Jurkat cells (RPMI+5% serum) were seeded at 50,000 cells per well were then treated with FLAG-FasL and anti-FLAG® mouse monoclonal antibody (200 ng/ml) and incubated at 37 C for 16 hrs to induce apoptosis. When TR6 or Fas-Fc was included in the assay, the decoy receptor protein was pre-incubated with FasL and anti-FLAG® antibody for 15 mins. To determine the degree of apoptosis, cells were harvested, stained with annexin and propidium iodide and evaluated using FACS analysis.

In Vitro Membrane Bound Murine FasL Mediated Cytotoxicity

To analyze the in vitro killing of Fas$^+$ target cells by murine FasL, murine effector L929 cells ($2.5 \times 10^5$ cells/well) were transfected with murine FasL and incubated with Fas$^+$ murine A20 target cells ($5 \times 10^3$ cells/well) labeled with Eu DTPA. After an 18 hour incubation at an effector:target cell ratio of 50:1, cells were centrifuged, and % release of Eu DTPA quantified as a measure of cell death.

In Vivo Cross-linked Flag-FasL Induced Mortality

Soluble human FLAG-FasL was synthesized at HGS. To induce cross-linking, FasL was incubated with anti-FLAG® antibody (Sigma, St Louis, Mo.) and injected iv into mice following a variation of the procedure used by Schneider et al. Fc-fusion proteins were injected iv or sc at various time points prior to FasL injection, and mortality recorded over time. Liver samples one centimeter square, were fixed in 10% neutral buffered formalin for 24 hours, then transferred to 70 percent methanol until time for embedding in paraffin. Sections were stained with H&E, and evaluated histologically. Blood was drawn from the heart and used in the measurement of serum AST and ALT levels.

Statistics

Statistical difference between groups was determined using a Student's unpaired t test. Error bars represent S.E.M.

Results of Example 22

BIAcore Analysis of TR6-Fc Binding to FasL

BIAcore chip technology provides the opportunity to identify and characterize ligands that bind to a given receptor, in this case TR6. The protein ligand can be immobilized and challenged with TR6 to calculate relative binding units (RU). Conversely, the TR6 receptor can be immobilized and exposed to various ligands to identify proteins with an affinity for the TR6 receptor.

BIAcore technology was used to determine if human TR6-Fc displayed any binding to human FasL immobilized on a BIAcore chip. The results indicated that TR6-Fc bound to FasL with the same affinity as the Fas receptor, approximately 100 RU. As a control, TR6-Fc interaction with another TNF ligand, BLyS, was examined. No significant binding was found.

To show the specificity of TR6-Fc for FasL, soluble FLAG-FasL was used to compete with the immobilized FasL for binding of TR6-Fc. Increasing concentrations of FasL-Flag were able to inhibit binding of TR6-Fc to immobilized FasL. At a concentration of 8 ug/ml, FasL-Flag inhibited binding of TR6-Fc (2 ug/ml) by 50 percent. When 17 ug/ml of FasL-Flag was used, inhibition rose to 75 percent.

When TR6-Fc was immobilized, and trimerized FLAG-FasL used as the soluble protein, the Kd of TR6-Fc was $4.6 \times 10^{-9}$ M, similar to the $7.4 \times 10^{-9}$ M Kd for FasFc. TR6 without the Fc portion had a fourfold reduction in affinity for FasL-Flag with a Kd of $1.7 \times 10^{-8}$ M.

In Vitro Effect of TR6 on Soluble Human FasL Mediated Cytotoxicity

The results of this experiment demonstrate the ability of TR6 to block cross-linked FLAG-FasL mediated HT-29 cell death. FLAG-FasL induced HT-29 cytotoxicity in a dose-dependent manner, with the maximal effect at a concentration between 1 and 10 ng/ml. In the presence of TR6-Fc (1 ug/ml), FasL failed to induce cell killing, in agreement with the proposed decoy receptor function of TR6. Unlike TR6-Fc, Fas-Fc did not totally abrogate FLAG-FasL mediated cell death, but did shift the cytotoxicity curve about 10 fold to the right. TR6-non-Fc also inhibited FasL mediated killing, but was not as potent as the Fc fusion protein. A number of other members of the TNF receptor family, such as TNFR1-Fc, LTBR-Fc, TR2-Fc, TR4-Fc, TR7-Fc, TR8-Fc, TR9-Fc, TR10-Fc and TR11-Fc were also tested in this assay and failed to block FasL induced killing of HT-29 cells. In a different cytotoxicity assay involving the eponymous TNF family member, TR6-Fc failed to inhibit TNFa-induced killing of L929 target cells.

The ability of TR6 to block antibody cross-linked FLAG-FasL killing in vitro was also observed using human Jurkat cells in a similar cytotoxicity assay. Treatment with FasL at 10 ng/ml resulted in an 80% decrease in cell viability as measured by fluorescence at 530/590. Fas-Fc as well as TR6-Fc and non-Fc significantly reduced FasL-induced cytotoxicity whether the decoy receptor level was kept constant and FasL increased, or the FasL level kept constant and the decoy receptor increased. In both assay systems TR6-Fc appeared to be at least 100 fold more potent than Fas-Fc.

In another Jurkat cell assay, treatment with FLAG-FasL resulted in an approximate 7-fold increase in the number of apoptotic cells over untreated controls, as measured by FACS analysis of annexin staining. FasL-mediated apoptosis was significantly reduced in a dose dependant fashion in the presence of TR6-Fc or Fas-Fc.

In Vitro Effect of TR6 on Membrane Bound Murine FasL Mediated Cytotoxicity

In an assay using $Fas^+$ murine A20 target cells labeled with Eu DTPA, TR6-Fc at a concentration of 10 ng/ml, completely inhibited killing by murine L929 cells transfected with murine FasL. In this assay, the $IC_{50}$ for both TR6-Fc and non-Fc was approximately 1 ng/ml. The potency of TR6 in this assay was 100 fold greater than that of Fas-Fc, which had an $IC_{50}$ of approximately 100 ng/ml. This assay demonstrated that the human TR6 protein was capable of recognizing, binding to, and blocking, the cytotoxic activity of murine FasL.

The In Vivo Effect of TR6-Fc on Flag-FasL-induced Mortality in Mice

Female Balb/c mice (n=20) were injected iv with 13 ug of FLAG-FasL mixed with 50 ug of murine antibody to FLAG. Half of the mice also received an iv injection of 96 ug of TR6-Fc, one hour prior to administration of cross-linked FLAG-FasL. Since TR6-Fc has a molecular weight of about 60,000 compared to 18,500 for FLAG-FasL, this resulted in a TR6-Fc:FLAG-FasL molar ratio of 2.3:1. However, each molecule of TR6-Fc is capable of binding two molecules of FasL.

Within one hour of FasL injection, all the mice injected only with cross-linked FLAG-FasL were dead. The hypotension was so great, that no blood could be obtained for analysis of serum alanine (ALT) and aspartate (AST) aminotransferase levels. In another group of mice injected with FLAG-FasL uncross-linked by anti-FLAG® antibody, there were no deaths. There were also no deaths in the cross-linked FLAG-FasL group treated with TR6-Fc. Analysis of blood drawn from mice 24 hours after TR6-Fc injection, showed an elevated, but not significantly higher serum AST level compared to normal controls (Normal=81±12 units/l; TR6-Fc=548±193 units/l)

To determine its minimum lethal dose, 1, 3, 6 or 13 ug of FLAG-FasL was mixed with 4, 12, 25 or 50 ug of anti-FLAG® antibody and injected iv into Balb/c mice (n=3). Only the mice injected with the lowest, 1 ug dose of FLAG-FasL survived. The mean serum AST level 24 hours after injection was 2663±1373 compared to the mean normal value of 67±17. The minimum lethal dose of cross-linked FLAG-FasL appeared to be about 3 ug/mouse.

To establish that the in vivo mechanism of FLAG-FasL-induced lethality was the binding of FasL to its cell bound Fas receptor, 5 ug of FLAG-FasL was mixed with 19 ug of anti-FLAG® antibody and injected into $Fas^-$ MRL/lpr mice and their $Fas^+$ littermates. Within 30 minutes, all the $Fas^+$ control mice were dead, while all the $Fas^-$ MRL/lpr mice survived. This indicated that in vivo FLAG-FasL killing was dependent on the expression of Fas receptor on the target cells.

In a dose response experiment, TR6-Fc was injected iv at a dose of 2, 8 or 24 ug/mouse, one hour before iv injection with FLAG-FasL (4 ug/mouse) mixed with 12 ug of anti-FLAG® antibody (Table VII). This results in a TR6-Fc:FLAG-FasL molar ratio of approximately 1:6, 1:2 and 2:1 respectively. In the FLAG-FasL control group, all but one of the ten mice died within two hours. The low dose of TR6-Fc (2 ug) had no protective activity, all the animals dying within two hours. The middle dose of TR6-Fc (8 ug) prolonged life an additional two hours. Only the high, 24 ug dose of TR6-Fc was efficacious, with seven of the ten mice surviving without weight loss to the end of the experiment on Day 7. This indicates not only that TR6-Fc was efficacious at a molar ratio of 2:1, but also that its protective effect was not lost over time. In contrast to the activity of TR6-Fc, the non Fc version of TR6 did not reduce FLAG-FasL (4 ug) induced mortality even when injected at 70 ug/mouse, a molar ratio of 11:1 (data not shown).

To determine if TR6-Fc exhibited protective activity when injected sc, as opposed to iv, 350 ug of TR6-Fc was injected sc, 1.5, 3 or 5 hours before iv injection of 4 ug of FLAG-FasL mixed with 15 ug of anti-FLAG® antibody (Table VIII). Even at the receptor:ligand molar ratio of 27:1, none of the animals injected sc with TR6-Fc survived for more than two hours, while all of the animals injected iv with 93 ug of TR6-Fc or Fas-Fc survived. A different member of the TNF receptor superfamily, TR-11(93 ug/mouse, iv) was used as a negative control, and failed to protect any animals from FLAG-FasL induced death. Analysis of blood drawn from mice, injected iv with TR-6-Fc+FasL showed no significant elevation of AST or ALT levels compared to normal controls.

TABLE VII

Dose dependant effect of TR6-Fc (iv) on cross-linked FLAG-FasL induced mortality

| Groups (n = 10) | Time/% Survival | | | | |
|---|---|---|---|---|---|
| (ug/mouse) | <2 Hrs | <4 Hrs | 1 Day | 4 Days | 7 Days |
| Normal | 100 | 100 | 100 | 100 | 100 |
| FLAG-FasL (3) + anti-FLAG ® Ab (12) | 10 | 10 | 10 | 10 | 10 |
| FasL + Ab + TR6-Fc (2) | 0 | 0 | 0 | 0 | 0 |
| FasL + Ab + TR6-Fc (8) | 100 | 10 | 10 | 10 | 10 |
| FasL + Ab + TR6-Fc (24) | 90 | 80 | 80 | 70 | 70 |

TR6-Fc and/or FLAG-FasL + anti-FLAG ® antibody was injected iv into female Balb/c mice as described in the Material and Methods.

TABLE VIII

Effect of TR6-Fc (sc, iv) and Fas-Fc (iv) on cross-linked FLAG-FasL induced mortality

| Groups | Time/% Survival | |
|---|---|---|
| | <2 Hours | >24 Hours |
| Normal | 100 | 100 |
| FLAG-FasL (4 µg/mouse) + anti-FLAG ® Ab (15 µg/mouse) | 0 | 0 |
| TR6Fc (350 µg/mouse) sc, −5 hr | 0 | 0 |
| TR6Fc (350 µg/mouse) sc, −3 hr | 0 | 0 |
| TR6Fc (350 µg/mouse) sc, −1.5 hr | 0 | 0 |
| TR6Fc (93 µg/mouse) iv, −1 hr | 100 | 100 |
| Fas-Fc (93 µg/mouse) iv, −1 hr | 100 | 100 |
| TR11-Fc(93 µg/mouse) iv, −1 hr | 0 | 0 |

All groups except normal controls received an iv injection of FLAG-FasL + anti-FLAG ® antibody at Time 0.

Example 23

Modulation of T Cell Responses by TNFR6:Soluble TNFR6 Inhibits Alloactivation and Heart Allograft Rejection The ability of TNFR6 to interact with LIGHT and the role of TNFR6 in modulating T cell activities and immunological responses that may be associated with LIGHT were analyzed according to the experiments detailed below.

Materials and Methods of Example 23

Mice

Twelve week-old female C57BL/6 (B6, H-$2^b$), BALB/c, and BALB/c×C57BL/6 F1 (H-$2^{bXd}$) mice were purchased from Jackson Laboratory (Bar Harbor, Me.) or Charles River (LaSalle, Quebec, Canada). 2C TCR transgenic mice were bred in an animal facility as described in Chen, H., et al., 1996. *J. Immunol.* 157:4297, which is hereby incorporated by reference in its entirety.

Expression and Purification of the Human TR6-Fc Fusion Protein

Full-length human TNFR-6 alpha cDNA (FIG. 1, aa 1-300; referred in this example hereafter as "TR6") was PCR-amplified using gene specific primers, fused to the sequence coding for the Fc domain of human IgG$_1$ and subcloned into a baculovirus expression vector pA2. The construct was named pA2-Fc:TR6. Sf9 cells infected pA2-Fc:TR6 were grown in media (100 L) containing 1% ultra low IgG serum (100 L). Conditioned culture supernatant from a bioreactor was harvested by continuous flow centrifugation. The pH of the supernatant was adjusted to pH 7.0, filtered through 0.22 um filter and loaded on to a Protein A column (BioSepra Ceramic HyperD, Life Technologies, Rockville, Md. 30 ml bed volume) previously conditioned with 20 mM phosphate buffer, 0.5 M NaCl (pH 7.2). The column was washed with 15 column volumes (CV) of 20 mM phosphate buffer (pH 7.2) containing 0.5 M NaCl followed by 5 CV of 0.1 M sodium citrate (pH 5.0). TR6-Fc was eluted with 0.1 M citric acid (pH 2.4), and 2 mL fractions were collected into tubes containing 0.6 ml Tris-HCl (pH 9.2). The TR6-Fc positive fractions were determined by SDS-PAGE. The peak fractions were pooled and concentrated with a Protein A column (7 mL bed volume) as described above. The concentrated TR6-Fc was loaded onto a Superdex 200 column (Amersham Pharmacia, Piscataway, N.J. 90 ml bed volume) and eluted with PBS containing 0.5 M NaCl. TR6-Fc positive fractions were determined by non-reducing SDS-PAGE. The pooled positive fractions were dialyzed against 12.5 mM HEPES buffer, pH 5.75 containing 50 mM NaCl. The dialysate was then passed through a 0.2 m filter (Minisart, Sartorius AG, Goettingen, Germany) followed by a Q15X-anion exchange membrane (Sartobind membrane, Sartorius AG, Goettingen, Germany).

Expression and Purification of Full-length Human TR6 (without Fc)

The full-length TR6 cDNA was PCR-amplified and cloned in to the baculovirus expression vector pA2 as describe above. Sf9 cells were infected with the viral construct, and the culture supernatant of the infected cells was loaded onto a Poros HS-50 column (Applied Biosystems, Foster City, Calif.) equilibrated in a buffer containing 50 mM Tris-HCl, pH 7, and 0.1M NaCl. The column was washed with 0.1 M NaCl and eluted stepwise with 0.3M, 0.5M, and 1.5M NaCl. The eluded fractions were analyzed by SDS-PAGE, and the 0.5 M NaCl fraction containing TR6 protein was diluted and loaded onto a set of Poros HQ-50/CM-20 columns in a tandem mode. TR6 was eluted from the CM column with a linear gradient from 0.2M to 1.0 M NaCl.

Expression and Purification of Human TR2-Fc, MCIF-Fc, and Fas-Fc Fusion Proteins The cDNA sequences coding for the extracellular domain of TR2 (aa 1-192), the extracellular domain of Fas (aa 1-169) and a beta chemokine MCIF (aa 1-92) were fused with the cDNA sequence coding for the Fc domain of human IgG$_1$, and cloned into a eukaryotic expression vector pC4. The construct was stably transfected into CHO cells. The Fc fusion proteins from the CHO supernatant were purified with methods used for TR6-Fc.

Expression and Purification of the Human LIGHT Protein

The coding sequence of the natural secreted form of LIGHT (aa 83-240) was cloned into a prokaryotic expression vector pHE4 (ATCC™ Deposit Number 209645, described in U.S. Pat. No. 6,194,168), and expressed in *E. coli*. Inclusion bodies from the transformed bacteria were dissolved for 48-72 hours at 4° C. in 3.5 M guanidine hydrochloride containing 100 mM Tris-HCl, pH 7.4 and 2 mM $CaCl_2$. The solution was quickly diluted with 20-30 volumes of a buffer containing 50 mM Tris-HCl, pH8 and 150 mM NaCl, adjusted to pH 6.6 and chromatographed with a strong cation exchange column (Poros HS-50). The protein was eluted with 3-5 CV of a stepwise gradient of 300 mM, 700 mM, and 1500 mM NaCl in 50 mM MES at pH 6.6. The fraction eluted with 0.7 M NaCl was diluted 3-fold with water, and applied to a set of strong anion (Poros HQ-50) and cation (Poros CM-20) exchange columns in a tandem mode. The CM column was eluted with 10-20 CV of a linear gradient from 50 mM MES pH6.6, 150 mM NaCl to 50 mM Tris-HCl pH 8, 500 mM NaCl. Fractions containing purified LIGHT as analyzed by SDS-PAGE were combined.

Quality Control of the Recombinant Proteins

The endotoxin levels in the purified recombinant proteins were determined by the LAL assay on a *Limulus* Amebocyte Lysate (LAL)-5000 Automatic Endotoxin Detection System (Associates of Cape Cod, Inc. Falmouth, Mass.), according to the standard procedure recommended by the manufacturer. All the recombinant proteins were subjected to N-terminal sequence using an ABI-494 sequencer (PE Biosystems, Inc. Foster City, Calif.) for their authenticity. The proteins was dialyzed against PBS containing 20% (v/v) glycerol for storage at −80° C. For applications such as CTL, cytokine secretion and heart transplantation, the proteins were subsequently dialyzed against PBS to remove the glycerol in the solution.

BIAcore Analysis

The binding of human LIGHT to human TR6-Fc was first assessed by BIAcore analysis (BIAcore Biosensor, Piscataway, N.J.). TR6-Fc or TR2-Fc fusion proteins were covalently immobilized to the BIAcore sensor chip (CM5 chip) via amine groups using N-ethyl-N'-(dimethylaminopropyl)carbodiimide/N-hydroxysuccinimide. Various dilutions of LIGHT were passed through the TR6-Fc- or TR2-Fc-conjugated flow cells at 15 microliters/min for a total volume of 50 microliters. The amount of bound protein was determined during washing of the flow cell with HBS buffer (10 mM HEPES, pH 7.4, 150 mM NaCl, 3.4 mM EDTA, 0.005% Surfactant P20). The flow cell surface was regenerated by washing off the bound proteins with 20 microliters of 10 mM glycine-HCl pH 2.3. For kinetic analysis the flow cells were tested at different flow rates and with different density of the conjugated TR6-Fc or TR2-Fc proteins. The on- and off-rates were determined according a kinetic evaluation program in the BiaEvaluation 3 software using a 1:1 binding model and the global analysis method.

Generation of Stable Cell Lines that Express Human LIGHT

The full-length human LIGHT genes were PCR amplified and subcloned into pcDNA3.1. The parental vector and the LIGHT expression vectors were then transfected into 293F cells (Life Technologies, Grand Island, N.Y.) using Lipofectamine (Life Technology) and stable clones resistant to 0.5 mg/ml geneticin were selected.

Flow Cytometry

Cells were incubated with Fc-fusion proteins in 100 ul FACS buffer (d-PBS with 0.1% sodium azide and 0.1% BSA) for 15-20 minutes at room temperature. The cells were washed once and reacted with goat F (ab)$_2$ anti-human IgG (Southern Biotechnology, Birmingham, Ala.) for 15 minutes at room temperature. After wash, the cells were resuspended in 0.5 ug/ml propidium iodide, and live cells were gated and analyzed on a FACScan (BD Biosciences, Mansfield, Mass.).

Stimulation of Human T Cells for Light Expression

Briefly, T cells were purified from human peripheral blood and stimulated with anti-CD3 in the presence of rhuIL-2 for 5 days. The cells were restimulated with PMA (100 ng/ml) and ionomycin (1 mg/ml) for additional 4 hours. LIGHT expression on the cells was assessed by the binding of TR6-Fc (10 ng/sample), TR2-Fc (250 ng/sample) or Fas-Fc (250 ng/sample) to the cells using flow cytometry.

Three-Way MLR of Human PBMC

PBMC from human donors were purified by density gradient using Lymphocyte Separation Medium (LSM, density at 1.0770 g/ml, Organon Teknika Corporation, West Chester, Pa.). PBMC from three donors were mixed at a ratio of 2:2:0.2 for a final density of $4.2 \times 10^6$ cells/ml in RPMI-1640 (Life Technologies) containing 10% FCS and 2 mM glutamine. The cells were cultured for 5-6 days in round-bottomed microtitre plates (200 microliters/well) in triplicate, pulsed with [$^3$H] thymidine for the last 16 h of culture, and the thymidine uptake was measured as describe before (Chen, H., et al., 1996. *J. Immunol.* 157:4297, which is hereby incorporated by reference in its entirety).

One-Way Ex Vivo MLR after In Vivo Stimulation in Mice

The F1 of C57BL/6×BALB/c mice ($H-2^{bxd}$) were transfused i.v. with $1.5 \times 10^8$ spleen cells from C57BL/6 mice ($H-2^b$) on day 1. TR6-Fc or a control fusion protein was administered i.v. daily for 9 days at 3 mg/kg/day starting one day before the transfusion. The spleen cells of the recipient F1 mice were harvested on day 8 for in vitro proliferation and cytokine assays.

Ex Vivo Mouse Splenocyte Proliferation

Single splenocyte suspensions from normal and transfused F1 mice were cultured in triplicate in 96-well flat-bottomed plates ($4 \times 10^5$ cells/200 microliters/well) for 2-5 days as with the human MLR. After removing 100 microliters of supernatants per well on the day of harvest, 10 microliters alamar Blue (Biosource, Camarillo, Calif.) was added to each well and the cells were cultured for additional 4 h. The cell number in each well was assessed according to $OD_{590}$ using a CytoFlu apparatus (PerSeptive Biosystems, Framingham, Mass.).

Mouse Cytokine Assays

Cytokines in the culture supernatants of mouse spleen cells were measured with commercial ELISA kits from Endogen (Cambridge, Mass.) or R & D Systems (Minneapolis, Minn.).

Mouse Cytotoxic T Lymphocyte (CTL) Assay

Transgenic mice carrying $L^d$-specific TCR (2C mice) were used in this experiment. In the 2C mice, the majority (about 75%) of their T cells are CD8$^+$, and almost all the CD8$^+$ cells carry clonotypic TCR recognized by mAb 1B2. The 2C mice in our colony are of an H-2b background. 2C spleen cells were stimulated with an equal number of mitomycin C-treated BALB/c spleen cells in 24-well plates at a final density of $4 \times 10^6$ cells/2 ml/well. After 5 days of culture in the presence of 10 U/ml recombinant human IL-2, the viable cells were counted and assayed for their $H-2^d$-specific cytotoxic activity using $^{51}$Cr-labeled P815 cells ($H-2^d$) as targets. A standard 4-h $^{51}$Cr release assay (Chen, H., et al., 1996. *J. Immunol.* 157:4297, which is hereby incorporated by reference in its entirety) was carried out in 96-well round-bottomed plates with $0.15 \times 10^6$ target cells/well/200 microliters at different ratios of effector/target cells (10:1, 3:1, 1:1 and 0.3:1). After 4-h incubation, 100 microliters of supernatant was collected from each well and counted in a gamma-counter. The percentage lysis of the test sample is calculated as follows:

$$\% \text{ lysis} = \frac{\text{cpm of the test sample} - \text{cpm of spontaneous release}}{\text{cpm of maximal release} - \text{cpm of spontaneous release}}$$

where the spontaneous release is derived from 100 microliters supernatant of the target cells cultured alone for 4 h, and the maximal release is derived from 100 microliters lysate of $0.15 \times 10^6$ target cells which were lysed by SDS in a total volume of 200 microliters.

Mouse Heart Transplantation

Three- to four-month-old C57BL/6 mice (H-2b) were used as recipients, and 2- to 3-month-old BALB/c mice (H-$2^d$) were used as donors. The procedure of heterotopic heart transplantation was detailed in Chen, H., et al., 1996. *J. Immunol.* 157:4297, which is hereby incorporated by reference in its entirety. The contraction of the transplanted heart was assessed daily by abdominal palpation. The duration between the day of the operation and the first day when a graft totally lost its palpable activity was defined as the graft survival time. Animals that lost palpable activity of the graft within three days after transplantation were classified as technical failures (<5%) and were omitted from the analysis.

Results of Example 23

Preparation of Recombinant Proteins of Human TR6-Fc, TR6, LIGHT, TR2-Fc, Fas-Fc and MCIF-Fc The purified TR6-Fc protein was analyzed with SDS-PAGE under reducing and nonreducing conditions. The result demonstrate that the protein is a disulfide-linked dimer under the non-reducing condition. Light scattering analysis also confirmed that the protein behaves as a dimer in solution. N-terminal sequencing revealed that the mature secreted TR6-Fc had the predicted sequence of VAETP starting at aa 30. The estimated purity of the protein preparation was more than 98% according to SDS-PAGE. Endotoxin levels in the purified proteins were below 10 EU/mg. Human TR6 without Fc, TR2-Fc, Fas-Fc and MCIF-Fc were also prepared to a similar purity as TR6-Fc and their authenticity was verified with N-terminal sequencing.

The Kinetics of Binding Between of TR6 and LIGHT

TR6-Fc has been previously shown to bind both LIGHT and FasL. We determined the kinetics of binding of LIGHT to both the Fc and non-Fc versions of TR6 according to BIAcore analysis. The Kd for LIGHT binding to TR6-Fc and non-Fc forms was 5.46 nM and 14.3 nM, respectively. The off rate (kd) for TR6 (4.83E-03 1/s) was approximately 2-fold higher than that of TR6-Fc (2.30E-03 1/s). The on-rates, ka, were 4.22E05 and 3.38E05 1/Ms for TR6-Fc and TR6, respectively, with TR6-Fc having a slightly higher on rate. The exact reason for the apparent higher Kd value for TR6-Fc compared to TR6-Fc is not known, but a comparable difference in binding affinity was also observed with FasL. The binding of LIGHT to TR2-Fc was also determined. The Kd was 4.56 nM, which is essentially the same as that between LIGHT and TR6-Fc.

TR6-Fc Binds Light Directly and can Compete with TR2 for the Binding of Light Overexpressed on 293 Cell Surface After it was shown that TR6-Fc could bind to LIGHT in BIAcore chips, the ability of TR6-Fc to bind to LIGHT expressed on cell surface was analyzed. This was tested on 293 cells overexpressing LIGHT according to flow cytometry. Fas-Fc was used as a control, and it did not bind to the transfected cells. TR6-Fc could bind to the LIGHT-transfectants, but not on untransfected cells. The specificity of the binding was further demonstrated by competition of TR6-Fc binding with soluble non-Fc form of TR6. Dose-dependent competition of TR6-Fc binding was attained using increasing concentrations of TR6 protein, and nearly complete inhibition was achieved with 10 micrograms of TR6.

It has been shown that TR2 can bind to LIGHT. Since TR6 also binds to LIGHT as shown above, its ability to interfere with the binding between TR2 and LIGHT was analyzed. This possibility was examined with flow cytometry. TR2-Fc could bind to the 293 cells overexpressing LIGHT as expected. TR6 could compete off the binding in a dose-dependent fashion. At 10 micrograms of TR6, the binding of TR2-Fc to the 293 cells was almost completely disappeared.

The results from this section indicate that TR-6 can bind to the cell membrane LIGHT, and it can also compete with TR2 for the binding of LIGHT.

TR6-Fc Reactivity with Activated T Cells

LIGHT expression is upregulated on T cells activated with anti-CD3 and IL-2 followed by PMA and ionomycin treatment (Mauri, D. N., et al., 1998, *Immunity*. 8:21). Using this activation regimen, we confirmed previous results according to flow cytometry that TR2-Fc bound to T cells thus activated. We then extended this observation by showing that as with TR2-Fc, TR6-Fc also bound to these activated T cells. The binding was specific because a control Fc fusion protein Fas-Fc did not bind to these cells, and the binding could be competed off with soluble TR6. The interaction between TR6 and the activated T cells was mediated via LIGHT expressed on these T cells, because the same soluble TR6 protein could also compete off the binding of TR2-Fc and LTbetaR-Fc with the T cells, TR2 and LTbetaR being receptors of LIGHT. These results demonstrate that soluble TR6 could associate with endogenous LIGHT expressed on the activated T cells, and it can interfere with the interaction between LIGHT and TR2 in immune cells.

TR6-Fc Inhibits Human MLR

It has been shown that soluble LIGHT can enhance a 3-way MLR, and soluble recombinant TR2-Fc can inhibit the 3-way MLR or dendritic cells-stimulated alloresponse of the T cells. These immune regulations are likely via the interaction between soluble LIGHT and its cell surface receptor TR2. Since TR6 could interfere with the interaction between LIGHT and TR2 as shown in our flow cytometry, we analyzed its ability to alter T cell alloresponses by testing the effect of TR6 in a three-way human MLR. The results show that TR6-Fc inhibited the T cell proliferation in this system. A control Fc fusion protein had no effect, whereas TR6-Fc at 1 microgram/ml caused nearly 50% inhibition. Further increase of the TR6-Fc concentrations had no additional suppressive effect.

TR6-Fc Inhibits Splenocyte Alloactivation Ex Vivo in Mice

It has been shown previously that T cells stimulated by alloantigen in vivo have increased spontaneous proliferation ex vivo, and alloreactive T cells depend on LIGHT for some costimulation in certain case. We tested whether TR6 had any immune regulatory effects in vivo on alloantigen-stimulated T cells. Parental splenocytes (H-$2^b$) were transfused i.v. into H-$2^{bxd}$ F1 mice, and the recipient mice were given TR6-Fc i.v. at 3 mg/kg/day for 8 days starting on day-1 (the day of transfusion was designated as day 0). The F1 mice were sacrificed on day 8 and the spleen weight of the mice were registered. The splenocytes were then cultured without additional stimulation to measure their spontaneous proliferation and cytokine production. Treatment with TR6-Fc reduced splenomagaly considerably, decreased spontaneous splenocyte proliferation as measured on day 4 after the culture, and inhibited the IFN-gamma and GM-CSF production by the spleen cells as measured from day 2 to day 5 of the culture. In contrast, all mice treated with control Fc or buffer had significantly more severe splenomagaly, higher splenocyte proliferation and higher INF-gamma and GM-CSF productions. Thus, our results show that TR6-Fc is immunologically active and can indeed modulate T cell-mediated alloactivation in vivo.

TR6-Fc and TR6 Inhibits Mouse CTL Activity Developed Against Alloantigens $L^d$-specific transgenic 2C T cells were then used as a model system to evaluate the effect of TR6 on the differentiation of alloantigen-specific CD8 cells into effector cells, since the CD8 cells are mainly responsible to the alloresponsiveness, and the high alloreactive CD8 CTL precursors in the 2C mice gives out elevated read-out signals for easy detection of possible changes exerted by TR6. In the presence of either TR6-Fc or TR6, the CTL activity was decreased significantly compared with the cultures containing no recombinant protein or containing normal human IgG. The detection of similar effect of TR6 and TR6-Fc in this experiment is of significant importance, because it excludes the possibility that the effect seen with TR6-Fc is Fc-mediated. The CTL assay presented in the figure was carried out on day 6 of the culture. When CTL were assayed on day 5 of the culture, there was no obvious difference between samples with or without TR6. This indicates that the repression of CTL seen on day 6 is not due to a kinetic shift.

TR6-Fc Modulates Lymphokine Production of 2C T Cells Stimulated with $H-2^d$ Alloantigens In Vitro The CTL differentiation and maturation are modulated by a plethora of lymphokines, and we examined the production of battery of lymphokines produced by 2C spleen cells upon stimulation of mitomycin C-treated BALB/c spleen cells ($H-2^d$) in the presence of TR6-Fc. There was a suppression of IL-2 production between 24-72 h after the stimulation, while the levels of IL-10 were upregulated.

TR6-Fc Prolongs Heart Allograft Survival of the Mice

Since TR6-Fc could repress ex vivo T cell proliferation after the alloantigen stimulation, and inhibit CTL development in in vitro assays, we speculated that it could also modulate a more complete immune response such as graft rejection. This was tested in a model of mouse heterotopic heart allografting, with C57BL/6 as recipients and BALB/c as donors. The recipients were administrated with TR6-Fc i.v. daily at 7.5 mg/kg/day for 7 days starting from one day before the operation. For this test group, the mean survival time (MST) of the grafts was 10.0+1.2 days, while the MST of the control group was 6.8+0.4 days. The difference between the two groups was highly significant (p=0.0001, non-paired Student's t test). This result shows that TR6-Fc could modulate an authentic immune response such as allograft rejection.

Example 24

TNFR-6 Alpha, TNFR-6 Beta and DR3 Interact with TNF-Gamma-beta

The premyeloid cell line TF-1 was stably transfected with SRE/SEAP (Signal Response Element/Secreted Alkaline Phosphatase) reporter plasmid that responds to the SRE signal transduction pathway. The TF1/SRE reporter cells were treated with TNF-gamma-beta (International Publication Numbers WO96/14328, WO00/66608, and WO00/08139) at 200 ng/mL and showed activation response as recorded by the SEAP activity. This activity can be neutralized by A TNFR-6 alpha Fc fusion protein (hereinafter TR6.Fc in this example) in a dose dependent manner. The TR6.Fc by itself, in contrast, showed no activity on the TF1/SRE reporter cells. The results demonstrate that 1) TF-1 is a target cell for TNF-gamma-beta ligand activity; and 2) TR6 interacts with TNF-gamma-beta and inhibits its activity on TF-1 cells. TR6 is known to have two splice forms, TR6-alpha and TR6-beta; both splice forms have been shown to interact with TNF-gamma-beta.

Similarly, the interaction of DR3 (International Publication Numbers WO97/33904 and WO/0064465) and TNF-gamma-beta can be demonstrated using TF-1/SRE reporter cells. The results indicate that DR3.Fc interacts with TNF-gamma-beta, either by competing naturally expressed DR3 on TF-1 cells or forming inactive TNF-gamma-beta/DR3.fc complex, or both.

At least three additional pieces of evidence demonstrate an interaction between TNF-gamma-beta and DR3 and TR6. First, both TR6.Fc and DR3.Fc are able to inhibit TNF-gamma-beta activation of NFkB in 293T cells, whereas in the same experiment, TNFR1.Fc was not able to inhibit TNF-gamma-beta activation of NFkB in 293T cells. Secondly, both TR6.Fc and DR3.Fc can be used to immunoprecipitate TNF-gamma-beta. Thirdly, TR6.Fc proteins can be detected by FACS analysis to specifically bind cells transfected with TNF-gamma-beta.

Example 25

TNF-gamma-beta is a Novel Ligand for DR3 and TR6-alpha (DcR3) and Functions as a T cell Costimulator Introduction Members of the TNF and TNFR superfamilies of proteins are involved in the regulation of many important biological processes, including development, organogenesis, innate and adaptive immunity (Locksley et al., Cell 104:487-501 (2001)). Interaction of TNF ligands such as TNF, Fas, LIGHT and BLyS with their cognate receptor (or receptors) has been shown to affect the immune responses, as they are able to activate signaling pathways that link them to the regulation of inflammation, apoptosis, homeostasis, host defense, and autoimmunity. The TNFR superfamily can be divided into two groups based on the presence of different domains in the intracellular portion of the receptor. One group contains a TRAF binding domain that enables them to couple to TRAFs (TNFR-associated factor); these in turn activate a signaling cascade that results in the activation of NF-κB and initiation of transcription. The other group of receptors is characterized by a 60 amino acid globular structure named Death Domain (DD). Historically death domain-containing receptors have been described as inducers of apoptosis via the activation of caspases. These receptors include TNFR1, DR3, DR4, DR5, DR6 and Fas. More recent evidence (Siegel et al., Nature Immunology 1:469-474 (2000) and references within) has shown that some members of this subgroup of receptors, such as Fas, also have the ability to positively affect T cell activation. A third group of receptors has also been described. The members of this group, that include DcR1, DcR2, OPG, and TNFR-6 alpha (also called DcR3, and hereinafter in this example referred to as "TR6"), have been named decoy receptors, as they lack a cytoplasmic domain and may act as inhibitors by competing with the signal transducing receptor for the ligand (Ashkenazi et al., Curr. Opin. Cell Biol. 11:255-260 (1999)). TR6, which exhibits closest homology to OPG, associates with high affinity to FasL and LIGHT, and inhibits FasL-induced apoptosis both in vitro and in vivo (Pitti et al., Nature 396:699-703 (1998), Yu, et al., J. Biol. Chem. 274: 13733-6 (1999); Connolly, et al., J. Pharmacol. Exp. Ther. 298:25-33 (2001)). Its role in down-regulating immune responses was strongly suggested by the observation that TR6 suppresses T-cell responses against alloantigen (Zhang et al., J. Clin. Invest. 107:1459-68 (2001)) and certain tumors over-express TR6 (Pitti et al., Nature 396:699-703 (1998), Bai et al., Proc. natl. Acad. Sci. 97:1230-1235 (2000)).

DR3 (described in International Publication Numbers WO97/33904 and WO/0064465 which are herein incorporated by reference in their entireties) is a DD-containing receptor that shows highest homology to TNFR1 (Chinnaiyan et al., Science 274:990-2 (1996); Kitson et al., Nature 384:372-5 (1996), Marsters et al., Curr. Biol. 6:1669-76 (1996); Bodmer et al., Immunity 6:79-88 (1997); Screaton et al., Proc. Natl. Acad. Sci. 94:4615-19 (1997); Tan et al., Gene 204:35-46 (1997)). In contrast to TNFR1, which is ubiquitously expressed, DR3 appears to be mostly expressed by lymphocytes and is efficiently induced following T cell activation. TWEAK/Apo3L was previously shown to bind DR3 in vitro (Marsters et al., Curr. Biol. 8:525-528 (1998)). However, more recent work raised doubt about this interaction and showed that TWEAK was able to induce NF-κB and caspase activation in cells lacking DR3 (Schneider et al., Eur. J. Immunol. 29:1785-92 (1999); Kaptein et al., FEBS Letters 485:135-141 (2000)).

In this example, the characterization of the ligand, TNF-gamma-beta (also known as TL1β; described in International Publication Numbers: WO00/08139 and WO00/66608 which are herein incorporated by reference in their entireties), for both DR3 and TR6/DcR3 is described. TNF-gamma-beta is a longer variant of TNF-gamma-alpha (also known as VEGI and TL1; described in International Publication Numbers WO96/14328, WO99/23105, WO00/08139 and WO00/66608 which are herein incorporated by reference in their entireties), which was previously identified as an endothelial-derived factor that inhibited endothelial cell growth in vitro and tumor progression in vivo (Tan et al., Gene 204:35-46 (1997); Zhai et al., FASEB J. 13:181-9 (1999); Zhai et al., Int. J. Cancer 82:131-6 (1999); Yue et al., J. Biol. Chem. 274: 1479-86 (1999)). It was found that TNF-gamma-beta is the more abundant form than TNF-gamma-alpha and is upregulated by TNFα and IL-1α. U.S. Pat. No. 5,876,969

As shown herein, the interaction between TNF-gamma-beta and DR3 in 293T cells and in the erythroleukemic line TF-1 results in activation of NF-κB and induction of caspase activity, respectively. TR6 is able to inhibit these activities by competing with DR3 for TNF-gamma-beta. More importantly, it was found that in vitro, TNF-gamma-beta functions specifically on activated T cells to promote survival and secretion of the proinflammatory cytokines IFNγ and GMCSF, and it markedly enhances acute graft-versus-host reactions in mice.

Results

TNF-gamma-beta is a Longer Variant of TNF-gamma-alpha, a Member of the TNF Superfamily of Ligands To identify novel TNF like molecules, a database of over three million human expressed sequence tag (EST) sequences was analyzed using the BLAST algorithm. Several EST clones with high homology to TNF like molecule 1, TNF-gamma-alpha (Tan et al., Gene 204:35-46 (1997); Zhai et al., FASEB J. 13:181-9 (1999); Yue et al., J. Biol. Chem. 274: 1479-86 (1999)) were identified from endothelial cell cDNA libraries)) Sequence analysis of these cDNA clones revealed a 2080 base pair (bp) insert encoding an open reading frame of 251 amino acids (aa) with two upstream in-frame stop codons. The predicted protein lacks a leader sequence but contains a hydrophobic transmembrane domain near the N-terminus, and a carboxyl domain that shares 20-30% sequence similarity with other TNF family members. Interestingly, the C-terminal 151-aa of this protein (residues 101-251) is identical to residues 24 to 174 of TNF-gamma-alpha, whereas the amino-terminal region shares no sequence similarity. The predicted extracellular receptor-interaction domain of TNF-gamma-beta contains two potential N-linked glycosylation sites and shows highest amino acid sequence identity to TNF (24.6%), followed by FasL (22.9%) and LTα (22.2%). A 337-bp stretch of the TNF-gamma-beta cDNA, containing most of the 5' untranslated region and the sequences encoding the first 70 amino acids of the TNF-gamma-beta protein, matches a genomic clone on human chromosome 9 (Genbank Accession: AL390240, clone RP11-428F18). Further analysis of the human genomic sequences reveals that TNF-gamma-alpha and TNF-gamma-beta are likely derived from the same gene. While TNF-gamma-beta is encoded by four putative exons, similar to most TNF-like molecules, TNF-gamma-alpha is encoded by only the last exon and the extended N-terminal intron region, and therefore lacks a putative transmembrane domain and the first conserved β-sheet Mouse and rat TNF-gamma-beta cDNAs isolated from normal kidney cDNAs each encode a 252-aa protein. The overall amino acid sequence homology between human and mouse, and human and rat TNF-gamma-beta proteins is 63.7% and 66.1%, respectively. Higher sequence homology was found in the predicted extracellular receptor-interaction domains, of which human and mouse share 71.8% and human and rat share 75.1% sequence identity. An 84.2% sequence identity is seen between the mouse and rat TNF-gamma-beta proteins.

Like most TNF ligands, TNF-gamma-beta exists as a membrane-bound protein and can also be processed into a soluble form when ectopically expressed. The N-terminal sequence of soluble TNF-gamma-beta protein purified from full length TNF-gamma-beta transfected 293T cells was determined to be Leu 72.

TNF-gamma-beta is Predominantly Expressed by Endothelial Cells, a More Abundant Form than TNF-gamma-alpha, and is Inducible by TNF and IL-1α

To determine the expression pattern of TNF-gamma-beta, TNF-gamma-beta specific primer and fluorescent probe were used for quantitative real-time polymerase chain reaction (TaqMan) and reverse transcriptase polymerase chain reaction (RT-PCR) (see Experimental Procedures below). TNF-gamma-beta is expressed predominantly by human endothelial cells, including the umbilical vein endothelial cells (HUVEC), the adult dermal microvascular endothelial cells (HMVEC-Ad), and uterus myometrial endothelial cells (UtMEC-Myo), with highest expression seen in HUVEC. A ~750 bp DNA fragment was readily amplified from these endothelial cells by RT-PCR, indicating the presence of full length TNF-gamma-beta transcripts. Very little expression was seen in human aortic endothelial cells (HAEC) or other human primary cells including adult dermal fibroblast (NHDF-Ad and HFL-1), aortic smooth muscle cells (AoSMC), skeletal muscle cells (SkMC), adult keratinocytes (NHEK-Ad), tonsillar B cells, T cells, NK cells, monocytes, or dendritic cells. Consistent with these results, TNF-gamma-beta RNA was detected in human kidney, prostate, stomach, and low levels were seen in intestine, lung, and thymus, but not in heart, brain, liver, spleen, or adrenal gland. No significant levels of TNF-gamma-beta mRNA in any of the cancer cell lines tested, including 293T, HeLa, Jurkat, Molt4, Raji, IM9, U937, Caco-2, SK-N-MC, HepG2, KS4-1, and GH4C were detected.

As the expression pattern of TNF-gamma-beta is very similar to that of TNF-gamma-alpha (Tan et al., Gene 204: 35-46 (1997); Zhai et al., FASEB J. 13:181-9 (1999)), the relative abundance of the two RNA species was analyzed using TNF-gamma-alpha and TNF-gamma-beta specific primers and fluorescence probes for conventional and quantitative RT-PCR. More TNF-gamma-beta mRNA was detected than that of TNF-gamma-alpha using both methods. The amount of TNF-gamma-beta mRNA is at least 15-fold higher than that of TNF-gamma-alpha in the same RNA samples. To determine if TNF-gamma-beta mRNA levels were inducible, HUVEC cells were stimulated with either TNF, IL-1α, PMA, bFGF or IFNγ. PMA and IL-1α rapidly induced high levels of TNF-gamma-beta mRNA, with a peak in expression reached at 6 hours after treatment. TNF was also able to induce TNF-gamma-beta mRNA, but the time course of induction appeared to be delayed compared to PMA and IL-1α. In contrast, bFGF and IFNγ did not significantly affect the expression of TNF-gamma-beta. TNF-gamma-beta protein levels in the supernatants of activated HUVEC cells were analyzed by ELISA and a similar profile of induction was observed.

Identification of DR3 and TR6 as Receptors for TL1β

To identify the receptor for TNF-gamma-beta, we generated HEK293F stable transfectants expressing full length TNF-gamma-beta on the cell surface (confirmed by Taqman and flow cytometric analysis using TNF-gamma-beta monoclonal antibody). These cells were used to screen the Fc-fusion form of the extracellular domain of TNFR family members, including TNFR1, Fas, HveA, DR3, DR4, DR5, DR6, DcR1, DcR2, TR6, OPG, RANK, AITR, TACI, CD40, and OX40. DR3-Fc and TR6-Fc bound efficiently to cells expressing TNF-gamma-beta but not to vector control transfected cells. In contrast, HveA-Fc and all the other receptors tested did not bind to the TNF-gamma-beta expressing cells. TR6 has been previously described as a decoy receptor (Pitti et al., Nature 396:699-703 (1998); Yu et al., J. Biol. Chem. 274:13733-6 (1999)) capable of competing with Fas and HveA for binding of FasL and LIGHT, respectively. Whether TR6 could compete with DR3 for TNF-gamma-beta binding was tested. When a 2:1 molar ratio of a non-tagged form of TR6 and DR3-Fc were used, no binding of DR3-Fc was detected on TNF-gamma-beta expressing cells. These results demonstrated that both DR3 and TR6 can bind to membrane-bound form of the TNF-gamma-beta protein.

Whether TNF-gamma-beta protein could bind to membrane-bound form of the receptor, DR3 was tested. A FLAG-tagged soluble form of the TL1 (aa 72-251) protein was tested for binding of cells transiently transfected with different members of the TNFR family, including TNFR2, LTβ R, 4-1BB, CD27, CD30, BCMA, DR3, DR4, DR5, DR6, DcR1, DcR2, RANK, HveA, and AITR. Binding of FLAG-TL1β, to cells expressing full length or DD-deleted DR3, but not to any of the other receptors tested, was consistently detected, demonstrating that TNF-gamma-beta interacts with membrane-associated DR3. The small shift (~30%) seen when full length DR3 was used is likely due to the presence of low DR3-expressing cells while DR3 overexpressed cells undergone apoptosis.

Communoprecipitation studies were also performed to confirm that TNF-gamma-beta could specifically bind DR3 and TR6. Consistent with what we observed in FACS analysis, we found that DR3-Fc and TR6-Fc specifically interacted with FLAG-TNF-gamma-beta. In contrast, Fas-Fc or TACI-Fc could not immunoprecipitate FLAG-TNF-gamma-beta, but efficiently bound their known ligands, FLAG-FasL and FLAG-BlyS, respectively.

To verify that the TNF-gamma-beta binding to DR3 and TR6 was specific and exhibited characteristics that were similar to those observed with other TNF family members to their cognate receptors, a BIAcore analysis using a non-tagged TNF-gamma-beta (aa 72-251) protein purified from *E. coli* was performed. The kinetics of TNF-gamma-beta binding to DR3-Fc was determined using three different batches of the TNF-gamma-beta protein. The ka and kd values were found to be 6.39E+05 Ms$^{-1}$ and 4.13E-03M$^{-1}$, respectively. The average Kd value was 6.45±10.2 nM. TNF-gamma-beta was also examined for its ability to bind to several other TNF-related receptors (HveA, BCMA, TACI, and TR6). In addition to DR3, only TR6 was found to have significant and specific binding to TNF-gamma-beta. The ka and kd values were 1.04E+06 Ms and 1.9E-03 M respectively, which gives a Kd of 1.8 nM. The specificity of binding of TL1β to DR3-Fc and TR6-Fc were confirmed by the competition of TNF-gamma-beta binding in the presence of excess soluble receptor-Fc. These Kd values for binding of TNF-gamma-beta to DR3-Fc and TR6-Fc are comparable to those determined for other TNFR-ligand interactions.

Interaction of TL1β with DR3 Induces Activation of NF-κB

Previous reports have demonstrated that ectopic expression of DR3 results in the activation of the transcription factor NF-κB (Chinnaiyan et al., Science 274:990-2 (1996); Kitson et al., Nature 384:372-5 (1996), Marsters et al., Curr. Biol. 6:1669-76 (1996); Bodmer et al., Immunity 6:79-88 (1997)). TNF-gamma-beta induced signaling in a reconstituted system in 293T cells in which DR3 and a NF-κB-SEAP reporter were introduced by transient transfection was studied. To avoid spontaneous apoptosis or NF-κB activation accompanied with DR3 overexpression, a limited amount of DR3-expression DNA that by itself minimally activated these pathways was used. Under these conditions, cotransfection of cDNAs encoding full length or the soluble form of TNF-gamma-beta resulted in significant NF-κB activation. This signaling event was dependent on the ectopic expression of DR3 and the intactness of the DR3 death domain, as TNF-gamma-beta alone or in combination with a DD-deleted DR3 did not induce NF-κB activation in these cells. Cotransfection of DR3 with cDNAs encoding TNF-gamma-alpha (full length or N-terminal 24-aa truncated) failed to induce NF-κB activation. A similar induction of NF-κB activity was observed when increasing amounts of recombinant TL1β protein (aa 72-251, with or without FLAG® tag) were added to DR3 expressing cells. This induction of NF-κB was specifically inhibited by the addition of excess amount of DR3-Fc or TR6-Fc, but not by the addition of Fas-Fc or TNFR1-Fc. These results demonstrated that TNF-gamma-beta is a signaling ligand for DR3 that induces NF-κB activation, and TR6 can specifically inhibit this event.

TL1β Induces IL-2 Responsiveness and Cytokine Secretion from Activated T Cells

As DR3 expression is mostly restricted to the lymphocytes (Chinnaiyan et al., Science 274:990-2 (1996); Kitson et al., Nature 384:372-5 (1996); Marsters et al., Curr. Biol. 6:1669-76 (1996); Bodmer et al., Immunity 6:79-88 (1997); Screaton et al., Proc. Natl. Acad. Sci. 94:4615-19 (1997); Tan et al., Gene 204:35-46 (1997)) and is upregulated upon T cell activation, we examined the biological activity of TNF-gamma-beta on T cells. Recombinant TNF-gamma-beta (aa 72-251) protein was tested for its ability to induce proliferation of resting or costimulated T cells (treated with amounts of anti- CD3 and anti-CD28 that are not sufficient to induce proliferation). In resting or costimulated T cells, no significant increase in proliferation over background was observed. Interestingly, cells that were previously treated with TNF-gamma-beta for 72 hours were able to proliferate significantly in the presence of IL-2 than cells without TNF-gamma-beta preincubation, indicating that TNF-gamma-beta increases the IL-2 responsiveness of costimulated T cells.

As enhanced IL-2 responsiveness has been associated with increased IL-2 receptor expression and altered cytokine secretion, it was of interest to assess these responses on costimulated T cells treated with TNF-gamma-beta. TNF-gamma-beta treatment indeed upregulated IL-2Rα (CD25) and IL-2Rβ (CD 122) expression from these cells. The extent of the increase in IL-2 receptor expression is consistent with the moderate increase in IL-2 responsiveness compared with IL-2 itself. We next measured cytokine secretion from these cells and found that both IFNγ and GMCSF were significantly induced, whereas IL-2, IL-4, IL-10, or TNF were not. This effect was mostly dependent on the T cell coactivator CD28, as treatment of the cells with anti-CD3 and TNF-gamma-beta only minimally induced cytokine secretion. The effect that we observed on T cells was specifically mediated by TNF-gamma-beta, as addition of monoclonal neutralizing antibody to TL1β, or addition of DR3-Fc or TR6-Fc proteins was able to inhibit TNF-gamma-beta-mediated IFNγ secretion. TNF-gamma-beta was also tested on a variety of primary cells, including B cells, NK cells, and monocytes, but no significant activity was detected, suggesting a specific activity of TNF-gamma-beta on T cells.

TL1β Induces Caspase Activation in TF-1 Cells but not in T Cells

Overexpression of DR3 in cell lines induces capase activation (Chinnaiyan et al., Science 274:990-2 (1996); Kitson et al., Nature 384:372-5 (1996); Marsters et al., Curr. Biol. 6:1669-76 (1996); Bodmer et al., Immunity 6:79-88 (1997)). We tested whether TL1β could induce caspase activation in primary T cells. Purified T cells were activated with PHA and incubated with recombinant TNF-gamma-beta or FasL in the presence or absence of cycloheximide (CHX). No induction of caspase activity was detected in TNF-gamma-beta treated T cells, but was readily measured when cells were triggered with FasL, suggesting that under this experimental condition, TNF-gamma-beta does not activate caspases in T cells (the assay we used detects activation of caspases 2, 3, 6, 7, 8, 9, and 10). Various cell lines for the expression of DR3 and found that the erythroleukimic cell line TF-1 expressed high levels of DR3 were then analyzed. The effect of recombinant TNF-gamma-beta protein on caspase activation in TF-1 cells was then measured. In the absence of cycloheximide, no significant increase in caspase activity was detected following TNF-gamma-beta treatment, while TNF-gamma-beta was able to efficiently induce caspase activation in the presence of cycloheximide. This effect was inhibited by either DR3-Fc or TR6-Fc protein but not by LIGHT-Fc. An anti-TNF-gamma-beta monoclonal antibody was also shown to completely inhibit this activity, confirming that the caspase activation was mediated by TNF-gamma-beta.

TL1β Promotes Splenocyte Alloactivation in Mice

To determine if the in vitro activities of TNF-gamma-beta could be reproduced in vivo, a mouse model of acute graft-versus-host-response (GVHR) was developed in which parental C57BL/6 splenocytes were injected intravenously into (BALB/c X C57 BL/6) F1 mice (CB6F1), and the recipient's immune responses were measured. Typical alloactivation results in increased splenic weight of the recipient mice and enhanced proliferation and cytokine production of the splenocytes cultured ex-vivo (Via, J. Immunol. 146:2603-9 (1991); Zhang et al., J. Clin. Invest. 107:1459-68 (2001)). The large number of T cells in the spleen and their expected upregulation of DR3 in response to alloactivation makes this an ideal model to assess the effect of TNF-gamma-beta on a defined in vivo immune response. Five day administration of 3 mg/kg of the recombinant TNF-gamma-beta protein markedly enhanced the graft-versus-host responses. The mean (n=4) weight of normal spleens obtained from naive CB6F1 mice was 0.091 g. Alloactivation resulted in a 2.5 fold increase in splenic weight (~0.228 g). Treatment of allografted CB6F1 mice with recombinant TNF-gamma-beta protein (aa 72-251) further increased splenic weight about 50%, to a mean value of 0.349 g. TNF-gamma-beta treatment also significantly enhanced ex-vivo splenocyte expansion, and secretion of IFNγ and GMCSF. Thus, TNF-gamma-beta strongly enhances GVHR in vivo, and this effect is consistent with TNF-gamma-beta's in vitro activities.

Experimental Procedures

Cells, Constructs, and Other Reagents

All human cancer cell lines and normal lung fibroblast (HFL-1) were purchased from American Tissue Culture Collection. Human primary cells were purchased from Clonetics Corp. Cells were cultured as recommended. Human cDNA encoding the full length TNF-gamma-alpha, TNF-gamma-beta, DR3; the extracellular domain of TNF-gamma-alpha (aa 25-174), TNF-gamma-beta (aa 72-251), BlyS (aa 134-285), FasL (aa 130-281), and death domain truncated DR3 (DR3ADD, aa 1-345) were amplified by PCR and cloned into the mammalian expression vectors pC4 and/or pFLAG-CMV™1 (Sigma). The extracellular domain of human DR3 (aa 1-199), TACI (aa 1-159), HveA (aa 1-192), Fas (aa 1-169), and full length TR6 (aa 1-300), was each fused in-frame, at its C-terminus, to the Fc domain of human IgG1 and cloned into pC4. Rabbit polyclonal TNF-gamma-beta antibody was generated using recombinant TNF-gamma-beta (aa 72-251) protein and purified on a TNF-gamma-beta affinity column. Monoclonal antibodies were raised against recombinant TNF-gamma-beta as described (Kohler and Milstein, Nature 256:503-519 (1975)).

Cloning of Human, Mouse, and Rat TNF-gamma-beta cDNA

TNF-gamma-beta was identified by screening a human EST database for sequence homology with the extracellular domain of TNF, using the blastn and tblastn algorithms. The extracellular domain of the mouse and rat TNF-gamma-beta cDNA was isolated by PCR amplification from mouse or rat kidney Marathon-Ready cDNAs (Clontech) using human TNF-gamma-beta specific primers. The resulting sequences were then used to design mouse and rat TNF-gamma-beta specific primers to amplify the 5' and 3' ends of the cDNA using Marathon cDNA Amplification kit (Clontech). Each sequence was derived and confirmed from at least two independent PCR products.

Generation of TNF-gamma-beta Stable Cell Line

HEK293F cells were transiently transfected with pcDNA3.1(+) (vector control) or pcDNA3.1(+) containing full length TNF-gamma-beta. Cells resistant to 0.5 mg/ml Genticin (Invitrogen) were selected and expanded. Expression of TNF-gamma-beta mRNA was confirmed by quantitative RT-PCR analysis and surface expression of TNF-gamma-beta protein confirmed by FACS analyses using TNF-gamma-beta monoclonal antibodies.

Quantitative Real-Time PCR (TaqMan) and RT-PCR Analysis

Total RNA was isolated from human cell lines and primary cells using TriZOL (Invitrogen). TaqMan was carried out in a 25 microliter reaction containing 25 ng of total RNA, 0.6 µM each of gene-specific forward and reverse primers and 0.2 µM of gene-specific fluorescence probe. TNF-gamma-beta specific primers (forward: 5'-CACCTCTTAGAGCAGACG-GAGATAA-3' (SEQ ID NO:34), reverse: 5'-TTAAAGT-GCTGTGTGGGAGTTTGT-3' (SEQ ID NO:35), and probe: 5'-CCAAGGGCACACCTGACAGTTGTGA-3' (SEQ ID NO:36)) amplify an amplicon span nucleotide 257 to 340 of the TNF-gamma-beta cDNA (aa 86-114 of the protein), while TNF-gamma-alpha specific primers (forward: 5'-CAAAGTCTACAGTTTCCCAATGAGAA-3' (SEQ ID NO:37); reverse: 5'-GGGAACTGATTTTTAAAGTGCT-GTGT-3' (SEQ ID NO:38); probe: 5'-TCCTCTTTCT-TGTCTTTCCAGTTGTGAGACAAAC-3' (SEQ ID NO:39)) amplify nucleotide 17 to 113 of the TNF-gamma-alpha cDNA (aa 7-37 of the protein). Gene-specific PCR products were measured using an ABI PRISM 7700 Sequence Detection System following the manufacturer's instruction (PE Corp.). The relative mRNA level of TNF-gamma-beta was normalized to the 18S ribosomal RNA internal control in the same sample.

For RT-PCR analysis, 0.5 micrograms of total RNA was amplified with TNF-gamma-alpha (5'-GCAAAGTCTA-CAGTTTCCCAATGAGAAAATTAATCC-3' (SEQ ID NO:40)) or TNF-gamma-beta specific sense primer (5'-ATG-GCCGAGGATCTGGGACTGAGC-3' (SEQ ID NO:41)) and an antisense primer (5'-CTATAGTAAGAAGGCTC-CAAAGAAGGTTTTATCTTC-3' (SEQ ID NO:42)) using SuperScript One-Step RT-PCR System (Invitrogen). β-actin was used as internal control.

Transfection and NF-κB Reporter Assay 293T cells were transiently transfected using LipofectAMINE and PLUS reagents according to the manufacturer's instruction (Invitrogen). For reporter assays, 293T cells, at $5 \times 10^5$ cells/well, were seeded in 6-well plates and transfected with a total of 1 microgram of DNA. pC4 DNA was used as filler DNA. Conditioned supernatant was collected 24 hr post-transfection and assayed for secreted alkaline phosphatase (SEAP) activity using the Phospha-Light™ chemiluminescent reporter gene assay system (Tropix). pCMV-lacZ was used as internal control for transfection efficiency normalization.

Recombinant Protein Purification

FLAG fusion proteins were produced from 293T cells by transient transfection, and purified on anti-FLAG® M2 affinity columns (Sigma) according to manufacturer's instruction. Receptor proteins with or without Fc fusion were produced from Baculovirus or CHO stable cell lines as described (Zhang et al., J. Clin. Invest. 107:1459-68 (2001)). Recombinant, untagged TNF-gamma-beta protein (aa 72-251) was generated and purified from E. coli. Briefly, E. Coli cell extract was separated on a HQ-50 anion exchange column (Applied Biosystems) and eluted with a salt gradient. The 0.2 M NaCl elution was diluted and loaded on a HQ-50 column, and the flow through was collected, adjusted to 0.8 M ammonia sulfate and loaded on a Butyl-650s column (Toso Haus). The column was eluted with a 0.6M to 0 M ammonia sulfate gradient and the fractions containing TNF-gamma-beta protein were pooled and further purified by size exclusion on a Superdex-200 column (Pharmacia) in PBS. All recombinant proteins were confirmed by $NH_2$-terminal sequencing on a ABI-494 sequencer (Applied Biosystem). The endotoxin level of the purified protein was less than 10 EU/mg as measured on a LAL-5000E (Cape Cod Associates).

Flow Cytometry, Immunoprecipitation, and Western Blot Analysis

One million cells, in 0.1 ml of FACS buffer (PBS, 0.1% BSA, 0.1% $NaN_3$), were incubated with 0.1-1 microgram of protein or antibody at RT for 15 min. The cells were washed with 3 ml of FACS buffer, reacted with biotinylated primary antibody, and stained with PE-conjugated secondary antibody at RT for 15 min. Cells were then washed again, resuspended in 0.5 microgram/ml of propidium iodide, and live cells were gated and analyzed on a FACScan using the CellQuest software (BD Biosciences).

For communoprecipiation studies, 2 micrograms each of purified TNFR-Fc proteins was incubated with 1 microgram of Flag-tagged TNF-gamma-beta, FasL or BlyS protein and 20 microliters of protein A-Sepharose beads in 0.5 ml of IP buffer (DMEM, 10% FCS, 0.1% Triton X-100) at 4° C. for 4 hr. The beads were then precipitated and washed extensively with PBST buffer (PBS, 0.5% Triton X-100) before boiled in SDS-sample buffer. Proteins were resolved on 4-20% Tris-Glycine gels (NOVEX), transferred to nitrocellulose membranes, and blotted with anti-FLAG®M2 monoclonal antibody (1 microgram/ml, Sigma) and horseradish peroxidase (HRP)-conjugated goat anti-mouse IgG antibody (0.5 microgram/ml).

BIAcore Analysis

Recombinant TNF-gamma-beta (from E. Coli) binding to various human TNF receptors was analyzed on a BIAcore 3000 instrument. TNFR-Fc were covalently immobilized to the BIAcore sensor chip (CM5 chip) via amine groups using N-ethyl-N'-(dimethylaminopropyl) carbodiimide/N-hydroxysuccinimide chemistry. A control receptor surface of identical density was prepared, BCMA-Fc, that was negative for TNF-gamma-beta binding and used for background subtraction. Eight different concentrations of TNF-gamma-beta (range: 3-370 nM) were flowed over the receptor-derivatized flow cells at 15 microliters/min for a total volume of 50 microliters. The amount of bound protein was determined during washing of the flow cell with HBS buffer (10 mM HEPES, pH 7.4, 150 mM NaCl, 3.4 mM EDTA, 0.005% Surfactant P20). The flow cell surface was regenerated by displacing bound protein by washing with 20 microliters of 10 mM glycine-HCl, pH 2.3. For kinetic analysis, the on and off rates were determined using the kinetic evaluation program in BIAevaluation 3 software using a 1:1 binding model and the global analysis method.

T Cell Proliferation Assays.

Whole blood from human donors was separated by Ficoll (ICN Biotechnologies) gradient centrifugation and cells were cultured overnight in RPMI containing 10% FCS (Biofluids). T cells were separated using the MACS PanT separation kit (Milteny Biotech), the T cell purity achieved was usually higher that 90%. The cells were seeded on anti-CD3 (0.3 microgram/ml, Pharmingen) and anti-CD28 (5.0 microgram/ml) coated 96-well plates at $2 \times 10^4$/well, and were incubated with medium alone, 1 ng/ml of IL-2 (R & D Systems), or 100 ng/ml of TNF-gamma-beta (aa 72-251) at 37° C. After 72 hour in culture, the cells were either untreated or treated with 1 ng/ml of IL-2, and pulsed with 0.5 µCi of $^3$H-thymidine for another 24 hours and incorporation of H measured on a scintillation counter.

Cytokine ELISA Assays for Primary Cells $1 \times 10^5$ cells/ml of purified T cells were seeded in a 24-well tissue culture plate that had been coated with anti-CD3 (0.3 microgram/ml) and anti-CD28 (5.0 microgram/ml) overnight at 4° C. Recombinant TNF-gamma-beta (aa72-251) protein (100 ng/ml) was added to cells and supernatants were collected 72 hours later. ELISA assay for IFNγ, GM-CSF, IL-2

IL-4, IL-10 and TNFα were performed using kits purchased from R & D Systems. Recombinant human IL-2 (5 ng/ml) was used as a positive control. All samples were tested in duplicate and results were expressed as an average of duplicate samples plus or minus error.

Caspase Assay

TF-1 cells or PHA-activated primary T cells were seeded at 75,000 cells/well in a black 96-well plate with clear bottom (Becton Dickinson) in RPMI Medium containing 1% fetal bovine serum (Biowhittaker). Cells were treated with TNF-gamma-beta (aa72-251, 100 ng/ml) in the presence or absence of cycloheximide (10 micrograms/ml). Caspase activity was measured directly in the wells by adding equal volume of a lysis buffer containing 25 μM DEVD-rodamine 110 (Roche Molecular Biochemicals), and allowed the reaction to proceed at 37 C for 1 to 2 hours. Release of rodamine 110 was monitored with a Wallac Victor2 fluorescence plate reader with excitation filter 485 nm and emission filter 535 nm.

For the inhibition studies using Fc-proteins or antibodies, the indicated amount of each protein was mixed with either medium or 100 ng/ml of TNF-gamma-beta in the presence or absence of cycloheximide. The reagents were incubated for 1 hour at RT to allow the formation of protein-TNF-gamma-beta complexes and then added to the cells. Caspase activity was measured as described above.

Murine Graft-Versus-Host Reaction

The F1 (CB6F1) of C57BL/6×BALB/c mice (H-2$^{bxd}$) were transfused intravenously with 1.5×10$^8$ spleen cells from C57BL/6 mice (H-2$^b$) on day 0. Recombinant TNF-gamma-beta (aa 72-251) protein or buffer alone was administered intravenously daily for 5 days at 3 mg/kg/day starting on the same day as the transfusion. The spleens of the recipient F1 mice were harvested on day 5, weighed and single cell suspensions prepared for in vitro assays.

Ex-vivo Mouse Splenocyte Alamar Blue and Cytokine Assays

Splenocytes from normal and the transfused F1 mice were cultured in triplicate in 96-well flat-bottomed plates (4×10$^5$ cells/200 microliters/well) for 2-4 days. After removing 100 microliters of supernatant per well on the day of harvest, 10 microliters Alamar Blue (Biosource) was added to each well and the cells cultured for additional 4 h. The cell number in each well was assessed according to OD590 nm minus OD530 nm background, using a CytoFluor apparatus (PerSeptive Biosystems). Cytokines in the culture supernatant were measured with commercial ELISA kits from Endogen or R & D Systems following manufacturer's instructions.

Example 26

Refolding of TNFR-6 Alpha from Inclusion Bodies

Materials and Methods

Reagents were of analytical grade and, unless stated otherwise in the protocol, purchased from Merck Eurolab. L-arginine was obtained from Ajinimoto Inc, kanamycin from Sigma, lysozyme from Sigma, Alamar Blue from Biosource and FasL-FALG from Alexis. Water was filtrated with a Milli-Q system (Millipore).

| Protein marker: LMW-marker (Pharmacia, 17-0615-01), stock solution: | | |
|---|---|---|
| Protein | Molecular Weight (kDa) | Concentration (ug/mL) |
| phosphorylase b | 97.0 | 67 |
| albumin | 66.0 | 83 |
| Ovalbumin | 45.0 | 147 |
| Carboanhydrase | 30.0 | 83 |
| Trypsin inhibitor | 20.1 | 80 |
| Alpha-lactalbumin | 14.4 | 116 |

Methods

SDS-PAGE

The method of Laemmli (1970) was used as the basis for SDS-PAGEs. Concentration of acrylamide was always 15%. Every protein sample was boiled at 95 C for 5 min after addition of SDS-sample buffer and subsequently centrifugated for 5 min at 13,000 rpm (Centrifuge: Biofuge Pico, Heraeus). SDS-PAGE gels ran 70 min at 150 V in a Mini-Protean system (BioRad). Silver staining of SDS gels was done according to the protocol of Nesterenko et al. J. Biochem. Biophys. Meth. 28 (1984) 239-242).

Buffer Systems:
  SDS-sample buffer: 250 mM Tris/HCl, pH 8.0; 40% (v/v) glycerine; 5% (w/v) SDS; 5% (v/v) mercaptoethanol
  Running buffer: 50 mM Tris/HCl; 19 mM glycine; 0.2% (w/v) SDS
  Lower gel buffer (end concentration): 600 mM Tris/HCl, pH 8.0; 0.8% (w/v) SDS
  Upper gel buffer (end concentration): 100 mM Tris/HCl, pH 6.8; 0.8% (w/v) SDS Methods for Determination of Protein Concentrations
1. Bio-RAD protein assay (Cat. No. 500-0006) with BSA as a standard.
2. UV-vis-spectra using the theoretical $\epsilon_{280nm}$ (23390 M$^{-1}$ cm$^{-1}$; http://www.expasy.ch/cgi-bin/protparam) were carried out on a Cary 300 system (Varian Inc.). An OD$_{280}$ of 0.716 corresponds to a solution of TNFR-6 alpha amino acid residues 30-300 of SEQ ID NO:2, hereinafter in this example "TNFR-alpha") with a concentration of 1 mg/ml.

Bacterial Strains and Growth Media

| | |
|---|---|
| BL21 (DE3) | purchased from Novagen |
| LB | 0.5 g NaCl, 0.5 g yeast extract, 1 g tryptone in 1 L water |
| LB-Agar | LB with 15 g Agar-Agar per L water |
| 2xYT | 17 g tryptone, 10 g yeast extract, 5 g NaCl in 1 L water |
| SOC | 20 g tryptone, 5 g yeast extract, 10 mM NaCl, 2.5 mM KCl, 10 mM MgS0$_4$, 10 mM MgCl$_2$, 0.4 g glucose in 1 L water |

Mammalian Cells.
  Jurkat E6-1 cells (ATCC™: TIB-1 52) were used in the apoptosis assay Experimental Protocol:
  Transformation of *E. coli* BL21 (DE3) and Cultivation
  *E. coli* BL21 (DE3) cells were transformed with the pHE4 vector (ATCC™ Deposit Number 209645, described in U.S. Pat. No. 6,194,168) containing a polynucleotide encoding amino acid residues 30-300 of SEQ ID NO:2) using a Bio-Rad GenePulser 11 system (2.5 kV, 200 Q, Cuvette with a 2 mm gap). Cells were immediately transferred to SOC medium and shaken for 40 min at 37 degrees C. and 600 rpm (Eppendorf Thermomixer Compact). They were subsequently plated on LB-Agar petri dishes containing 50 micrograms/ml kanamycin and grown overnight at 37 degrees C. A single colony was used for an overnight culture and grown in 175 ml LB medium containing 50 micrograms/ml kanamycin at 37 degrees C. and 200 rpm for 14 h. 4×5 L erlenmeyer flasks containing 1.5 L 2xYT medium with 50 micrograms/ml kanamycin were inoculated with 30 ml overnight culture each and grown at 37 degrees C. and 200 rpm for 4 h (until the $OD_{600}$ reached 1). Afterwards, cells were induced by addition of 3 mM IPTG and cultivated as before for 3 h more. Harvest was done using a Beckman Avanti J-20 centrifuge and a JLA 8.1000 rotor at 5000 g and 4 degrees C. for 10 min. Cell pellets were frozen and stored at −20 degrees C.

Preparation of Inclusion Bodies 15 g cells were thawed and homogenized in 75 ml 0.1 M Tris-HCl, pH 7.0, 1 mM EDTA using an ultraturrax. After addition of 23 mg lysozyme, the cells were mixed shortly with an ultraturrax and incubated at 4 degrees C. for 30 min. Subsequently 15,000 U benzonase and 3 mM $MgCl_2$ were added and the mixture was incubated at 25 degrees C. for 10 min. Cells were disrupted using a Constant Systems Z-Plus high-pressure homogenizer at 1,800 bar (two passages). 0.5 vol. of 67 mM EDTA, 6% Triton X-100, 1.5 M NaCl pH 7.0 were added and the homogenate was incubated at 4 degrees C. for 30 min. Inclusion bodies were sedimented by centrifugation at 4 degrees C. and 32,000 g for 10 min (Beckman Avanti J-25 centrifuge; JLA 16.250 rotor). Inclusion bodies were resuspended in 120 ml 0.1 M Tris-HCl, pH 7.0, 20 mM EDTA using an ultraturrax. The centrifugation step and the resuspension were repeated 4 times and the resulting inclusion bodies were stored at −20 degrees C. For following analysis of inclusion bodies in SDS-PAGE a very diminutive amount is sufficient.

Solubilization of TNFR-6 Alpha Inclusion Bodies

TNFR-6 alpha inclusion bodies were solubilized by dilution of approximately 1 g IBs into 15 ml solubilization buffer (100 mM Tris, pH 8.0; 8 M guanidiniumhydrochloride; 100 mM dithiothreitol, 1 mM EDTA) and incubated on a roller shaker at room temperature for 3 h. After centrifugation at 75,000 g (4 degrees C.; 1 h; Beckman centrifuge Avanti J-25; JA 25.50 rotor) the pH of the supernatant was lowered to 3-4 by dropwise addition of 1 M HCl Two dialysis steps for 2 h at room temperature against 4 M guanidiniumhydrochloride, 10 mM HCl using Spectra/Por dialysis membranes (MWCO 6000-8000 Da; Reorder-No. 132 650) followed by a dialysis against 4 M guanidiniumhydrochloride at 7 degrees C. overnight were carried out to remove dithiothreitol. Protein concentration was determined by UV-vis spectroscopy using the theoretical extinction coefficient of TNFR-6 alpha (see materials and methods).

Refolding of TNFR-6 Alpha 16.7 mg solubilized TNFR-6 alpha (21.6 mg/ml concentration) were added dropwise (under stirring) to 200 ml refolding buffer (50 mM BICINE, pH 9.0, 1 M L-arginine, 0.5 M NaCl, 5 mM oxidized glutathione, 1 mM reduced glutathione) at a temperature of 7 degrees C. This addition was repeated twice after 2 and 4 h, respectively. The solution was stirred gently overnight (approximately 20 h). After centrifugation at 4 degrees C. and 75,000 g (Beckman Avanti J-25 centrifuge, JA 25.50 rotor) for 1 h, the supernatant was used for buffer exchange.

Buffer Exchange

Buffer exchange took place by applying 60 ml of the refolding samples on an XK 50/20 column packed with 300 ml sephadex G-25 fine (Amersham Pharmacia Biotech; Cat. No. 170032-01), equilibrated with elution buffer (50 mM $Na_2HPO_4$, pH 7.5; 50 mM NaCl). The flow rate was S (injection) or 10 ml/min (elution) using a Pharmacia FPLC system at 7 degrees C. At the elution peak of proteins (rise of extinction at 280 nm) 10 fractions of 10 ml each were collected and fractions 2-7 pooled. Buffer exchange was repeated twice and the fractions containing TNFR-6 alpha were pooled. The protein concentration of the supernatant was determined and samples were taken for SDS-PAGE and activity assay.

Further Purification of TNFR-6 Alpha Using Ion Exchange Chromatography

TNFR-6 alpha fractions from buffer exchange were applied on a 1 ml HiTrap column packed with SP sepharose XL (Amersham Pharmacia Cat.-No. 17-5160-01), equilibrated with 50 mM $Na_2BPO_4$, pH 7.5; 50 mM NaCl. The flow rate was 0.5 ml/min. Afterwards the column was washed with 20 column volumes 50 mM $Na_2HP04$, pH 7.5; 50 mM NaCl. TNFR-6 alpha was eluted by a step-gradient to 50 mM $Na_2HPO_4$, pH 7.5; 390 mM NaCl and collected in fractions of 1 ml each. Samples of peak fractions were used for determination of protein concentration and SDS/PAGE. Fractions containing TNFR-6 alpha were pooled and tested in the activity assay.

Determination of Activity

The determination of refolded TNFR-6-alpha protein activity was assessed using the in vitro soluble human FasL mediated cytoxicity assay largely as described in Example 22. A few minor modifications to the assay were made: Jurkat-E6 cells were used rather than HT-29 cells; the cell number per well was 10,000 rather than 50,000; the incubation time in the presence of alamar blue was 56 hours rather than 4 hours; and absorption measurements were carried out at 620 nm. Concentrations of TNFR-6 alpha tested in the assay were 100 ng/ml, 1 microgram/ml and 10 micrograms/ml.

Aliquoting of Samples

Because TNFR-6 alpha tends to aggregate at concentrations above 1 mg/ml the sample was diluted to 0.7 mg/ml with 50 mM $Na_2BP04$, pH 7.5; 390 mM NaCl. Samples of 1 ml were aliquoted into 1.5 ml eppendorf tubes, frozen in liquid nitrogen and stored at −80 degrees C.

Results of Example 26

Cultivation and Preparation of Inclusion Bodies

From 6 L shake flask culture, 24 grams cells (wet weight) were obtained. These cells yielded approximately 1.5 grams inclusion bodies. The inclusion body preparation contained about 70% TNFR-6-alpha (residues 30-300) (estimation from SDS-PAGE).

Solubilization of TNFR-6 Alpha

From 1 grams inclusion bodies approximately 400 mg solubilized protein could be prepared. In general it is preferable to have protein solubilisate with a high protein content to prevent adding too much guanidiniumhydrochloride to the refolding reaction. With our procedure we were able to obtain a solubilisate with 22 mg/ml protein content (estimated with the theoretical extinction coefficient of TNFR-6 alpha).

Refolding of TNFR-6 Alpha and Buffer Exchange

Optimal time for refolding was one day. After two days of refolding the yield decreased by approximately 40%. To find the optimal protein concentration for the refolding of TNFR-6 alpha, we tested concentrations ranging from 50-400 micrograms/ml. Although the yield of soluble protein was slightly higher at lower concentrations we chose 250 micrograms/ml, a concentration that yielded at least 55% soluble protein after refolding and avoided working with high refolding volumes. Even though only a small aggregation pellet appeared, about 60% of the initial protein amount were detected by protein determination using Bio-Rad protein assay after centrifugation (refolding yield). The pooled fractions obtained after buffer exchange contained 95% of the applied protein amount.

Purification of Refolded TNFR-6 Alpha by Ion Exchange Chromatography

Because TNFR-6 alpha inclusion bodies and solubilisate contained a high content of other proteins that may interfere with the activity assay we attempted to purify the protein using liquid chromatography. Because of the high theoretical pI we have chosen cation exchange chromatography. TNFR-6 alpha bound to SP sepahroseXL in the presence of 50 mM NaCl and could be eluted with 390 mM NaCl. The main protein contaminants did not bind to this material or eluted at a higher concentration of NaCl. TNFR-6 alpha could be purified to at least 90% (estimated from a silver stained SDS-PAGE). Typical fractions contained 0.5-1.5 mg/ml TNFR-6 alpha. At concentrations above 1 mg/ml, the solution became sometimes turbid indicating aggregation of TNFR-6 alpha. We therefore diluted the pooled samples to a concentration below 1 mg/ml. To avoid aggregation we recommend to use a linear gradient to keep the protein concentration during elution low. Fractions eluted by a 100% step of high salt contained TNFR-6 alpha only at approximately 50%.

Because of aggregation, the yield of this purification procedure was less than 50% of the applied TNFR-6 alpha. So the overall yield of this step-gradient procedure, referred to the TNFR-6 alpha content, is 20% (Table IX).

absorption was around 0.4 and with apoptotic cells (with FasL FLAG without TNFR-6 alpha) the absorption rose to 0.7. The refolded samples of TNFR-6 alpha and the positive control showed activity in a range from 1-10 micrograms/ml, but not below (e.g., at 100 ng/ml). The further purified material from refolding showed a higher activity than samples after buffer exchange without further purification. This may be due to the lower purity of the samples from buffer exchange, that only contain approximately 70% TNFR-6 alpha. But it clearly shows that active (and not just soluble) TNFR-6 alpha can be obtained by refolding even at this high refolding yield (approximately 60% refolding yield).

Storage of refolded TNFR-6 alpha at −80 degrees C. has only a slight influence on the activity in the apoptosis assay.

Conclusions

This refolding protocol in connection with the purification of TNFR-6 alpha by cation exchange chromatography can be used to produce TNFR-6 alpha at a mg-scale. From 6 L shake flask culture (24 grams wet cell weight) approximately 70 mg active TNFR-6 alpha with a purity of at least 90% can be obtained. After refolding and buffer exchange, a yield of 60%, referred to the employed amount of solubilized protein at the beginning of refolding.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. In addition, the sequence listing submitted herewith and the corresponding computer readable form are both incorporated herein by reference in their entireties. The specification and sequence listing of each of the following U.S. applications are herein incorporated by reference in their entirety: 60/303,224 filed Jul. 6, 2001; 60/252,131 filed Nov. 21, 2000; 60/227,598 filed

TABLE IX

Calculation of yield of the used refolding and purification steps

| Step | Applied protein | Estimated purity of TNFR-6 alpha (from SDS-PAGE) before | Estimated purity of TNFR-6 alpha (from SDS-PAGE) after | Yield (referred to total protein content) | | Overall yield (referred to TNFR-6 alpha) |
|---|---|---|---|---|---|---|
| Refolding | 50 mg | 70% | 70% | 30 mg | 60% | 60% |
| Buffer exchange | 28 mg | 70% | 70% | 27 mg | 95% | 57% |
| Ion exchange chromatography | 17 mg | 70% | >90% | 4.6 mg | 27% | 20% |

Pooled fractions of purified TNFR-6 alpha were tested for activity immediately or frozen in liquid nitrogen, stored at −80 degrees C. and tested after 5 days in the activity assay.

Activity of the Refolded and Purified Samples

We used the determination of the absorption at 620 nm for the activity assay. With viable cells (without FasL-FLAG) the Aug. 25, 2000; 09/518,931 filed Mar. 3, 2000; 60/168,235 filed Dec. 1, 1999; 60/146,371 filed Aug. 2, 1999; 60/131,964 filed Apr. 30, 1999; 60/131,270 filed Apr. 27, 1999; 60/124,092 filed Mar. 12, 1999; 60/121,774 filed Mar. 4, 1999; 09/006,352 filed Jan. 13, 1998 and 60/035,496 filed Jan. 14, 1997.

What is claimed is:

1. A method for detecting over-expression of a polypeptide in a sample derived from a human comprising:
   (a) detecting the level of a polypeptide in a sample derived from a human, wherein the sample derived from the human is selected from the group consisting of blood, serum, plasma, a tissue biopsy, cancerous tissue, urine, saliva, synovial fluid, and spinal fluid; and
   (b) comparing the detected level in step (a) to a normal control-sample, wherein an increased detected level in step (a) as compared to the normal control is indicative of over-expression of the polypeptide in the sample derived from the human, wherein the polypeptide is selected from the group consisting of:
      (i) a polypeptide having the amino acid sequence of SEQ ID NO:2;
      (ii) a polypeptide encoded by the cDNA clone of ATCC Deposit No. 97810;
      (iii) a polypeptide comprising amino acid residues 31-300 of SEQ ID NO:2;
      (iv) a polypeptide comprising amino acid residues 31-283 of SEQ ID NO :2;
      (v) a polypeptide comprising the mature form of a polypeptide encoded by the cDNA clone of ATCC Deposit No. 97810, wherein the mature form lacks the leader sequence; and
      (vi) a polypeptide comprising the soluble extracellular domain of a polypeptide encoded by the cDNA clone of ATCC Deposit No. 97810.

2. The method of claim 1 wherein the polypeptide is detected with an antibody or fragment thereof specific to the polypeptide.

3. The method of claim 2 wherein the antibody or fragment thereof is monoclonal.

4. The method of claim 2 wherein the antibody or fragment thereof is polyclonal.

5. The method of claim 2 wherein the antibody or fragment thereof is selected from the group consisting of:
   (a) a chimeric antibody or fragment thereof;
   (b) a humanized antibody or fragment thereof;
   (c) a F(ab')$_2$ fragment; and
   (d) a Fab fragment.

6. The method of claim 2 wherein the antibody or fragment thereof is labeled.

7. The method of claim 1 wherein the sample derived from the human is blood.

8. The method of claim 1 wherein the sample derived from the human is serum.

9. The method of claim 1 wherein the sample derived from the human is plasma.

10. The method of claim 1 wherein the sample derived from the human is a tissue biopsy.

11. The method of claim 1 wherein the sample derived from the human is cancerous tissue.

12. The method of claim 1 wherein the sample derived from the human is urine.

13. The method of claim 1 wherein the sample derived from the human is saliva.

14. The method of claim 1 wherein the sample derived from the human is synovial fluid.

15. The method of claim 1 wherein the sample derived from the human is spinal fluid.

* * * * *

SEQUENCE LISTING

<160> NUMBER OF SEQ ID NOS: 42

<210> SEQ ID NO 1
<211> LENGTH: 1077
<212> TYPE: DNA
<213> ORGANISM: Homo sapiens
<220> FEATURE:
<221> NAME/KEY: CDS
<222> LOCATION: (25)..(924)

<400> SEQUENCE: 1

| | | | | | | | | | | | | | | | |
|---|---|---|---|---|---|---|---|---|---|---|---|---|---|---|---|
| gctctccctg ctccagcaag gacc | | | atg<br>Met<br>1 | agg<br>Arg | gcg<br>Ala | ctg<br>Leu | gag<br>Glu<br>5 | ggg<br>Gly | cca<br>Pro | ggc<br>Gly | ctg<br>Leu | | | 51 |

| tcg<br>Ser | ctg<br>Leu<br>10 | ctg<br>Leu | tgc<br>Cys | ctg<br>Leu | gtg<br>Val<br>15 | ttg<br>Leu | gcg<br>Ala | ctg<br>Leu | cct<br>Pro | gcc<br>Ala<br>20 | ctg<br>Leu | ctg<br>Leu | ccg<br>Pro | gtg<br>Val<br>25 | ccg<br>Pro | 99 |
|---|---|---|---|---|---|---|---|---|---|---|---|---|---|---|---|---|

| gct<br>Ala | gta<br>Val | cgc<br>Arg | gga<br>Gly<br>30 | gtg<br>Val | gca<br>Ala | gaa<br>Glu | aca<br>Thr | ccc<br>Pro<br>35 | acc<br>Thr | tac<br>Tyr | ccc<br>Pro | tgg<br>Trp | cgg<br>Arg<br>40 | gac<br>Asp | gca<br>Ala | 147 |
|---|---|---|---|---|---|---|---|---|---|---|---|---|---|---|---|---|

| gag<br>Glu | aca<br>Thr | ggg<br>Gly<br>45 | gag<br>Glu | cgg<br>Arg | ctg<br>Leu | gtg<br>Val | tgc<br>Cys<br>50 | gcc<br>Ala | cag<br>Gln | tgc<br>Cys | ccc<br>Pro | cca<br>Pro<br>55 | ggc<br>Gly | acc<br>Thr | ttt<br>Phe | 195 |
|---|---|---|---|---|---|---|---|---|---|---|---|---|---|---|---|---|

| gtg<br>Val | cag<br>Gln<br>60 | cgg<br>Arg | ccg<br>Pro | tgc<br>Cys | cgc<br>Arg | cga<br>Arg<br>65 | gac<br>Asp | agc<br>Ser | ccc<br>Pro | acg<br>Thr | acg<br>Thr<br>70 | tgt<br>Cys | ggc<br>Gly | ccg<br>Pro | tgt<br>Cys | 243 |
|---|---|---|---|---|---|---|---|---|---|---|---|---|---|---|---|---|

| cca<br>Pro | ccg<br>Pro<br>75 | cgc<br>Arg | cac<br>His | tac<br>Tyr | acg<br>Thr<br>80 | cag<br>Gln | ttc<br>Phe | tgg<br>Trp | aac<br>Asn | tac<br>Tyr<br>85 | ctg<br>Leu | gag<br>Glu | cgc<br>Arg | tgc<br>Cys | cgc<br>Arg | 291 |
|---|---|---|---|---|---|---|---|---|---|---|---|---|---|---|---|---|

| tac<br>Tyr | tgc<br>Cys<br>90 | aac<br>Asn | gtc<br>Val | ctc<br>Leu | tgc<br>Cys<br>95 | ggg<br>Gly | gag<br>Glu | cgt<br>Arg | gag<br>Glu | gag<br>Glu<br>100 | gag<br>Glu | gca<br>Ala | cgg<br>Arg | gct<br>Ala | tgc<br>Cys<br>105 | 339 |
|---|---|---|---|---|---|---|---|---|---|---|---|---|---|---|---|---|

| cac<br>His | gcc<br>Ala | acc<br>Thr | cac<br>His | aac<br>Asn<br>110 | cgt<br>Arg | gcc<br>Ala | tgc<br>Cys | cgc<br>Arg | tgc<br>Cys<br>115 | cgc<br>Arg | acc<br>Thr | ggc<br>Gly | ttc<br>Phe | ttc<br>Phe<br>120 | gcg<br>Ala | 387 |
|---|---|---|---|---|---|---|---|---|---|---|---|---|---|---|---|---|

| cac<br>His | gct<br>Ala | ggt<br>Gly<br>125 | ttc<br>Phe | tgc<br>Cys | ttg<br>Leu | gag<br>Glu | cac<br>His<br>130 | gca<br>Ala | tcg<br>Ser | tgt<br>Cys | cca<br>Pro | cct<br>Pro<br>135 | ggt<br>Gly | gcc<br>Ala | ggc<br>Gly | 435 |
|---|---|---|---|---|---|---|---|---|---|---|---|---|---|---|---|---|

| gtg<br>Val | att<br>Ile | gcc<br>Ala<br>140 | ccg<br>Pro | ggc<br>Gly | acc<br>Thr | ccc<br>Pro | agc<br>Ser<br>145 | cag<br>Gln | aac<br>Asn | acg<br>Thr | cag<br>Gln | tgc<br>Cys<br>150 | cag<br>Gln | ccg<br>Pro | tgc<br>Cys | 483 |
|---|---|---|---|---|---|---|---|---|---|---|---|---|---|---|---|---|

| ccc<br>Pro | cca<br>Pro<br>155 | ggc<br>Gly | acc<br>Thr | ttc<br>Phe | tca<br>Ser | gcc<br>Ala<br>160 | agc<br>Ser | agc<br>Ser | tcc<br>Ser | agc<br>Ser | tca<br>Ser<br>165 | gag<br>Glu | cag<br>Gln | tgc<br>Cys | cag<br>Gln | 531 |
|---|---|---|---|---|---|---|---|---|---|---|---|---|---|---|---|---|

| ccc<br>Pro | cac<br>His | cgc<br>Arg<br>170 | aac<br>Asn | tgc<br>Cys | acg<br>Thr | gcc<br>Ala | ctg<br>Leu<br>175 | ggc<br>Gly | ctg<br>Leu | gcc<br>Ala | ctc<br>Leu | aat<br>Asn<br>180 | gtg<br>Val | cca<br>Pro | ggc<br>Gly<br>185 | 579 |
|---|---|---|---|---|---|---|---|---|---|---|---|---|---|---|---|---|

| tct<br>Ser | tcc<br>Ser | tcc<br>Ser | cat<br>His | gac<br>Asp<br>190 | acc<br>Thr | ctg<br>Leu | tgc<br>Cys | acc<br>Thr | agc<br>Ser<br>195 | tgc<br>Cys | act<br>Thr | ggc<br>Gly | ttc<br>Phe | ccc<br>Pro<br>200 | ctc<br>Leu | 627 |
|---|---|---|---|---|---|---|---|---|---|---|---|---|---|---|---|---|

| agc<br>Ser | acc<br>Thr | agg<br>Arg | gta<br>Val<br>205 | cca<br>Pro | gga<br>Gly | gct<br>Ala | gag<br>Glu | gag<br>Glu<br>210 | tgt<br>Cys | gag<br>Glu | cgt<br>Arg | gcc<br>Ala | gtc<br>Val<br>215 | atc<br>Ile | gac<br>Asp | 675 |
|---|---|---|---|---|---|---|---|---|---|---|---|---|---|---|---|---|

| ttt<br>Phe | gtg<br>Val | gct<br>Ala<br>220 | ttc<br>Phe | cag<br>Gln | gac<br>Asp | atc<br>Ile | tcc<br>Ser<br>225 | atc<br>Ile | aag<br>Lys | agg<br>Arg | ctg<br>Leu | cag<br>Gln<br>230 | cgg<br>Arg | ctg<br>Leu | ctg<br>Leu | 723 |
|---|---|---|---|---|---|---|---|---|---|---|---|---|---|---|---|---|

| cag<br>Gln | gcc<br>Ala | ctc<br>Leu<br>235 | gag<br>Glu | gcc<br>Ala | ccg<br>Pro | gag<br>Glu | ggc<br>Gly<br>240 | tgg<br>Trp | ggt<br>Gly | ccg<br>Pro | aca<br>Thr | cca<br>Pro<br>245 | agg<br>Arg | gcg<br>Ala | ggc<br>Gly | 771 |
|---|---|---|---|---|---|---|---|---|---|---|---|---|---|---|---|---|

```
cgc gcg gcc ttg cag ctg aag ctg cgt cgg cgg ctc acg gag ctc ctg     819
Arg Ala Ala Leu Gln Leu Lys Leu Arg Arg Arg Leu Thr Glu Leu Leu
250                 255                 260                 265 ggg gcg cag gac ggg gcg ctg ctg gtg cgg ctg ctg cag gcg ctg cgc     867
Gly Ala Gln Asp Gly Ala Leu Leu Val Arg Leu Leu Gln Ala Leu Arg
                270                 275                 280 gtg gcc agg atg ccc ggg ctg gag cgg agc gtc cgt gag cgc ttc ctc     915
Val Ala Arg Met Pro Gly Leu Glu Arg Ser Val Arg Glu Arg Phe Leu
            285                 290                 295 cct gtg cac tgatcctggc ccctcttat ttattctaca tccttggcac              964
Pro Val His
        300 cccacttgca ctgaaagagg ctttttttta aatagaagaa atgaggtttc ttaaagctta   1024 tttttataaa gcttttcat aaaaaaaaaa aaaaaaaaa aaaaaaaaaa aaa            1077

<210> SEQ ID NO 2
<211> LENGTH: 300
<212> TYPE: PRT
<213> ORGANISM: Homo sapiens

<400> SEQUENCE: 2
```

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
                20                  25                  30

Thr Pro Thr Tyr Pro Trp Arg Asp Ala Glu Thr Gly Glu Arg Leu Val
            35                  40                  45

Cys Ala Gln Cys Pro Pro Gly Thr Phe Val Gln Arg Pro Cys Arg Arg
        50                  55                  60

Asp Ser Pro Thr Thr Cys Gly Pro Cys Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
        115                 120                 125

His Ala Ser Cys Pro Pro Gly Ala Gly Val Ile Ala Pro Gly Thr Pro
    130                 135                 140

Ser Gln Asn Thr Gln Cys Gln Pro Cys Pro Pro Gly Thr Phe Ser Ala
145                 150                 155                 160

Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
        195                 200                 205

Glu Glu Cys Glu Arg Ala Val Ile Asp Phe Val Ala Phe Gln Asp Ile
    210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270

```
Leu Val Arg Leu Leu Gln Ala Leu Arg Val Ala Arg Met Pro Gly Leu
        275                 280                 285

Glu Arg Ser Val Arg Glu Arg Phe Leu Pro Val His
        290                 295                 300

<210> SEQ ID NO 3
<211> LENGTH: 1667
<212> TYPE: DNA
<213> ORGANISM: Homo sapiens
<220> FEATURE:
<221> NAME/KEY: CDS
<222> LOCATION: (73)..(582)

<400> SEQUENCE: 3
tggcatgtcg gtcaggcaca gcagggtcct gtgtccgcgc tgagccgcgc tctccctgct      60
ccagcaagga cc atg agg gcg ctg gag ggg cca ggc ctg tcg ctg ctg tgc    111
              Met Arg Ala Leu Glu Gly Pro Gly Leu Ser Leu Leu Cys
                1               5                  10 ctg gtg ttg gcg ctg cct gcc ctg ctg ccg gtg ccg gct gta cgc gga      159
Leu Val Leu Ala Leu Pro Ala Leu Leu Pro Val Pro Ala Val Arg Gly
     15                  20                  25 gtg gca gaa aca ccc acc tac ccc tgg cgg gac gca gag aca ggg gag      207
Val Ala Glu Thr Pro Thr Tyr Pro Trp Arg Asp Ala Glu Thr Gly Glu
 30                  35                  40                  45 cgg ctg gtg tgc gcc cag tgc ccc cca ggc acc ttt gtg cag cgg ccg      255
Arg Leu Val Cys Ala Gln Cys Pro Pro Gly Thr Phe Val Gln Arg Pro
             50                  55                  60 tgc cgc cga gac agc ccc acg acg tgt ggc ccg tgt cca ccg cgc cac      303
Cys Arg Arg Asp Ser Pro Thr Thr Cys Gly Pro Cys Pro Pro Arg His
                 65                  70                  75 tac acg cag ttc tgg aac tac ctg gag cgc tgc cgc tac tgc aac gtc      351
Tyr Thr Gln Phe Trp Asn Tyr Leu Glu Arg Cys Arg Tyr Cys Asn Val
             80                  85                  90 ctc tgc ggg gag cgt gag gag gag gca cgg gct tgc cac gcc acc cac      399
Leu Cys Gly Glu Arg Glu Glu Glu Ala Arg Ala Cys His Ala Thr His
         95                 100                 105 aac cgt gcc tgc cgc tgc cgc acc ggc ttc ttc gcg cac gct ggt ttc      447
Asn Arg Ala Cys Arg Cys Arg Thr Gly Phe Phe Ala His Ala Gly Phe
110                 115                 120                 125 tgc ttg gag cac gca tcg tgt cca cct ggt gcc ggc gtg att gcc ccg      495
Cys Leu Glu His Ala Ser Cys Pro Pro Gly Ala Gly Val Ile Ala Pro
                130                 135                 140 ggt gag agc tgg gcg agg gga ggg gcc ccc agg agt ggt ggc cgg agg      543
Gly Glu Ser Trp Ala Arg Gly Gly Ala Pro Arg Ser Gly Gly Arg Arg
            145                 150                 155 tgt ggc agg ggt cag gtt gct ggt ccc agc ctt gca ccc tgagctagga      592
Cys Gly Arg Gly Gln Val Ala Gly Pro Ser Leu Ala Pro
160                 165                 170 caccagttcc cctgaccctg ttcttccctc ctggctgcag caccccag ccagaacacg     652 cagtgccagc cgtgcccccc aggcaccttt tcagccagca gctccagctc agagcagtgc     712
cagccccacc gcaactgcac ggccctgggc ctggccctca atgtgccagg ctcttcctcc     772
catgacaccc tgtgcaccag ctgcactggc ttcccctca gcaccaggt accaggtgag     832 ccagaggcct gagggggcag cacactgcag gccaggccca cttgtgccct cactcctgcc     892
cctgcacgtg catctagcct gaggcatgcc agctggctct gggaaggggc cacagtggat     952
ttgaggggtc aggggtccct ccactagatc cccaccaagt ctgccctctc aggggtggct    1012
gagaatttgg atctgagcca gggcacagcc tcccctggag agctctggga aagtgggcag    1072
```

```
caatctccta actgcccgag gggaaggtgg ctggctcctc tgacacgggg aaaccgaggc    1132
ctgatggtaa ctctcctaac tgcctgagag gaaggtggct gcctcctctg acatggggaa    1192
accgaggccc aatgttaacc actgttgaga agtcacaggg ggaagtgacc cccttaacat    1252
caagtcaggt ccggtccatc tgcaggtccc aactcgcccc ttccgatggc ccaggagccc    1312
caagcccttg cctgggcccc cttgcctctt gcagccaagg tccgagtggc cgctcctgcc    1372
ccctaggcct ttgctccagc tctctgaccg aaggctcctg ccccttctcc agtccccatc    1432
gttgcactgc cctctccagc acggctcact gcacagggat ttctctctcc tgcaaacccc    1492
ccgagtgggg cccagaaagc agggtacctg gcagcccccg ccagtgtgtg tgggtgaaat    1552
gatcggaccg ctgcctcccc accccactgc aggagctgag gagtgtgagc gtgccgtcat    1612
cgactttgtg gctttccagg acatctccat caagaggagc ggctgctgca ggccc         1667
```

<210> SEQ ID NO 4
<211> LENGTH: 170
<212> TYPE: PRT
<213> ORGANISM: Homo sapiens

<400> SEQUENCE: 4

```
Met Arg Ala Leu Glu Gly Pro Gly Leu Ser Leu Leu Cys Leu Val Leu
 1               5                  10                  15

Ala Leu Pro Ala Leu Leu Pro Val Pro Ala Val Arg Gly Val Ala Glu
                20                  25                  30

Thr Pro Thr Tyr Pro Trp Arg Asp Ala Glu Thr Gly Glu Arg Leu Val
            35                  40                  45

Cys Ala Gln Cys Pro Pro Gly Thr Phe Val Gln Arg Pro Cys Arg Arg
        50                  55                  60

Asp Ser Pro Thr Thr Cys Gly Pro Cys Pro Arg His Tyr Thr Gln
 65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
        115                 120                 125

His Ala Ser Cys Pro Pro Gly Ala Gly Val Ile Ala Pro Gly Glu Ser
    130                 135                 140

Trp Ala Arg Gly Gly Ala Pro Arg Ser Gly Arg Arg Cys Gly Arg
145                 150                 155                 160

Gly Gln Val Ala Gly Pro Ser Leu Ala Pro
                165                 170
```

<210> SEQ ID NO 5
<211> LENGTH: 455
<212> TYPE: PRT
<213> ORGANISM: Homo sapiens

<400> SEQUENCE: 5

```
Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
```

```
            50                  55                  60
Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
             85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
            165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
            210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
            290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
            405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
450                 455

<210> SEQ ID NO 6
```

<211> LENGTH: 461
<212> TYPE: PRT
<213> ORGANISM: Homo sapiens

<400> SEQUENCE: 6

Met Ala Pro Val Ala Val Trp Ala Ala Leu Ala Val Gly Leu Glu Leu
1               5                   10                  15

Trp Ala Ala His Ala Leu Pro Ala Gln Val Ala Phe Thr Pro Tyr
        20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln

```
             385                 390                 395                 400
Ala Ser Ser Thr Met Gly Asp Thr Asp Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Glu Lys Pro
                435                 440                 445

Leu Pro Leu Gly Val Pro Asp Ala Gly Met Lys Pro Ser
                450                 455                 460

<210> SEQ ID NO 7
<211> LENGTH: 427
<212> TYPE: PRT
<213> ORGANISM: Homo sapiens

<400> SEQUENCE: 7

Met Gly Ala Gly Ala Thr Gly Arg Ala Met Asp Gly Pro Arg Leu Leu
 1               5                  10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
                35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
                115                 120                 125

Glu Ala Gly Ser Gly Leu Val Phe Ser Cys Gln Asp Lys Gln Asn Thr
        130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
                195                 200                 205

Ala Pro Ser Thr Gln Glu Pro Glu Ala Pro Glu Gln Asp Leu Ile
        210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
                260                 265                 270

Lys Arg Trp Asn Ser Cys Lys Gln Asn Lys Gln Gly Ala Asn Ser Arg
                275                 280                 285

Pro Val Asn Gln Thr Pro Pro Pro Glu Gly Glu Lys Leu His Ser Asp
        290                 295                 300
```

```
Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 8
<211> LENGTH: 415
<212> TYPE: PRT
<213> ORGANISM: Homo sapiens

<400> SEQUENCE: 8

Met Arg Leu Pro Arg Ala Ser Ser Pro Cys Gly Leu Ala Trp Gly Pro
1               5                   10                  15

Leu Leu Leu Gly Leu Ser Gly Leu Leu Val Ala Ser Gln Pro Gln Leu
                20                  25                  30

Val Pro Pro Tyr Arg Ile Glu Asn Gln Thr Cys Trp Asp Gln Asp Lys
            35                  40                  45

Glu Tyr Tyr Glu Pro Met His Asp Val Cys Cys Ser Arg Cys Pro Pro
50                  55                  60

Gly Glu Phe Val Phe Ala Val Cys Ser Arg Ser Gln Asp Thr Val Cys
65                  70                  75                  80

Lys Thr Cys Pro His Asn Ser Tyr Asn Glu His Trp Asn His Leu Ser
                85                  90                  95

Thr Cys Gln Leu Cys Arg Pro Cys Asp Ile Val Leu Gly Phe Glu Glu
            100                 105                 110

Val Ala Pro Cys Thr Ser Asp Arg Lys Ala Glu Cys Arg Cys Gln Pro
        115                 120                 125

Gly Met Ser Cys Val Tyr Leu Asp Asn Glu Cys Val His Cys Glu Glu
    130                 135                 140

Glu Arg Leu Val Leu Cys Gln Pro Gly Thr Glu Ala Glu Val Thr Asp
145                 150                 155                 160

Glu Ile Met Asp Thr Asp Val Asn Cys Val Pro Cys Lys Pro Gly His
                165                 170                 175

Phe Gln Asn Thr Ser Ser Pro Arg Ala Arg Cys Gln Pro His Thr Arg
            180                 185                 190

Cys Glu Ile Gln Gly Leu Val Glu Ala Ala Pro Gly Thr Ser Tyr Ser
        195                 200                 205

Asp Thr Ile Cys Lys Asn Pro Pro Glu Pro Gly Ala Met Leu Leu Leu
    210                 215                 220

Ala Ile Leu Leu Ser Leu Val Leu Phe Leu Leu Phe Thr Thr Val Leu
225                 230                 235                 240

Ala Cys Ala Trp Met Arg His Pro Ser Leu Cys Arg Lys Leu Gly Thr
                245                 250                 255
```

-continued

Leu Leu Lys Arg His Pro Glu Gly Glu Ser Pro Pro Cys Pro Ala
            260                 265                 270

Pro Arg Ala Asp Pro His Phe Pro Asp Leu Ala Glu Pro Leu Leu Pro
        275                 280                 285

Met Ser Gly Asp Leu Ser Pro Ser Pro Ala Gly Pro Pro Thr Ala Pro
290                 295                 300

Ser Leu Glu Glu Val Val Leu Gln Gln Ser Pro Leu Val Gln Ala
305                 310                 315                 320

Arg Glu Leu Glu Ala Glu Pro Gly Glu His Gly Gln Val Ala His Gly
                325                 330                 335

Ala Asn Gly Ile His Val Thr Gly Gly Ser Val Thr Val Thr Gly Asn
            340                 345                 350

Ile Tyr Ile Tyr Asn Gly Pro Val Leu Gly Thr Arg Gly Pro Gly
        355                 360                 365

Asp Pro Pro Ala Pro Pro Glu Pro Pro Tyr Pro Thr Pro Glu Glu Gly
370                 375                 380

Ala Pro Gly Pro Ser Glu Leu Ser Thr Pro Tyr Gln Glu Asp Gly Lys
385                 390                 395                 400

Ala Trp His Leu Ala Glu Thr Glu Thr Leu Gly Cys Gln Asp Leu
                405                 410                 415

<210> SEQ ID NO 9
<211> LENGTH: 335
<212> TYPE: PRT
<213> ORGANISM: Homo sapiens

<400> SEQUENCE: 9

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu

```
            210                 215                 220
Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
                275                 280                 285

Glu Ala Tyr Asp Thr Leu Ile Lys Asp Leu Lys Lys Ala Asn Leu Cys
            290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 10
<211> LENGTH: 260
<212> TYPE: PRT
<213> ORGANISM: Homo sapiens

<400> SEQUENCE: 10

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255
```

```
Ala Cys Ser Pro
        260

<210> SEQ ID NO 11
<211> LENGTH: 595
<212> TYPE: PRT
<213> ORGANISM: Homo sapiens

<400> SEQUENCE: 11

Met Arg Val Leu Leu Ala Ala Leu Gly Leu Leu Phe Leu Gly Ala Leu
 1               5                  10                  15

Arg Ala Phe Pro Gln Asp Arg Pro Phe Glu Asp Thr Cys His Gly Asn
             20                  25                  30

Pro Ser His Tyr Tyr Asp Lys Ala Val Arg Arg Cys Cys Tyr Arg Cys
         35                  40                  45

Pro Met Gly Leu Phe Pro Thr Gln Gln Cys Pro Gln Arg Pro Thr Asp
     50                  55                  60

Cys Arg Lys Gln Cys Glu Pro Asp Tyr Tyr Leu Asp Glu Ala Asp Arg
 65                  70                  75                  80

Cys Thr Ala Cys Val Thr Cys Ser Arg Asp Asp Leu Val Glu Lys Thr
                 85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365
```

```
Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Gly Lys Glu Asp Pro Leu Pro Thr Ala Ala
            580                 585                 590

Ser Gly Lys
        595

<210> SEQ ID NO 12
<211> LENGTH: 277
<212> TYPE: PRT
<213> ORGANISM: Homo sapiens

<400> SEQUENCE: 12

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
```

-continued

```
            130                 135                 140
Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
            275

<210> SEQ ID NO 13
<211> LENGTH: 255
<212> TYPE: PRT
<213> ORGANISM: Homo sapiens

<400> SEQUENCE: 13

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
        210                 215                 220
```

```
Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 14
<211> LENGTH: 277
<212> TYPE: PRT
<213> ORGANISM: Homo sapiens

<400> SEQUENCE: 14

Met Cys Val Gly Ala Arg Arg Leu Gly Arg Gly Pro Cys Ala Ala Leu
  1               5                  10                  15

Leu Leu Leu Gly Leu Gly Leu Ser Thr Val Thr Gly Leu His Cys Val
                 20                  25                  30

Gly Asp Thr Tyr Pro Ser Asn Asp Arg Cys Cys His Glu Cys Arg Pro
             35                  40                  45

Gly Asn Gly Met Val Ser Arg Cys Ser Arg Ser Gln Asn Thr Val Cys
         50                  55                  60

Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 15
<211> LENGTH: 349
<212> TYPE: PRT
<213> ORGANISM: Homo sapiens

<400> SEQUENCE: 15

Met Lys Ser Val Leu Tyr Leu Tyr Ile Leu Phe Leu Ser Cys Ile Ile
  1               5                  10                  15
```

Ile Asn Gly Arg Asp Ala Ala Pro Tyr Thr Pro Pro Asn Gly Lys Cys
            20                  25                  30

Lys Asp Thr Glu Tyr Lys Arg His Asn Leu Cys Cys Leu Ser Cys Pro
        35                  40                  45

Pro Gly Thr Tyr Ala Ser Arg Leu Cys Asp Ser Lys Thr Asn Thr Gln
    50                  55                  60

Cys Thr Pro Cys Gly Ser Gly Thr Phe Thr Ser Arg Asn Asn His Leu
65                  70                  75                  80

Pro Ala Cys Leu Ser Cys Asn Gly Arg Cys Asn Ser Asn Gln Val Glu
                85                  90                  95

Thr Arg Ser Cys Asn Thr Thr His Asn Arg Ile Cys Glu Cys Ser Pro
            100                 105                 110

Gly Tyr Tyr Cys Leu Leu Lys Gly Ser Ser Gly Cys Lys Ala Cys Val
        115                 120                 125

Ser Gln Thr Lys Cys Gly Ile Gly Tyr Gly Val Ser Gly His Thr Ser
    130                 135                 140

Val Gly Asp Val Ile Cys Ser Pro Cys Gly Phe Gly Thr Tyr Ser His
145                 150                 155                 160

Thr Val Ser Ser Ala Asp Lys Cys Glu Pro Val Pro Asn Asn Thr Phe
                165                 170                 175

Asn Tyr Ile Asp Val Glu Ile Thr Leu Tyr Pro Val Asn Asp Thr Ser
            180                 185                 190

Cys Thr Arg Thr Thr Thr Thr Gly Leu Ser Glu Ser Ile Leu Thr Ser
        195                 200                 205

Glu Leu Thr Ile Thr Met Asn His Thr Asp Cys Asn Pro Val Phe Arg
    210                 215                 220

Glu Glu Tyr Phe Ser Val Leu Asn Lys Val Ala Thr Ser Gly Phe Phe
225                 230                 235                 240

Thr Gly Glu Asn Arg Tyr Gln Asn Ile Ser Lys Val Cys Thr Leu Asn
                245                 250                 255

Phe Glu Ile Lys Cys Asn Asn Lys Gly Ser Ser Phe Lys Gln Leu Thr
            260                 265                 270

Lys Ala Lys Asn Asp Asp Gly Met Met Ser His Ser Glu Thr Val Thr
        275                 280                 285

Leu Ala Gly Asp Cys Leu Ser Ser Val Asp Ile Tyr Ile Leu Tyr Ser
    290                 295                 300

Asn Thr Asn Ala Gln Asp Tyr Glu Thr Asp Thr Ile Ser Tyr Arg Val
305                 310                 315                 320

Gly Asn Val Leu Asp Asp Asp Ser His Met Pro Gly Ser Cys Asn Ile
                325                 330                 335

His Lys Pro Ile Thr Asn Ser Lys Pro Thr Arg Phe Leu
            340                 345

<210> SEQ ID NO 16
<211> LENGTH: 355
<212> TYPE: PRT
<213> ORGANISM: Homo sapiens

<400> SEQUENCE: 16

Met Lys Ser Tyr Ile Leu Leu Leu Leu Ser Cys Ile Ile Ile
1               5                   10                  15

Asn Ser Asp Ile Thr Pro His Glu Pro Ser Asn Gly Lys Cys Lys Asp
            20                  25                  30

Asn Glu Tyr Lys Arg His His Leu Cys Cys Leu Ser Cys Pro Pro Gly
        35                  40                  45

```
               Thr Tyr Ala Ser Arg Leu Cys Asp Ser Lys Thr Asn Thr Asn Thr Gln
                50                  55                  60

Cys Thr Pro Cys Ala Ser Asp Thr Phe Thr Ser Arg Asn Asn His Leu
                65                  70                  75                  80

Pro Ala Cys Leu Ser Cys Asn Gly Arg Cys Asp Ser Asn Gln Val Glu
                            85                  90                  95

Thr Arg Ser Cys Asn Thr Thr His Asn Arg Ile Cys Asp Cys Ala Pro
                           100                 105                 110

Gly Tyr Tyr Cys Phe Leu Lys Gly Ser Ser Gly Cys Lys Ala Cys Val
                           115                 120                 125

Ser Gln Thr Lys Cys Gly Ile Gly Tyr Gly Val Ser Gly His Thr Pro
                130                 135                 140

Thr Gly Asp Val Val Cys Ser Pro Cys Gly Leu Gly Thr Tyr Ser His
                145                 150                 155                 160

Thr Val Ser Ser Val Asp Lys Cys Glu Pro Val Pro Ser Asn Thr Phe
                                165                 170                 175

Asn Tyr Ile Asp Val Glu Ile Asn Leu Tyr Pro Val Asn Asp Thr Ser
                           180                 185                 190

Cys Thr Arg Thr Thr Thr Thr Gly Leu Ser Glu Ser Ile Ser Thr Ser
                           195                 200                 205

Glu Leu Thr Ile Thr Met Asn His Lys Asp Cys Asp Pro Val Phe Arg
                210                 215                 220

Asn Gly Tyr Phe Ser Val Leu Asn Glu Val Ala Thr Ser Gly Phe Phe
               225                 230                 235                 240

Thr Gly Gln Asn Arg Tyr Gln Asn Ile Ser Lys Val Cys Thr Leu Asn
                               245                 250                 255

Phe Glu Ile Lys Cys Asn Asn Lys Asp Ser Tyr Ser Ser Lys Gln
                           260                 265                 270

Leu Thr Lys Thr Lys Asn Asp Asp Ser Ile Met Pro His Ser Glu
                           275                 280                 285

Ser Val Thr Leu Val Gly Asp Cys Leu Ser Ser Val Asp Ile Tyr Ile
                290                 295                 300

Leu Tyr Ser Asn Thr Asn Thr Gln Asp Tyr Glu Thr Asp Thr Ile Ser
               305                 310                 315                 320

Tyr His Val Gly Asn Val Leu Asp Val Asp Ser His Met Pro Gly Arg
                               325                 330                 335

Cys Asp Thr His Lys Leu Ile Thr Asn Ser Asn Ser Gln Tyr Pro Thr
                           340                 345                 350

His Phe Leu
                       355

<210> SEQ ID NO 17
<211> LENGTH: 499
<212> TYPE: DNA
<213> ORGANISM: Homo sapiens
<220> FEATURE:
<221> NAME/KEY: misc_feature
<222> LOCATION: (20)
<223> OTHER INFORMATION: n equals a, t, g, or c
<220> FEATURE:
<221> NAME/KEY: misc_feature
<222> LOCATION: (41)
<223> OTHER INFORMATION: n equals a, t, g, or c
<220> FEATURE:
<221> NAME/KEY: misc_feature
<222> LOCATION: (160)..(161)
<223> OTHER INFORMATION: n equals a, t, g, or c
<220> FEATURE:
```

-continued

```
<221> NAME/KEY: misc_feature
<222> LOCATION: (164)
<223> OTHER INFORMATION: n equals a, t, g, or c
<220> FEATURE:
<221> NAME/KEY: misc_feature
<222> LOCATION: (181)
<223> OTHER INFORMATION: n equals a, t, g, or c
<220> FEATURE:
<221> NAME/KEY: misc_feature
<222> LOCATION: (205)
<223> OTHER INFORMATION: n equals a, t, g, or c
<220> FEATURE:
<221> NAME/KEY: misc_feature
<222> LOCATION: (207)
<223> OTHER INFORMATION: n equals a, t, g, or c
<220> FEATURE:
<221> NAME/KEY: misc_feature
<222> LOCATION: (212)
<223> OTHER INFORMATION: n equals a, t, g, or c
<220> FEATURE:
<221> NAME/KEY: misc_feature
<222> LOCATION: (231)
<223> OTHER INFORMATION: n equals a, t, g, or c
<220> FEATURE:
<221> NAME/KEY: misc_feature
<222> LOCATION: (248)
<223> OTHER INFORMATION: n equals a, t, g, or c
<220> FEATURE:
<221> NAME/KEY: misc_feature
<222> LOCATION: (277)
<223> OTHER INFORMATION: n equals a, t, g, or c
<220> FEATURE:
<221> NAME/KEY: misc_feature
<222> LOCATION: (322)
<223> OTHER INFORMATION: n equals a, t, g, or c
<220> FEATURE:
<221> NAME/KEY: misc_feature
<222> LOCATION: (330)
<223> OTHER INFORMATION: n equals a, t, g, or c
<220> FEATURE:
<221> NAME/KEY: misc_feature
<222> LOCATION: (353)
<223> OTHER INFORMATION: n equals a, t, g, or c
<220> FEATURE:
<221> NAME/KEY: misc_feature
<222> LOCATION: (372)
<223> OTHER INFORMATION: n equals a, t, g, or c
<220> FEATURE:
<221> NAME/KEY: misc_feature
<222> LOCATION: (378)
<223> OTHER INFORMATION: n equals a, t, g, or c
<220> FEATURE:
<221> NAME/KEY: misc_feature
<222> LOCATION: (391)
<223> OTHER INFORMATION: n equals a, t, g, or c
<220> FEATURE:
<221> NAME/KEY: misc_feature
<222> LOCATION: (394)
<223> OTHER INFORMATION: n equals a, t, g, or c
<220> FEATURE:
<221> NAME/KEY: misc_feature
<222> LOCATION: (402)
<223> OTHER INFORMATION: n equals a, t, g, or c
<220> FEATURE:
<221> NAME/KEY: misc_feature
<222> LOCATION: (407)
<223> OTHER INFORMATION: n equals a, t, g, or c
<220> FEATURE:
<221> NAME/KEY: misc_feature
<222> LOCATION: (421)
<223> OTHER INFORMATION: n equals a, t, g, or c
<220> FEATURE:
<221> NAME/KEY: misc_feature
<222> LOCATION: (437)..(438)
<223> OTHER INFORMATION: n equals a, t, g, or c
<220> FEATURE:
<221> NAME/KEY: misc_feature
<222> LOCATION: (446)
<223> OTHER INFORMATION: n equals a, t, g, or c
```

```
<220> FEATURE:
<221> NAME/KEY: misc_feature
<222> LOCATION: (460)
<223> OTHER INFORMATION: n equals a, t, g, or c
<220> FEATURE:
<221> NAME/KEY: misc_feature
<222> LOCATION: (466)
<223> OTHER INFORMATION: n equals a, t, g, or c
<220> FEATURE:
<221> NAME/KEY: misc_feature
<222> LOCATION: (474)
<223> OTHER INFORMATION: n equals a, t, g, or c
<220> FEATURE:
<221> NAME/KEY: misc_feature
<222> LOCATION: (482)..(484)
<223> OTHER INFORMATION: n equals a, t, g, or c
<220> FEATURE:
<221> NAME/KEY: misc_feature
<222> LOCATION: (486)
<223> OTHER INFORMATION: n equals a, t, g, or c
<220> FEATURE:
<221> NAME/KEY: misc_feature
<222> LOCATION: (496)
<223> OTHER INFORMATION: n equals a, t, g, or c

<400> SEQUENCE: 17
ggcacgagca gggtcctgtn tccgccctga gccgcgctct ncctgctcca gcaaggacca      60
tgagggcgct ggaggggcca ggcctgtcgc tgctgtgcct ggtgttggcg ctgcctgccc     120
tgctgccggt gccggctgta cgcggagtgg cagaaacacn nacntacccc tggcgggacg     180
nagagacagg ggagcggctg gtgtntnccc antgccccc aggcacctttt ntgcagcggc     240 cgtgccgncg agacagcccc acgacgtgtg gcccgtntcc accgcgccac tacacgcatt     300
ctggaactac ctggagcgct gncgttactn caacgtcctc tgcggggagc gtnaggagga     360
ggcacgggtt tnccacgnca accacaaccg nggnttaccg tngccgnacc ggtttcttcg     420
nggcaagttg gttttttnntt tggagnaagg attcgtgttn caattnattg acgnagtgat     480
tnnncncggg aaactnaaa                                                   499

<210> SEQ ID NO 18
<211> LENGTH: 191
<212> TYPE: DNA
<213> ORGANISM: Homo sapiens
<220> FEATURE:
<221> NAME/KEY: misc_feature
<222> LOCATION: (42)
<223> OTHER INFORMATION: n equals a, t, g, or c
<220> FEATURE:
<221> NAME/KEY: misc_feature
<222> LOCATION: (106)
<223> OTHER INFORMATION: n equals a, t, g, or c
<220> FEATURE:
<221> NAME/KEY: misc_feature
<222> LOCATION: (125)
<223> OTHER INFORMATION: n equals a, t, g, or c
<220> FEATURE:
<221> NAME/KEY: misc_feature
<222> LOCATION: (188)
<223> OTHER INFORMATION: n equals a, t, g, or c

<400> SEQUENCE: 18
cgcaactgca cggccctggg actggccctc aatgtgccag gntcttcctc ccatgacacc      60
ctgtgcacca gctgcactgg cttcccctc agcaccaggg taccangagc tgaggagtgt     120
gagcntgccg tcatcgactt tttggctttc caggacatct ccatcaagag gctgcagcgg     180
ctgctcangc c                                                          191

<210> SEQ ID NO 19
```

<211> LENGTH: 26
<212> TYPE: DNA
<213> ORGANISM: Artificial sequence
<220> FEATURE:
<223> OTHER INFORMATION: TNFR-6 alpha forward primer containing Nco I
      restriction site

<400> SEQUENCE: 19
cgcccatggc agaaacaccc acctac                                          26

<210> SEQ ID NO 20
<211> LENGTH: 26
<212> TYPE: DNA
<213> ORGANISM: Artificial sequence
<220> FEATURE:
<223> OTHER INFORMATION: TNFR-6 alpha reverse primer containing Hind III
      restriction site

<400> SEQUENCE: 20
cgcaagcttc tctttcagtg caagtg                                          26

<210> SEQ ID NO 21
<211> LENGTH: 28
<212> TYPE: DNA
<213> ORGANISM: Artificial sequence
<220> FEATURE:
<223> OTHER INFORMATION: TNFR-6 beta reverse primer containing Hind III
      restriction site

<400> SEQUENCE: 21
cgcaagcttc tcctcagctc ctgcagtg                                        28

<210> SEQ ID NO 22
<211> LENGTH: 36
<212> TYPE: DNA
<213> ORGANISM: Artificial sequence
<220> FEATURE:
<223> OTHER INFORMATION: TNFR-6 alpha and TNFR-6 beta forward primer
      containing Bam HI restriction site

<400> SEQUENCE: 22
cgcggatccg ccatcatgag ggcgtggagg ggccag                               36

<210> SEQ ID NO 23
<211> LENGTH: 26
<212> TYPE: DNA
<213> ORGANISM: Artificial sequence
<220> FEATURE:
<223> OTHER INFORMATION: TNFR-6 alpha reverse primer containing Asp 718
      restriction site

<400> SEQUENCE: 23
cgcggtaccc tctttcagtg caagtg                                          26

<210> SEQ ID NO 24
<211> LENGTH: 28
<212> TYPE: DNA
<213> ORGANISM: Artificial sequence
<220> FEATURE:
<223> OTHER INFORMATION: TNFR-6 beta reverse primer containing Asp 718
      restriction site

<400> SEQUENCE: 24
cgcggtaccc tcctcagctc ctgcagtg                                        28

<210> SEQ ID NO 25
<211> LENGTH: 33

<212> TYPE: DNA
<213> ORGANISM: Artificial sequence
<220> FEATURE:
<223> OTHER INFORMATION: TNFR-6 alpha forward primer

<400> SEQUENCE: 25
agacccaagc ttcctgctcc agcaaggacc atg              33

<210> SEQ ID NO 26
<211> LENGTH: 50
<212> TYPE: DNA
<213> ORGANISM: Artificial sequence
<220> FEATURE:
<223> OTHER INFORMATION: TNFR-6 alpha reverse primer

<400> SEQUENCE: 26
agacgggatc cttagtggtg gtggtggtgg tgcacaggga ggaagcgctc              50

<210> SEQ ID NO 27
<211> LENGTH: 733
<212> TYPE: DNA
<213> ORGANISM: Homo sapiens

<400> SEQUENCE: 27
gggatccgga gcccaaatct tctgacaaaa ctcacacatg cccaccgtgc ccagcacctg       60
aattcgaggg tgcaccgtca gtcttcctct tccccccaaa acccaaggac accctcatga      120
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta caacagcacg taccgtgtgg tcagcgtcct caccgtcctg caccaggact      300
ggctgaatgg caaggagtac aagtgcaagg tctccaacaa agccctccca acccccatcg      360
agaaaaccat ctccaaagcc aaagggcagc ccgagaacc acaggtgtac accctgcccc       420
catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat              733

<210> SEQ ID NO 28
<211> LENGTH: 1796
<212> TYPE: DNA
<213> ORGANISM: Homo sapiens
<220> FEATURE:
<221> NAME/KEY: intron
<222> LOCATION: 425-560
<220> FEATURE:
<221> NAME/KEY: intron
<222> LOCATION: 756-1512

<400> SEQUENCE: 28
atgagggcgc tggaggggcc aggcctgtcg ctgctgtgcc tggtgttggc gctgcctgcc       60
ctgctgccgg tgccggctgt acgcggagtg gcagaaacac ccacctaccc ctggcgggac      120
gcagagacag gggagcggct ggtgtgcgcc cagtgccccc aggcaccttt gtgcagcgg       180
ccgtgccgcc gagacagccc cacgacgtgt ggccgtgtc accgcgcca ctacacgcag        240
ttctggaact acctrgagcg ctgccgctac tgcaacgtcc tctgcgggga gcgtgaggag      300

```
gaggcacggg cttgccacgc cacccacaac cgtgcctgcc gctgccgcac cggcttcttc    360
gcgcacgctg gtttctgctt ggagcacgca tcgtgtccac ctggtgccgg cgtgattgcc    420
ccgggtgaga gctgggcgag gggaggggcc cccaggagtg gtggccggag gtgtggcagg    480
ggtcaggttg ctggtcccag ccttgcaccc tgagctagga caccagttcc cctgaccctg    540
ttcttccctc ctggctgcag gcaccccag ccagaacacg cagtgccagc cgtgccccc     600 aggcaccttc tcagccagca gctccagctc agagcagtgc cagccccacc gcaactgcac    660
ggccctgggc ctggccctca atgtgccagg ctcttcctcc catgacaccc tgtgcaccag    720
ctgcactggc ttccccctca gcaccagggt accaggtgag ccagaggcct gaggggcag     780 cacactgcag gccaggccca cttgtgccct cactcctgcc cctgcacgtg catctagcct    840
gaggcatgcc agctggctct gggaagggc cacagtggat tgaggggtc aggggtccct      900 ccactagatc cccaccaagt ctgccctctc aggggtggct gagaatttgg atctgagcca    960
gggcacagct cccctggggg agctctggga aagtgggcag caatctccta actgcccgag    1020
gggaaggtgg ctggctcctc tgacacgggg aaaccgaggc ctgatggtaa ctctcctaac    1080
tgcctgagag gaaggtggct gcctcctctg acatggggaa accgaggccc aatgttaacc    1140
actgttgaga agtcacaggg ggaagtgacc cccttaacat caagtcaggt ccggtccatc    1200
tgcaggtccc aactcgcccc ttccgatggc ccaggagccc caagcccttg cctgggcccc    1260
cttgcctctt gcagccaagg tccgagtggc cgctcctgcc ccctaggcct ttgctccagc    1320
tctctgaccg aaggctcctg cccccttctcc agtccccatc gttgcactgc cctctccagc    1380
acggctcact gcacagggat ttctctctcc tgcaaacccc ccgagtgggg cccagaaagc    1440
agggtacctg gcagccccg ccagtgtgtg tgggtgaaat gatcggaccg ctgcctcccc    1500 acccactgc aggagctgag gagtgtgagc gtgccgtcat cgactttgtg gctttccagg    1560
acatctccat caagaggctg cagcggctgc tgcaggccct cgaggccccg gagggctggg    1620
gtccgacacc aagggcgggc cgcgcggcct tgcagctgaa gctgcgtcgg cggctcacgg    1680
agctcctggg ggcgcaggac ggggcgctgc tggtgcggct gctgcaggcg ctgcgcgtgg    1740
ccaggatgcc cgggctggag cggagcgtcc gtgagcgctt cctccctgtg cactga       1796
```

<210> SEQ ID NO 29
<211> LENGTH: 17
<212> TYPE: PRT
<213> ORGANISM: Homo Sapiens
<220> FEATURE:
<221> NAME/KEY: SIGNAL
<222> LOCATION: (1)..(22)
<223> OTHER INFORMATION: stanniocalcin signal sequence

<400> SEQUENCE: 29

Met Leu Gln Asn Ser Ala Val Leu Leu Leu Val Ile Ser Ala Ser
 1               5                  10                  15

Ala

<210> SEQ ID NO 30
<211> LENGTH: 22
<212> TYPE: PRT
<213> ORGANISM: Artificial Sequence
<220> FEATURE:
<221> NAME/KEY: SIGNAL
<222> LOCATION: (1)..(22)
<223> OTHER INFORMATION: consensus signal sequence

<400> SEQUENCE: 30

```
Met Pro Thr Trp Ala Trp Trp Leu Phe Leu Val Leu Leu Ala Leu
1               5                   10                  15

Trp Ala Pro Ala Arg Gly
                20

<210> SEQ ID NO 31
<211> LENGTH: 283
<212> TYPE: PRT
<213> ORGANISM: Homo sapiens

<400> SEQUENCE: 31

Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
        50                  55                  60

Glu Ala Cys Gly Glu Leu Thr Gly Thr Val Cys Glu Pro Cys Pro Pro
65              70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280

<210> SEQ ID NO 32
<211> LENGTH: 903
<212> TYPE: DNA
<213> ORGANISM: Artificial Sequence
<220> FEATURE:
<223> OTHER INFORMATION: Mammalian synthetic TNFR-6 alpha

<400> SEQUENCE: 32
atgagggcgc tggaggggcc aggcctgtcg ctgctgtgcc tggtgttggc gctgcctgcc    60
```

```
ctgctgccgg tgccggctgt acgcggagtg gctgaaacac ctacatatcc atggagagat      120
gctgaaacag gagaaaggct ggtgtgtgct cagtgtcctc ctggaacatt tgtgcaaagg      180
ccttgtaggc gcgattctcc tacgacgtgt ggcccttgcc ctcctaggca ctatacacag      240
ttttggaact atctcgagcg ctgtaggtat tgcaacgtgc tctgtggaga agggaagag       300 gaagcaaggg cttgtcatgc aacacacaac agggcatgta ggtgtcgcac aggcttcttt      360
gctcatgctg gattttgtct ggaacacgct tcttgtcctc ctggtgctgg agtgatcgct      420
cctggtacac cctctcagaa cacccaatgc cagccctgtc ctcctggcac cttctctgca      480
tctagctcca gctctgaaca atgccaacct caccgcaatt gtacagctct gggactggct      540
ctgaacgtgc ctggttcctc ctcccatgat actctgtgta caagctgtac tggctttcct      600
ctctctaccc gcgtgcctgg cgctgaagag tgcgaacgcg ctgtgatcga ctttgtggcc      660
ttccaggata tctctatcaa aaggctgcaa cgcctgctgc aagctctgga agctcctgag      720
ggctggggtc ccacaccaag ggctggcagg gctgcactgc aactgaagct tcgcaggagg      780
ctcactgaac tcctgggagc tcaagatgga gctctgctgg tgaggctgct gcaagctctg      840
agggtggcaa ggatgcctgg actggagcgc tctgtgaggg aacgcttcct gcctgtgcac      900
tga                                                                    903

<210> SEQ ID NO 33
<211> LENGTH: 1550
<212> TYPE: DNA
<213> ORGANISM: Artificial Sequence
<220> FEATURE:
<223> OTHER INFORMATION: Codon optimized TNFR-6 alpha

<400> SEQUENCE: 33
atgagggcgc tggaggggcc aggcctgtcg ctgctgtgcc tggtgttggc gctgcctgcc       60
ctgctgccgg tgccggctgt acgcggagtg gctgaaacac ctacatatcc atggagagat      120
gctgaaacag gagaaaggct ggtgtgtgct cagtgtcctc ctggaacatt tgtgcaaagg      180
ccttgtaggc gcgattctcc tacgacgtgt ggcccttgcc ctcctaggca ctatacacag      240
ttttggaact atctcgagcg ctgtaggtat tgcaacgtgc tctgtggaga agggaagag       300 gaagcaaggg cttgtcatgc aacacacaac agggcatgta ggtgtcgcac aggcttcttt      360
gctcatgctg gattttgtct ggaacacgct tcttgtcctc ctggtgctgg agtgatcgct      420
cctggtacac cctctcagaa cacccaatgc cagccctgtc ctcctggcac cttctctgca      480
tctagctcca gctctgaaca atgccaacct caccgcaatt gtacagctct gggactggct      540
ctgaacgtgc ctggttcctc ctcccatgat actctgtgta caagctgtac tggctttcct      600
ctctctaccc gcgtgcctgg cgctgaagag tgcgaacgcg ctgtgatcga atgagggcgc      660
tggaggggcc aggcctgtcg ctgctgtgcc tggtgttggc gctgcctgcc ctgctgccgg      720
tgccggctgt acgcggagtt gctgaaacac caacutaccc atggagagat gctgaaactg      780
gtgaaagact ggtttgtgct caatgtccac caggtacttt tgttcaaaga ccatgtagaa      840
gagattctcc aactacttgt ggtccatgtc caccaagaca ttacactcaa ttttggaact      900
acctggaaag atgtagatac tgtaacgttc tttgtggtga aagagaagaa gaagctagag      960
cttgtcatgc tactcataac agagcttgta gatgtagaac tggttttttt gctcatgctg     1020 gttttttgttt ggaacatgct tcttgtccac ctggtgctgg tgttattgct cctggtactc     1080
cttctcaaaa cactcaatgt cagccatgtc caccaggtac tttttctgct tcttcttctt     1140
```

```
cttctgaaca atgtcaacca catagaaact gtactgcttt gggtctggct ttgaatgttc    1200
caggttcttc ttctcatgat actttgtgta cttcttgtac tggttttcct ttgtctacta    1260
gagttccagg tgctgaagaa tgtgaaagag ctgttattga ttttgttgct tttcaagata    1320
tttctattaa gagactgcaa agactgctgc aagctctgga agctccagaa ggttggggtc    1380
caactccaag agctggtaga gctgctttgc aattgaagtt gagaagaaga ttgacagaat    1440
tgttgggtgc tcaagatggt gctttgttgg ttagattgtt gcaagctttg agagttgcta    1500
gaatgcctgg tttggaaaga tctgttagag aaagattttt gccagttcac              1550

<210> SEQ ID NO 34
<211> LENGTH: 25
<212> TYPE: DNA
<213> ORGANISM: Artificial Sequence
<220> FEATURE:
<223> OTHER INFORMATION: Forward TNF-gamma-beta primer useful for
      amplifying nucleotides encoding amino acids 86-114 of TNF-gamma-
      beta protein Mammalian synthetic TNFR-6 alpha

<400> SEQUENCE: 34
cacctcttag agcagacgga gataa                                            25

<210> SEQ ID NO 35
<211> LENGTH

```
-continued gggaactgat ttttaaagtg ctgtgt                                         26

<210> SEQ ID NO 39
<211> LENGTH: 34
<212> TYPE: DNA
<213> ORGANISM: Artificial Sequence
<220> FEATURE:
<223> OTHER INFORMATION: Probe that hybridizes to TNF-gamma-alpha cDNA

<400> SEQUENCE: 39
tcctctttct tgtctttcca gttgtgagac aaac                                34

<210> SEQ ID NO 40
<211> LENGTH: 36
<212> TYPE: DNA
<213> ORGANISM: Artificial Sequence
<220> FEATURE:
<223> OTHER INFORMATION: Forward TNF-gamma-alpha primer

<400> SEQUENCE: 40
gcaaagtcta cagtttccca atgagaaaat taatcc                              36

<210> SEQ ID NO 41
<211> LENGTH: 24
<212> TYPE: DNA
<213> ORGANISM: Artificial Sequence
<220> FEATURE:
<223> OTHER INFORMATION: Forward TNF-gamma-beta primer

<400> SEQUENCE: 41
atggccgagg atctgggact gagc                                           24

<210> SEQ ID NO 42
<211> LENGTH: 36
<212> TYPE: DNA
<213> ORGANISM: Artificial Sequence
<220> FEATURE:
<223> OTHER INFORMATION: Reverse TNF-gamma-alpha/beta primer

<400> SEQUENCE: 42
ctatagtaag aaggctccaa agaaggtttt atcttc                              36
```